US008058233B2

(12) United States Patent
Cowley et al.

(10) Patent No.: US 8,058,233 B2
(45) Date of Patent: *Nov. 15, 2011

(54) MODIFICATION OF FEEDING BEHAVIOR USING PYY AND GLP-1

(75) Inventors: Michael Cowley, Portland, OR (US); Roger Cone, Oregon City, OR (US); Malcolm James Duncan Low, Lake Oswego, OR (US); Andrew Butler, Baton Rouge, LA (US); Stephen Robert Bloom, Hampstead (GB); Caroline Jane Small, London (GB); Rachel Louise Batterham, London (GB); Mohammad Ali Ghatei, Ruislip (GB)

(73) Assignees: Oregon Health and Science University, Portland, OR (US); Imperial Innovations Limited (GB)

( * ) Notice: Subject to any disclaimer, the term of this patent is extended or adjusted under 35 U.S.C. 154(b) by 903 days.

This patent is subject to a terminal disclaimer.

(21) Appl. No.: 10/501,411

(22) PCT Filed: Jan. 10, 2003

(86) PCT No.: PCT/GB03/00062
§ 371 (c)(1),
(2), (4) Date: Jul. 7, 2005

(87) PCT Pub. No.: WO03/057235
PCT Pub. Date: Jul. 17, 2003

(65) Prior Publication Data
US 2006/0014678 A1 Jan. 19, 2006

Related U.S. Application Data

(60) Provisional application No. 60/392,109, filed on Jun. 28, 2002.

(30) Foreign Application Priority Data

Jan. 10, 2002 (GB) .................................. 0200507.2

(51) Int. Cl.
*A61K 38/00* (2006.01)
*C07K 14/00* (2006.01)
(52) U.S. Cl. ............................ 514/2; 530/300; 536/23.5
(58) Field of Classification Search .................. None
See application file for complete search history.

(56) References Cited

U.S. PATENT DOCUMENTS

| 3,773,919 | A | 11/1973 | Boswell et al. |
|---|---|---|---|
| 4,002,531 | A | 1/1977 | Royer |
| 4,175,122 | A | 11/1979 | Lazarus |
| 4,179,337 | A | 12/1979 | Davis et al. |
| 4,220,653 | A | 9/1980 | Vivino |
| 4,223,017 | A | 9/1980 | Lazarus |
| 4,355,025 | A | 10/1982 | Lazarus |
| 4,485,045 | A | 11/1984 | Regen |
| 4,544,545 | A | 10/1985 | Ryan et al. |
| 4,619,794 | A | 10/1986 | Hauser |
| 4,698,327 | A | 10/1987 | Nagarajan |
| 4,701,441 | A | 10/1987 | Kalra |
| 4,829,076 | A | 5/1989 | Szilagyi et al. |
| 5,021,234 | A | 6/1991 | Ehrenfeld |
| 5,026,685 | A | 6/1991 | Boublik et al. |
| 5,122,614 | A | 6/1992 | Zalipsky |
| 5,284,839 | A | 2/1994 | Siren et al. |
| 5,349,052 | A | 9/1994 | Delgado et al. |
| 5,428,128 | A | 6/1995 | Mensi-Fattohi et al. |
| 5,432,156 | A | 7/1995 | Matsuno |
| 5,512,549 | A | 4/1996 | Chen et al. |
| 5,574,010 | A * | 11/1996 | McFadden ..................... 514/12 |
| 5,604,203 | A | 2/1997 | Balasubramaniam |
| 5,635,503 | A | 6/1997 | Poindexter et al. |
| 5,643,575 | A | 7/1997 | Martinez et al. |
| 5,696,093 | A | 12/1997 | Tseng et al. |
| 5,700,486 | A | 12/1997 | Canal et al. |
| 5,728,396 | A | 3/1998 | Peery et al. |
| 5,858,975 | A | 1/1999 | Yano |
| 5,880,131 | A | 3/1999 | Greenwald et al. |
| 5,889,016 | A | 3/1999 | Bruce et al. |
| 5,912,227 | A | 6/1999 | Croom et al. |
| 5,919,901 | A | 7/1999 | Hu et al. |
| 5,936,092 | A | 8/1999 | Shen et al. |
| 5,939,380 | A | 8/1999 | Wang |
| 5,965,392 | A | 10/1999 | Hun et al. |
| 5,989,920 | A | 11/1999 | Gerald et al. |
| 5,993,414 | A | 11/1999 | Haller |
| 6,001,836 | A | 12/1999 | Poindexter et al. |

(Continued)

FOREIGN PATENT DOCUMENTS

CA          2431800          6/2002

(Continued)

OTHER PUBLICATIONS

Yang Y., Emerging therapeutic targets in obesity: new approaches to controlling body weight, Emerging Therapeutic Targets (1999), 3(1), pp. 165-176.* U.S. Appl. No. 60/256,216, filed Dec. 14, 2000, Pittener et al.
U.S. Appl. No. 60/324,406, filed Sep. 24, 2001, Cowley, et al.
Abuchowski, et al., "Cancer therapy with chemically modified enzymes. I. Antitumor properties of polyethylene glycol-asparaginase conjugates," *Cancer Biochem Biophys.*, 7(2):175-86 (1984).
Adrian, et al., "Distribution and postprandial release of porcine peptide YY," *J Endocrinol.*, 113:11-4, (1987).
Adrian, et al., "Release of peptide YY (PYY) after resection of small bowel, colon, or pancreas in man," *Surgery*, 101(6):715-9 (1987).

(Continued)

*Primary Examiner* — Anand Desai
(74) *Attorney, Agent, or Firm* — Lando & Anastasi LLP

(57) ABSTRACT

Methods are disclosed for decreasing calorie intake, food intake, and appetite in a subject. The methods include peripherally administering PYY or an agonist thereof and GLP-1 or an agonist thereof to the subject, simultaneously or sequentially, thereby decreasing the calorie intake of the subject.

28 Claims, 16 Drawing Sheets

U.S. PATENT DOCUMENTS

| | | | |
|---|---|---|---|
| 6,001,970 A | 12/1999 | Cascieri et al. | |
| 6,046,167 A | 4/2000 | Balasubramaniam | |
| 6,048,900 A | 4/2000 | Connell et al. | |
| 6,093,692 A | 7/2000 | Shen et al. | |
| 6,127,355 A | 10/2000 | Greenwald et al. | |
| 6,140,354 A | 10/2000 | Dax et al. | |
| 6,191,102 B1 | 2/2001 | Dimarchi et al. | |
| 6,201,025 B1 | 3/2001 | Dax et al. | |
| 6,218,408 B1 | 4/2001 | Marzabadi et al. | |
| 6,225,330 B1 | 5/2001 | Marzabadi et al. | |
| 6,225,445 B1 | 5/2001 | Shen et al. | |
| 6,268,343 B1 | 7/2001 | Knudsen | |
| 6,316,203 B1 | 11/2001 | Gerald et al. | |
| 6,340,683 B1 | 1/2002 | Marzabadi et al. | |
| 6,348,472 B1 | 2/2002 | Poindexter et al. | |
| 6,355,478 B1 | 3/2002 | Baez et al. | |
| 6,372,743 B1 | 4/2002 | Darrow et al. | |
| 6,380,224 B1 | 4/2002 | Dax et al. | |
| 6,391,877 B1 | 5/2002 | Islam et al. | |
| 6,391,881 B2 | 5/2002 | Sit | |
| 6,399,631 B1 | 6/2002 | Elliot et al. | |
| 6,407,120 B1 | 6/2002 | Carpino et al. | |
| 6,410,707 B2 | 6/2002 | Wagner et al. | |
| 6,410,792 B1 | 6/2002 | Connell et al. | |
| 6,420,532 B1 | 7/2002 | Gerald et al. | |
| 6,432,960 B2 | 8/2002 | Sit et al. | |
| 6,436,091 B1 | 8/2002 | Harper et al. | |
| 6,444,675 B2 | 9/2002 | Sit | |
| 6,447,743 B1 | 9/2002 | Devic et al. | |
| 6,447,753 B2 | 9/2002 | Edwards et al. | |
| 6,458,924 B2 | 10/2002 | Knudsen | |
| 6,583,111 B1 | 6/2003 | DiMarchi et al. | |
| 6,586,403 B1 | 7/2003 | Mathison | |
| 6,608,098 B1 | 8/2003 | Nagase et al. | |
| 6,620,910 B1 | 9/2003 | Calas et al. | |
| 6,645,774 B1 | 11/2003 | Gerald et al. | |
| 6,667,319 B2 | 12/2003 | Stamford et al. | |
| 6,699,891 B1 | 3/2004 | Kawanishi et al. | |
| 6,890,898 B2 | 5/2005 | Bachovchin et al. | |
| 6,956,026 B2 * | 10/2005 | Beeley et al. | 514/12 |
| 7,078,381 B2 | 7/2006 | Bachovchin et al. | |
| 7,157,429 B1 | 1/2007 | Bachovchin et al. | |
| 7,166,575 B2 | 1/2007 | Quay | |
| 7,265,125 B2 | 9/2007 | Breu et al. | |
| 7,396,809 B1 | 7/2008 | Lu et al. | |
| 7,459,432 B2 | 12/2008 | Cowley et al. | |
| 2001/0011071 A1 | 8/2001 | Knudsen | |
| 2001/0046956 A1 | 11/2001 | Hadcock | |
| 2002/0141985 A1 * | 10/2002 | Pittner et al. | 424/94.1 |
| 2002/0156010 A1 | 10/2002 | Lustig | |
| 2004/0018975 A1 | 1/2004 | DiMarchi et al. | |
| 2005/0070469 A1 | 3/2005 | Bloom | |
| 2005/0176630 A1 | 8/2005 | Cowley et al. | |
| 2005/0176643 A1 | 8/2005 | Bridon et al. | |
| 2006/0014678 A1 | 1/2006 | Cowley et al. | |
| 2006/0171920 A1 | 8/2006 | Shechter | |
| 2006/0189522 A1 | 8/2006 | Bloom et al. | |
| 2008/0064636 A1 | 3/2008 | Bloom et al. | |
| 2009/0181885 A1 | 7/2009 | Bloom | |
| 2009/0209461 A1 | 8/2009 | Cowley et al. | |

FOREIGN PATENT DOCUMENTS

| | | |
|---|---|---|
| CN | 1490333 | 4/2004 |
| DE | 3 218 121 | 11/1983 |
| EP | 0 036 676 | 9/1981 |
| EP | 0 052 322 | 5/1982 |
| EP | 0 058 481 | 8/1982 |
| EP | 0 102 324 | 3/1984 |
| EP | 0 133 988 | 3/1985 |
| EP | 0 143 949 | 6/1985 |
| EP | 0 267 050 | 5/1988 |
| EP | 0 401 384 | 12/1990 |
| EP | 0619332 | 10/1994 |
| EP | 0708179 | 4/1996 |
| EP | 0795562 | 9/1997 |
| EP | 0920864 | 11/1998 |
| JP | 60-007934 | 1/1985 |
| JP | 11-228447 | 8/1999 |
| JP | 2001-011095 | 1/2001 |
| WO | WO 80/01882 | 9/1980 |
| WO | WO 93/09227 | 5/1993 |
| WO | WO 93/19175 | 9/1993 |
| WO | WO 94/22467 | 10/1994 |
| WO | WO 95/06058 | 3/1995 |
| WO | WO 96/22783 | 1/1996 |
| WO | WO 97/37998 | 10/1997 |
| WO | WO 97/46579 | 11/1997 |
| WO | WO 98/20885 | 5/1998 |
| WO | WO 98/20895 | 5/1998 |
| WO | WO 98/30231 | 7/1998 |
| WO | WO 98/32466 | 7/1998 |
| WO | WO 99/39702 | 8/1999 |
| WO | WO 99/43707 | 9/1999 |
| WO | WO 00/34236 | 6/2000 |
| WO | WO 00/42026 | 7/2000 |
| WO | WO 00/47219 | 8/2000 |
| WO | WO 00/59887 | 10/2000 |
| WO | WO 00/68197 | 11/2000 |
| WO | WO 00/78333 | 12/2000 |
| WO | WO 01/04156 | 1/2001 |
| WO | WO 01/14368 | 3/2001 |
| WO | WO 01/14386 | 3/2001 |
| WO | WO 01/35988 | 5/2001 |
| WO | WO 01/51078 | 7/2001 |
| WO | WO 01/66135 | 9/2001 |
| WO | WO 01/68699 | 9/2001 |
| WO | WO 01/76631 | 10/2001 |
| WO | WO 01/87335 | 11/2001 |
| WO | WO 01/89554 | 11/2001 |
| WO | WO 02/03978 | 1/2002 |
| WO | WO 02/47712 | 6/2002 |
| WO | WO 02/066479 | 8/2002 |
| WO | WO 02/067918 | 9/2002 |
| WO | WO 03/022304 | 3/2003 |
| WO | WO 03/026591 | 4/2003 |
| WO | WO 03/057235 | 7/2003 |
| WO | WO 2004/062685 | 7/2004 |
| WO | WO 2005/035761 | 4/2005 |
| WO | WO 2005/118642 | 12/2005 |
| WO | WO 2006/082517 | 8/2006 |
| WO | WO 2006/095166 | 9/2006 |
| WO | WO 2006/134340 | 12/2006 |
| WO | WO 2007/056362 | 5/2007 |
| WO | WO 2007/100535 | 9/2007 |
| WO | WO 2007/146038 | 12/2007 |
| WO | WO 2008/003947 | 1/2008 |
| WO | WO 2008/071972 | 6/2008 |

OTHER PUBLICATIONS

Adrian, et al., "Elevated plasma peptide YY in human neonates and infants," *Pediatr Res.*, 20(12):1225-7 (1986).

Adrian, et al., "Peptide YY abnormalities in gastrointestinal diseases," *Gastroenterology*, 90:379-84 (1986).

Adrian, et al., "Plasma peptide YY (PYY) in dumping syndrome," *Digestive Diseases & Sciences*, 30(12):1145-8 (1985).

Adrian, et al., "Effect of peptide YY on gastric, pancreatic, and biliary function in humans," *Gastroenterology*, 89:494-9 (1985).

Adrian et al., "Human distribution and release of a putative new gut hormone, peptide yy" *Gastroenterology* 89:1070-1077 (1985).

Allen, et al., "Effects of peptide YY and neuropeptide Y on gastric emptying in man," *Digestion*, 30:255-62 (1984).

Allen, et al., "Radioimmunoassay of neuropeptide Y," *Regul Pept.*, 8(461-70 (1984).

Allen, et al., "Two novel related peptides, neuropeptide Y (NPY) and peptide YY (PYY) inhibit the contraction of the electrically stimulated mouse vas deferens," *Neuropeptides*, 3:71-9 (1982).

Asakawa, et al., "Mouse pancreatic polypeptide modulates food intake, while not influencing anxiety in mice," *Peptides*, 20:1445-8 (1999).

Bagnol, et al., "Anatomy of an endogenous antagonist: relationship between Agouti-related protein and proopiomelanocortin in brain," *J Neurosci*, 19(18)RC26:1-7 (1999).

Balasubramaniam, et al., "Syntheses and receptor affinities of partial sequences of peptide yy (pyy)" *Pept Res.*, 1(1):32-5 (1998).

Barlow and Dietz, "Obesity Evaluation and Treatment: Expert Committee recommendations," *Pediatrics*, 102:E29-40 (1998).
Barrachina, et al., "Leptin-induced decrease in food intake is not associated with changes in gastric emptying in lean mice" *Am. J. Physiol.*, 272:R1007-11 (1997).
Barsh, et al., "Genetics of body-weight regulation," *Nature*, 404(6778):644-51 (2000).
Batterham and Bloom, "The gut hormone peptide YY regulates appetite," *Ann N Y Acad Sci.*, 994:162-8 (2003).
Batterham, et al., "Gut hormone PYY(3-36) physiologically inhibits food intake," *Nature*, 418(6898):650-4 (2002).
Beck-Sickinger and Jung, "Structure-activity relationships of neuropeptide y analogues with respect to $Y_1$ and $Y_2$ receptors" *Biopolymers*, 37:123-142 (1995).
Beer, et al., "The effect of a 72-h fast on plasma levels of pituitary, adrenal, thyroid, pancreatic and gastrointestinal hormones in healthy men and women," *J Endocrinol*, 120:337-50 (1989).
Berglund, MM, Binding Properties of Three Neuropeptide Y Receptor Subtypes from Zebrafish: Comparison with Mammalian Y1 Receptors *Biochem Pharmacol*, 60(12):1815-22 (2000).
Broberger, et al., "Subtypes Y1 and Y2 of the neuropeptide Y receptor are respectively expressed in pro-opiomelanocortin- and neuropeptide-Y-containing neurons of the rat hypothalamic arcuate nucleus" *Neuroendocrinology*, 66:393-408 (1997).
Buchwald, et al., "Long-term, continuous intravenous heparin administration by an implantable infusion pump in ambulatory patients with recurrent venous thrombosis" *Surgery*, 88:507-16 (1980).
Butler, et al., "Melanocortin-4 receptor is required for acute homeostatic responses to increased dietary fat" *Nature Neuroscience*, 4:605-611 (2001).
Butler, et al., "A unique metabolic syndrome causes obesity in the melanocortin-3 receptor-deficient mouse," *Endocrinology*, 141:3518-21 (2000).
Cabrele, et al., "Molecular characterization of the ligand-receptor interaction of the neuropeptide Y family" *J Pept Sci.*, 6(3):97-122 (2000).
Calam, et al., "Regional differences in concentrations of regulatory peptides in human colon mucosal biopsy," *Digestive Diseases & Sciences*, 34(8):1193-8 (1989).
Caliceti, et al., "Biopharmaceutical properties of uricase conjugated to neutral and amphiphilic polymers," *Bioconjug Chem.*, 10(4):638-46 (1999).
Campbell, et al., "Oxygen-dependent K+ influxes in Mg2+-clamped equine red blood cells," *J. Physiol.* 515:431-7 (1999).
Campfeild, et al., "Recombinant mouse OB protein: evidence for a peripheral signal linking adiposity and central neural networks," *Science*, 269:546-9 (1995).
Chelikani, et al., "Intravenous infusion of peptide YY(3-36) potently inhibits food intake in rats," *Endocrinology*, 146(2):879-88 (2005).
Clapham, et al., "Anti-obesity drugs: a critical review of current therapies and future opportunities," *Pharmacol Ther.*, 89(1):81-121 (2001).
Clinical Guidelines on the Identification, Evaluation, and Treatment of Overweight and Obesity in Adults—The Evidence Report. National Institutes of health, *ObesityRresearch* 6(Suppl 2):51S-209S (1998).
Comuzzie, et al., "A major quantitative trait locus determining serum leptin levels and fat mass is located on human chromosome 2," *Nature Genetics*, 15:273-6 (1997).
Cone, "The central melanocortin system and energy homeostasis," *Trends Endocrinot Metab.*, 10:211-16 (1999).
Cowley, et al., "Leptin activates anorexigenic POMC neurons through a neural network in the arcuate nucleus" *Nature*, 411:480-484 (2001).
Cowley, et al., "Integration of NPY, AGRP, and melanocortin signals in the hypothalamic paraventricular nucleus: evidence of a cellular basis for the adipostat," *Neuron*, 24:155-63 (1999).
Cox and Randich, "Enhancement of feeding suppression by PYY(3-36) in rats with area postrema ablations," *Peptides*, 25(6):985-9 (2004).

Csiffary, et al., "Neuropeptide Y innervation of ACTH-immunoreactive neurons in the arcuate nucleus of rats: a correlated light and electron microscopic double immunolabeling study," *Brain Research*, 506:215-222 (1990).
Delgado, et al., "The uses and properties of PEG-linked proteins," *Crit Rev Ther Drug Carrier Syst.*, 9(3-4):249-304 (1992).
Donckier, et al., "Age-related changes in regulatory peptides in rectal mucosa," *Acta Gastro-Enterologica Belgica*, 50(4):405-10 (1987).
Doods, H.N., "Pharmacological characterization of the selective nonpeptide neuropeptide Y Y1 receptor antagonist BIBP 3226" *J Pharmacol Exp Ther.*, 275(1):136-42 (1995).
Dreborg, et al., "Immunotherapy with monomethoxypolyethylene glycol modified allergens," *Crit Rev Ther Drug Carrier Syst.*, 6(4):315-65 (1990).
Dumont, et al., "Characterization of a selective neuropeptide Y/peptide YY Y2 receptor radioligand" *Society for Neuroscience Abstracts*, 19:726 (1993).
Eberlein, et al., "A new molecular form of PYY: structural characterization of human PYY(3-36) and PYY(1-36)" *Peptides*, 10:797-803 (1989).
Edwards, et al., "Exendin-4 reduces fasting and postprandial glucose and decreases energy intake in healthy volunteers" *Am. J. Physiol. Endocrinol. Metab.*, 281:E155-E166, (2001).
Ekblad and Sundler, "Distribution of pancreatic polypeptide and peptide YY," *Peptides*, 23:251-61 (2002).
Elias, et al., "Leptin differentially regulates NPY and POMC neurons projecting to the lateral hypothalamic area," *Neuron*, 23:775-86 (1999).
Eng, et al., "Isolation and characterization of exendin-4, an exendin-3 analogue, from Heloderma suspectum venom. Further evidence for an exendin receptor on dispersed acini from guinea pig pancreas," *J Biol Chem.*, 267(11):7402-5 (1992).
Epstein, et al., "Biological activity of liposome-encapsulated murine interferon gamma is mediated by a cell membrane receptor" *Proc. Natl. Acad. Sci. U.S.A.*, 82:3688-3692 (1985).
Fan, et al., "Role of melanocortinergic neurons in feeding and the agouti obesity syndrome," *Nature*, 385:165-8 (1997).
Farooqi, et al., "Effects of recombinant leptin therapy in a child with congenital leptin deficiency," New Engl. J. Med., 341:879-84 (1999).
Ferri, et al., "Intramural distribution of regulatory peptides in the sigmoid-recto-anal region of the human gut," *Gut*, 29:762-8 (1988).
Fournier, et al., "Conformational and biological studies of neuropeptide Y analogs containing structural alterations" *Mol Pharmacol.*, 45(1):93-101 (1994).
Francis, et al., "PEGylation of cytokines and other therapeutic proteins and peptides: the importance of biological optimisation of coupling techniques," *Int J Hematol.*, 68(1):1-18 (1998).
Fried, et al., "Temporal relationships of cholecystokinin release, pancreatobiliary secretion, and gastric emptying of a mixed meal," *Gastroenterology*, 95:1344-50 (1988).
Fueßl, et al., "Peptide YY in Diabetes Treated Chronically with an Intestinal Glucosidae Inhibitor,"*Klinische Wochen-schrift*, 66:985 (1988).
Fuessl, et al., "The effect of a long-acting somatostatin analogue (SMS 201-995) on intermediary metabolism and gut hormones after a test meal in normal subjects," *Aliment. Pharmacol. Therap.*, 1:321-30 (1987).
Gehlert, et al., "Multiple receptors for the pancreatic polypeptide (pP-fold) family: Physiological implications" *Proc Soc Exp Biol Med.*, 218:7-22 (1998).
Ghatei, et al., "Fermentable dietary fibre, intestinal microflora and plasma hormones in the rat," *Clinical Science*, 93:109-12 (1997).
Glaum, et al., Leptin, the Obese Gene Product, Rapidly Modulates Synaptic Transmission in the Hypothalamus, *Mol. Pharmacol.*, 50:230-235 (1996).
Goodlad, et al., "Does the response of the intestinal epithelium to keratinocyte growth factor vary according to the method of administration?" *Regul Pept*, 87:83-90 (2000).
Goodlad, et al., "Insulin and intestinal epithelial cell proliferation," *Exp Physiol.* 78(5):697-705 (1993).
Goodlad, et al., "Glucagon 1-21 reduces intestinal epithelial cell proliferation in parenterally fed rats," *Experimental Physiology*, 76:943-9 (1991).

Goodlad, et al., "Is peptide YY trophic to the intestinal epithelium of parenterally fed rats," "*Digestion*, 46(S2)177-81 (1990)."

Goodlad, et al, "Plasma enteroglucagon, gastrin and peptide YY in conventional and germ-free rats refed with a fibre-free or fibre-supplemented diet," *Q J Exp Physiol.*, 74(4):437-42 (1989).

Proliferative effects of 'fibre' on the intestinal epithelium: relationship to gastrin, enteroglucagon and PYY, *Gut*, 28(S1):221-6 (1987).

Googlad, et al, "Effects of an elemental diet, inert bulk and different types of dietary fibre on the response of the intestinal epithelium to refeeding in the rat and relationship to plasma gastrin, enteroglucagon, and PYY concentrations", *Gut*, 28:171-80 (1987).

Graffner, et al., Effects of physiological increases of plasma noradrenaline on gastric acid secretion and gastrointestinal hormones, *Digestive Diseases & Sciences*, 32(7):715-9 (1987).

Grandt, et al., "Two molecular forms of peptide YY (PYY) are abundant in human blood: characterization of a radioimmunoassay recognizing PYY 1-36 and PYY 3-36" *Regulatory Peptides*, 67(1):151-159 (1996).

Grandt, et al., "Characterization of two forms of peptide YY, PYY(1-36) and PYY(3-36), in the rabbit" *Regul. Pept.*, 51:815-20 (1994).

Grandt, et al., "Neuropeptide Y 3-36 is an endogenous ligand selective for Y2 receptors" *Peptides*, 15(5):33-37 (1994).

Grieco, et al., "D-Amino acid scan of gamma-melanocyte-stimulating hormone: importance of Trp(8) on human MC3 receptor selectivity," *J. Med. Chem.*, 43:4998-5002 (2000).

Grove, et al., "Neuropeptide Y Y5 receptor protein in the cortical/limbic system and brainstem of the rat: expression on gamma-aminobutyric acid and corticotropin-releasing hormone neurons," *Neuroscience*, 100(4):731-40 (2000).

Grundemar, et al., "Ligand binding and functional effects of systematic double D-amino acid residue substituted neuropeptide Y analogs on Y1 and Y2 receptor types" *Regulatory Peptides*, 62:131-136 (1996).

Hagan, "Peptide YY: a key mediator of orexigenic behavior," *Peptides*, 23:377-82 (2002).

Hager, et al., "A genome-wide scan for human obesity genes reveals a major susceptibility locus on chromosome 10," *Nature Genetics*, 20, 304-8 (1998).

Hakansson, et al., "Leptin receptor immunoreactivity in chemically defined target neurons of the hypothalamus" *J Neurosci.*, 18:559-72 (1998).

Hammer, et al., Pituitary-Specific and Hormonally Regulated Gene Expression Directed by the Raf Prooiomelanocortin Promoter in Transgenic Mice, *Mol. Endocrin.*, 4(11), 1689-97 (1990).

Harding, et al., "Identification and characterization of the emetic effects of peptide YY," *Peptides*, 10:21-4 (1989).

Haynes, et al., "Interactions between the melanocortin system and leptin in control of sympathetic nerve traffic," *Hypertension*, 33(1):542-7 (1999).

Haynes, et al., "Receptor-mediated regional sympathetic nerve activation by leptin," *J. Clin. Invest.*, 100:270-8 (1997).

Heisler, et al., "Activation of central melanocortin pathways by fenfluramine," *Science*, 297(5581):609-11 (2002).

Hoffman, et al., "c-Fos and related immediate early gene products as markers of activity in neuroendocrine systems," *Front. Neuroendocrinol.*, 14:173-213 (1993).

Horvath, et al., "Heterogeneity in the neuropeptide Y-containing neurons of the rat arcuate nucleus: GABAergic and non-GABAergic subpopulations," *Brain Res.*, 756:283-6 (1997).

Horvath, et al., "Gabaergic and Cathcholaminergic Innervation of Mediobasal Hypothalamic β-Endorphin Cells Projecting to the Medial Preoptic Area." *Neuroscience*, 51:391-9 (1992).

Hwang, et al., "Hepatic uptake and degradation of unilamellar sphingomyelin/cholesterol liposomes: A kinetic study" *Proc. Natl. Acad. Sci. U.S.A.*, 77:4030-4034 (1980).

Iyengar, et al., "Characterization of neuropeptide Y-induced feeding in mice: do Y1-Y6 receptor subtypes mediate feeding?" *J Pharmacol Exp Ther.*, 289(2):1031-40 (1999).

Jequier, et al., "Energy, obesity, and body weight standard," *Am. J. Clin.Nutr.*, 45:1035-47 (1987).

Kalra, et al., "Interacting appetite-regulating pathways in the hypothalamic regulation of body weight" *Endocr. Rev.*, 20:68-100 (1999).

Kanatani, A., "L-152,804: Orally active and selective neuropeptide Y Y5 receptor antagonist" *Biochem Biophys Res Commun.*, 272(1):169-73 (2000).

Keire, et al., "Primary structures of PYY, [Pro(34)]PYY, and PYY-(3-36) confer different conformations and receptor selectivity," *Am. J. Physiol. Gastrointest. Liver Physiol.*, 279:G126-31 (2000).

Kelly, et al., "Opiods Hyperpolarize β-Endorphin Neurons via μ-Receptor Activation of a Potassium Conductance," *Neuroendocrinology*, 52:268-75 (1990).

Kenchaiah, et al., "Obesity and the risk of heart failure," *N Engl J Med.*, 347(5):305-13 (2002).

Kim, et al., "Hypothalamic localization of the feeding effect of agouti-related peptide and alpha-melanocyte-stimulating hormone" *J. Clin. Invest.*, 105:1005-11 (2000).

Kim, et al., "The central melanocortin system affects the hypothalamopituitary thyroid axis and may mediate the effect of leptin" *Diabetes*, 49:177-82 (2000).

Kimmel, et al., "Isolation and characterization of chicken insulin" *Endocrinology*, 83:1323-30 (1968).

King, et al., "Regulation of neuropeptide Y release by neuropeptide Y receptor ligands calcium channel antagonists in hypothalamic slices" *J Neurochem.*, 73:641-6 (1999).

Kirby, et al., "Neuropeptide Y: Y1 and Y2 affinities of the complete series of analogues with single D-residue substitutions" *J Med Chem*, 38:4579-86 (1995).

Kirby, et al., "Defining structural requirements for neuropeptide Y receptors using truncated and conformationally restricted analogues," *J. Med. Chem.*, 36:385-93 (1993).

Kirby, et al., "Y1 and Y2 receptor selective neuropeptide Y analogues: Evidence of a Y1 receptor subclass" *J Med Chem*, 36:3802-08 (1993).

Kopelman, "Obesity as a medical problem," *Nature*, 404(6778):635-43 (2000).

Kreymann, et al., "Developmental patterns of glucagon-like peptide-1-(7-36) amide and peptide-YY in rat pancreas and gut," *Endocrinology*, 129:1001-5 (1991).

Krude and Gruters, "Implications of proopiomelanocortin (POMC) mutations in humans: the POMC deficiency syndrome," *Trends Endocrinol. Metab.*, 11(1):15-22 (2000).

Krude, et al., "Sever early-onset obesity, adrenal insufficiency and red-hair pigmentation caused by POMC mutations in humans," *Nature Genetics*, 19:155-7 (1998).

Langer, et al., "New methods of drug discovery," *Science*, 249:1527-1533 (1998).

Langer, "Controlled release of macromolecules" *Chem. Tech.*, 12:98-105 (1982).

Langer, et al., "Biocompatibility of polymeric delivery systems for macromolecules" *J. Biomed. Mater. Res.*, 15:167-277 (1981).

Leban, et al., "Novel modified carboxy terminal fragments of neuropeptide Y with high affinity for Y2-type receptors and potent functional antagonism at a Yl-type receptor" *J Med Chem*, 38:1150-57 (1995).

Liu, et al., "Synthetic peptide YY analog binds to a cell membrane receptor and delivers fluorescent dye to pancreatic cancer cells" *J Gastrointest Surg*, 5(2):147-52 (2001).

Liu, et al., "DNA elements with AT-rich core sequences direct pituitary cell-specific expression of the pro-opiomelanocortin gene in transgenic mice," *Biochem. J.*, 312(Pt 3):827-32 (1995).

Liu, et al., "Identification of DNA elements cooperatively activating proopiomelanocortin gene expression in the pituitary glands of transgenic mice," *Mol Cell Biol.* 12(9):3978-90 (1992).

Low, et al., "Post-translational processing of proopiomelanocortin (POMC) in mouse pituitary melanotroph tumors induced by a POMC-simian virus 40 large T antigen transgene," *J. Biol. Chem.*, 268(33):24967-75 (1993).

Lundberg and Modin, "Inhibition of sympathetic vasoconstriction in pigs in vivo by the neuropeptide Y-Y1 receptor antagonist BIBP 3226" *Br J Pharmacol* 116(7):2971-82 (1995).

Lyznicki, et al., "Obesity: assessment and management in primary care," *Am Fam Physician.*, 63(11):2185-96 (2001).

Malaisse-Lagae, et al., "Pancreatic polypeptide: a possible role in the regulation of food intake in the mouse: Hypothesis," *Experientia*, 33(7):915-7 (1977).

Malik, et al., Polyethylene glycol (PEG)-modified granulocyte-macrophage colony-stimulating factor (GM-CSF) with conserved biological activity, *Exp Hematol.*, 20(8):1028-35 (1992).

Malmstrom, "Existence of both neuropeptide Y, Y1 and Y2 receptors in pig spleen evidence using subtype-selective antagonists in vivo" *Life Sci*, 69(17):1999-2005 (2001).

Malmstrom, "Pharmacology of H 394/84, a dihydropyridine neuropeptide Y Y1 receptor antagonist, in vivo" *Eur J Pharmacol*, 418(1-2):95-104 (2001).

Marks, et al., "Role of the central melanocortin system in cachexia," *Cancer Res.*, 61:1432-8 (2001).

Massie, "Obesity and heart failure—risk factor or mechanism?" *N Engl J Med.*, 347(5):358-9 (2002).

McGowan and Bloom, "Peptide YY and appetite control," *Curr Opin Pharmacol.*, 4(6):583-8 (2004).

Meleagros, et al., "Release of vasodilator, but not vasoconstrictor, neuropeptides and of enteroglucagon by intestinal ischaemia/reperfusion in the rat," *Gut*, 35:1701-6 (1994).

Moran, et al., "Peptide YY(3-36) inhibits gastric emptying and produces acute reductions in food intake in rhesus monkeys," *Am J Physiol Regul Integr Comp Physiol.*, 288(2):R384-8 (2005).

Moran, "Cholecystokinin and satiety: Current perspectives" *Nutrition*, 16:858-865 (2000).

Morgan, et al., "Inhibition of glucose stimulated insulin secretion by neuropeptide Y is mediated via the Y1 receptor and inhibition of adenylyl cyclase in RIN 5AH rat insulinoma cells," *Diabetologia*, 41:1482-91 (1998).

Morgan, et al., "Reduced NPY induced feeding in diabetic but not steroid-treated rats: lack of evidence for changes in receptor number or affinity," *J Neuroendocrinol*, 8:283-90 (1996).

Morpurgo, et al., "Covalent modification of mushroom tyrosinase with different amphiphic polymers for pharmaceutical and biocatalysis applications," *Appl Biochem Biotechnol.*, 56(1):59-72 (1996).

Naveilham, et al., "Attenuation of hypercholesterolemia and hyperglycemia in ob/ob mice by NPY Y2 receptor ablation," *Peptides*, 23(6):1087-91 (2002).

Naveilhan, et al., "Distinct roles of the Y1 and Y2 receptors on neuropeptide Y-induced sensitization to sedation," *J. Neurochem*, 78:1201-7 (2001).

Naveilhan, et al., "Normal feeding behavior, body weight and leptin response require the neuropeptide Y Y2 receptor," *Nature Medicine*, 5(10):1188-93 (1999).

Nightingale, et al., "Gastrointestinal hormones in short bowel syndrome. Peptide YY may be the 'colonic brake' to gastric emptying," *Gut*, 39:267-72 (1996).

Okada, et al., Abstract 520, p. 180, 75th Meeting of Endocrine Society (1993).

Pedersen-Bjergaard, et al., "Influence of meal composition on postprandial peripheral plasma concentrations of vasoactive peptides in man" *Scand. J. Clin. Lab. Invest.* 56:497-503 (1996).

Pittner, et al., "Effects of PYY[3-36] in rodent models of diabetes and obesity," *Int J Obes Relat Metab Disord.*, 28(8):963-71 (2004).

Playford, et al., "Comparison of the effects of transforming growth factor alpha and epidermal growth factor on gastrointestinal proliferation and hormone release," *Digestion*, 57:362-7 (1996).

Playford, et al., "Effects of peptide YY on the human cardiovascular system: reversal of responses to vasoactive intestinal peptide," *Am J Physiol.* 263(4 Pt 1):E740-7 (1992).

Playford, et al., "Preliminary report: role of peptide YY in defence against diarrhoea," *Lancet*, 335:1555-7, (1990).

Potter, et al., "A novel neuropeptide Y analog, N-acetyl[Leu28, Leu31]neuropeptide Y-(24-36), with functional specificity for the presynaptic (Y2) receptor" *Eur J Pharmacol*, 267(3):253-262 (1994).

Powis, et al., "Leptin depolarizes rat hypothalamic paraventricular nucleus neurons," *Am J Physiol.*, 274(5 Pt 2):R1468-72 (1998).

Qin, et al., "Direct interaction of gbetagamma with a C-terminal gbetagamma-binding domain of the Ca2+ channel alpha1 subunit is responsible for channel inhibition by G protein-coupled receptors," *PNAS*, 94(16):8866-71 (1997).

Raben, et al., "The reproducibility of subjective appetite scores" *Br. J. Nutr.*, 73:517-30, (1995).

Rissanen, et al., "Risk of disability and mortality due to overweight in a Finnish population," *BMJ*, 301(6756):835-7 (1990).

Rist, et al., "The bioactive conformation of neuropeptide Y analogues at the human Y2-receptor" *Eur J Biochem.*, 247:1019-1028 (1997).

Rossi and Bloom, "Central Nervous SYStem Neuropeptides Involved in Obesity," in *Handbook of Experimental Pharmacology*, pp. 313-341; eds. D.H. Lockwood and T.G. Heffner, Springer, New York, (2000).

Rubinstein, et al., "Rat and Mouse Proopiomelanocortin Gene Sequences Target Tissue-Specific Expression to the Pituiary Gland but not to the Hypothalamus of Transgenic Mice," *Neuroendocrinology*, 58:373-80 (1993).

Saudek, et al., "A preliminary trial of the programmable implantable medication system for insulin delivery" *N. Engl. J. Med.*, 321:574-9 (1989).

Savage, et al., "Effects of peptide YY (PYY) on mouth to caecum intestinal transit time and on the rate of gastric emptying in healthy volunteers," *Gut*, 28:166-70 (1987).

Savage, et al., "Is raised plasma peptide YY after intestinal resection in the rat responsible for the trophic response?" *Gut*, 26:1353-8 (1985).

Schober, "The neuropeptide Y Y1 antagonist, 1229U91, a potent agonist for the human pancreatic polypeptide-preferring (NPY Y4) receptor" *Peptides*, 19(3):537-42 (1998).

Schutz, "Exercise and postprandial thermogenesis in obese women before and after weight loss," *Am J Clin Nutr.*, 45(6):1424-32 (1987).

Schwartz et al., "Central nervous system control of food intake" *Nature*, 404:661-671 (2000).

Sefton, "Implantable pumps" *CRC Crit. Ref. Biomed. Eng.*, 14:201-40 (1987).

Sheikh, et al., "Neuropeptide Y and peptide YY: major modulators of gastrointestinal blood flow and function" *Am J Physiol.*, 261:G701-15 (1991).

Shiraishi, et al., "Leptin effects on feeding-related hypothalamic and peripheral neuronal activities in normal and obese rats," *Nutrition*, 15:576-9 (1999).

Sidman, et al., "Controlled release of macromolecules and pharmaceuticals form synthetic polypeptides based on glutamic acid" *Biopolymers*, 22:547-556 (1983).

Simanowski, et al., "Effects of acute and chronic ethanol administration on the gastrointestinal hormones gastrin, enteroglucagon, pancreatic glucagon and peptide YY in the rat," *Digestion*, 42:167-73 (1989).

Slugg, et al., "Effect of the µ-Opiod Agonist DAMGO on Medial Basa Hypothalamic Neurons in Beta-Endorphin Knockout Mice," *Neuroendocrinology*, 72:208 (2000).

Small, et al., "Peptide analogue studies of the hypothalamic neuropeptide Y receptor mediating pituitary adrenocorticotrophic hormone release" *Proc. Natl. Acad. Sci. U.S.A.*, 94:11686-91 (1997).

Soderberg, et al., "Zebrafish genes for neuropeptide Y and peptide YY reveal origin by chromosome duplication from an ancestral gene linked to the homeobox cluster" *J. Neurochem.*, 75:908-18 (2000).

Soll, et al., "Novel analogues of neuroppeitde Y with a preference for the Yl-receptor" *Eur J Biochem*, 268(10):2828-37 (2001).

Spanswick, et al., "Leptin inhibits hypothalamic neurons by activation of ATP-sensitive potassium channels," *Nature*, 390:521-5 (1997).

Spiller, et al., "Further characterisation of the 'ileal brake' reflex in man—effect of ileal infusion of partial digests of fat, protein, and starch on jejunal motility and release of neurotensin, enteroglucagon, and peptide YY," *Gut*, 29:1042-51 (1988).

Tarling, et al., "A model gastric emptying using paracetamol absorption in intensive care patients" *Intensive Care Med.*, 23:256-260 (1997).

Tatemoto, et al., "Neuropeptide Y: Complete amino acid sequence of the brain peptide" *Proc Natl Aced Sci* U.S.A., 79:5485-9 (1982).

Tsukada, et al., "Functional analysis of the cell-specific enhancer in the human proopiomelanocortin gene by beta-galactosidase histochemical staining," *DNA and Cell Biol.*, 13(7):755-62 (1994).

Verma, et al., "Human fos gene," *Cold Spring Harb Symp Quant Biol.*, 51:949-58 (1986).

Vorobjev, et al., "Oligonucleotide conjugated to linear and branched high molecular weight polyethylene glycol as substrates for RNase H," *Nucleosides & Nucleotides*, 18(11-12):2745-50 (1999).
Walker, et al., "Neuropeptide Y modulates Neurotransmitter Release and $Ca^{2+}$ Currents in Rat Sensory Neurons," *J. Neuroscience*, 8:2438-2446 (1988).
Wang and Hanson, "Parenteral Formulations of Proteins and Peptides: Stability and Stabilizers," *Journal of Parenteral Science and technical Technology*, 42:S4-S26 (1988).
Wardlaw, et al., "Obesity as a Neuroendocrine Disease: Lessons to Be Learned from Proopiomelanocortin and Melanocortin Receptor Mutations in Mice and Men," *J. Clin. Endocrin. & Metab.*, 86(4):1442-46 (2001).
Yoshinaga, et al., "Structural requirements of peptide YY for biological activity at enteric sites," *Am. J. Physiol. Gastrointest. Liver Physiol.*, 263:G695-701 (1992).
Young, et al., "Authentic cell-specific and developmentally regulated expression of pro-opiomelanocortin genomic fragments in hypothalamic and hindbrain neurons of transgenic mice," *J. Neurosci.*, 18:6631-40 (1998).
Zhang, et al., "Positional cloning of the mouse *obese* gene and its human homologue," *Nature*, 372:425 (1994).
P01275 (gi45644939): "Glucagon precursor", GenBank Record dated Jan. 23, 2007, (GenBank [online] Bethesda, MD USA: United States National Library of Medicine, retrieved on Jun. 9, 2007, retrieved from internet using <URL: www.ncbl.nlm.nih.gov/entrezlviewer.fcgi?db=protein&val=45644939>, GenBank Accession No. P01275 (gi45644939).
P01275 (gi121484): "Glucagon precursor", GenBank Record dated Aug. 20, 2001, (GenBank [online] Bethesda, MD USA: United States National Library of Medicine, retrieved on Jun. 9, 2007, retrieved from internet using <URL//www.ncbi.nlm.nih.gov/entrezlviewer.fcgi?121484: )OLD09:43184>, GenBank Accession No. P01275 (gi121484).
P01273 (gi1346151): "Glucagon precursor", GenBank Record dated Jul. 10, 2007, (GenBank [online] Bethesda, MD USA: United States National Library of Medicine, retrieved on Jun. 9, 2007, retrieved from internet using <URL www.ncbi.nlm.nih.gov/entrezlviewer.fcgi?db=protein&val=1346151 >, GenBank Accession No. P01273 (gi1346151).
P01275: "GLUe_HUMAN", ExPASy [online] Swiss Institute of Bioinformatics (SIB), Gasteiger E., Gattiker A., Hoogland C., Ivanyi I., Appel R.D., Bairoch A. ExPASy: the proteomics server for in-depth protein knowledge and analysis Nucleic Acids Res. 31:3784-3788(2003), retrieved on May 27, 2005, retrieved from internet using <URLwww.au.expasy.org/cgi-bin/sprot-ft-details.pl?P01275@PEPTIDE@53@89>, ExPASy Accession No. P01275.
P01272 (gi121479): "Glucagon precursor", GenBank Record dated Aug. 21, 2007, (GenBank [online] Bethesda, MD USA: United States National Library of Medicine, retrieved on Jun. 9, 2007, retrieved from internet using <URL://www.ncbi.nlm.nih.gov/entrezlviewer.fcgi?db=protein&val=121479>, GenBank Accession No. P01272 (gi121479).
P06883 (gi121496): "Glucagon precursor", GenBank Record dated Jul. 10, 2007, (GenBank [online] Bethesda, MD USA: United States National Library of Medicine, retrieved on Jun. 9, 2007, retrieved from internet using <URL//www.ncbi.nlm.nih.gov/entrezlviewer.fcgi?db=protein&val=121496>, GenBank Accession No. P06883 (gi121496).
Allen, "Radioimmunoassay of neuropeptide Y", *Histochemistry*, 80:487 (1984).
Anderson & Rasmussen, "Cimetidine and obesity: Conflicting evidence", *Intl. J. Obesity* 23:550 (1999).
Assuncao, "Weight gain management in patients with schizophrenia during treatment with olanzapine in association with nizalidine", *Rev. Bras. Psiquiatr* 28(4):270-276 (2006).
Bagger, "Nasal bioavailability of peptide T in rabbits: Absorption enhancement by sodium glycocholate and glycofurol" Eur. J. Pharm. Sci. 14:69-74 (2001).
Bays, "Current and investigational antiobesity agents and obesity therapeutic treatment targets", *Obes Res* 12(8):1197-211 (2004).
Bowie, "Deciphering the message in protein sequences: tolerance to amino acid substitutions", *Science*, 247:1306-1310 (1990).
Buse, "Effects of exenatide (exendin-4) on glycemic control over 30 weeks in sulfonylurea-treated patients with type 2 diabetes", *Diabetes Care*, 27(11):2628-2635 (2004).
Cohen, Oxyntomodulin suppresses appetite and reduces food intake in humans•, *J. Clin, Endocrino/. Metab.*, 88(10):4696-4701 (2003).
Cummings, "A preprandial rise in plasma ghrelin levels suggest a role in meal initiation in humans", *Diabetes*, 50:1714-1719 (2001).
Dakin, "Oxyntomodulin inhibits food intake in the rat", *Endocrinology*, 142:4244-4250 (2001).
Dakin, "Peripheral oxyntomodulin reduces food intake and body weight gain in rats", *Endocrinology*, 145:2687-2695 (2004).
Dakin, "Repeated ICV administration of oxyntomodulin causes a greater reduction in body weight gain than in pair-fed rats", *Am. J. Physiol. Endocrinol. Metab.*, 283:E1173-E1177(2002).
Dakin, "Novel Actions of Oxyntomodulin in the Central Nervous System", Dept. of Endocrinology & Metabolism, Imperial College School Medicine, Hammersmith Hospital, Du Cane Road, London. W12.
Onn, Journal of Endocrinology, Mar. 2000, vol. 164 Supplement (Abstract #181).
Dakin, "Novel Actions of Oxyntomodulin in the Central Nervous System", Dept. of Endocrinology & Metabolism, Imperial College School Medicine, Hammersmith Hospital, Du Cane Road, London. W12 Onn. UK presented at 19th Joint Meeting of the British Endocrine Societies, with the European Federation of Endocrine Societies, Mar. 13-16, 2000.
CAA27627 (gi762941): "unnamed protein product [*Homo sapiens*]", NCBI Record dated Dec. 3, 2009, (Database Medline [online], Bethesda, MD, USA: US National Library of Medicine (NLM), retrieved from internet using <URL://www.ncbi.nlm.nih.gov/protein/762941, NCBI Accession No. CAA27627 (gi762941).
English, "Food fails to suppress ghrelin levels in obese humans", *J Clin Endocrinol Metab*, 87:2984-87 (2002).
ExPasy Proteomics Tools, Compute pI/MW, //ca.expasy.org/cgi-bin/pi_tool, printed on Apr. 10, 2007.
Garrow, "Does cimetidine cause weight loss?", *8MJ.*, 306(6885):1084 (1993).
Holst, "Enteroglucagon", *Ann. Rev. PhysioJ.*, 59:257-271 (1997).
Holz and Habener, "Black widow spider alpha-Ialrotoxin: a presynaptic neurotoxin that shares structural homology with the glucagon-like peptide-1 family of insulin secretagogic hormones", *Camp. Biochem. Physiol. Part B* 121:177-184 (1998).
International Preliminary Examination Report dated Jan. 28, 2005 from International Application No. PCT/US02/31944.
Kawana, "Nasal immunization of mice with peptide having a cross-neutralization epitope on minor capsid protein L2 of human papillomavirus type 16 elicit systemic and mucosal antibodies" Vaccine 19:1496-1502 (2001).
Leger, "Identification of CJC-1131-Albumin Bioconjugate as a Stable and Bioactive GLP-1(7-36) Analog", Bioorganic & Medicinal Chemistry Letters, Oxford, GB, 14:17 (2004) 4395-4398.
McNeely, "Sibutramine. A review of its contribution to the management of obesity", *Drugs*, 56(6):1093-1124 (1998).
Messer, "Vasopressin and Oxytocin", web documents updated Apr. 3, 2000; <http://neurosci.pharm.utoledo.edu/MBC3329Ivassopressin.htm>.
National Institutes of Health, National Heart, Lung, and Blood Institute (NHLBI), "Clinical Guidelines on the Identification, Evaluation, and Treatment of Overweight and Obesity in Adults—The Evidence Report. National Institutes of Health", *Obes. Res.*, 6 (suppl. 2):51S-209S (1998).
"Oxyntomodulin" Internet Document http://www.glucagon,com/oxyntomodulin,htm> Mar. 3, 2001 2 pages, accessed Aug. 30, 2006.
Parker, Internet Document http://www.futurepundit.com/archives/002946.html> 8/17105, accessed Aug. 29, 2006.
Rasmussen, Cimetidine suspension as adjuvant to energy restricted diet in treating obesity•, *BMJ.*, 306(6885):1093-1096 (1993).
Rudinger, In: Peptide Hormones, JA Parsons, Ed. (1976) 1-7.
Sarson, "Gut hormone changes after jejunoileal (JIB) or biliopancrealic (BPB) bypass surgery for morbid obesity", *Int. J. Obes.*, 5:471-480 (1981).

Schjoldager, "Oxyntomodulin: a potential hormone from the distal gut. Pharmacokinetics and effects on gastric acid and insulin secretion in man", *Eur. J. CUn.Invest.*, 18(5):499-503 (1988).

Search Report dated Jan. 23, 2003 from International Application No. PCT/GB02/04082.

Search Report dated Apr. 9, 2004 from International Application No. PCT/US02/31944.

Search Report dated Sep. 19, 2003 from International Application No. PCT/GB03/00062.

Search Report dated Mar. 13, 2007 from International Application No. PCT/GB2006/002155.

Search Report dated Oct. 19, 2007 from International Application No. PCT/GB2007/002473.

Search Report dated May 21, 2008 from International Application No. PCT/GB2007/004779.

Senel, Drug permeation enhancement via buccal route: possibilities and limitations,• *J, ControJ Release*, 72(1-3):133-144 (2001).

Sherwood, "The origin and function of the pituitary adenylate cyclase-activating polypeptide (PACAP)/glucagon superfamily", *Endocrine Reviews*, 21 (6):619-670 (2000).

Smilek, "A Single amino acid change in a myelin basic protein peptide confers the capacity to prevent rather than induce experimental autoimmune encephalomyelitis", *Proc. Natl. Acad. Sci. U.S.A.*, 1:88(21):9633-7 (1991).

Stoa-Bi Rketvedt, "Cimetidine reduces weight and improves metabolic control in overweight patients with Type 2 diabetes", *International Journal of Obesity Relat. Metab. Disord.*, 22(11):1041-1045 (1998).

Stoa-Birketvedt, "Effect of cimetidine suspension on appetite and weight in overweight subjects", *BMJ.*, 306(6885):1091-1093 (1993).

Stoa-Birketvedt, "H2-Receptor antagonist reduces food intake and weight gain in rats by non-gastric acid secretory mechanisms", *Scandinavian Physiological SOCiety*, 161(4):489-494 (1997).

Tani, "Oxyntomodulin and related peptides control somatostatin secretion in RIN T3 cells" Biochim. Biophys. Acta 1095:249-254 (1991).

Tzotsas, "Use of somatostatin analoQues in obesity" Drugs 68: 1963-1973(2008).

"The Wonders of Weight Loss", *American Fitness*, Jan./Feb. p. 18 (2006).

Uesaka, "Glucagon-like peptide isolated from the eel intestine: effects on atrial beating", *Journal of Experimental Biology*, 204:3019-3026 (2001).

Voet and Voet, Biochemistry, 2nd Edition, pp. 235-241 (1995).

Walan and Strom, "Metabolic consequences of reduced gastric acidity", Scand. J. GastroenteroL Suppl., 111 :24-30 (1985).

Wilkosz, "Transdermal Drug delivery", *u.s. Pharmacist, Ajobson publication*, 28(4):1-15(2003).

Wolfe and Morton, "Weighing in on bariatric surgery: procedure use, readmission rates, and mortality", *JAMA*, 294:1960-1963(2005).

Wren, "Ghrelin enhances appetite and increases food intake in humans", *J Clin Endocrinol Metab*, 86:5992-5 (2001).

Wynne, "Oxyntomodulin increases energy expenditure in addition to decreasing energy intake in overweight and obese humans: a randomised controlled trial", *Intenational Journal of Obesity*, 12:1729-1736 (2006).

Wynne, "Subcutaneous oxyntomodulin reduces body weight in overweight and obese subjects: a double-blind, randomized, controlled trial!", *Diabetes*, 54: 2390-2395 (2005).

Bado, A. et al., "Neurotensin and oxyntomodulin-(30-37) potentiate PYY regulation of gastric acid and somatostatin secretions," Am. J. Physiol., 1993, vol. 265, No. 1 Pt. 1, p. G113-7.

Statement of the Substance of the Interview dated Dec. 26, 2008 from U.S. Appl. No. 10/490,776.

Examiner Interview Summary Record (PTOL-413) dated Nov. 26, 2008 from U.S. Appl. No. 10/490,776.

Gantz et al., "Efficacy and safety of intranasal peptide PYY(3-36) for weight reduction in obese adults", J Clin Endocrinol & Metabol 92(5):1754-1757, 2007.

Extended European Search Report from European Application No. 10186174.8 dated Apr. 29, 2011.

Fung, L.C., "Glucagon-Like Peptide-1-(7-36) Amide and Peptide YY Mediate Intraduodenal Fat-Induced Inhibition of Acid Secretion in Dogs", Endocrinology, 139(1):189-194, 1998.

Gutzwiller, J-P, "Glucagon-like peptide-1: a potent regulator of food intake in humans", Gut, 44:81-86, 1999.

Steinert, R.E., "Oral administration of glucagon-like peptide 1 or peptide YY 3-36 affects food intake in healthy male subjects superscript 1-3", The Amer. Journal of Clin. Nutrition, 92(4), 2010.

Wettergren, A., "Glucagon-Like Peptide-1 7-36 Amide and Peptide YY Have Additive Inhibitory Effect on Gastric Acid Secretion in Man", Scand. Journal of Gastroenterology, 32(6):552-555, 1997.

* cited by examiner

Fig. 4d
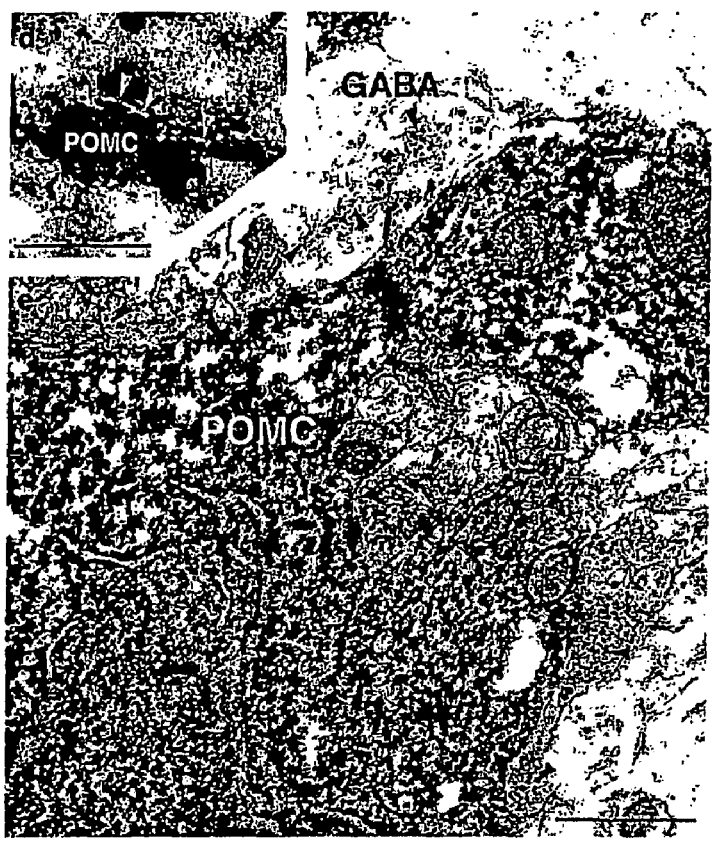
Fig. 4e
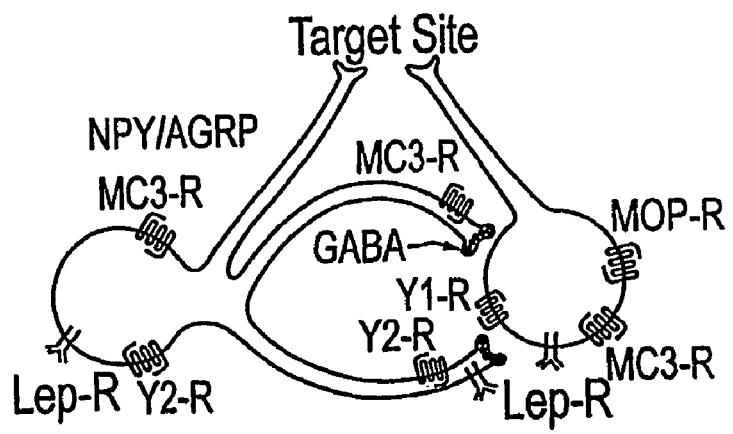
Fig. 4f

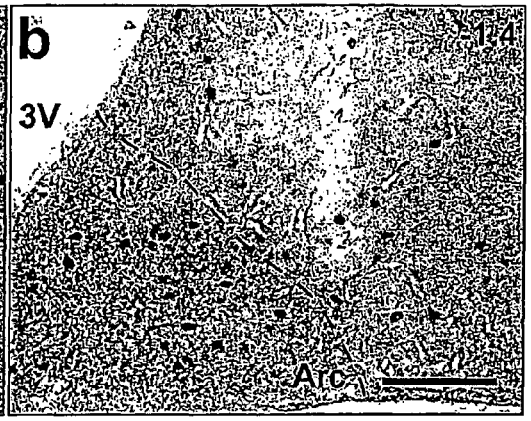
Fig. 6a　　　　　　　　　　Fig. 6b
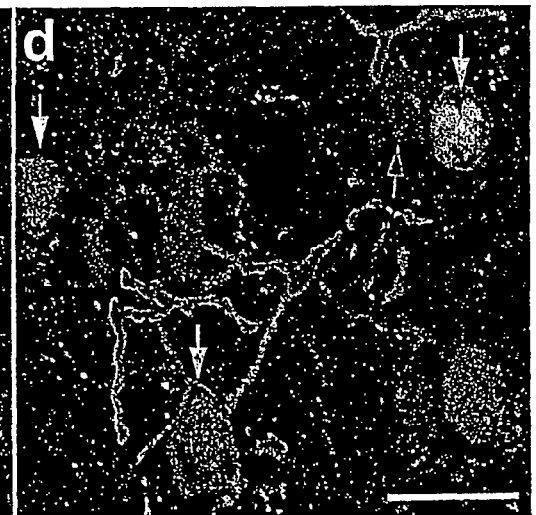
● c-Fos　● EGFP　colocalisation
Fig. 6c　　　　　　　　　　Fig. 6d

SEQUENCE LISTING

```
<160> NUMBER OF SEQ ID NOS: 344

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 36
<212> TYPE: PRT
<213> ORGANISM: Homo sapiens
```

```
<400> SEQUENCE: 2

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Tyr
            35

<210> SEQ ID NO 3
<211> LENGTH: 36
<212> TYPE: PRT
<213> ORGANISM: Homo sapiens

<400> SEQUENCE: 3

Ala Ser Leu Glu Pro Glu Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
                20                  25                  30

Arg Pro Arg Tyr
            35

<210> SEQ ID NO 4

<400> SEQUENCE: 4

000

<210> SEQ ID NO 5
<211> LENGTH: 36
<212> TYPE: PRT
<213> ORGANISM: Rattus sp.

<400> SEQUENCE: 5

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
            35

<210> SEQ ID NO 6
<211> LENGTH: 36
<212> TYPE: PRT
<213> ORGANISM: Sus sp.

<400> SEQUENCE: 6

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
            35

<210> SEQ ID NO 7
<211> LENGTH: 36
<212> TYPE: PRT
<213> ORGANISM: Cavia porcellus

<400> SEQUENCE: 7

Tyr Pro Ser Lys Pro Glu Ala Pro Gly Ser Asp Ala Ser Pro Glu Glu
1               5                   10                  15
```

Leu Ala Arg Tyr Tyr Ala Ser Leu Arg His Tyr Leu Asn Leu Val Thr
            20                  25                  30

Arg Gln Arg Tyr
            35

<210> SEQ ID NO 8
<211> LENGTH: 36
<212> TYPE: PRT
<213> ORGANISM: Rana sp.

<400> SEQUENCE: 8

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
            35

<210> SEQ ID NO 9
<211> LENGTH: 36
<212> TYPE: PRT
<213> ORGANISM: Raja sp.

<400> SEQUENCE: 9

Tyr Pro Pro Lys Pro Glu Asn Pro Gly Asp Asp Ala Ala Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
            35

<210> SEQ ID NO 10
<211> LENGTH: 36
<212> TYPE: PRT
<213> ORGANISM: Unknown
<220> FEATURE:
<221> NAME/KEY: source
<223> OTHER INFORMATION: /note="Description of Unknown: Dogfish PYY
      polypeptide"

<400> SEQUENCE: 10

Tyr Pro Pro Lys Pro Glu Asn Pro Gly Glu Asp Ala Pro Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
            35

<210> SEQ ID NO 11
<211> LENGTH: 36
<212> TYPE: PRT
<213> ORGANISM: Lampetra sp.

<400> SEQUENCE: 11

Phe Pro Pro Lys Pro Asp Asn Pro Gly Asp Asn Ala Ser Pro Glu Gln
1               5                   10                  15

Met Ala Arg Tyr Lys Ala Ala Val Arg His Tyr Ile Asn Leu Ile Thr
            20                  25                  30

Arg Gln Arg Tyr
            35

```
<210> SEQ ID NO 12
<211> LENGTH: 36
<212> TYPE: PRT
<213> ORGANISM: Unknown
<220> FEATURE:
<221> NAME/KEY: source
<223> OTHER INFORMATION: /note="Description of Unknown: Petromyzontidae
      PYY polypeptide"

<400> SEQUENCE: 12

Met Pro Pro Lys Pro Asp Asn Pro Ser Pro Asp Ala Ser Pro Glu Glu
1               5                   10                  15

Leu Ser Lys Tyr Met Leu Ala Val Arg Asn Tyr Ile Asn Leu Ile Thr
            20                  25                  30

Arg Gln Arg Tyr
        35

<210> SEQ ID NO 13
<211> LENGTH: 36
<212> TYPE: PRT
<213> ORGANISM: Rattus sp.

<400> SEQUENCE: 13

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 14
<211> LENGTH: 36
<212> TYPE: PRT
<213> ORGANISM: Oryctolagus cuniculus

<400> SEQUENCE: 14

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 15
<211> LENGTH: 36
<212> TYPE: PRT
<213> ORGANISM: Canis familiaris

<400> SEQUENCE: 15

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 16
<211> LENGTH: 36
<212> TYPE: PRT
<213> ORGANISM: Sus sp.

<400> SEQUENCE: 16

Tyr Pro Ser Lys Pro Asp Asn Pro Gly Glu Asp Ala Pro Ala Glu Asp
```

```
                1               5                  10                 15
Leu Ala Arg Tyr Tyr Ser Ala Leu Arg His Tyr Ile Asn Leu Ile Thr
            20                  25                 30

Arg Gln Arg Tyr
            35

<210> SEQ ID NO 17
<211> LENGTH: 36
<212> TYPE: PRT
<213> ORGANISM: Bos taurus

<400> SEQUENCE: 17

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 18
<211> LENGTH: 36
<212> TYPE: PRT
<213> ORGANISM: Ovis aries

<400> SEQUENCE: 18

Tyr Pro Ser Lys Pro Asp Asn Pro Gly Asp Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 19
<211> LENGTH: 36
<212> TYPE: PRT
<213> ORGANISM: Cavia porcellus

<400> SEQUENCE: 19

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 20
<211> LENGTH: 36
<212> TYPE: PRT
<213> ORGANISM: Unknown
<220> FEATURE:
<221> NAME/KEY: source
<223> OTHER INFORMATION: /note="Description of Unknown: Avian
      Neuropeptide Y polypeptide"

<400> SEQUENCE: 20

Tyr Pro Ser Lys Pro Asp Ser Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35
```

-continued

```
<210> SEQ ID NO 21
<211> LENGTH: 36
<212> TYPE: PRT
<213> ORGANISM: Rana sp.

<400> SEQUENCE: 21

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Ile Thr
            20                  25                  30

Arg Gln Arg Tyr
        35

<210> SEQ ID NO 22
<211> LENGTH: 36
<212> TYPE: PRT
<213> ORGANISM: Carassius auratus

<400> SEQUENCE: 22

Tyr Pro Thr Lys Pro Asp Asn Pro Gly Glu Gly Ala Pro Ala Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
        35

<210> SEQ ID NO 23
<211> LENGTH: 36
<212> TYPE: PRT
<213> ORGANISM: Unknown
<220> FEATURE:
<221> NAME/KEY: source
<223> OTHER INFORMATION: /note="Description of Unknown: Dogfish
      Neuropeptide Y polypeptide"

<400> SEQUENCE: 23

Tyr Pro Ser Lys Pro Asp Asn Pro Gly Glu Gly Ala Pro Ala Glu Asp
1               5                   10                  15

Leu Ala Lys Tyr Tyr Ser Ala Leu Arg His Tyr Ile Asn Leu Ile Thr
            20                  25                  30

Arg Gln Arg Tyr
        35

<210> SEQ ID NO 24
<211> LENGTH: 36
<212> TYPE: PRT
<213> ORGANISM: Lampetra sp.

<400> SEQUENCE: 24

Pro Pro Asn Lys Pro Asp Ser Pro Gly Glu Asp Ala Pro Ala Glu Asp
1               5                   10                  15

Leu Ala Arg Tyr Leu Ser Ala Val Arg His Tyr Ile Asn Leu Ile Thr
            20                  25                  30

Arg Gln Arg Tyr
        35

<210> SEQ ID NO 25
<211> LENGTH: 36
<212> TYPE: PRT
<213> ORGANISM: Ovis aries

<400> SEQUENCE: 25
```

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 26
<211> LENGTH: 36
<212> TYPE: PRT
<213> ORGANISM: Sus sp.

<400> SEQUENCE: 26

Ala Pro Leu Glu Pro Val Tyr Pro Gly Asp Asp Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 27
<211> LENGTH: 36
<212> TYPE: PRT
<213> ORGANISM: Canis familiaris

<400> SEQUENCE: 27

Ala Pro Leu Glu Pro Val Tyr Pro Gly Asp Asp Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 28
<211> LENGTH: 36
<212> TYPE: PRT
<213> ORGANISM: Felis catus

<400> SEQUENCE: 28

Ala Pro Leu Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 29
<211> LENGTH: 36
<212> TYPE: PRT
<213> ORGANISM: Bos taurus

<400> SEQUENCE: 29

Ala Pro Leu Glu Pro Glu Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 30
<211> LENGTH: 36

```
<212> TYPE: PRT
<213> ORGANISM: Rattus sp.

<400> SEQUENCE: 30

Ala Pro Leu Glu Pro Met Tyr Pro Gly Asp Tyr Ala Thr His Glu Gln
1               5                   10                  15

Arg Ala Gln Tyr Glu Thr Gln Leu Arg Arg Tyr Ile Asn Thr Leu Thr
            20                  25                  30

Arg Pro Arg Tyr
        35

<210> SEQ ID NO 31
<211> LENGTH: 36
<212> TYPE: PRT
<213> ORGANISM: Mus musculus

<400> SEQUENCE: 31

Ala Pro Leu Glu Pro Met Tyr Pro Gly Asp Tyr Ala Thr Pro Glu Gln
1               5                   10                  15

Met Ala Gln Tyr Glu Thr Gln Leu Arg Arg Tyr Ile Asn Thr Leu Thr
            20                  25                  30

Arg Pro Arg Tyr
        35

<210> SEQ ID NO 32
<211> LENGTH: 37
<212> TYPE: PRT
<213> ORGANISM: Cavia porcellus

<400> SEQUENCE: 32

Ala Pro Leu Glu Pro Val Tyr Pro Gly Asp Asn Ala Thr Pro Glu Gln
1               5                   10                  15

Gln Met Ala Gln Tyr Ala Ala Glu Met Arg Arg Tyr Ile Asn Met Leu
            20                  25                  30

Thr Arg Pro Arg Tyr
        35

<210> SEQ ID NO 33
<211> LENGTH: 36
<212> TYPE: PRT
<213> ORGANISM: Gallus gallus

<400> SEQUENCE: 33

Gly Pro Ser Gln Pro Thr Tyr Pro Gly Asp Asp Ala Pro Val Glu Asp
1               5                   10                  15

Leu Ile Arg Phe Tyr Asn Asp Leu Gln Gln Tyr Leu Asn Val Val Thr
            20                  25                  30

Arg His Arg Tyr
        35

<210> SEQ ID NO 34
<211> LENGTH: 36
<212> TYPE: PRT
<213> ORGANISM: Unknown
<220> FEATURE:
<221> NAME/KEY: source
<223> OTHER INFORMATION: /note="Description of Unknown: Alligator
      Pancreatic polypeptide"

<400> SEQUENCE: 34

Thr Pro Leu Gln Pro Lys Tyr Pro Gly Asp Gly Ala Pro Val Glu Asp
1               5                   10                  15
```

```
Leu Ile Gln Phe Tyr Asn Asp Leu Gln Gln Tyr Leu Asn Val Val Thr
            20                  25                  30

Arg Pro Arg Phe
        35

<210> SEQ ID NO 35
<211> LENGTH: 36
<212> TYPE: PRT
<213> ORGANISM: Rana catesbeiana

<400> SEQUENCE: 35

Ala Pro Ser Glu Pro His His Pro Gly Asp Gln Ala Thr Pro Asp Gln
1               5                   10                  15

Leu Ala Gln Tyr Tyr Ser Asp Leu Tyr Gln Tyr Ile Thr Phe Ile Thr
            20                  25                  30

Arg Pro Arg Phe
        35

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Lys His Tyr Leu Asn Leu Val Thr Arg Gln Arg Tyr
1               5                   10

<210> SEQ ID NO 37
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Arg His Thr Leu Asn Leu Val Thr Arg Gln Arg Tyr
1               5                   10

<210> SEQ ID NO 38
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg His Phe Leu Asn Leu Val Thr Arg Gln Arg Tyr
1               5                   10

<210> SEQ ID NO 39
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39
```

Arg His Tyr Ile Asn Leu Val Thr Arg Gln Arg Tyr
1               5                   10

<210> SEQ ID NO 40
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Arg His Tyr Val Asn Leu Val Thr Arg Gln Arg Tyr
1               5                   10

<210> SEQ ID NO 41
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg His Tyr Leu Gln Leu Val Thr Arg Gln Arg Tyr
1               5                   10

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg His Tyr Leu Asn Ile Val Thr Arg Gln Arg Tyr
1               5                   10

<210> SEQ ID NO 43
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Arg His Tyr Leu Asn Val Val Thr Arg Gln Arg Tyr
1               5                   10

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Arg His Tyr Leu Asn Leu Ile Thr Arg Gln Arg Tyr
1               5                   10

<210> SEQ ID NO 45

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg His Tyr Leu Asn Leu Leu Thr Arg Gln Arg Tyr
1               5                   10

<210> SEQ ID NO 46
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg His Tyr Leu Asn Leu Val Ser Arg Gln Arg Tyr
1               5                   10

<210> SEQ ID NO 47
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Arg His Tyr Leu Asn Leu Val Thr Lys Gln Arg Tyr
1               5                   10

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg His Tyr Leu Asn Leu Val Thr Arg Asn Arg Tyr
1               5                   10

<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg His Tyr Leu Asn Leu Val Thr Arg Gln Lys Tyr
1               5                   10

<210> SEQ ID NO 50
<211> LENGTH: 12
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 50

Arg His Tyr Leu Asn Leu Val Thr Arg Gln Arg Thr
1               5                   10

<210> SEQ ID NO 51
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Arg His Tyr Leu Asn Leu Val Thr Arg Gln Arg Phe
1               5                   10

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Lys His Thr Leu Asn Leu Val Thr Arg Gln Arg Tyr
1               5                   10

<210> SEQ ID NO 53
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Lys His Phe Leu Asn Leu Val Thr Arg Gln Arg Tyr
1               5                   10

<210> SEQ ID NO 54
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Lys His Tyr Ile Asn Leu Val Thr Arg Gln Arg Tyr
1               5                   10

<210> SEQ ID NO 55
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Lys His Tyr Val Asn Leu Val Thr Arg Gln Arg Tyr
1               5                   10

<210> SEQ ID NO 56
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Lys His Tyr Leu Gln Leu Val Thr Arg Gln Arg Tyr
1               5                   10

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Lys His Tyr Leu Asn Ile Val Thr Arg Gln Arg Tyr
1               5                   10

<210> SEQ ID NO 58
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Lys His Tyr Leu Asn Val Val Thr Arg Gln Arg Tyr
1               5                   10

<210> SEQ ID NO 59
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Lys His Tyr Leu Asn Leu Ile Thr Arg Gln Arg Tyr
1               5                   10

<210> SEQ ID NO 60
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Lys His Tyr Leu Asn Leu Leu Thr Arg Gln Arg Tyr
1               5                   10

<210> SEQ ID NO 61

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Lys His Tyr Leu Asn Leu Val Ser Arg Gln Arg Tyr
1               5                   10

<210> SEQ ID NO 62
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Lys His Tyr Leu Asn Leu Val Thr Lys Gln Arg Tyr
1               5                   10

<210> SEQ ID NO 63
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Lys His Tyr Leu Asn Leu Val Thr Arg Asn Arg Tyr
1               5                   10

<210> SEQ ID NO 64
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Lys His Tyr Leu Asn Leu Val Thr Arg Gln Lys Tyr
1               5                   10

<210> SEQ ID NO 65
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Lys His Tyr Leu Asn Leu Val Thr Arg Gln Arg Thr
1               5                   10

<210> SEQ ID NO 66
<211> LENGTH: 12
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 66

Lys His Tyr Leu Asn Leu Val Thr Arg Gln Arg Phe
1               5                   10

<210> SEQ ID NO 67
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Arg His Thr Ile Asn Leu Val Thr Arg Gln Arg Tyr
1               5                   10

<210> SEQ ID NO 68
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Arg His Thr Val Asn Leu Val Thr Arg Gln Arg Tyr
1               5                   10

<210> SEQ ID NO 69
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Arg His Thr Leu Gln Leu Val Thr Arg Gln Arg Tyr
1               5                   10

<210> SEQ ID NO 70
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Arg His Thr Leu Asn Ile Val Thr Arg Gln Arg Tyr
1               5                   10

<210> SEQ ID NO 71
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

-continued

Arg His Thr Leu Asn Val Val Thr Arg Gln Arg Tyr
1               5                   10

<210> SEQ ID NO 72
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Arg His Thr Leu Asn Leu Ile Thr Arg Gln Arg Tyr
1               5                   10

<210> SEQ ID NO 73
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Arg His Thr Leu Asn Leu Leu Thr Arg Gln Arg Tyr
1               5                   10

<210> SEQ ID NO 74
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Arg His Thr Leu Asn Leu Val Ser Arg Gln Arg Tyr
1               5                   10

<210> SEQ ID NO 75
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Arg His Thr Leu Asn Leu Val Thr Lys Gln Arg Tyr
1               5                   10

<210> SEQ ID NO 76
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Arg His Thr Leu Asn Leu Val Thr Arg Asn Arg Tyr
1               5                   10

<210> SEQ ID NO 77

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Arg His Thr Leu Asn Leu Val Thr Arg Gln Lys Tyr
1               5                   10

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Arg His Thr Leu Asn Leu Val Thr Arg Gln Arg Thr
1               5                   10

<210> SEQ ID NO 79
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Arg His Thr Leu Asn Leu Val Thr Arg Gln Arg Phe
1               5                   10

<210> SEQ ID NO 80
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Arg His Phe Ile Asn Leu Val Thr Arg Gln Arg Tyr
1               5                   10

<210> SEQ ID NO 81
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Arg His Phe Val Asn Leu Val Thr Arg Gln Arg Tyr
1               5                   10

<210> SEQ ID NO 82
<211> LENGTH: 12
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 82

Arg His Phe Leu Gln Leu Val Thr Arg Gln Arg Tyr
1               5                   10

<210> SEQ ID NO 83
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Arg His Phe Leu Asn Ile Val Thr Arg Gln Arg Tyr
1               5                   10

<210> SEQ ID NO 84
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Arg His Phe Leu Asn Val Val Thr Arg Gln Arg Tyr
1               5                   10

<210> SEQ ID NO 85
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Arg His Phe Leu Asn Leu Ile Thr Arg Gln Arg Tyr
1               5                   10

<210> SEQ ID NO 86
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Arg His Phe Leu Asn Leu Leu Thr Arg Gln Arg Tyr
1               5                   10

<210> SEQ ID NO 87
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg His Phe Leu Asn Leu Val Ser Arg Gln Arg Tyr
1               5                   10

<210> SEQ ID NO 88
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Arg His Phe Leu Asn Leu Val Thr Lys Gln Arg Tyr
1               5                   10

<210> SEQ ID NO 89
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Arg His Phe Leu Asn Leu Val Thr Arg Asn Arg Tyr
1               5                   10

<210> SEQ ID NO 90
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Arg His Phe Leu Asn Leu Val Thr Arg Gln Lys Tyr
1               5                   10

<210> SEQ ID NO 91
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Arg His Phe Leu Asn Leu Val Thr Arg Gln Arg Thr
1               5                   10

<210> SEQ ID NO 92
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Arg His Phe Leu Asn Leu Val Thr Arg Gln Arg Phe
1               5                   10

<210> SEQ ID NO 93

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Arg His Tyr Leu Gln Ile Val Thr Arg Gln Arg Tyr
1               5                   10

<210> SEQ ID NO 94
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Arg His Tyr Leu Gln Val Val Thr Arg Gln Arg Tyr
1               5                   10

<210> SEQ ID NO 95
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Arg His Tyr Leu Gln Leu Ile Thr Arg Gln Arg Tyr
1               5                   10

<210> SEQ ID NO 96
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Arg His Tyr Leu Gln Leu Leu Thr Arg Gln Arg Tyr
1               5                   10

<210> SEQ ID NO 97
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Arg His Tyr Leu Gln Leu Val Ser Arg Gln Arg Tyr
1               5                   10

<210> SEQ ID NO 98
<211> LENGTH: 12
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 98

Arg His Tyr Leu Gln Leu Val Thr Lys Gln Arg Tyr
1               5                   10

<210> SEQ ID NO 99
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Arg His Tyr Leu Gln Leu Val Thr Arg Asn Arg Tyr
1               5                   10

<210> SEQ ID NO 100
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Arg His Tyr Leu Gln Leu Val Thr Arg Gln Lys Tyr
1               5                   10

<210> SEQ ID NO 101
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Arg His Tyr Leu Gln Leu Val Thr Arg Gln Arg Thr
1               5                   10

<210> SEQ ID NO 102
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg His Tyr Leu Gln Leu Val Thr Arg Gln Arg Phe
1               5                   10

<210> SEQ ID NO 103
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Arg His Tyr Leu Asn Ile Ile Thr Arg Gln Arg Tyr
1               5                   10

<210> SEQ ID NO 104
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Arg His Tyr Leu Asn Ile Leu Thr Arg Gln Arg Tyr
1               5                   10

<210> SEQ ID NO 105
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Arg His Tyr Leu Asn Ile Val Ser Arg Gln Arg Tyr
1               5                   10

<210> SEQ ID NO 106
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Arg His Tyr Leu Asn Ile Val Thr Lys Gln Arg Tyr
1               5                   10

<210> SEQ ID NO 107
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Arg His Tyr Leu Asn Ile Val Thr Arg Asn Arg Tyr
1               5                   10

<210> SEQ ID NO 108
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Arg His Tyr Leu Asn Ile Val Thr Arg Gln Lys Tyr
1               5                   10

<210> SEQ ID NO 109

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Arg His Tyr Leu Asn Ile Val Thr Arg Gln Arg Thr
1               5                   10

<210> SEQ ID NO 110
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Arg His Tyr Leu Asn Ile Val Thr Arg Gln Arg Phe
1               5                   10

<210> SEQ ID NO 111
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Arg His Tyr Leu Asn Val Ile Thr Arg Gln Arg Tyr
1               5                   10

<210> SEQ ID NO 112
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Arg His Tyr Leu Asn Val Leu Thr Arg Gln Arg Tyr
1               5                   10

<210> SEQ ID NO 113
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Arg His Tyr Leu Asn Val Val Ser Arg Gln Arg Tyr
1               5                   10

<210> SEQ ID NO 114
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 114

Arg His Tyr Leu Asn Val Val Thr Lys Gln Arg Tyr
1               5                   10

<210> SEQ ID NO 115
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Arg His Tyr Leu Asn Val Val Thr Arg Asn Arg Tyr
1               5                   10

<210> SEQ ID NO 116
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg His Tyr Leu Asn Val Val Thr Arg Gln Lys Tyr
1               5                   10

<210> SEQ ID NO 117
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Arg His Tyr Leu Asn Val Val Thr Arg Gln Arg Thr
1               5                   10

<210> SEQ ID NO 118
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Arg His Tyr Leu Asn Val Val Thr Arg Gln Arg Phe
1               5                   10

<210> SEQ ID NO 119
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119
```

Arg His Tyr Leu Asn Leu Ile Ser Arg Gln Arg Tyr
1               5                   10

<210> SEQ ID NO 120
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Arg His Tyr Leu Asn Leu Ile Thr Lys Gln Arg Tyr
1               5                   10

<210> SEQ ID NO 121
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Arg His Tyr Leu Asn Leu Ile Thr Arg Asn Arg Tyr
1               5                   10

<210> SEQ ID NO 122
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Arg His Tyr Leu Asn Leu Ile Thr Arg Gln Lys Tyr
1               5                   10

<210> SEQ ID NO 123
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Arg His Tyr Leu Asn Leu Ile Thr Arg Gln Arg Thr
1               5                   10

<210> SEQ ID NO 124
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Arg His Tyr Leu Asn Leu Ile Thr Arg Gln Arg Phe
1               5                   10

<210> SEQ ID NO 125

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Arg His Tyr Leu Asn Leu Leu Ser Arg Gln Arg Tyr
1               5                   10

<210> SEQ ID NO 126
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Arg His Tyr Leu Asn Leu Leu Thr Lys Gln Arg Tyr
1               5                   10

<210> SEQ ID NO 127
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Arg His Tyr Leu Asn Leu Leu Thr Arg Asn Arg Tyr
1               5                   10

<210> SEQ ID NO 128
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Arg His Tyr Leu Asn Leu Leu Thr Arg Gln Lys Tyr
1               5                   10

<210> SEQ ID NO 129
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Arg His Tyr Leu Asn Leu Leu Thr Arg Gln Arg Thr
1               5                   10

<210> SEQ ID NO 130
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 130

Arg His Tyr Leu Asn Leu Leu Thr Arg Gln Arg Phe
1               5                   10

<210> SEQ ID NO 131
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Arg His Tyr Leu Asn Leu Val Ser Lys Gln Arg Tyr
1               5                   10

<210> SEQ ID NO 132
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Arg His Tyr Leu Asn Leu Val Ser Arg Asn Arg Tyr
1               5                   10

<210> SEQ ID NO 133
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Arg His Tyr Leu Asn Leu Val Ser Arg Gln Lys Tyr
1               5                   10

<210> SEQ ID NO 134
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Arg His Tyr Leu Asn Leu Val Ser Arg Gln Arg Thr
1               5                   10

<210> SEQ ID NO 135
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135
```

-continued

Arg His Tyr Leu Asn Leu Val Ser Arg Gln Arg Tyr
1               5                   10

<210> SEQ ID NO 136
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Arg His Tyr Leu Asn Leu Val Thr Lys Asn Arg Tyr
1               5                   10

<210> SEQ ID NO 137
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Arg His Tyr Leu Asn Leu Val Thr Lys Gln Lys Tyr
1               5                   10

<210> SEQ ID NO 138
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Arg His Tyr Leu Asn Leu Val Thr Lys Gln Arg Thr
1               5                   10

<210> SEQ ID NO 139
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Arg His Tyr Leu Asn Leu Val Thr Lys Gln Arg Phe
1               5                   10

<210> SEQ ID NO 140
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Arg His Tyr Leu Asn Leu Val Thr Arg Asn Lys Tyr
1               5                   10

<210> SEQ ID NO 141

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Arg His Tyr Leu Asn Leu Val Thr Arg Asn Arg Thr
1               5                   10

<210> SEQ ID NO 142
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Arg His Tyr Leu Asn Leu Val Thr Arg Asn Arg Phe
1               5                   10

<210> SEQ ID NO 143
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Arg His Tyr Leu Asn Leu Val Thr Arg Gln Lys Thr
1               5                   10

<210> SEQ ID NO 144
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Arg His Tyr Leu Asn Leu Val Thr Arg Gln Lys Phe
1               5                   10

<210> SEQ ID NO 145
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Leu Arg His Tyr Leu Asn Leu Val Thr Arg Gln Arg Tyr
1               5                   10

<210> SEQ ID NO 146
<211> LENGTH: 13
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 146

Ile Arg His Tyr Leu Asn Leu Val Thr Arg Gln Arg Tyr
1               5                   10

<210> SEQ ID NO 147
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Val Arg His Tyr Leu Asn Leu Val Thr Arg Gln Arg Tyr
1               5                   10

<210> SEQ ID NO 148
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Ser Leu Arg His Tyr Leu Asn Leu Val Thr Arg Gln Arg Tyr
1               5                   10

<210> SEQ ID NO 149
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Thr Leu Arg His Tyr Leu Asn Leu Val Thr Arg Gln Arg Tyr
1               5                   10

<210> SEQ ID NO 150
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ala Ser Leu Arg His Tyr Leu Asn Leu Val Thr Arg Gln Arg Tyr
1               5                   10                  15

<210> SEQ ID NO 151
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151
```

Ser Ser Leu Arg His Tyr Leu Asn Leu Val Thr Arg Gln Arg Tyr
1               5                   10                  15

<210> SEQ ID NO 152
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Tyr Ala Ser Leu Arg His Tyr Leu Asn Leu Val Thr Arg Gln Arg Tyr
1               5                   10                  15

<210> SEQ ID NO 153
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Thr Ala Ser Leu Arg His Tyr Leu Asn Leu Val Thr Arg Gln Arg Tyr
1               5                   10                  15

<210> SEQ ID NO 154
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Phe Ala Ser Leu Arg His Tyr Leu Asn Leu Val Thr Arg Gln Arg Tyr
1               5                   10                  15

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Tyr Tyr Ala Ser Leu Arg His Tyr Leu Asn Leu Val Thr Arg Gln Arg
1               5                   10                  15

Tyr

<210> SEQ ID NO 156
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Thr Tyr Ala Ser Leu Arg His Tyr Leu Asn Leu Val Thr Arg Gln Arg
1               5                   10                  15

Tyr

<210> SEQ ID NO 157
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Phe Tyr Ala Ser Leu Arg His Tyr Leu Asn Leu Val Thr Arg Gln Arg
1               5                   10                  15

Tyr

<210> SEQ ID NO 158
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Arg Tyr Tyr Ala Ser Leu Arg His Tyr Leu Asn Leu Val Thr Arg Gln
1               5                   10                  15

Arg Tyr

<210> SEQ ID NO 159
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Lys Tyr Tyr Ala Ser Leu Arg His Tyr Leu Asn Leu Val Thr Arg Gln
1               5                   10                  15

Arg Tyr

<210> SEQ ID NO 160
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Asn Arg Tyr Tyr Ala Ser Leu Arg His Tyr Leu Asn Leu Val Thr Arg
1               5                   10                  15

Gln Arg Tyr

<210> SEQ ID NO 161
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 161

Gln Arg Tyr Tyr Ala Ser Leu Arg His Tyr Leu Asn Leu Val Thr Arg
1               5                   10                  15

Gln Arg Tyr

<210> SEQ ID NO 162
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Leu Asn Arg Tyr Tyr Ala Ser Leu Arg His Tyr Leu Asn Leu Val Thr
1               5                   10                  15

Arg Gln Arg Tyr
            20

<210> SEQ ID NO 163
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Ile Asn Arg Tyr Tyr Ala Ser Leu Arg His Tyr Leu Asn Leu Val Thr
1               5                   10                  15

Arg Gln Arg Tyr
            20

<210> SEQ ID NO 164
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Val Asn Arg Tyr Tyr Ala Ser Leu Arg His Tyr Leu Asn Leu Val Thr
1               5                   10                  15

Arg Gln Arg Tyr
            20

<210> SEQ ID NO 165
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Glu Leu Asn Arg Tyr Tyr Ala Ser Leu Arg His Tyr Leu Asn Leu Val
1               5                   10                  15

Thr Arg Gln Arg Tyr
            20
```

```
<210> SEQ ID NO 166
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Asp Leu Asn Arg Tyr Tyr Ala Ser Leu Arg His Tyr Leu Asn Leu Val
1               5                   10                  15

Thr Arg Gln Arg Tyr
            20

<210> SEQ ID NO 167
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 168
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Asp Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 169
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 170
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 170

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 171
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Thr Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 172
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 173
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Ser Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 174
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 175
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 175

Glu Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 176
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 176

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 177
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 177

Asp Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 178
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 178

Gly Glu Asp Ala Ser Pro Glu Glu Leu Asn Arg Tyr Tyr Ala Ser Leu
1               5                   10                  15

Arg His Tyr Leu Asn Leu Val Thr Arg Gln Arg Tyr
            20                  25

<210> SEQ ID NO 179
<211> LENGTH: 29
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 179

Pro Gly Glu Asp Ala Ser Pro Glu Glu Leu Asn Arg Tyr Tyr Ala Ser
1               5                   10                  15

Leu Arg His Tyr Leu Asn Leu Val Thr Arg Gln Arg Tyr
            20                  25

<210> SEQ ID NO 180
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Ala Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 181
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Ser Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 182
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Glu Ala Pro Gly Glu Asp Ala Ser Pro Glu Glu Leu Asn Arg Tyr Tyr
1               5                   10                  15

Ala Ser Leu Arg His Tyr Leu Asn Leu Val Thr Arg Gln Arg Tyr
            20                  25                  30

<210> SEQ ID NO 183
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Asp Ala Pro Gly Glu Asp Ala Ser Pro Glu Glu Leu Asn Arg Tyr Tyr
1               5                   10                  15
```

Ala Ser Leu Arg His Tyr Leu Asn Leu Val Thr Arg Gln Arg Tyr
            20                  25                  30

<210> SEQ ID NO 184
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 185
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 186
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Arg Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 187
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Gln Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 188
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Asn Pro Glu Ala Pro Gly Glu Asp Ala Ser Pro Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 189
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Leu Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 190
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Val Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 191
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Leu Lys His Tyr Leu Asn Leu Val Thr Arg Gln Arg Tyr
1               5                   10

<210> SEQ ID NO 192
<211> LENGTH: 14
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Ser Leu Lys His Tyr Leu Asn Leu Val Thr Arg Gln Arg Tyr
1               5                   10

<210> SEQ ID NO 193
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Ala Ser Leu Lys His Tyr Leu Asn Leu Val Thr Arg Gln Arg Tyr
1               5                   10                  15

<210> SEQ ID NO 194
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Tyr Ala Ser Leu Lys His Tyr Leu Asn Leu Val Thr Arg Gln Arg Tyr
1               5                   10                  15

<210> SEQ ID NO 195
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Tyr Tyr Ala Ser Leu Lys His Tyr Leu Asn Leu Val Thr Arg Gln Arg
1               5                   10                  15

Tyr

<210> SEQ ID NO 196
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Arg Tyr Tyr Ala Ser Leu Lys His Tyr Leu Asn Leu Val Thr Arg Gln
1               5                   10                  15

Arg Tyr

<210> SEQ ID NO 197
<211> LENGTH: 19
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 197

Asn Arg Tyr Tyr Ala Ser Leu Lys His Tyr Leu Asn Leu Val Thr Arg
1               5                   10                  15

Gln Arg Tyr

<210> SEQ ID NO 198
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Leu Asn Arg Tyr Tyr Ala Ser Leu Lys His Tyr Leu Asn Leu Val Thr
1               5                   10                  15

Arg Gln Arg Tyr
            20

<210> SEQ ID NO 199
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Glu Leu Asn Arg Tyr Tyr Ala Ser Leu Lys His Tyr Leu Asn Leu Val
1               5                   10                  15

Thr Arg Gln Arg Tyr
            20

<210> SEQ ID NO 200
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Glu Glu Leu Asn Arg Tyr Tyr Ala Ser Leu Lys His Tyr Leu Asn Leu
1               5                   10                  15

Val Thr Arg Gln Arg Tyr
            20

<210> SEQ ID NO 201
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Pro Glu Glu Leu Asn Arg Tyr Tyr Ala Ser Leu Lys His Tyr Leu Asn
1               5                   10                  15
```

Leu Val Thr Arg Gln Arg Tyr
            20

<210> SEQ ID NO 202
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ser Glu Glu Leu Asn Arg Tyr Tyr Ala Ser Leu Lys His Tyr Leu Asn
1               5                   10                  15

Leu Val Thr Arg Gln Arg Tyr
            20

<210> SEQ ID NO 203
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Ala Ser Glu Glu Leu Asn Arg Tyr Tyr Ala Ser Leu Lys His Tyr Leu
1               5                   10                  15

Asn Leu Val Thr Arg Gln Arg Tyr
            20

<210> SEQ ID NO 204
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Asp Ala Ser Glu Glu Leu Asn Arg Tyr Tyr Ala Ser Leu Lys His Tyr
1               5                   10                  15

Leu Asn Leu Val Thr Arg Gln Arg Tyr
            20                  25

<210> SEQ ID NO 205
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Glu Asp Ala Ser Glu Glu Leu Asn Arg Tyr Tyr Ala Ser Leu Lys His
1               5                   10                  15

Tyr Leu Asn Leu Val Thr Arg Gln Arg Tyr
            20                  25

<210> SEQ ID NO 206
<211> LENGTH: 28
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Gly Glu Asp Ala Ser Pro Glu Glu Leu Asn Arg Tyr Tyr Ala Ser Leu
1               5                   10                  15

Lys His Tyr Leu Asn Leu Val Thr Arg Gln Arg Tyr
            20                  25

<210> SEQ ID NO 207
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Pro Gly Glu Asp Ala Ser Pro Glu Leu Asn Arg Tyr Tyr Ala Ser
1               5                   10                  15

Leu Lys His Tyr Leu Asn Leu Val Thr Arg Gln Arg Tyr
            20                  25

<210> SEQ ID NO 208
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ala Pro Gly Glu Asp Ala Ser Glu Glu Leu Asn Arg Tyr Tyr Ala Ser
1               5                   10                  15

Leu Lys His Tyr Leu Asn Leu Val Thr Arg Gln Arg Tyr
            20                  25

<210> SEQ ID NO 209
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Glu Ala Pro Gly Glu Asp Ala Ser Glu Glu Leu Asn Arg Tyr Tyr Ala
1               5                   10                  15

Ser Leu Lys His Tyr Leu Asn Leu Val Thr Arg Gln Arg Tyr
            20                  25                  30

<210> SEQ ID NO 210
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

```
Pro Glu Ala Pro Gly Glu Asp Ala Ser Pro Glu Leu Asn Arg Tyr
1               5                   10                  15

Tyr Ala Ser Leu Lys His Tyr Leu Asn Leu Val Thr Arg Gln Arg Tyr
            20                  25                  30
```

<210> SEQ ID NO 211
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 211

```
Lys Pro Glu Ala Pro Gly Glu Asp Ala Ser Glu Glu Leu Asn Arg Tyr
1               5                   10                  15

Tyr Ala Ser Leu Lys His Tyr Leu Asn Leu Val Thr Arg Gln Arg Tyr
            20                  25                  30
```

<210> SEQ ID NO 212
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 212

```
Ile Lys Pro Glu Ala Pro Gly Glu Asp Ala Ser Glu Glu Leu Asn Arg
1               5                   10                  15

Tyr Tyr Ala Ser Leu Lys His Tyr Leu Asn Leu Val Thr Arg Gln Arg
            20                  25                  30

Tyr
```

<210> SEQ ID NO 213
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (1)..(1)
<223> OTHER INFORMATION: /note="N-terminus acetylation"

<400> SEQUENCE: 213

```
Leu Arg His Tyr Ile Asn Leu Ile Thr Arg Gln Arg Tyr
1               5                   10
```

<210> SEQ ID NO 214
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (1)..(1)
<223> OTHER INFORMATION: /note="N-terminus acetylation"

<400> SEQUENCE: 214

Leu Arg His Tyr Leu Asn Leu Leu Thr Arg Gln Arg Tyr

```
<210> SEQ ID NO 215
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Leu Arg His Tyr Leu Asn Leu Leu Thr Arg Gln Arg Tyr
1               5                   10

<210> SEQ ID NO 216
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Pro Ala Glu Asp Leu Ala Gln Tyr Ala Ala Glu Leu Arg His Tyr Leu
1               5                   10                  15

Asn Leu Leu Thr Arg Gln Arg Tyr
            20

<210> SEQ ID NO 217
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

<400> SEQUENCE: 217

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 218
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

<400> SEQUENCE: 218
```

```
Met Ala Arg Tyr Tyr Ser Ala Leu Arg His Tyr Ile Asn Leu Ile Thr
1               5                   10                  15

Arg Gln Arg Tyr
            20

<210> SEQ ID NO 219
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 219

Ala Arg Tyr Tyr Ser Ala Leu Arg His Phe Ile Asn Leu Ile Thr Arg
1               5                   10                  15

Gln Arg Tyr

<210> SEQ ID NO 220
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus acetylation"
<220> FEATURE:
<221> NAME/KEY: MOD_RES
<222> LOCATION: (1)..(1)
<223> OTHER INFORMATION: D-Ala
<220> FEATURE:
<221> NAME/KEY: misc_feature
<222> LOCATION: (20)..(20)
<223> OTHER INFORMATION: /note="C-terminus amidation"

<400> SEQUENCE: 220

Ala Ala Arg Tyr Tyr Ser Ala Leu Arg His Tyr Ile Asn Leu Ile Thr
1               5                   10                  15

Arg Gln Arg Tyr
            20

<210> SEQ ID NO 221
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (18)..(18)
<223> OTHER INFORMATION: /note="C-terminus amidation"
```

<400> SEQUENCE: 221

Arg Tyr Tyr Ser Ala Leu Arg His Tyr Ile Asn Leu Ile Thr Arg Gln
1               5                   10                  15

Arg Tyr

<210> SEQ ID NO 222
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: Norleucine
<220> FEATURE:
<221> NAME/KEY: misc_feature
<222> LOCATION: (20)..(20)
<223> OTHER INFORMATION: /note="C-terminus amidation"

<400> SEQUENCE: 222

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 223
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: D-Ser
<220> FEATURE:
<221> NAME/KEY: misc_feature
<222> LOCATION: (19)..(19)
<223> OTHER INFORMATION: /note="C-terminus amidation"

<400> SEQUENCE: 223

Ser Arg Tyr Tyr Ser Ala Leu Arg His Tyr Ile Asn Leu Ile Thr Arg
1               5                   10                  15

Gln Arg Tyr

<210> SEQ ID NO 224
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:

```
<221> NAME/KEY: misc_feature
<222> LOCATION: (20)..(20)
<223> OTHER INFORMATION: /note="C-terminus amidation"

<400> SEQUENCE: 224

Ala Ala Arg Tyr Ser His Ala Leu Arg His Tyr Ile Asn Leu Ile Thr
1               5                   10                  15

Arg Gln Arg Tyr
            20

<210> SEQ ID NO 225
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Ile
<220> FEATURE:
<221> NAME/KEY: misc_feature
<222> LOCATION: (19)..(19)
<223> OTHER INFORMATION: /note="C-terminus amidation"

<400> SEQUENCE: 225

Ile Arg Tyr Tyr Ser Ala Leu Arg His Tyr Ile Asn Leu Ile Thr Arg
1               5                   10                  15

Gln Arg Tyr

<210> SEQ ID NO 226
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus acetylation"
<220> FEATURE:
<221> NAME/KEY: misc_feature
<222> LOCATION: (20)..(20)
<223> OTHER INFORMATION: /note="C-terminus amidation"

<400> SEQUENCE: 226

Arg Ala Arg Tyr Tyr Ser Ala Leu Arg His Tyr Ile Asn Leu Ile Thr
1               5                   10                  15

Arg Gln Arg Tyr
            20

<210> SEQ ID NO 227
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (18)..(18)
<223> OTHER INFORMATION: /note="C-terminus amidation"
```

<400> SEQUENCE: 227

Gln Tyr Tyr Ser Ala Leu Arg His Tyr Ile Asn Leu Ile Thr Arg Gln
1               5                   10                  15

Arg Tyr

<210> SEQ ID NO 228
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 228

Ala Arg Phe Tyr Ser Ala Leu Arg His Tyr Ile Asn Leu Ile Thr Arg
1               5                   10                  15

Gln Arg Tyr

<210> SEQ ID NO 229
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: C-MeLeu
<220> FEATURE:
<221> NAME/KEY: misc_feature
<222> LOCATION: (20)..(20)
<223> OTHER INFORMATION: /note="C-terminus amidation"

<400> SEQUENCE: 229

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 230
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: N-MeLeu

```
<220> FEATURE:
<221> NAME/KEY: misc_feature
<222> LOCATION: (20)..(20)
<223> OTHER INFORMATION: /note="C-terminus amidation"

<400> SEQUENCE: 230

Leu Ala Arg Tyr Tyr Ser Ala Leu Arg His Tyr Ile Asn Leu Ile Thr
1               5                   10                  15

Arg Gln Arg Tyr
            20

<210> SEQ ID NO 231
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: desamino-Ala
<220> FEATURE:
<221> NAME/KEY: misc_feature
<222> LOCATION: (19)..(19)
<223> OTHER INFORMATION: /note="C-terminus amidation"

<400> SEQUENCE: 231

Ala Arg Tyr Tyr Ser Ala Leu Arg His Tyr Ile Asn Leu Ile Thr Arg
1               5                   10                  15

Gln Arg Tyr

<210> SEQ ID NO 232
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus formylation"
<220> FEATURE:
<221> NAME/KEY: misc_feature
<222> LOCATION: (19)..(19)
<223> OTHER INFORMATION: /note="C-terminus amidation"

<400> SEQUENCE: 232

Ala Arg Tyr Tyr Ser Glu Leu Arg Arg Tyr Ile Asn Leu Ile Thr Arg
1               5                   10                  15

Gln Arg Tyr

<210> SEQ ID NO 233
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: Norvaline
```

```
<220> FEATURE:
<221> NAME/KEY: misc_feature
<222> LOCATION: (20)..(20)
<223> OTHER INFORMATION: /note="C-terminus amidation"

<400> SEQUENCE: 233

Val Ala Arg Tyr Ala Ser Ala Leu Arg His Tyr Leu Asn Leu Ile Thr
1               5                   10                  15

Arg Gln Arg Tyr
            20

<210> SEQ ID NO 234
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 234

Ala Arg Tyr Tyr Thr Gln Leu Arg His Tyr Ile Asn Leu Ile Thr Arg
1               5                   10                  15

Gln Arg Tyr

<210> SEQ ID NO 235
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: desamino-Leu
<220> FEATURE:
<221> NAME/KEY: misc_feature
<222> LOCATION: (20)..(20)
<223> OTHER INFORMATION: /note="C-terminus amidation"

<400> SEQUENCE: 235

Leu Ala Arg Tyr Tyr Ser Asn Leu Arg His Tyr Ile Asn Val Ile Thr
1               5                   10                  15

Arg Gln Arg Tyr
            20

<210> SEQ ID NO 236
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
```

```
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 236

Ala Arg Tyr Tyr Asp Ser Leu Arg His Tyr Ile Asn Thr Ile Thr Arg
1               5                   10                  15

Gln Arg Tyr

<210> SEQ ID NO 237
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 237

Ala Arg Tyr Tyr Ser Ala Leu Gln His Tyr Ile Asn Leu Leu Thr Arg
1               5                   10                  15

Pro Arg Tyr

<210> SEQ ID NO 238
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

<400> SEQUENCE: 238

Leu Ala Arg Tyr Tyr Ser Ala Leu Arg Gln Tyr Arg Asn Leu Ile Thr
1               5                   10                  15

Arg Gln Arg Phe
            20

<210> SEQ ID NO 239
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (18)..(18)
```

<223> OTHER INFORMATION: /note="C-terminus amidation"

<400> SEQUENCE: 239

Arg Tyr Tyr Ala Ser Leu Arg His Tyr Leu Asn Leu Val Thr Arg Gln
1               5                   10                  15

Arg Phe

<210> SEQ ID NO 240
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 240

Ser Arg Tyr Tyr Ala Ser Leu Arg His Tyr Leu Asn Leu Val Thr Arg
1               5                   10                  15

Gln Arg Tyr

<210> SEQ ID NO 241
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus acetylation"
<220> FEATURE:
<221> NAME/KEY: misc_feature
<222> LOCATION: (19)..(19)
<223> OTHER INFORMATION: /note="C-terminus amidation"

<400> SEQUENCE: 241

Ser Arg Tyr Tyr Ala Ser Leu Arg His Phe Leu Asn Leu Val Thr Arg
1               5                   10                  15

Gln Arg Tyr

<210> SEQ ID NO 242
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: Norleucine
<220> FEATURE:
<221> NAME/KEY: misc_feature
<222> LOCATION: (20)..(20)
<223> OTHER INFORMATION: /note="C-terminus amidation"

<400> SEQUENCE: 242

Leu Ala Arg Tyr Tyr Asn Ala Leu Arg His Phe Ile Asn Leu Ile Thr
1               5                   10                  15

Arg Gln Arg Tyr
            20

<210> SEQ ID NO 243
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: D-Ala
<220> FEATURE:
<221> NAME/KEY: misc_feature
<222> LOCATION: (19)..(19)
<223> OTHER INFORMATION: /note="C-terminus amidation"

<400> SEQUENCE: 243

Ala Arg Tyr Glu Ser Ala Leu Arg His Tyr Ile Asn Leu Ile Thr Arg
1               5                   10                  15

His Arg Tyr

<210> SEQ ID NO 244
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Bz-Leu
<220> FEATURE:
<221> NAME/KEY: misc_feature
<222> LOCATION: (20)..(20)
<223> OTHER INFORMATION: /note="C-terminus amidation"

<400> SEQUENCE: 244

Leu Ala Arg Tyr Tyr Ser Ala Leu Arg His Tyr Ile Asn Leu Ile Thr
1               5                   10                  15

Arg Pro Arg Phe
            20

<210> SEQ ID NO 245
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)

<223> OTHER INFORMATION: /note="C-terminus amidation"

<400> SEQUENCE: 245

Ala Leu Tyr Tyr Ser Ala Leu Arg His Phe Val Asn Leu Ile Thr Arg
1               5                   10                  15

Gln Arg Tyr

<210> SEQ ID NO 246
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Ala
<220> FEATURE:
<221> NAME/KEY: misc_feature
<222> LOCATION: (19)..(19)
<223> OTHER INFORMATION: /note="C-terminus amidation"

<400> SEQUENCE: 246

Ala Arg Tyr Tyr Ser Ala Leu Arg His Tyr Val Asn Leu Ile Phe Arg
1               5                   10                  15

Gln Arg Tyr

<210> SEQ ID NO 247
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: C-MeSer
<220> FEATURE:
<221> NAME/KEY: misc_feature
<222> LOCATION: (18)..(18)
<223> OTHER INFORMATION: /note="C-terminus amidation"

<400> SEQUENCE: 247

Ser Tyr Tyr Ser Ala Leu Arg His Tyr Ile Asn Met Ile Thr Arg Gln
1               5                   10                  15

Arg Phe

<210> SEQ ID NO 248
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

```
<400> SEQUENCE: 248

Arg Ile Arg Tyr Tyr Ser Ala Leu Arg His Phe Ile Asn Leu Ile Thr
1               5                   10                  15

Arg Gln Arg Phe
            20

<210> SEQ ID NO 249
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

<400> SEQUENCE: 249

Leu Ser Arg Tyr Tyr Ser Ala Leu Arg His Phe Ile Asn Leu Ile Thr
1               5                   10                  15

Arg Gln Arg Tyr
            20

<210> SEQ ID NO 250
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: N-MeIle
<220> FEATURE:
<221> NAME/KEY: misc_feature
<222> LOCATION: (19)..(19)
<223> OTHER INFORMATION: /note="C-terminus amidation"

<400> SEQUENCE: 250

Ile Arg Tyr Tyr Ser Ala Leu Gln His Phe Ile Asn Leu Ile Thr Arg
1               5                   10                  15

Gln Arg Tyr

<210> SEQ ID NO 251
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: MOD_RES
<222> LOCATION: (1)..(1)
<223> OTHER INFORMATION: D-Ser
<220> FEATURE:
<221> NAME/KEY: misc_feature
<222> LOCATION: (19)..(19)
```

<223> OTHER INFORMATION: /note="C-terminus amidation"

<400> SEQUENCE: 251

Ser Arg Tyr Tyr Ser Ala Leu Arg His Tyr Ile Asn Leu Ile Thr Arg
1               5                   10                  15

Gln Arg Phe

<210> SEQ ID NO 252
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (20)..(20)
<223> OTHER INFORMATION: /note="C-terminus amidation"

<400> SEQUENCE: 252

Met Ala Arg Tyr Tyr Ser Asp Leu Arg Arg Tyr Ile Asn Leu Ile Thr
1               5                   10                  15

Arg Gln Arg Tyr
            20

<210> SEQ ID NO 253
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (19)..(19)
<223> OTHER INFORMATION: /note="C-terminus amidation"

<400> SEQUENCE: 253

Ala Arg Tyr Tyr Ser Glu Leu Arg His Tyr Ile Ile Leu Ile Thr Arg
1               5                   10                  15

Gln Arg Tyr

<210> SEQ ID NO 254
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Ala
<220> FEATURE:
<221> NAME/KEY: misc_feature
<222> LOCATION: (15)..(15)
<223> OTHER INFORMATION: /note="C-terminus OH"

<400> SEQUENCE: 254

```
Ala Ala Arg Tyr Tyr Ser Ala Leu Arg His Tyr Ile Asn Leu Ile Thr
1               5                   10                  15

Arg Gln Arg Tyr
            20
```

<210> SEQ ID NO 255
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (1)..(1)
<223> OTHER INFORMATION: /note="N-terminus N-alpha"
<220> FEATURE:
<221> NAME/KEY: misc_feature
<222> LOCATION: (15)..(15)
<223> OTHER INFORMATION: /note="C-terminus amidation"

<400> SEQUENCE: 255

```
Ala Ser Leu Arg His Trp Leu Asn Leu Val Thr Arg Gln Arg Tyr
1               5                   10                  15
```

<210> SEQ ID NO 256
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (25)..(25)
<223> OTHER INFORMATION: im-DNP-His
<220> FEATURE:
<221> NAME/KEY: misc_feature
<222> LOCATION: (35)..(35)
<223> OTHER INFORMATION: /note="C-terminus amidation"

<400> SEQUENCE: 256

```
Tyr Pro Ala Lys Glu Ala Pro Gly Glu Asp Ala Ser Pro Glu Glu Leu
1               5                   10                  15

Ser Thr Tyr Tyr Ala Ser Leu Arg His Tyr Leu Asn Leu Val Thr Arg
            20                  25                  30

Glx Arg Tyr
35
```

<210> SEQ ID NO 257
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (15)..(15)
<223> OTHER INFORMATION: /note="C-terminus amidation"

<400> SEQUENCE: 257

```
Ala Ser Leu Arg His Tyr Leu Asn Leu Val Thr Arg Gln Arg Tyr
1               5                   10                  15
```

<210> SEQ ID NO 258
<211> LENGTH: 15

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (15)..(15)
<223> OTHER INFORMATION: /note="C-terminus amidation"

<400> SEQUENCE: 258

Ala Ser Leu Arg His Tyr Leu Asn Leu Val Ala Arg Gln Arg Tyr
1               5                   10                  15

<210> SEQ ID NO 259
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (15)..(15)
<223> OTHER INFORMATION: /note="C-terminus amidation"

<400> SEQUENCE: 259

Ala Ala Leu Arg His Tyr Leu Asn Leu Val Ala Arg Gln Arg Tyr
1               5                   10                  15

<210> SEQ ID NO 260
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (15)..(15)
<223> OTHER INFORMATION: /note="C-terminus amidation"

<400> SEQUENCE: 260

Ala Ser Leu Arg His Tyr Glu Asn Leu Val Thr Arg Gln Arg Tyr
1               5                   10                  15

<210> SEQ ID NO 261
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (13)..(13)
<223> OTHER INFORMATION: Ornithine
<220> FEATURE:
<221> NAME/KEY: misc_feature
<222> LOCATION: (15)..(15)
<223> OTHER INFORMATION: /note="C-terminus amidation"

<400> SEQUENCE: 261

Ala Ser Leu Arg His Tyr Leu Asn Leu Val Thr Arg Xaa Arg Tyr
1               5                   10                  15
```

<210> SEQ ID NO 262
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (5)..(5)
<223> OTHER INFORMATION: p.CL.Phe
<220> FEATURE:
<221> NAME/KEY: misc_feature
<222> LOCATION: (15)..(15)
<223> OTHER INFORMATION: /note="C-terminus amidation"

<400> SEQUENCE: 262

Ala Ser Leu Arg Phe Tyr Leu Asn Leu Val Thr Arg Gln Arg Tyr
1               5                   10                  15

<210> SEQ ID NO 263
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 263

Ala Ser Leu Arg His Tyr Glu Asn Leu Val Thr Arg Gln Arg Tyr
1               5                   10                  15

<210> SEQ ID NO 264
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (15)..(15)
<223> OTHER INFORMATION: N-Me-Tyr
<220> FEATURE:
<221> NAME/KEY: misc_feature
<222> LOCATION: (15)..(15)
<223> OTHER INFORMATION: /note="C-terminus amidation"

<400> SEQUENCE: 264

Ala Ser Leu Arg His Phe Glu Asn Leu Val Thr Arg Gln Arg Tyr
1               5                   10                  15

<210> SEQ ID NO 265

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (13)..(13)
<223> OTHER INFORMATION: Ornithine
<220> FEATURE:
<221> NAME/KEY: MOD_RES
<222> LOCATION: (15)..(15)
<223> OTHER INFORMATION: N-Me-Tyr
<220> FEATURE:
<221> NAME/KEY: misc_feature
<222> LOCATION: (15)..(15)
<223> OTHER INFORMATION: /note="C-terminus amidation"

<400> SEQUENCE: 265

Ala Ser Leu Arg His Tyr Glu Asn Leu Val Thr Arg Xaa Arg Tyr
1               5                   10                  15

<210> SEQ ID NO 266
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-myristoyl"
<220> FEATURE:
<221> NAME/KEY: misc_feature
<222> LOCATION: (15)..(15)
<223> OTHER INFORMATION: /note="C-terminus amidation"

<400> SEQUENCE: 266

Ala Ser Leu Arg His Tyr Leu Asn Leu Val Thr Arg Gln Arg Tyr
1               5                   10                  15

<210> SEQ ID NO 267
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-naphthateneacetyl"
<220> FEATURE:
<221> NAME/KEY: misc_feature
<222> LOCATION: (15)..(15)
<223> OTHER INFORMATION: /note="C-terminus amidation"

<400> SEQUENCE: 267

Ala Ser Leu Arg His Tyr Leu Asn Leu Val Thr Arg Gln Arg Tyr
1               5                   10                  15

<210> SEQ ID NO 268
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (13)..(13)
<223> OTHER INFORMATION: Ornithine
<220> FEATURE:
<221> NAME/KEY: MOD_RES
<222> LOCATION: (15)..(15)
<223> OTHER INFORMATION: N-Me-Tyr
<220> FEATURE:
<221> NAME/KEY: misc_feature
<222> LOCATION: (15)..(15)
<223> OTHER INFORMATION: /note="C-terminus amidation"

<400> SEQUENCE: 268

Ala Ser Leu Arg His Phe Glu Asn Leu Val Thr Arg Xaa Arg Tyr
1               5                   10                  15

<210> SEQ ID NO 269
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 269

Ala Ser Leu Arg His Tyr Leu Asn Leu Val Thr Arg Gln Arg Tyr
1               5                   10                  15

<210> SEQ ID NO 270
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: 3 benzothienyalanine
<220> FEATURE:
<221> NAME/KEY: misc_feature
<222> LOCATION: (15)..(15)
<223> OTHER INFORMATION: /note="C-terminus amidation"

<400> SEQUENCE: 270

Ala Ser Leu Arg His Ala Leu Asn Leu Val Thr Arg Gln Arg Tyr
1               5                   10                  15

<210> SEQ ID NO 271
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: 4,4' biphenylalanine
<220> FEATURE:
<221> NAME/KEY: misc_feature
<222> LOCATION: (15)..(15)
<223> OTHER INFORMATION: /note="C-terminus amidation"

<400> SEQUENCE: 271

Ala Ser Leu Arg His Phe Tyr Leu Asn Leu Val Thr Arg Gln Arg Tyr
1               5                   10                  15

<210> SEQ ID NO 272
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: 3 benzothienylalanine
<220> FEATURE:
<221> NAME/KEY: misc_feature
<222> LOCATION: (15)..(15)
<223> OTHER INFORMATION: /note="C-terminus amidation"

<400> SEQUENCE: 272

Ala Ser Leu Arg His Ala Leu Asn Leu Val Thr Arg Gln Arg Tyr
1               5                   10              15

<210> SEQ ID NO 273
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: Naphthylalanine
<220> FEATURE:
<221> NAME/KEY: misc_feature
<222> LOCATION: (15)..(15)
<223> OTHER INFORMATION: /note="C-terminus amidation"

<400> SEQUENCE: 273

Ala Ser Leu Arg His Ala Leu Asn Leu Val Thr Arg Gln Arg Tyr
1               5                   10              15

<210> SEQ ID NO 274
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 274

Ala Ser Leu Arg His Trp Leu Asn Leu Val Thr Arg Gln Arg Tyr
1               5                   10                  15

<210> SEQ ID NO 275
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 275

Ala Ser Leu Arg His Trp Leu Asn Leu Val Thr Arg Gln Arg Tyr
1               5                   10                  15

<210> SEQ ID NO 276
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: 2 thienylalanine
<220> FEATURE:
<221> NAME/KEY: misc_feature
<222> LOCATION: (15)..(15)
<223> OTHER INFORMATION: /note="C-terminus amidation"

<400> SEQUENCE: 276

Ala Ser Leu Arg Asn Ala Leu Asn Leu Val Thr Arg Gln Arg Tyr
1               5                   10                  15

<210> SEQ ID NO 277
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: Tetrahydroisoquinoline
<220> FEATURE:
<221> NAME/KEY: misc_feature
<222> LOCATION: (15)..(15)
<223> OTHER INFORMATION: /note="C-terminus amidation"

<400> SEQUENCE: 277

Ala Ser Leu Arg His Xaa Leu Asn Leu Val Thr Arg Gln Arg Tyr
1               5                   10                  15

<210> SEQ ID NO 278

<400> SEQUENCE: 278

000

<210> SEQ ID NO 279
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation-H"
<220> FEATURE:
<221> NAME/KEY: misc_feature
<222> LOCATION: (11)..(11)
<223> OTHER INFORMATION: /note="C-terminus amidation"

<400> SEQUENCE: 279

His Phe Leu Asn Leu Val Thr Arg Gln Arg Tyr
1               5                   10

<210> SEQ ID NO 280
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (15)..(15)
<223> OTHER INFORMATION: 2 thienylalanine
<220> FEATURE:
<221> NAME/KEY: misc_feature
<222> LOCATION: (15)..(15)
<223> OTHER INFORMATION: /note="C-terminus amidation"

<400> SEQUENCE: 280

Ala Ser Leu Arg His Phe Leu Asn Leu Val Thr Arg Gln Arg Ala
1               5                   10                  15

<210> SEQ ID NO 281
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: Thiazolylalanine
<220> FEATURE:
<221> NAME/KEY: misc_feature
<222> LOCATION: (16)..(16)
<223> OTHER INFORMATION: /note="C-terminus amidation"

<400> SEQUENCE: 281

Ala Ser Leu Arg His Ala Phe Leu Asn Leu Val Thr Arg Gln Arg Tyr
1               5                   10                  15

<210> SEQ ID NO 282
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: Thiazolylalanine
<220> FEATURE:
<221> NAME/KEY: misc_feature
<222> LOCATION: (16)..(16)
<223> OTHER INFORMATION: /note="C-terminus amidation"

<400> SEQUENCE: 282

Ala Ser Leu Arg His Ala Phe Leu Asn Leu Val Thr Arg Gln Arg Tyr
1               5                   10                  15

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287
```

000

<210> SEQ ID NO 288

<400> SEQUENCE: 288

000

<210> SEQ ID NO 289
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 289

Phe Ser Leu Arg Asn Phe Leu Asn Leu Val Thr Arg Gln Arg Tyr
1               5                   10                  15

<210> SEQ ID NO 290
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 290

Tyr Ser Leu Arg His Phe Leu Asn Leu Val Thr Arg Gln Arg Tyr
1               5                   10                  15

<210> SEQ ID NO 291
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 291

Ala Ser Leu Arg His Tyr Trp Asn Leu Val Thr Arg Gln Arg Tyr
1               5                   10                  15

```
<210> SEQ ID NO 292
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 292

Ala Ser Leu Arg His Tyr Leu Asn Trp Val Thr Arg Gln Arg Tyr
1               5                   10                  15

<210> SEQ ID NO 293
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 293

Ala Ser Leu Arg Ala Phe Leu Asn Leu Val Thr Arg Gln Arg Tyr
1               5                   10                  15

<210> SEQ ID NO 294
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (5)..(5)
<223> OTHER INFORMATION: 3 benzothienyalanine
<220> FEATURE:
<221> NAME/KEY: misc_feature
<222> LOCATION: (14)..(14)
<223> OTHER INFORMATION: /note="C-terminus amidation"

<400> SEQUENCE: 294

Ala Ser Leu Arg Ala Leu Asn Leu Val Thr Arg Gln Arg Tyr
1               5                   10

<210> SEQ ID NO 295
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 295

Ala Ser Leu Arg His Phe Leu Asn Leu Val Thr Arg Gln Arg Tyr
1               5                   10                  15

<210> SEQ ID NO 296
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 296

Ala Ser Leu Arg His Phe Leu Asn Leu Val Thr Arg Gln Arg Phe
1               5                   10                  15

<210> SEQ ID NO 297
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (11)..(11)
<223> OTHER INFORMATION: D-Trp
<220> FEATURE:
<221> NAME/KEY: misc_feature
<222> LOCATION: (15)..(15)
<223> OTHER INFORMATION: /note="C-terminus amidation"

<400> SEQUENCE: 297

Ala Ser Leu Arg His Phe Leu Asn Leu Val Trp Arg Gln Arg Tyr
1               5                   10                  15

<210> SEQ ID NO 298
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: misc_feature
<222> LOCATION: (1)..(1)
<223> OTHER INFORMATION: /note="N-terminus CH3CO"
<220> FEATURE:
<221> NAME/KEY: misc_feature
```

```
<222> LOCATION: (13)..(13)
<223> OTHER INFORMATION: /note="C-terminus amidation"

<400> SEQUENCE: 298

Leu Arg His Tyr Leu Asn Leu Leu Thr Arg Gln Arg Tyr
1               5                   10

<210> SEQ ID NO 299
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus CH3CO"
<220> FEATURE:
<221> NAME/KEY: misc_feature
<222> LOCATION: (13)..(13)
<223> OTHER INFORMATION: /note="C-terminus amidation"

<400> SEQUENCE: 299

Leu Arg His Tyr Ile Asn Leu Ile Thr Arg Gln Arg Tyr
1               5                   10

<210> SEQ ID NO 300
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus amidation"
<220> FEATURE:
<221> NAME/KEY: misc_feature
<222> LOCATION: (13)..(13)
<223> OTHER INFORMATION: /note="C-terminus amidation"

<400> SEQUENCE: 300

Leu Arg His Tyr Leu Asn Leu Leu Thr Arg Gln Arg Tyr
1               5                   10

<210> SEQ ID NO 301
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus amidation"
<220> FEATURE:
<221> NAME/KEY: misc_feature
<222> LOCATION: (15)..(15)
<223> OTHER INFORMATION: /note="C-terminus amidation"

<400> SEQUENCE: 301

Leu Arg His Tyr Ile Asn Leu Ile Thr Arg Gln Arg Tyr
1               5                   10

<210> SEQ ID NO 302
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"

<400> SEQUENCE: 302

Ala Ser Leu Arg His Trp Leu Asn Leu Val Thr Arg Gln Arg Tyr
1               5                   10                  15

<210> SEQ ID NO 303
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"

<400> SEQUENCE: 303

Ala Ser Leu Arg His Trp Leu Asn Trp Val Thr Arg Gln Arg Tyr
1               5                   10                  15
```

```
<210> SEQ ID NO 304
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"

<400> SEQUENCE: 304

Ala Ser Leu Arg His Phe Leu Asn Leu Val Thr Arg Gln Arg Tyr
1               5                   10                  15

<210> SEQ ID NO 305
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"

<400> SEQUENCE: 305

Ala Ser Leu Arg His Phe Leu Asn Trp Val Thr Arg Gln Arg Tyr
1               5                   10                  15
```

```
<210> SEQ ID NO 306
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (11)..(12)
<223> OTHER INFORMATION: /note="Psi-Bond between residues"
<220> FEATURE:
<221> NAME/KEY: misc_feature
<222> LOCATION: (12)..(12)
<223> OTHER INFORMATION: /note="C-terminus amidation"

<400> SEQUENCE: 306

Arg His Tyr Leu Asn Trp Val Thr Arg Gln Arg Tyr
1               5                   10

<210> SEQ ID NO 307
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (12)..(12)
<223> OTHER INFORMATION: /note="C-terminus amidation"

<400> SEQUENCE: 307

Arg His Tyr Leu Asn Trp Val Thr Arg Gln Arg Tyr
1               5                   10

<210> SEQ ID NO 308
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"
```

<400> SEQUENCE: 308

Ala Ser Leu Arg His Tyr Leu Asn Trp Val Thr Arg Gln Arg Tyr
1               5                   10                  15

<210> SEQ ID NO 309
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (10)..(10)
<223> OTHER INFORMATION: Norvaline
<220> FEATURE:
<221> NAME/KEY: misc_feature
<222> LOCATION: (14)..(15)
<223> OTHER INFORMATION: /note="Psi-Bond between residues"
<220> FEATURE:
<221> NAME/KEY: misc_feature
<222> LOCATION: (15)..(15)
<223> OTHER INFORMATION: /note="C-terminus amidation"

<400> SEQUENCE: 309

Ala Ser Leu Arg His Tyr Leu Asn Trp Val Thr Arg Gln Arg Tyr
1               5                   10                  15

<210> SEQ ID NO 310
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (9)..(9)
<223> OTHER INFORMATION: /note="C-terminus OMe"

<400> SEQUENCE: 310

Ile Asn Pro Ile Tyr Arg Leu Arg Tyr
1               5

<210> SEQ ID NO 311
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)

```
<223> OTHER INFORMATION: /note="N-terminus H"
<220> FEATURE:
<221> NAME/KEY: misc_feature
<222> LOCATION: (9)..(9)
<223> OTHER INFORMATION: /note="C-terminus OMe"

<400> SEQUENCE: 311

Ile Asn Pro Cys Tyr Arg Leu Arg Tyr
1               5

<210> SEQ ID NO 312
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (6)..(6)
<223> OTHER INFORMATION: /note="C-terminus OMe"

<400> SEQUENCE: 312

Cys Tyr Arg Leu Arg Tyr
1               5

<210> SEQ ID NO 313
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (8)..(8)
<223> OTHER INFORMATION: /note="C-terminus OMe"

<400> SEQUENCE: 313

Ile Asn Pro Tyr Arg Leu Arg Tyr
1               5

<210> SEQ ID NO 314
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus H"
<220> FEATURE:
<221> NAME/KEY: misc_feature
<222> LOCATION: (1)..(5)
<223> OTHER INFORMATION: /note="Cyclic"
<220> FEATURE:
<221> NAME/KEY: misc_feature
<222> LOCATION: (5)..(5)
<223> OTHER INFORMATION: /note="C-terminus OMe"

<400> SEQUENCE: 314
```

```
Tyr Arg Leu Arg Tyr
1               5

<210> SEQ ID NO 315
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Ser Lys Pro Asp Asn Pro Gly Glu Asp Ala Pro Ala Glu Asp Met Ala
1               5                   10                  15

Arg Cys Tyr Ser Ala Cys Arg His Tyr Ile Asn Leu Ile Thr Arg Gln
            20                  25                  30

Arg Tyr

<210> SEQ ID NO 316
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus acetylation"

<400> SEQUENCE: 316

Arg His Tyr Leu Asn Leu Ile Gly Arg Gln Arg Tyr
1               5                   10

<210> SEQ ID NO 317
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus acetylation"

<400> SEQUENCE: 317

Arg His Gly Leu Asn Leu Leu Gly Arg Gln Arg Tyr
1               5                   10

<210> SEQ ID NO 318
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Tyr Ile Asn Leu Ile Tyr Arg Leu Arg Tyr
1               5                   10

<210> SEQ ID NO 319
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

His Tyr Ile Asn Leu Ile Tyr Arg Leu Arg Tyr
1               5                   10

<210> SEQ ID NO 320
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Arg His Tyr Ile Asn Leu Ile Tyr Arg Leu Arg Tyr
1               5                   10

<210> SEQ ID NO 321
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Tyr Ile Asn Leu Leu Tyr Arg Gln Arg Tyr
1               5                   10

<210> SEQ ID NO 322
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: 6 amino hexanoic acid

<400> SEQUENCE: 322

Tyr Pro Ser Leu Xaa Tyr Ile Asn Leu Ile Tyr Arg Leu Arg Tyr
1               5                   10                  15

<210> SEQ ID NO 323
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Ile Asn Leu Ile Tyr Arg Leu Arg Tyr
1               5

<210> SEQ ID NO 324
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (12)..(12)
<223> OTHER INFORMATION: /note="C-terminus amidation"

<400> SEQUENCE: 324

Arg His Phe Leu Asn Leu Val Thr Arg Gln Arg Tyr
1               5                   10

<210> SEQ ID NO 325
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 325

Ala Ser Leu Arg His Phe Leu Asn Leu Val Thr Arg Gln Arg Tyr
1               5                   10                  15

<210> SEQ ID NO 326
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (15)..(15)
<223> OTHER INFORMATION: /note="C-terminus amidation"

<400> SEQUENCE: 326

Ala Ser Leu Arg His Phe Leu Asn Leu Val Thr Arg Gln Arg Tyr
1               5                   10                  15

<210> SEQ ID NO 327
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (9)..(9)
<223> OTHER INFORMATION: /note="C-terminus amidation"

<400> SEQUENCE: 327
```

```
Ala Ser Leu Arg Thr Arg Gln Arg Tyr
1               5

<210> SEQ ID NO 328
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: MOD_RES
<222> LOCATION: (6)..(6)
<223> OTHER INFORMATION: 2 thienylalanine
<220> FEATURE:
<221> NAME/KEY: misc_feature
<222> LOCATION: (15)..(15)
<223> OTHER INFORMATION: /note="C-terminus amidation"

<400> SEQUENCE: 328

Ala Ser Leu Arg His Ala Leu Asn Leu Val Thr Arg Gln Arg Tyr
1               5                   10                  15

<210> SEQ ID NO 329
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus N-alpha-acetylation"
<220> FEATURE:
<221> NAME/KEY: misc_feature
<222> LOCATION: (15)..(15)
<223> OTHER INFORMATION: /note="C-terminus amidation"

<400> SEQUENCE: 329

Tyr Ser Leu Arg His Phe Leu Asn Leu Val Thr Arg Gln Arg Tyr
1               5                   10                  15

<210> SEQ ID NO 330
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Asp Asp Asp Asp Tyr
1               5

<210> SEQ ID NO 331
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331
```

Gly Pro Arg
1

<210> SEQ ID NO 332
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Ala Gly Gly
1

<210> SEQ ID NO 333
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

His Pro Phe His Leu
1               5

<210> SEQ ID NO 334
<211> LENGTH: 34
<212> TYPE: PRT
<213> ORGANISM: Homo sapiens

<400> SEQUENCE: 334

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 335
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 335

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 336
<211> LENGTH: 37
<212> TYPE: PRT
<213> ORGANISM: Homo sapiens

<400> SEQUENCE: 336

His Asp Glu Phe Glu Arg His Ala Glu Gly Thr Phe Thr Ser Asp Val
1               5                   10                  15

Ser Ser Tyr Leu Glu Gly Gly Ala Ala Lys Glu Phe Ile Ala Trp Leu
            20                  25                  30

Val Lys Gly Arg Gly
35

<210> SEQ ID NO 337
<211> LENGTH: 36
<212> TYPE: PRT
<213> ORGANISM: Homo sapiens
<220> FEATURE:
<221> NAME/KEY: misc_feature
<222> LOCATION: (36)..(36)
<223> OTHER INFORMATION: /note="C-terminus amidation"

<400> SEQUENCE: 337

His Asp Glu Phe Glu Arg His Ala Glu Gly Thr Phe Thr Ser Asp Val
1               5                   10                  15

Ser Ser Tyr Leu Glu Gly Gly Ala Ala Lys Glu Phe Ile Ala Trp Leu
            20                  25                  30

Val Lys Gly Arg
35

<210> SEQ ID NO 338
<211> LENGTH: 31
<212> TYPE: PRT
<213> ORGANISM: Homo sapiens

<400> SEQUENCE: 338

His Ala Glu Gly Thr Phe Thr Ser Asp Val Ser Ser Tyr Leu Glu Gly
1               5                   10                  15

Gly Ala Ala Lys Glu Phe Ile Ala Trp Leu Val Lys Gly Arg Gly
            20                  25                  30

<210> SEQ ID NO 339
<211> LENGTH: 30
<212> TYPE: PRT
<213> ORGANISM: Homo sapiens
<220> FEATURE:
<221> NAME/KEY: misc_feature
<222> LOCATION: (30)..(30)
<223> OTHER INFORMATION: /note="C-terminus amidation"

<400> SEQUENCE: 339

His Ala Glu Gly Thr Phe Thr Ser Asp Val Ser Ser Tyr Leu Glu Gly
1               5                   10                  15

Gly Ala Ala Lys Glu Phe Ile Ala Trp Leu Val Lys Gly Arg
            20                  25                  30

<210> SEQ ID NO 340
<211> LENGTH: 37
<212> TYPE: PRT
<213> ORGANISM: Homo sapiens

<400> SEQUENCE: 340

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Lys Asn Asn Ile Ala
35

<210> SEQ ID NO 341
<211> LENGTH: 463

```
<212> TYPE: PRT
<213> ORGANISM: Homo sapiens

<400> SEQUENCE: 341

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Phe Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
    370                 375                 380

Phe Thr Glu Leu Ser Phe Thr Ser Phe Gln Gly Leu Met Val Ala Ile
385                 390                 395                 400
```

```
Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
    450                 455                 460

<210> SEQ ID NO 342
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus may be H, C-Me, N-Me,
      desamino or an acyl group having 7 carbon atoms or less"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (5)..(6)
<223> OTHER INFORMATION: /replace="Ser"
<220> FEATURE:
<221> NAME/KEY: misc_feature
<222> LOCATION: (5)..(6)
<223> OTHER INFORMATION: /note="Residues given in the sequence have no
      preference with respect to those in the annotation for said
      positions"
<220> FEATURE:
<221> NAME/KEY: VARIANT
<222> LOCATION: (11)..(11)
<223> OTHER INFORMATION: /replace="Leu"
<220> FEATURE:
<221> NAME/KEY: misc_feature
<222> LOCATION: (11)..(11)
<223> OTHER INFORMATION: /note="Residue given in the sequence has no
      preference with respect the annotation for said position"
<220> FEATURE:
<221> NAME/KEY: VARIANT
<222> LOCATION: (14)..(14)
<223> OTHER INFORMATION: /replace="Val"
<220> FEATURE:
<221> NAME/KEY: misc_feature
<222> LOCATION: (14)..(14)
<223> OTHER INFORMATION: /note="Residue given in the sequence has no
      preference with respect the annotation for said position"
<220> FEATURE:
<221> NAME/KEY: misc_feature
<222> LOCATION: (19)..(19)
<223> OTHER INFORMATION: /note="C-terminus amidation"
<220> FEATURE:
<221> NAME/KEY: misc_feature
<222> LOCATION: (1)..(19)
<223> OTHER INFORMATION: /note="see specification as filed for
      detailed description of substitutions and preferred embodiments"

<400> SEQUENCE: 342

Ala Arg Tyr Tyr Ala Ala Leu Arg His Tyr Ile Asn Leu Ile Thr Arg
1               5                   10                  15

Gln Arg Tyr
```

```
<210> SEQ ID NO 343
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus may be H, C-Me, N-Me,
      desamino or an acyl group having 7 carbon atoms or less"
<220> FEATURE:
<221> NAME/KEY: VARIANT
<222> LOCATION: (1)..(1)
<223> OTHER INFORMATION: /replace="Leu"
<220> FEATURE:
<221> NAME/KEY: VARIANT
<222> LOCATION: (2)..(2)
<223> OTHER INFORMATION: /replace="Ala" or "Ile"
<220> FEATURE:
<221> NAME/KEY: misc_feature
<222> LOCATION: (1)..(2)
<223> OTHER INFORMATION: /note="Residues given in the sequence has
      no preference with respect to those in the annotations for
      said positions"
<220> FEATURE:
<221> NAME/KEY: VARIANT
<222> LOCATION: (11)..(11)
<223> OTHER INFORMATION: /replace="Tyr"
<220> FEATURE:
<221> NAME/KEY: misc_feature
<222> LOCATION: (11)..(11)
<223> OTHER INFORMATION: /note="Residue given in the sequence has no
      preference with respect to the annotation for said position"
<220> FEATURE:
<221> NAME/KEY: VARIANT
<222> LOCATION: (20)..(20)
<223> OTHER INFORMATION: /replace="Tyr"
<220> FEATURE:
<221> NAME/KEY: misc_feature
<222> LOCATION: (20)..(20)
<223> OTHER INFORMATION: /note="Residue given in the sequence has no
      preference with respect to the annotation for said position"
<220> FEATURE:
<221> NAME/KEY: misc_feature
<222> LOCATION: (20)..(20)
<223> OTHER INFORMATION: /note="C-terminus amidation"
<220> FEATURE:
<221> NAME/KEY: misc_feature
<222> LOCATION: (1)..(20)
<223> OTHER INFORMATION: /note="see specification as filed for
      detailed description of substitutions and preferred embodiments"

<400> SEQUENCE: 343

Arg Ser Arg Tyr Tyr Ser Ala Leu Arg His Phe Ile Asn Leu Ile Thr
1               5                   10                  15

Arg Gln Arg Phe
            20

<210> SEQ ID NO 344
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-terminus may be C-Me, N-Me or
      desamino"
<220> FEATURE:
<221> NAME/KEY: VARIANT
```

```
<222> LOCATION: (1)..(1)
<223> OTHER INFORMATION: /replace="Ser" or "Ile" or "D-Ala" or "D-Ser"
      or "D-Ile"
<220> FEATURE:
<221> NAME/KEY: misc_feature
<222> LOCATION: (1)..(1)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Gln"
<220> FEATURE:
<221> NAME/KEY: misc_feature
<222> LOCATION: (8)..(8)
<223> OTHER INFORMATION: /note="Residue given in the sequence has no
      preference with respect to the annotation for said position"
<220> FEATURE:
<221> NAME/KEY: VARIANT
<222> LOCATION: (10)..(10)
<223> OTHER INFORMATION: /replace="Tyr"
<220> FEATURE:
<221> NAME/KEY: misc_feature
<222> LOCATION: (10)..(10)
<223> OTHER INFORMATION: /note="Residue given in the sequence has no
      preference with respect to the annotation for said position"
<220> FEATURE:
<221> NAME/KEY: VARIANT
<222> LOCATION: (19)..(19)
<223> OTHER INFORMATION: /replace="Tyr"
<220> FEATURE:
<221> NAME/KEY: misc_feature
<222> LOCATION: (19)..(19)
<223> OTHER INFORMATION: /note="Residue given in the sequence has no
      preference with respect to the annotation for said position"
<220> FEATURE:
<221> NAME/KEY: misc_feature
<222> LOCATION: (19)..(19)
<223> OTHER INFORMATION: /note="C-terminus amidation"
<220> FEATURE:
<221> NAME/KEY: misc_feature
<222> LOCATION: (1)..(19)
<223> OTHER INFORMATION: /note="see specification as filed for
      detailed description of substitutions and preferred embodiments"

<400> SEQUENCE: 344

Ala Arg Tyr Tyr Ala Ser Leu Arg His Phe Leu Asn Leu Val Thr Arg
1               5                   10                  15

Gln Arg Phe
```

MODIFICATION OF FEEDING BEHAVIOR USING PYY AND GLP-1

PRIORITY CLAIM

This application is a nationalization of PCT Application Serial No. PCT/GB03/00062, filed Jan. 10, 2003; which claims priority to PCT Application Serial No. PCT/US02/31944, filed Sep. 24, 2002; and claims priority to U.S. Provisional Application No. 60/392,109, filed Jun. 28, 2002; and claims priority to UK Application No. GB 0200507.2, filed Jan. 10, 2002; each of which application is incorporated by reference in their entirety herein.

STATEMENT OF GOVERNMENT SUPPORT

This disclosure was made in part with United States government support pursuant to grants RR00163, DK51730 and DK55819, from the National Institutes of Health. The United States government has certain rights in the disclosure.

FIELD

This application relates to the use of agents to control appetite, feeding, food intake, energy expenditure and calorie intake, particularly in the field of obesity.

BACKGROUND

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347: 358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia.

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects.

SUMMARY

Disclosed herein are findings that peripheral administration of PYY, or an agonist thereof, to a subject results in decreased food intake, caloric intake, and appetite, and an alteration in energy metabolism. The subject can be any subject, including, but not limited to, a human subject. In several embodiments, the subject desires to lose weight, is obese, overweight, or suffers from a weight-related disorder. $PYY_{3-36}$ can preferably be administered to the subject.

Also disclosed are findings that co-administration of PYY, or an agonist thereof, for example, $PYY_{3-36}$, with GLP-1 or an agonist thereof to a subject results in a greater decrease in food intake, caloric intake, and appetite, than when PYY or an agonist thereof is administered alone. The effect is synergistic.

In one embodiment, a method is disclosed for decreasing calorie intake in a subject. The method includes peripherally administering a therapeutically effective amount of PYY or an agonist thereof and GLP-1 or an agonist thereof to the subject, thereby decreasing the calorie intake of the subject.

In another embodiment, a method is disclosed for decreasing appetite in a subject. The method includes peripherally administering a therapeutically effective amount of PYY or an agonist thereof and GLP-1 or an agonist thereof to the subject, thereby decreasing the appetite of the subject.

In a further embodiment, a method is disclosed for decreasing food intake in a subject. The method includes peripherally administering a therapeutically effective amount of PYY or an agonist thereof, and GLP-1 or an agonist thereof to the subject, thereby decreasing the food intake of the subject.

In yet another embodiment, a method is disclosed herein for increasing energy expenditure in a subject. The method includes peripherally administering a therapeutically effective amount of PYY or an agonist thereof, and GLP-1 or an agonist thereof to the subject, thereby increasing energy expenditure in the subject.

A method is also disclosed for decreasing calorie intake, food intake, or appetite in a human subject. The method includes peripherally injecting a therapeutically effective amount of PYY or an agonist thereof in a pharmaceutically acceptable carrier to the subject in a pulse dose, thereby decreasing the calorie intake, food intake, or appetite of the subject, and also administering GLP-1 or an agonist thereof.

In each method above, the GLP-1 or an agonist thereof maybe administered simultaneously or substantially simultaneously as the PYY or agonist thereof, or sequentially, in any order. The PYY or agonist thereof and the GLP-1 or agonist thereof may be administered in a single pharmaceutical composition or in separate compositions, and they may be administered by the same route or my different routes.

BRIEF DESCRIPTION OF THE FIGURES

FIG. 1 is a set of diagrams and digital images showing the generation of transgenic mice expressing EGFP in ARC POMC neurons.

FIG. 2 is a tracing and graphs showing activation of MOP-Rs hyperpolarizes the EGFP-labeled POMC neurons by opening G protein-coupled inwardly-rectifying potassium channels.

FIG. 3 are tracings and graphs demonstrating that leptin depolarizes POMC neurons via a non-specific cation channel, and decreases GABAergic tone onto POMC cells.

FIG. 4 is a set of images showing that the GABAergic inputs to POMC cells are from NPY neurons that co-express GABA. FIGS. 4a, 4b and 4c are representative. FIG. 4d is a set of digital images demonstrating that expression of NPY in nerve terminals adjacent to POMC neurons in the ARC. NPY nerve terminals (black); POMC neuronal soma (grey). Scale bar, 10 μm. FIG. 4e is a digital image showing expression of GABA and NPY in nerve terminals synapsing onto POMC neurons in the ARC. GABA immunoreactivity (10 nm gold particles, arrowheads without tail) and NPY immunoreactivity (25 nm gold particles) are in separate vesicle populations co-localized within synaptic boutons that make direct contact with the soma of POMC neurons (DAB contrasted with uranyl acetate and lead citrate, diffuse black in cytoplasm). Scale bar, 1 μm. FIG. 4f is a diagram of the model of NPY/GABA and POMC neurons in the ARC.

FIG. 5 is a set of graphs relating to the feeding response to $PYY_{3-36}$ in rats.

FIG. 6 is a set of digital images of c-fos expression in Pomc-EGFP mice. FIGS. 6a and 6b are digital images of representative sections (bregma—1.4 mm$^{22}$) of c-fos expression in the arcuate nucleus of Pomc-EGFP mice response to intraperitoneal saline (FIG. 6a) or $PYY_{3-36}$ (5 μg/100 g) (FIG. 6b). Scale bar 100 μm. 3V, third ventricle; Arc, arcuate nucleus. FIGS. 6c and 6d are digital images of representative sections showing POMC-EGFP neurons (FIG. 6c) and c-fos immunoreactivity (FIG. 6d) either co-localizing or alone. Scale bar 25 μm.

FIG. 7 is a set of bar graphs relating to intra-arcuate $PYY_{3-36}$ in rats and feeding effects of IP $PYY_{3-36}$ in Y2r-null mice.

FIG. 8 is a set of images relating to the electrophysiological and neuropeptide responses to $PYY_{3-36}$ and Y2A.

Inset shows a representative recording of membrane potential and action potential frequency.

FIG. 9 is a set of graphs showing the effect of $PYY_{3-36}$ infusion on appetite and food intake in human subjects.

SEQUENCE LISTING

Figure 1A:
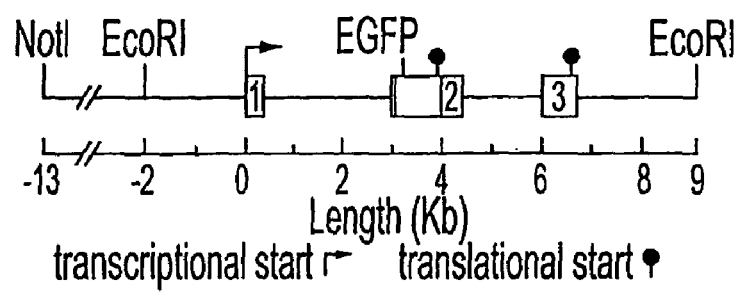
FIG. 1a is a schematic diagram of the structure of the POMC-EGFP transgene.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

I. Abbreviations
 α-MSH: alpha melanocortin stimulating hormone
 Arc: arcuate nucleus
 EPSP: excitatory postsynaptic potential
 GABA: γaminobutyric acid
 GFP, EGFP: green fluorescent protein
 GLP-1: glucagons-like peptide-1
 ICV: intracerebroventricular
 IP: intraperitoneal
 IPSC: inhibitory postsynaptic current
 kb: kilobase
 kg: kilogram
 MOP-R: μ-opiod receptor
 MV: millivolts
 NPY: neuropeptide Y
 Oxm: oxyntomodulin
 pmol: picomole
 POMC: proopiomelanocortin
 RIA: radioimmunoassay
 RPA: RNase protection assay
 s.e.m: standard error of the mean
 TH: tyrosine hydroxylase
 μM: micromolar
 V: volts
 Y2A: N-acetyl ($Leu^{28}$, $Leu^{31}$) NPY (24-36)

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Action potential: A rapidly propagated electrical message that speeds along an axon of a neuron and over the surface membrane of many muscle and glandular cells. In axons they are brief, travel at constant velocity, and maintain a constant amplitude. Like all electrical messages of the central nervous system, the action potential is a membrane potential change caused by the flow of ions through ion channels in the membrane. In one embodiment, an action potential is a regenerative wave of sodium permeability.

Animal: Living multi-cellular vertebrate organisms, a category that includes, for example, mammals and birds. The term mammal includes both human and non-human mammals. Similarly, the term "subject" includes both human and veterinary subjects.

Anorexia: A lack or loss of the appetite for food. In one embodiment, anorexia is a result of "anorexia nervosa." This is an eating disorder primarily affecting females, usually with onset in adolescence, characterized by refusal to maintain a normal minimal body weight, intense fear of gaining weight or becoming obese, and a disturbance of body image resulting in a feeling of being fat or having fat in certain areas even when extremely emaciated, undue reliance on body weight or shape for self-evaluation, and amenorrhea. Associated features often include denial of the illness and resistance to psychotherapy, depressive symptoms, markedly decreased libido, and obsessions or peculiar behavior regarding food, such as hoarding. The disorder is divided into two subtypes, a restricting type, in which weight loss is achieved primarily through diet or exercise, and a binge-eating/purging type, in which binge eating or purging behavior also occur regularly.

Antagonist: A substance that tends to nullify the action of another, as an agent that binds to a cell receptor without eliciting a biological response, blocking binding of substances that could elicit such responses.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Binding: A specific interaction between two molecules, such that the two molecules interact. Binding can be specific and selective, so that one molecule is bound preferentially when compared to another molecule. In one embodiment, specific binding is identified by a disassociation constant ($K_d$).

Body Mass Index (BMI: A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J. Clin. Nutr.* 45:1035-47, 1987). Ideal body weight will vary among species and individuals based on height, body build, bone structure, and sex.

c-fos: The cellular homologue of the viral v-fos oncogene found in FBJ (Finkel-Biskis-Jinkins) and FBR murine osteosarcoma viruses (MSV). The human fos gene maps to chromosome 14q21-q31. Human fos has been identified as TIS-28.

C-fos is thought to have an important role in signal transduction, cell proliferation, and differentiation. It is a nuclear protein which, in combination with other transcription factors (for example, jun) acts as a trans-activating regulator of gene expression. C-fos is an immediate early response gene, which are believed to play a key role in the early response of cells to growth factors. C-fos is involved also in the control of cell growth and differentiation of embryonic hematopoietic cells and neuronal cells. The human c-fos coding amino acid and nucleic sequences are known (e.g., see Verma et al., *Cold Spring Harb. Symp. Quant. Biol.* 51, 949, 1986; GenBank Accession Nos. K00650 and M16287, and is available on the internet).

Caloric intake or calorie intake: The number of calories (energy) consumed by an individual.

Calorie: A unit of measurement in food. A standard calorie is defined as 4.184 absolute joules, or the amount of energy it takes to raise the temperature of one gram of water from 15 to 16° C. (or 1/100th the amount of energy needed to raise the temperature of one gram of water at one atmosphere pressure from 0° C. to 100° C.), food calories are actually equal to 1,000 standard calories (1 food calorie=1 kilocalorie).

Conservative variation: The replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Non-limiting examples of conservative amino acid substitutions include those listed below:

| Original Residue | Conservative Substitutions |
| --- | --- |
| Ala | Ser |
| Arg | Lys |
| Asn | Gln, His |
| Asp | Glu |
| Cys | Ser |
| Gln | Asa |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Depolarization: An increase in the membrane potential of a cell. Certain stimuli reduce the charge across the plasma membrane. These can be electrical stimuli (which open voltage-gated channels), mechanical stimuli (which activate mechanically-gated channels) or certain neurotransmitters (which open ligand-gated channels). In each case, the facilitated diffusion of sodium into the cell increases the resting potential at that spot on the cell creating an excitatory postsynaptic potential (EPSP). Depolarizations can also be generated by decreasing the frequency of inhibitory postsynaptic currents (IPSCs), these are due to inhibitory neurotransmitters facilitating the influx of chloride ions into the cell, creating an IPSC. If the potential is increased to the threshold voltage (about −50 mV in mammalian neurons), an action potential is generated in the cell.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Exendin: A 39-amino acid peptide isolated from the salivary glands of the Gila monster (*Heloderma suspectum*) (Eng J et al *J Biol Chem* 267:7402-7405, 1992), see SEQ ID NO:341. Exendin is an example of an agonist at the GLP-1 receptor. Molecules derived from exendin-4 and that also have GLP-1 agonist activity are further examples of GLP-1 agonists.

Food intake: The amount of food consumed by an individual. Food intake can be measured by volume or by weight. In one embodiment, food intake is the total amount of food consumed by an individual. In another embodiment, food intake is the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Glucagon-like peptide-1: Peptides produced by processing of preproglucogon, which is a 160 amino acid polypeptide, in the central nervous system (CNS) and the intestine. GLP-1 (1-37) is the initial product. GLP-1 (1-37) is amidated by post-translational processing to yield GLP-1 (1-36) NH, or is enzymatically processed to give GLP-1 (7-37) (SEQ ID NO: 338). GLP-1 (7-37) can be amidated to give GLP-1 (7-36) amide (SEQ ID NO: 339), which is the most biologically active form. GLP-1 is released into the circulation in response to nutrient intake. Intestinal cells secrete GLP-1 (7-37) and GLP-1 (7-36) amide in a ratio of 1 to 5.

GLP-1 receptors are found in the brainstem, arcuate nucleus and paraventricular nucleus. Physiological actions of GLP-1 in man include stimulation of insulin release, suppression of gastric acid secretion and slowing of gastric emptying.

A GLP-1 agonist is a peptide, small molecule, or chemical compound that preferentially binds to the GLP-1 receptor and stimulates the same biological activity as GLP-1. In one embodiment, an agonist for the GLP-1 receptor binds to the receptor with an equal or greater affinity than a GLP-1 peptide. In another embodiment, an agonist selectively binds the GLP-1 receptor, as compared to binding to another receptor.

One of skill in the art can readily determine the dissociation constant ($K_d$) value of a given compound. This value is dependent on the selectivity of the compound tested. For example, a compound with a $K_d$ which is less than 10 nM is generally considered an excellent drug candidate. However, a compound that has a lower affinity, but is selective for the particular receptor, can also be a good drug candidate. In one specific, non-limiting example, an assay, such as a competition assay, is used to determine if a compound of interest is a GLP-1 receptor agonist.

GLP-1 agonists include GLP-1 related peptides and peptides that result from natural or synthetic enzymatic or chemical processing of a GLP-1 peptide or a related peptide.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is unchanged, a hyperpolarized cell requires a stronger excitatory stimulus to reach threshold.

Inhibitory Postsynaptic Current: A current that inhibits an electrophysiological parameter of a postsynaptic cell. The potential of a postsynaptic cell can be analyzed to determine an effect on a presynaptic cell. In one embodiment, the postsynaptic cell is held in voltage clamp mode, and postsynaptic currents are recorded. If necessary, antagonists of other classes of current can be added. In one specific, non-limiting example, to record GABAergic IPSCs, blockers of excitatory channels or receptors can be added. The instantaneous frequency over time is then determined.

In one embodiment, IPSCs give a measure of the frequency of GABA release from an NPY neuron. Thus, as NPY neurons release GABA onto POMC neurons, measurement of IPSC frequency is a gauge of the inhibitory tone that POMC neurons are receiving, and can be used to assess the effect of an agonist of PYY.

Membrane potential: The electrical potential of the interior of the cell with respect to the environment, such as an external bath solution. One of skill in the art can readily assess the membrane potential of a cell, such as by using conventional whole cell techniques. Activation of a cell is associated with less negative membrane potentials (for example shifts from about −50 mV to about −40 mV).—These changes in potential increase the likelihood of action potentials, and thus lead to an increase in the rate of action potentials.

The rate of action potentials can be assessed using many approaches, such as using conventional whole cell access, or using, for example, perforated-patch whole-cell and cell-attached configurations. In each event the absolute voltage or current is not assessed, rather the frequency of rapid deflections characteristic of action potentials is assessed, as a function of time (therefore this frequency is an instantaneous frequency, reported in "bins"). This time component can be related to the time at which a compound, such as a PYY agonist, is applied to the bath to analyze the effect of the compound, such as the PYY agonist, on action potential firing rate.

Neuropeptide Y (NPY): A 36-amino acid peptide that is a neuropeptide identified in the mammalian brain. NPY is believed to be an important regulator in both the central and peripheral nervous systems and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen, intestinal membranes, brain, aortic smooth muscle, kidney, testis, and placenta. In addition, binding sites have been reported in a number of rat and human cell lines.

Neuropeptide Y (NPY) receptor has structure/activity relationships within the pancreatic polypeptide family. This family includes NPY, which is synthesized primarily in neurons; peptide YY (PYY), which is synthesized primarily by endocrine cells in the gut; and pancreatic polypeptide (PP), which is synthesized primarily by endocrine cells in the pancreas. These 36 amino acid peptides have a compact helical structure involving an amino acid structure, termed a "PP-fold" in the middle of the peptide.

NPY binds to several receptors, including the Y1, Y2, Y3, Y4 (PP), Y5, Y6, and Y7 receptors. These receptors are recognized based on binding affinities, pharmacology, and sequence (if known). Most, if not all of these receptors are G protein-coupled receptors. The Y1 receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity (e.g., see PCT publication WO 93/09227).

Pharmacologically, the Y2receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provides improved affinity and selectivity (see Dumont et al., *Society for Neuroscience Abstracts* 19:726, 1993). Signal transmission through both the Y1 and the Y2 receptors are coupled to the inhibition of adenylate cyclase. Binding to the Y-2 receptor was also found to reduce the intracellular levels of calcium in the synapse by selective inhibition of N-type calcium channels. In addition, the Y-2 receptor, like the Y1 receptors, exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. Nos. 6,420,352 and 6,355,478).

A Y2 receptor agonist is a peptide, small molecule, or chemical compound that preferentially binds to the Y2 receptor and stimulates intracellular signaling. In one embodiment, an agonist for the Y2 receptor binds to the receptor with an equal or greater affinity than NPY. In another embodiment, an agonist selectively binds the Y2 receptor, as compared to binding to another receptor.

One of skill in the art can readily determine the dissociation constant ($K_d$) value of a given compound. This value is dependent on the selectivity of the compound tested. For example, a compound with a $K_d$ which is less than 10 nM is generally considered an excellent drug candidate. However, a compound that has a lower affinity, but is selective for the particular receptor, can also be a good drug candidate. In one specific, non-limiting example, an assay, such as a competition assay, is used to determine if a compound of interest is a Y2 receptor agonist. Assays useful for evaluating neuropeptide Y receptor antagonists are also well known in the art (see U.S. Pat. No. 5,284,839, which is herein incorporated by reference, and Walker et al., *Journal of Neurosciences* 8:2438-2446, 1988).

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. In one embodiment, the Body Mass Index (BMI) is used to assess obesity. In one embodiment, a BMI of 25.0 kg/m$^2$ to 29.9 kg/m$^2$ is overweight, while a BMI of 30 kg/m$^2$ is obese.

In another embodiment, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese, but is not necessarily obese. In one embodiment, an overweight individual is any individual who desires to decrease their weight. In another embodiment, an overweight individual is an individual with a BMI of 25.0 kg/m$^2$ to 29.9 kg/m$^2$ Oxyntomodulin: A further peptide produced by post-translational processing of preproglucagon in the CNS and intestine, see SEQ ID NO: 340. Agonists of oxyntomodulin may be identified as described above for agonists of GLP-1 and of NPY. include oxyntomodulins of other species and also modified sequences, for example, sequences in which The term OXM used in this text also covers any analogue of the above OXM sequence, wherein the histidine residue at position 1 is maintained or replaced by an aromatic moiety carrying a positive charge or a derivative thereof, preferably wherein the moiety is an amino acid, more preferably wherein it is a histidine derivative, while 1, 2, 3, 4, 5, 6, 7, 8, 9, 10, 11, 12, 13, 14, 15, 16, 17, 18, 19, 20, 21 or 22 of the other amino acids in the above OXM sequence can be independently replaced by any other independently chosen amino acid, with the exception of histidine in position 1.

Any one or more (to 22) other alpha-amino acid residue in the sequence can be independently replaced by any other one alpha-amino acid residue. Preferably, any amino acid residue other than histidine is replaced with a conservative replacement as well known in the art i.e. replacing an amino acid with one of a similar chemical type such as replacing one hydrophobic amino acid with another.

As discussed above, 1 to 22 of the amino acids can be replaced. In addition to the replacement option above, this may be by a non-essential or modified or isomeric form of an amino acid. For example, 1 to 22 amino acids can be replaced by an isomeric form (for example a D-amino acid), or a modified amino acid, for example a nor-amino acid (such as norleucine or norvaline) or a non-essential amino acid (such as taurine). Furthermore, 1 to 22 amino acids may be replaced by a corresponding or different amino acid linked via its side chain (for example gamma-linked glutamic acid). For each of the replacements discussed above, the histidine residue at position 1 is unaltered or defined above.

In addition, 1, 2, 3, 4 or 5 of the amino acid residues can be removed from the OXM sequence with the exception of histidine at the 1 position (or as defined above). The deleted residues may be any 2, 3, 4 or 5 contiguous residues or entirely separate residues.

The C-terminus of the OXM sequence may be modified to add further amino acid residues or other moieties.

Pancreatic Polypeptide: A 36 amino acid peptide produced by the pancreas that is has homology to PYY and NPY.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration Polypeptide: A polymer in which the monomers are amino acid residues which are joined together through amide bonds.

When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide, for example such a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

PYY: A peptide YY polypeptide obtained or derived from any species. Thus, PYY includes the human full length polypeptide (as set forth in SEQ ID NO: 1) and species variations of PYY, including e.g. murine, hamster, chicken, bovine, rat, and dog PYY (SEQ ID NOS: 5-12). In one embodiment, PYY agonists do not include NPY. PYY also includes $PYY_{3-36}$. A "PYY agonist" is any compound which binds to a receptor that specifically binds PYY, and elicits an effect of PYY. In one embodiment, a PYY agonist is a compound that affects food intake, caloric intake, or appetite, and/or which binds specifically in a Y receptor assay or competes for binding with PYY, such as in a competitive binding assay with labeled PYY. PYY agonists include, but are not limited to, compounds that bind to the Y2 receptor.

Substantially purified: A polypeptide which is substantially free of other proteins, lipids, carbohydrates or other materials with which it is naturally associated. For example, the polypeptide may be at least 50%, 80% or 90% free of other proteins, lipids, carbohydrates or other materials with which it is naturally associated.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effect of PYY or an agonist thereof is an amount sufficient to inhibit or halt weight gain, or an amount sufficient to decrease appetite, or an amount sufficient to reduce caloric intake or food intake or increase energy expenditure.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Altering Food Intake, Appetite, Caloric Intake and Energy Expenditure A method is disclosed herein for reducing food intake by peripherally administering to a subject a therapeutically effective amount of PYY or an agonist of PYY and GLP-1 or an agonist thereof. In one embodiment, administration of PYY, or an agonist of PYY, and GLP-1 or an agonist thereof, results in a decrease in the amount, either the total weight or the total volume of food. In other embodiment, administration of PYY, or an agonist thereof, and GLP-1 or an agonist thereof, results in a decrease of the intake of a food component, such as a decrease in the ingestion of lipids, carbohydrates, cholesterol, or proteins. In the any of the methods disclosed herein, a preferred compound, $PYY_{3-36}$ can be administered. This disclosure includes the corresponding uses of PYY or an agonist thereof and GLP-1 or an agonist thereof, for the manufacture of a medicament or medicaments for the purposes set herein, and includes the use of $PYY_{3-36}$.

A method is also disclosed herein for reducing caloric intake by peripherally administering to a subject a therapeutically effective amount of PYY or an agonist of PYY and GLP-1 or an agonist thereof In one embodiment, total caloric intake is reduced by peripheral administration of a therapeutically effective amount of PYY and GLP-1 or an agonist thereof In other embodiments, the caloric intake from the ingestion of a specific food component, such as, but not limited to, the ingestion of lipids, carbohydrates, cholesterol, or proteins, is reduced.

In an additional embodiment, a method is disclosed herein for reducing appetite by administering a therapeutically effective amount of PYY or an agonist thereof and GLP-1 or an agonist thereof. Appetite can be measured by any means known to one of skill in the art. For example, decreased appetite can be assessed by a psychological assessment. In this embodiment, administration of PYY and the other agent(s) results in a change in perceived hunger, satiety, and/or fullness. Hunger can be assessed by any means known to one of skill in the art. In one embodiment, hunger is assessed using psychological assays, such as by an assessment of hunger feelings and sensory perception using a questionnaire, such as, but not limited to, a Visual Analog Score (VAS) questionnaire (see the Examples section). In one specific, non-limiting example, hunger is assessed by answering questions relating to desire for food, drink, prospective food consumption, nausea, and perceptions relating to smell or taste.

In a further embodiment, a method is disclosed herein for altering energy metabolism in a subject. The method includes peripherally administering a therapeutically effective amount of PYY or an agonist thereof and GLP-1 or an agonist thereof, to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat. In a further embodiment a method is disclosed herein for any and all manipulations of the arcuate circuitry described in this application, that alter food intake coordinately and reciprocally alter energy expenditure. Energy expenditure is a result of cellular metabolism, protein synthesis, metabolic rate, and calorie utilization. Thus, in this embodiment, peripheral administration of PYY and administration of GLP-1 or an agonist thereof, results in increased energy expenditure, and decreased efficiency of calorie utilization. In one embodiment, a therapeutically effective amount of PYY or an agonist and GLP-1 or an agonist thereof, thereof is administered to a subject, thereby increasing energy expenditure.

In several embodiments, PYY (e.g., $PYY_{3-36}$) or an agonist thereof and GLP-1 or an agonist thereof, are used for weight control and treatment, reduction or prevention of obesity, in particular any one or more of the following: preventing and reducing weight gain; inducing and promoting weight loss; and reducing obesity as measured by the Body Mass Index. The disclosure further relates to the use of PYY or an agonist and GLP-1 or an agonist thereof, in control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. The disclosure further relates to the use of PYY an agonist thereof and GLP-1 or an agonist thereof, in maintaining any one or more of a desired body weight, a desired Body Mass Index, a desired appearance and good health.

The subject can be any subject, including both human and veterinary mammalian subjects. Thus, the subject can be a human, or can be a non-human primate, a farm animal such as swine, cattle, and poultry, a sport animal or pet such as dogs, cats, horses, hamsters, rodents, or a zoo animal such as lions, tigers, or bears.

Obesity is currently a poorly treatable, chronic, essentially intractable metabolic disorder. A therapeutic drug useful in weight reduction of obese persons could have a profound beneficial effect on their health. Thus, the subject can be, but is not limited to, a subject who is overweight or obese. In one embodiment, the subject has, or is at risk of having, a disorder wherein obesity or being overweight is a risk factor for the disorder. Disorders of interest include, but are not limited to, cardiovascular disease, (including, but not limited to, hypertension, atherosclerosis, congestive heart failure, and dyslipidemia), stroke, gallbladder disease, osteoarthritis, sleep apnea, reproductive disorders such as, but not limited to, polycystic ovarian syndrome, cancers (e.g., breast, prostate, colon, endometrial, kidney, and esophagus cancer), varicose veins, acnthosis nigricans, eczema, exercise intolerance, insulin resistance, hypertension hypercholesterolemia, cholithiasis, osteoarthritis, orthopedic injury, insulin resistance (such as, but not limited to, type 2 diabetes and syndrome X) and tromboembolic disease (see Kopelman, *Nature* 404:635-43; Rissanen et al., *British Med. J.* 301, 835, 1990).

Other associated disorders also include depression, anxiety, panic attacks, migraine headaches, PMS, chronic pain states, fibromyalgia, insomnia, impulsivity, obsessive compulsive disorder, and myoclonus. Obesity is a recognized risk factor for increased incidence of complications of general anesthesia. (See e. g., Kopelman, *Nature* 404:635-43, 2000). It reduces life span and carries a serious risk of co-morbidities listed above.

Other diseases or disorders associated with obesity are birth defects (maternal obesity associated with increased incidence of neural tube defects), carpal tunnel syndrome (CTS), chronic venous insufficiency (CVI), daytime sleepiness, deep vein thrombosis (DVT), end stage renal disease (ESRD), gout, heat disorders, impaired immune response, impaired respiratory function, infertility, liver disease, lower back pain, obstetric and gynecologic complications, pancreatititis, as well as abdominal hernias, acanthosis nigricans, endocrine abnormalities, chronic hypoxia and hypercapnia, dermatological effects, elephantitis, gastroesophageal reflux, heel spurs, lower extremity edema, mammegaly (causing considerable problems such as bra strap pain, skin damage, cervical pain, chronic odors and infections in the skin folds under the breasts, etc.), large anterior abdominal wall masses (abdominal panniculitis with frequent panniculitis, impeding walking, causing frequent infections, odors, clothing difficulties, low back pain), musculoskeletal disease, pseudo tumor cerebri (or benign intracranial hypertension), and sliding hiatil hernia.

The present disclosure relates to treating, prevention, ameliorating or alleviating conditions or disorders caused by, complicated by, or aggravated by a relatively high nutrient availability. By "condition or disorder which can be alleviated by reducing caloric (or nutrient) availability," it is meant any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus (e.g., type 1, 2 or gestational diabetes) can also benefit from this disclosure.

Such conditions or disorders are disorders associated with increased caloric intake, insulin resistance, or glucose intolerance and include, but are not limited to, obesity, diabetes, including type 2 diabetes, eating disorders, insulin-resistance syndromes, and Alzheimer's disease.

In another embodiment, the subject is a subject who desires weight loss, such as female and male subject who desire a change in their appearance. In yet a further embodiment, the subject is a subject who desires decreased feelings of hunger, such as, but not limited to, a person involved in a lengthy task that requires a high level of concentration (e.g., soldiers on active duty, air traffic controllers, or truck drivers on long distance routes, etc.).

A suitable administration format may be best determined by the subject or by a medical practitioner. In one embodiment, the pharmaceutical compositions that include PYY, or an agonist thereof, will preferably be formulated in unit dosage form, suitable for individual administration of precise dosages. An effective amount of PYY or an agonist thereof can be administered in a single dose, or in multiple doses, for example daily, during a course of treatment. In one embodiment, PYY is administered whenever the effect (e.g., appetite suppression, decreased food intake, or decreased caloric intake) is desired. In another embodiment, PYY or an analog thereof is administered slightly prior to whenever the effect is desired, such as, but not limited to about 10 minutes, about 15 minutes, about 30 minutes, about 60 minutes, about 90 minutes, or about 120 minutes, prior to the time the effect is desired. In another embodiment, a time release formulation is utilized.

In one embodiment, a therapeutically effective amount of PYY or an agonist thereof is administered as a single pulse dose, as a bolus dose, or as pulse doses administered over time. Thus, in pulse doses, a bolus administration of PYY is provided, followed by a time period wherein no PYY is administered to the subject, followed by a second bolus administration. In specific, non-limiting examples, pulse doses of PYY are administered during the course of a day, during the course of a week, or during the course of a month.

The therapeutically effective amount of PYY or an agonist thereof will be dependent on the molecule utilized, the subject being treated, the severity and type of the affliction, and the manner of administration. For example, a therapeutically effective amount of PYY or an agonist thereof can vary from about 0.01 µg per kilogram (kg) body weight to about 1 g per kg body weight, such as about 1 µg to about 5 mg per kg body weight, or about 5 µg to about 1 mg per kg body weight. In another embodiment, PYY or an agonist thereof is administered to a subject at 0.5 to 135 picomole (pmol) per kg body weight, or about 72 pmol per kg body weight. In one specific, non-limiting example about 5 to about 50 nmol is administered as a subcutaneous injection, such as about 2 to about 20 nmol, or about 10 nmol is administered as a subcutaneous injection. The exact dose is readily determined by one of skill in the art based on the potency of the specific compound (such as the PYY polypeptide, or agonist) utilized, the age, weight, sex and physiological condition of the subject. The dose of an agonist can be a molar equivalent of the therapeutically effective dose of PYY or $PYY_{3-36}$.

The compositions or pharmaceutical compositions can be administered by any route, including intravenous, intraperitoneal, subcutaneous, sublingual, transdermal, intramuscular, oral, topical, transmucosal, or by pulmonary inhalation. Compositions useful in the disclosure may conveniently be provided in the form of formulations suitable for parenteral (including intravenous, intramuscular and subcutaneous), nasal or oral administration. The term "parenteral" as used herein refers to modes of administration which include intravenous, intramuscular, intraperitoneal, intrasternal, subcutaneous and intraarticular injection and infusion. PYY, including $PYY_{3-36}$, an agonist of PYY, or an antagonist of PYY, can be administered subcutaneously. It is well known in the art that subcutaneous injections can be easily self-administered.

In some cases, it will be convenient to provide a PYY or a PYY agonist and another food-intake-reducing, plasma glucose-lowering or plasma lipid-altering agent, in a single composition or solution for administration together. In other cases, it may be more advantageous to administer the additional agent separately from said PYY or PYY agonist.

A suitable administration format may best be determined by a medical practitioner for each patient individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

PYY and PYY agonists useful in the methods of this disclosure can be provided as parenteral compositions, e.g., for injection or infusion. Preferably, they are suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Since the PYY and agonists are amphoteric, they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. Such products are readily prepared by procedures well known to those skilled in the art.

For use by the physician, the compositions can be provided in dosage unit form containing an amount of a PYY or a PYY agonist with or without another active ingredient, e.g., a food intake-reducing, plasma glucose-lowering or plasma lipid-altering agent. Administration may begin whenever the suppression of nutrient availability, food intake, weight, blood glucose or plasma lipid lowering is desired, for example, at the first sign of symptoms of a weight-related disorder or shortly after diagnosis of obesity, diabetes mellitus, or insulin resistance syndrome.

Therapeutically effective amounts of a PYY or a PYY agonist for use in reducing nutrient availability are those that suppress appetite at a desired level. As will be recognized by those in the field, an effective amount of therapeutic agent will vary with many factors including the potency of the particular compound, age and weight of the patient, the patient's physical condition, the blood sugar level, the weight level to be obtained, and other factors. As will be recognized by those in the field, an effective amount of this therapeutic agent will also vary with many factors including the potency of the particular compound, age and weight of the patient, the patient's physical condition, the blood sugar level, the weight level to be obtained, and other factors. Administration may begin whenever the increased of nutrient availability, food intake, weight, blood glucose or plasma lipid lowering is desired, such as, but not limited to, at the first sign of symptoms of a anorexia or at the onset of weight loss due to AIDS.

The optimal formulation and mode of administration of PYY or a PYY agonist to a patient depend on factors known in the art such as the particular disease or disorder, the desired effect, and the type of patient. While the PYY and PYY agonists will typically be used to treat human subjects they may also be used to treat similar or identical diseases in other vertebrates such as other primates, farm animals such as swine, cattle and poultry, and sport animals and pets such as horses, dogs and cats.

As a pharmaceutical medicament the PYY and PYY agonists of the present disclosure may be administered directly by any suitable technique, including parenterally, intranasally, orally, or by absorption through the skin. The specific route of administration of each agent will depend, e.g., on the medical history of the animal.

For parenteral administration, in one embodiment, PYY and PYY agonists can be formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. "Pharmaceutically acceptable carrier" refers to a non-toxic solid, semisolid or liquid filler, diluent, encapsulating material or formulation auxiliary of any type. For example, the formulation preferably does not include oxidizing agents and other compounds that are known to be deleterious to PYY and PYY agonists.

Generally, the formulations are prepared by contacting the PYY or PYY agonist uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

PPY and PYY agonists are also suitably administered by sustained-release systems. Suitable examples of sustained-release PYY and PYY agonists include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt). Sustained-release PPY and PYY agonist compositions may be administered orally, rectally, parenterally, intracisternally, intravaginally, intraperitoneally, topically (as by powders, ointments, gels, drops or transdermal patch), bucally, or as an oral or nasal spray.

Sustained release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., *Id.*) or poly-D-(–)-3-hydroxybutyric acid (EP 133,988).

Sustained-release PPY and PYY agonists include liposomally PPY and PYY agonists (see generally, Langer, *Science* 249:1527-1533, 1990; Treat et al., in *Liposomes in the Therapy of Infectious Disease and Cancer*, Lopez-Berestein and Fidler (eds.), Liss, New York, pp. 317-327 and 353-365, 1989). Liposomes containing PPY peptide and peptide analogs are prepared by methods known per se: DE 3,218,121; Epstein et al., *Proc. Natl. Acad. Sci. U.S.A.* 82:3688-3692, 1985; Hwang et al., *Proc. Natl. Acad. Sci. U.S.A.* 77:4030-4034, 1980; EP 52,322; EP 36,676; EP 88,046; EP 143,949; EP 142,641; Japanese Patent Application No. 83-118008; U.S. Pat. Nos. 4,485,045, 4,544,545; and EP 102,324. Ordinarily, the liposomes are of the small (about 200-800 Angstroms) unilamellar type in which the lipid content is greater than about 30 mole percent cholesterol, the selected proportion being adjusted for the optimal performance.

Preparations for administration can be suitably formulated to give controlled release of PYY and PYY agonists. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

In yet an additional embodiment, PPY and PYY agonists are delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321: 574, 1989) or by continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249: 1527-1533, 1990).

In another aspect of the disclosure, PPY and PYY agonists are delivered by way of an implanted pump, described, for example, in U.S. Pat. Nos. 6,436,091; 5,939,380; 5,993,414.

Implantable drug infusion devices are used to provide patients with a constant and long term dosage or infusion of a drug or any other therapeutic agent. Essentially such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed™ pump further includes an antenna to permit the remote programming of the pump. Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a patient, thereby negating the need for a percutaneous catheter. These implanted pumps can provide the patient with PYY or a PYY agonist at a constant or a programmed delivery rate, e.g., to give pulsed doses at or around meal time. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions that comprise a PYY, or an agonist thereof, as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Other medicinal and pharmaceutical agents, for instance other appetite suppressants, or protease inhibitors, also may be included. Actual methods of preparing such dosage forms are known, or will be apparent, to those skilled in the art.

The dosage form of the pharmaceutical composition will be determined by the mode of administration chosen. For instance, in addition to injectable fluids, inhalation, suppository, and oral formulations can be employed. The pharmaceutical compositions can be produced of conventional mixing, granulating, confectioning, dissolving or lyophilizing processes.

Oral formulations may be liquid (e.g., syrups, solutions or suspensions), or solid (e.g., powders, pills, tablets, or capsules). For example, pharmaceutical compositions for oral use can be obtained by combining the active ingredient with one or more solid carriers, optionally granulating a resulting mixture, and, if desired, processing the mixture or granules, if appropriate with the addition of additional excipients, to form tablets or dragee cores.

Suitable carriers include fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

For parenteral administration compositions include suitable aqueous solutions of an active ingredient in water-soluble form, for example in the form of a water-soluble salt, or aqueous injection suspensions that contain viscosity-altering substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

For inhalation, PYY or an agonist thereof is administered as an aerosol or a dispersion in a carrier. In one specific, non-limiting example, PYY or an agonist thereof is administered as an aerosol from a conventional valve, such as, but not limited to, a metered dose valve, through an aerosol adapter also known as an actuator. A suitable fluid carrier can be also included in the formulation, such as, but not limited to, air, a hydrocarbon, such as n-butane, propane, isopentane, amongst others, or a propellant, such as, but not limited to a fluorocarbon. Optionally, a stabilizer is also included, and/or porous particles for deep lung delivery are included (e.g., see U.S. Pat. No. 6,447,743).

Compounds with poor solubility in aqueous systems require formulation by using solubilizing agents such as ionic surfactants, cholates, polyethylene glycol (PEG), ethanol, or other agents which may have undesirable effects when used for inhalation. In addition, a treatment requiring successful delivery into alveoli of the lower pulmonary region may preclude from the formulation the use of certain irritants such as chlorofluorocarbons and should involve a minimum number of required doses. Alternatively, to avoid such limitations, liposomes or hydrophobic particles can be used. In one embodiment, an inhalation formulation for a sustained release includes using aerosol droplet particles approximately 1-2.1 μm in size, or of less than 1 μm in size. Small particle aerosol liposomes and liposome-drug combinations for medical use have been previously described (e.g., see EP 87309854.5).

According to the invention, a therapeutically effective amount of PYY or an agonist thereof is administered with a therapeutically effective amount of GLP-1 or an agonist thereof.

The PYY or agonist thereof and the GLP-1 or an agonist thereof may be administered simultaneously or substantially simultaneously, or sequentially, in any order. The PYY or agonist thereof and the GLP-1 or an agonist thereof may be administered in a single pharmaceutical composition or in separate compositions, and they may be administered by the same route or my different routes.

If the PYY and the GLP-1 or an agonist thereof are to be administered in a single pharmaceutical composition, that composition may be any of those described above for PYY or an agonist thereof. The composition may enable simultaneous or substantially simultaneous administration of the PYY or agonist thereof and the GLP-1 or an agonist thereof. If desired, the PYY or agonist thereof and the GLP-1 or an agonist thereof may be compartmentalized in the composition, for example, in different layers of a tablet, or in different granules in a capsule. If desired, such compartmentalization may be designed to give different release properties to the two components to enable delivery of the PYY or agonist component and the GLP-1 or an agonist thereof at different times, for example, sequentially.

Alternatively, the PYY or agonist thereof and the GLP-1 or an agonist thereof may be formulated in separate pharmaceutical compositions, for example, any of the pharmaceutical compositions described above for PYY and agonists thereof. Such separate compositions may be administered simultaneously or substantially simultaneously, or they may be administered sequentially, in any order.

If administered separately, whether sequentially or simultaneously (or substantially simultaneously), the PYY or agonist thereof and the GLP-1 or an agonist thereof may be administered by the same route or by different routes. It is generally more convenient to administer all the active agents in a single composition. However, in some cases it may be necessary or appropriate to administer the active agents by different routes. For example, peptides are generally not stable on oral administration unless modified or formulated in a special way, so must generally be administered via a non-oral route. Some agonists, for example, GLP-1 agonists, are chemical compounds that are stable when administered orally. It may be appropriate to administer OXM non-orally and the other component by a non-oral route.

When PYY or an agonist thereof and GLP-1 or an agonist thereof are used in the manufacture of a medicament for use in a treatment as described herein, the medicament may be a single pharmaceutical composition comprising both components, as described above, or may be a two-component medicament, one component being a pharmaceutical composition comprising PYY or an agonist thereof, the other component being a pharmaceutical composition comprising GLP-1 or an agonist thereof, see above. The medicament, whether a one component medicament or a two component medicament as described above, will generally be packaged with instructions relating to its use. Such instructions will refer to the timing, dose and route of administration of the component(s).

If desired, a further agent that influences food intake and/or appetite may also be administered. Such agents include naturally-occurring agents and agonists thereof, for example, amylin and amylin agonists, leptin and leptin agonosts, and oxyntomodulin.

If desired, one or more other agents, such as, but not limited to, an additional appetite suppressant, may also be administered. Specific, non-limiting example of an additional appetite suppressant include amfepramone (diethylpropion), phentermine, mazindol and phenylpropanolamine, fenfluramine, dexfenfluramine, and fluoxetine.

PYY or a PYY agonist, or GLP-1 or a GLP-1 agonist, or both, can be administered simultaneously with the additional agent(s), or the various substances may be administered sequentially, and in any order. Thus, in one embodiment, PYY or an agonist thereof and GLP-1 or an agonist thereof is formulated and administered with an additional agent, for example, oxyntomodulin or an agonist thereof, or an appetite suppressant as a single composition.

Additionally, a method of treating obesity is disclosed herein. The method includes administering to an obese subject a therapeutically effective amount of PYY or a PYY agonist, and GLP-1 or an agonist thereof. The PYY agonist can have potency in at least one of food intake or gastric emptying greater than NPY. PYY or a PYY agonist can be administered peripherally, such as in a single or divided dose. Suitable single or divided doses include, but are not limited to, 1 µg to about 5 mg or about 0.01 µg/kg to about 500 µg/kg per dose. The subject can be insulin resistant or glucose intolerant, or both. In addition to being obese, the subject can have diabetes mellitus.

A method of reducing food intake is also disclosed herein. The method includes administering to an obese subject a therapeutically effective amount of PYY or a PYY agonist, and GLP-1 or an agonist thereof. The PYY agonist can have potency in at least one of food intake or gastric emptying greater than NPY. PYY or a PYY agonist can be administered peripherally, such as in a single or divided dose. Suitable single or divided doses include, but are not limited to, 1 µg to about 5 mg or about 0.01 µg/kg to about 500 µg/kg per dose. The subject can have -Type II diabetes, and/or can be overweight.

A method is disclosed herein for improving lipid profile in a subject. The method includes administering to the subject an effective amount of PYY or a PYY agonist, and GLP-1 or antagonist thereof. An improvement in lipid profile includes, but is not limited to, at least one method of reducing cholesterol levels, reducing triglyceride levels and increasing HDL cholesterol levels. PYY or a PYY agonist can be administered peripherally, such as in a single or divided dose. PYY or a PYY agonist can be administered peripherally, such as in a single or divided dose. Suitable single or divided doses include, but are not limited to, 1 µg to about 5 mg or about 0.01 µg/kg to about 500 µg/kg per dose. The PYY agonist can have potency in at least one of food intake or gastric emptying greater than NPY.

In another embodiment, a method is disclosed herein for alleviating a condition or disorder which can be alleviated by reducing nutrient availability. The method includes administering to a subject a therapeutically effective amount of PYY or a PYY agonist, and GLP-1 or an agonist thereof. Suitable disorders include any of the disorders mentioned above.

The PYY or a PYY agonist and GLP-1 or GLP-1 agonist can be administered peripherally, such as in a single or divided dose. Suitable single or divided doses include, but are not limited to, 1 µg to about 5 mg or about 0.01 µg/kg to about 500 µg/kg of PYY or a PYY agonist per dose. The PYY agonist can have potency in at least one of food intake or gastric emptying greater than NPY. Suitable doses also include those that raise the concentration of PYY and/or the agonist thereof significantly above the basal concentration of PYY, such as, but not limited to, a dose that that mimic postparandial serum concentrations of PYY (or the agonist). Thus, in one embodiment, PYY or an agonist thereof is administered to achieve the level of to effect a reduction in calorie intake, food intake, or appetite equivalent to the reduction in calorie intake, food intake, or appetite, or to increase the energy expenditure, caused by the postprandial level of $PYY_{3-36}$. Specific, non-limiting examples of doses include, but are not limited doses that produce the effect demonstrated when the serum levels of PYY are from about 40 pM/liter to about 60 pM/liter, for example, from about 40 pM/liter to about 50 pM/liter, or from about 40 pM/liter to about 45 pM/liter, or to about 43 pM/liter.

For all methods disclosed herein, the dose of PYY or $PYY_{3-36}$ can be based on the physiological levels observed post-prandially. The normal circulating levels of $PYY_{3-36}$ are about 8 pmol/liter, typically rising to about 40 to 60 pmol/liter after a meal. Agonists of PYY can be used at analogous doses. A single dose may be administered per day, or divided doses can be used (see above).

As indicated above, $PYY_{3-36}$ has a prolonged and sustained action, continuing to act even after it has been cleared from the circulating blood, for example, for up to 12 and even up to 24 hours. Accordingly, PYY or an agonist thereof may be administered twice per day or even just once. If desired, more doses may be administered, for example, three or four per day. For example, it may be desired to administer PYY or an agonist thereof before a meal, for example, about half an hour before a meal. It may be desired to administer PYY or an agonist thereof before each meal. Alternately, it may be desired to administer as few doses as possible, in which case a regime or one or two doses per day may be used.

GLP-1 or an agonist may be administered according to the same regime as the PYY or agonist thereof, whether administered simultaneously or substantially simultaneously with the PYY or PYY agonist, or sequentially. Alternatively, the GLP-1 may be administered in a different regime, for example, with more doses of GLP-1 than of PYY, for example, the PYY or PYY agonist may be administered once or twice per day, and the GLP-1 or agonist thereof may be administered three or four times per day. For example, PYY or a PYY agonist may be administered in the morning and evening, for example, before breakfast and before the evening meal, and the GLP-1 agonist thereof may also be administered before the mid-day meal.

In one embodiment, when administered peripherally, PYY, including $PYY_{3-36}$ has its effects at physiological levels. No side effects are observed when $PYY_{3}$-36 is used at such levels. Without being bound by theory, $PYY_{3-36}$ does not affect Y2 receptors throughout the brain, which could cause side effects. It should be noted, without being limiting, that a further advantage of $PYY_{3-36}$ is that $PYY_{3-36}$ does not increase blood pressure. The effects of $PYY_{3-36}$ are as long lasting as 24 hours. Recipients claim a decrease in appetite over that period, and a reduction of food intake of about one third has been reported.

In one specific, non-limiting example, $PYY_{3-36}$ is administered in a dose of about 1 nmol or more, 2 nmol or more, or 5 nmol or more. In this example, the dose of $PYY_{3-36}$ is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, exemplar non-limiting dose ranges include a dose of $PYY_{3-36}$ may be within the range of form 1 to 100 nmols, from 1 to 90 mols, from 1 to 80 nmols. Exemplary, non-limiting dose ranges include, from 2 to 100 nmols, from 2 to 90 n mols, for example, from 2 to 80 nmols etc., from 5 nmols to 100 mols, from 5 nmols to 90 nmols, from 5 nmols to 80 nmols etc. By way of example, a dose of from about 5 to about 50 nmol may be administered such as, but not limited to, from about 2 to about 20 nmol, for example, about 10 nmol. The selected dose may be administered for example, by injection, for example, as a subcutaneous injection. A PYY agonist may be administered at the same dose.

In a further, non-limiting example, $PYY_{3-36}$ may be administered peripherally at a dose of 0.1 nmoles or more per kg body weight of the subject, for example, 0.2 nmoles or more, for example, 0.4 nmoles or more, for example, 0.6 nmoles or more, for example, 0.8 nmoles or more, for example, 1.0 nmole or more, for example, 1.2 nmoles or more, for example, 1.4 nmoles or more, for example, 1.6 nmoles or more, for example, 1.8 nmoles or more, for example, 2.0 nmoles or more, for example, 2.2 nmoles or more, for example, 2.4 nmoles or more, for example, 2.6 nmoles or more, for example, 2.8 nmoles, for example, 3.0 nmoles or more, for example, up to 3.2 nmoles per kg body weight. $PYY_{3-36}$ or a PYY agonist and may be administered peripherally in an amount of up to 3.0 nmoles per kg body weight, for example, up to 2.8 nmoles, for example, up to 2.6 nmoles, for example, up to 2.4 nmoles, for example, up to 2.2 nmoles, for example, up to 2.0 nmoles, for example, up to 1.8 nmoles, for example, up to 1.4 nmoles, for example, up to 1.2 nmoles, for example, up to 1.0 nmoles, for example, up to 0.8 nmoles, for example, up to 0.6 nmoles, for example, up to 0.4 nmoles, for example, up to 0.2 nmoles per kg body weight.

For subcutaneous administration, a dose of PYY for example $PYY_{3-36}$ or a -PYY agonist of 10 nmoles or more, for example, 20 nmoles or more, for example, 30 nmoles or more, for example, 40 nmoles or more may be used. It is generally preferable to use up to about 70 nmoles, for example, up to about 60 nnmoles. A dose of about 40 nmoles may be used. In one embodiment, a dose of PYY or $PYY_{3-36}$ at 0.143 n moles ($\frac{1}{7}^{th}$ of a mole) is administered per kilogram, to achieve a dose that is similar to the postprandial level of PYY.

If PYY itself or an agonist thereof is used, the dose is preferably a molar equivalent of a $PYY_{3-36}$ dose, or achieves the same effect as a $PYY_{3}$_36 dose, as described above. The doses can be calculated on the basis of a subject, such as a subject weighing from 70 to 75 kg. The exact dose is readily determined by one of skill in the art based on the potency of the specific compound (such as the PYY polypeptide, or agonist) utilized, and the age, weight, sex and physiological condition of the subject.

All the teachings given above in relation to $PYY_{3-36}$ also apply to PYY itself and to PYY agonists. For example, the teachings relating to routes of administration and dosage regimes.

The GLP-1 or an agonist thereof should be administered in an therapeutically effective dose, see the section relating to GLP-1 and agonists thereof below. GLP-1 or an agonist thereof may be used in amounts or doses in the ranges described above for PYY or a PYY agonist. The doses of the various agent may be independent of each other or, for example, equimolar doses may be used, for example, equimolar doses of GLP-1 or an agonist thereof and PYY or an agonist thereof.

As disclosed herein, a naturally occurring peptide, PYY or $PYY_{3-36}$ can be used to achieve a physiological effect. This results in minimal side effects and enables long term use, if necessary. The dose of PYY or $PYY_{3-36}$ can be based on the physiological levels observed post-prandially. The normal circulating levels of $PYY_{3-36}$ are about 8 pmol/liter, typically rising to about 40 to 60 pmol/liter after a meal. PYY (e.g., $PYY_{3-36}$) and agonists can be used at analogous doses.

The considerations set out above in relation to the administration regime also relate to administration using the subcutaneous route.

The various uses of PYY, or an agonist thereof, and GLP-1 or an agonist thereof, as set out above may be in a method of treatment of a mammalian subject in need of such treatment, or may be in the manufacture of a medicament for such treatment. PYY (e.g., $PYY_{3-36}$) or an agonist thereof, and GLP-1 or an agonist thereof, should be administered in an amount effective to achieve the stated object. Some of the treatments described above are medical treatments, for example, the treatment of obesity. Others, however, do not relate to medical treatment, and are part of the maintenance of a healthy lifestyle, or are for cosmetic purposes.

The use of a combination of any of OXM and GLP-1 or an agonist thereof and PYY or an agonist thereof may serve to increase the effectiveness of any of the agents compared with its use alone, for example, as described above. Alternatively or in addition, use of the two or three agents in combination may reduce any tendency for "escape" when using an agent alone. The term "escape" is used to denote a reduction in effect of an agent with time. For example, if any one of the agents above has been used alone, its effect may reduce with time. Use of one or both of the other agents in addition may reduce or prevent the tendency for that reduction in effectiveness. For example, PYY has a sustained effect and may be used for prolonged periods. If the effect of PYY should appear to reduce, or to reduce or prevent any such reduction in effect, OXM may be administered in addition to the PYY. GLP-1 may also be used for the same purpose, with OXM or with OXM and PYY.

In another aspect the present invention provides a pharmaceutical composition that comprises PYY or a PYY agonist as the active ingredient and a pharmaceutically suitable carrier in a form suitable for subcutaneous administration, for example, as an injectable solution. Such a composition may comprise an amount of PYY for example $PYY_{3-36}$ or a PYY agonist of 10 nmoles or more, for example, 20 nmoles or more, for example, 30 nmoles or more, for example, 40 nmoles or more may be used. It is generally preferable to use up to about 70 nmoles, for example, up to about 60 nnmoles. An amount of about 40 nmoles may present. Suitable formulations for subcutaneous administration are well known, and are described above. One or more further active ingredient(s) may also be present in the composition, in particular GLP-1 or an agonist thereof, which may be used in amounts and doses as described above. Further active ingredients may be present, for example, as described above, for example, oxyntomodulin or an agonist thereof, or an appetite suppressant as described above.

A further aspect of the invention relates to methods as disclosed above, including a method for decreasing calorie intake in a subject, a method for decreasing appetite in a subject, a method for decreasing food intake in a subject, a method for weight control or treatment in a subject, and a method for reduction or prevention of obesity, in particular any one or more of the following: preventing and reducing weight gain; inducing and promoting weight loss; and reducing obesity as measured by the Body Mass Index. The methods include control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. The methods further include maintaining any one or more of a desired body weight, a desired Body Mass Index, a desired appearance and good health. In the methods of this aspect of the invention, PYY, for example, $PYY_{3-36}$ or a PYY agonist is administered subcutaneously to the subject.

Preferably the PYY or PYY agonist is administered at dose of 10 nmoles or more, for example, 20 nmoles or more, for example, 30 nmoles or more, for example, 40 nmoles or more may be used. It is generally preferable to use up to about 70 nmoles, for example, up to about 60 nnmoles. An dose of about 40 nmoles be used. As indicated above, $PYY_{3-36}$ has a prolonged and sustained action, continuing to act even after it has been cleared from the circulating blood, for example, for up to 12 and even up to 24 hours. Accordingly, PYY or an agonist thereof may be administered twice per day or even just once. If desired, more doses may be administered, for example, three or four per day. For example, it may be desired to administer PYY or an agonist thereof before a meal, for example, about half an hour before a meal. It may be desired to administer PYY or an agonist thereof before each meal. Alternately, it may be desired to administer as few doses as possible, in which case a regime or one or two doses per day may be used.

In this aspect of the invention, PYY or an agonist thereof may be administered alone or PYY or an agonist thereof and GLP-1 or an agonist thereof may be administered. If GLP-1 or an agonist thereof is used in addition to the PYY or PYY agonist, the GLP-1 or agonist thereof may be administered simultaneously or substantially simultaneously with the PYY or agonist thereof, or sequentially, in either order. The PYY or agonist thereof and the GLP-1 or agonist thereof may be administered in a single pharmaceutical composition or in separate compositions, and they may be administered by the same route or by different routes. Further active ingredients may also be administered, for example, as described above for subcutaneous PYY pharmaceutical compositions.

The present invention also includes PYY or an agonist thereof for use in the manufacture of a medicament for subcutaneous administration for any of the methods of treatment described above.

PYY Agonists

A PYY agonist, of use in the methods of the present disclosure, is a molecule that binds to a receptor that specifically binds PYY, and elicits an effect of PYY. Assays for binding to PYY receptors, and eliciting a response in a cell with a PYY receptor, are known in the art. A specific assay for detecting a PYY agonist is also disclosed herein. Thus, in one embodiment, a PYY agonist binds to a NPY neuron in the arcuate nucleus, which results in an electrophysiological effect on an NPY neuron. As disclosed herein, NPY neurons synapse with POMC neurons. Thus, the electrophysiological effect on the NYP neuron can result in a further electrophysiological effect on a POMC neuron. In one specific, non-limiting example, an administration of PYY agonist results in hyperpolization of the membrane potential of a POMC neuron. In another specific, non-limiting example, administration of a PYY agonist results in an increase in IPSCs in a POMC neuron.

In another embodiment, PYY agonists do not include NPY. Suitable PYY agonists include molecules that bind NPY neurons, but do not cross the blood/brain barrier. The arcuate nucleus neurons upon which PYY exerts its effects are not protected by the blood/brain barrier, and thus are readily accessible to peripherally available molecules. In addition, other brain sites that express the Y2 receptor are protected by the blood/brain barrier. Without being bound by theory, agents able to bind to the arcuate Y2R, but that do not cross the blood/brain barrier following peripheral administration, are likely to be of use.

In one embodiment, a PYY agonist is a compound that affects food intake, caloric intake, or appetite, and/or which binds specifically in a Y receptor assay or competes for binding with PYY, such as in a competitive binding assay with labeled PYY. PYY agonists include, but are not limited to, compounds that bind to the Y2 receptor.

PYY and agonists useful in the methods disclosed herein include, but are not limited to, polypeptides comprising, or alternatively consisting of, the amino acid sequence for PPY and agonists thereof, e.g., mutants, fragments and/or variants thereof Variants include deletions, insertions, inversions, repeats and substitutions (e.g., conservative substitutions and non-conservative substitutions; see, e.g., Tables 1 and 2, infra). More than one amino acid (e.g., 2, 3, 4, 5, 6, 7, 8, 9, 10, etc.) can be deleted or inserted or substituted with another amino acid. Typically conservative substitutions are the replacements, one for another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly. Guidance concerning how to make phenotypically silent amino acid substitutions is provided in Bowie et al., *Science* 247:1306-1310, 1990.

As another example, polypeptide fragments may contain a continuous series of deleted residues from the amino (N)- or the carboxyl (C)-terminus, or both (see, e.g., Tables 1 and 2, infra). Any number of amino acids, ranging from 1 to 24, can be deleted from the N-terminus, the C-terminus or both.

Furthermore, the agonist polypeptides may also include, but are not limited to, polypeptides comprising, or alternatively consisting of, internal deletions of the amino acid sequences for PPY and/or agonist thereof (see, e.g., Table 2, infra). Such deletions may comprise one or more amino acid residue deletions (e.g., one, two, three, four, five, six, seven, eight, nine, ten, etc.) and may begin at any amino acid position (e.g., two, three, four, five, six, seven, eight, nine, ten, etc.). In addition, the polypeptides of this disclosure may contain one or more such internal deletions. Such deletions are contemplated in PPY, NPY and PP.

Also contemplated are agonist peptides that are PPY, NPY and/or PP chimeras having high affinity and/or selectivity for the Y2 receptor. These chimeras may comprise amino acid substitutions of one or more amino acids (e.g., 1, 2, 3, 4, 5, 6, 7, 8, 9, 10, etc.) from PPY, NPY and/or PP, variants, mutants and/or deletions thereof, with one or more amino acids (e.g., 1, 2, 3, 4, 5, 6, 7, 8, 9, 10, etc.) from a second PPY, NPY, or PP, variants, mutations and/or deletions thereof. These substitutions may begin at any amino acid position (e.g., two, three, four, five, six, seven, eight, nine, ten, etc.).

Preferably, the peptide is selective for the Y2 receptor. That is, it binds with higher affinity to Y2 compared to other receptors, such as Y1, Y2, Y3, Y4, Y5 and Y6. In another embodiment, the peptide is selective for the Y2 and Y5 receptors over the Y1, Y3, Y4 and Y6 receptors.

Other polypeptide fragments are fragments comprising structural or functional domain of the polypeptides of this disclosure. Such fragments include amino acid residues that comprise a polyproline-type II helix (residues 1-8), beta-turn (residues 9-14), amphipathic alpha-helix (residues 15-32) and/or a C-terminal turn structure (residues 33-36). See, Kirby et al., *J Med Chem* 36:385-393, 1993.

In addition, this disclosure includes the use of a polypeptide or agonist comprising, or alternatively consisting of, the amino acid sequence for PPY, NPY and PP species variants (see Table 1, infra) and/or mutants, and fragments thereof.

Also contemplated are fusion proteins, whereby a PYY or PYY agonist will be fused to another protein or polypeptide (the fusion partner) using recombinant methods known in the art. Alternatively, such a fusion protein may be synthetically synthesized by any known method. Any known peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be designed linking the carboxy-terminus of the fusion partner to the amino-terminus of the PYY or agonist peptide, or vice versa. Optionally, a cleavable linker region may be used linking the PYY or PYY agonist to the fusion partner, and may be cleaved in vivo thereby resulting in the release of an active form of PYY or a PYY agonist. Examples of such cleavage regions include, but are not limited to, the linker regions D-D-D-D-Y (SEQ ID NO: 330), G-P-R (SEQ ID NO: 331), A-G-G (SEQ ID NO: 332) and H-P-F-H-L (SEQ ID NO 333), which can be cleaved by enterokinase, thrombin, ubiquitin cleaving enzyme and renin, respectfully. See, e.g., U.S. Pat. No. 6,410,707.

Also contemplated as useful PYY agonists are Y2 specific NPY peptide agonists as described in U.S. Pat. Nos. 5,026, 685; 5,574,010; 5,604,203; 5,696,093; 6,046,167. See below:

Preferred PPY agonists are described herein as follows.

TABLE 1

| PYY: Variation Among Species | | |
|---|---|---|
| PEPTIDE YY | AA SEQUENCE | |
| Human | YPIKPEAPGEDASPEELNRYYASLRHYLNLVTRQRY | (SEQ ID NO: 1) |
| Rat | YPAKPEAPGEDASPEELSRYYASLRHYLNLVTRQRY | (SEQ ID NO: 5) |
| Pig | YPAKPEAPGEDASPEELSRYYASLRHYLNLVIRQRY | (SEQ ID NO: 6) |
| Guinea pig | YPSKPEAPGSDASPEELARYYASLRHYLNLVTRQRY | (SEQ ID NO: 7) |
| Frog | YPPKPENPGEDASPEEMTKYLTALRHYINLVTRQRY | (SEQ ID NO: 8) |
| Raja | YPPKPENPGDDAAPEELAKYYSALRHYINLITRQRY | (SEQ ID NO: 9) |
| Dogfish | YPPKPENPGEDAPPEELAKYYSALRHYINLITRQRY | (SEQ ID NO: 10) |
| Lampetra | FPPKPDNPGDNASPEQMARYKAAVRHYINLITRQRY | (SEQ ID NO: 11) |
| Petromyzon | MPPKPDNPSPDASPEELSKYMLAVRNYINLITRQRY | (SEQ ID NO: 12) |
| NEUROPEPTIDE Y | AA SEQUENCE | |
| Human | YPSKPDNPGEDAPAEDMARYYSALRHYINLITRQRY | (SEQ ID NO: 2) |
| Rat | YPSKPDNPGEDAPABDMARYYSALRHYINLITRQRY | (SEQ ID NO: 13) |
| Rabbit | YPSKPDNPGEDAPAEDMARYYSALRHYINLITRQRY | (SEQ ID NO: 14) |
| Dog | YPSKPDNPGEDAPAEDMARYYSALRHYINLITRQRY | (SEQ ID NO: 15) |
| Pig | YPSKPDNPGEDAPABDLARYYSALRHYINLITRQRY | (SEQ ID NO: 16) |
| Cow | YPSKPDNPGEDAPAEDLARYYSALRHYINLITRQRY | (SEQ ID NO: 17) |
| Sheep | YPSKPDNPGDDAPAEDLARYYSALRHYINLITRQRY | (SEQ ID NO: 18) |
| Guinea pig | YPSKPDNPGEDAPABDMARYYSALRHYINLITRQRY | (SEQ ID NO: 19) |
| Avian | YPSKPDSPGEDAPAEDMARYYSALRHYINLITRQRY | (SEQ ID NO: 20) |
| Rana | YPSKPDNPGEDAPAEDMAKYYSALRHYINLITRQRY | (SEQ ID NO: 21) |

TABLE 1-continued

PYY: Variation Among Species

| | | |
|---|---|---|
| Goldfish | YPTKPDNPGEGAPAEELAKYYSALRHYINLITRQRY | (SEQ ID NO: 22) |
| Dogfish | YPSKPDNPGEGAPAEDLAKYYSALRHYINLITRQRY | (SEQ ID NO: 23) |
| Lampetra | PPNKPDSPGEDAPAEDLARYLSAVRHYINLITRQRY | (SEQ ID NO: 24) |
| PANCREATIC POLYPEPTIDE | AA SEQUENCE | |
| Human | ASLEPEYPGDNATPEQMAQYAAELRRYINMLTRPRY | (SEQ ID NO: 3) |
| Sheep | APLEPVYPGDNATPEQMAQYAADLRRYINMLTRPRY | (SEQ ID NO: 25) |
| Pig | APLEPVYPGDDATPEQMAQYAAELRRYINMLTRPRY | (SEQ ID NO: 26) |
| Dog | APLEPVYPGDDATPEQMAQYAAELRRYINMLTRPRY | (SEQ ID NO: 27) |
| Cat | APLEPVYPGDNATPEQMAQYAAELRRYINMLTRPRY | (SEQ ID NO: 28) |
| Cow | APLEPEYPGDNATPEQMAQYAAELRRYINMLTRPRY | (SEQ ID NO: 29) |
| Rat | APLEPMYPGDYATHEQRAQYETQLRRYTNTLTRPRY | (SEQ ID NO: 30) |
| Mouse | APLEPMYPGDYATPEQMAQYETQLRRYINTLTRPRY | (SEQ ID NO: 31) |
| Guinea pig | APLEPVYPGDNATPEQQMAQYAAEMRRYINMLTRPRY | (SEQ ID NO: 32) |
| Chicken | GPSQPTYPGDDAPVEDLIRFYNDLQQYLNVVTRHRY | (SEQ ID NO: 33) |
| Alligator | TPLQPKYPGDGAPVEDLIQFYNDLQQYLNVVTRPRF | (SEQ ID NO: 34) |
| Bullfrog | APSEPHHPGDQATPDQLAQYYSDLYQYITFITRPRF | (SEQ ID NO: 35) |

Ref: Beck-Sickinger, A. G., Jung, G., Biopolymers 37:123-142, 1995.

TABLE 2

PEPTIDE AGONIST OF PYY

| PEPTIDE | SEQUENCE | |
|---|---|---|
| PPY(3-36)human) | IKPEAPGEDASPEELNRYYASLRHYLNLVTRQRY | (SEQ ID NO: 334) |

Ref: Eberlein et al., Peptides 10:797-803, 1989; Grandt et al., Peptides 15(5):815-20, 1994.

Variations of PPY(3-36)

N-Terminal Deletions of PYY, including but not limited to:

PYY(26-36), PYY(25-36), PYY(24-36), PYY(23-36), PYY(22-36),

PYY(21-36), PYY(20-36), PYY(19-36), PYY(18-36), PYY(17-36),

PYY(16-36), PYY(15-36), PYY(14-36), PYY(13-36), PYY(12-36),

PYY(11-36), PYY(10-36), PYY(9-36), PYY(8-36), PYY(7-36),PYY(6-36),

PYY(5-36), PYY(4-36), PYY(3-36).

Ref: See, e.g., Balasubramaniam et at., Pept Res 1(1):32-5, Sep-Oct 1998; Liu et al., J Gastrointest Surg 5(2):147-52, Mar-Apr 2001.

| PEPTIDE | SEQUENCE | |
|---|---|---|
| NPY (human) | YPSKPDNPGEDAPAEDMARYYSALRHYINLITRQRY | (SEQ ID NO: 2) |

Ref: Tatemoto et al., Proc Natl Acad Sci U.S.A. 79:5485-9, 1982.

Variations of NPY

N-Terminal Deletions of NPY, including but not limited to:
NPY(26-36), NPY(25-36), NPY(24-36), NPY(23-36), NPY(22-36),

NPY(21-36), NPY(20-36), NPY(19-36), NPY(18-36), NPY(17-36),

NPY(16-36), NPY(15-36), NPY(14-36), NPY(13-36), NPY(12-36),

TABLE 2-continued

PEPTIDE AGONIST OF PYY

NPY(11-36), NPY(10-36), NPY(9-36), NPY(8-36), NPY(7-36), NPY(6-36), NPY(5-36), NPY(4-36), NPY(3-36).

Ref: See e.g., Gehlert et al., Proc Soc Exp Biol Med 218:7-22, 1998; Sheikh et al., Am J Physiol 261:G701-15, Nov. 1991.

Internal Deletions, including but not limited to:
(1-4)-Aca-(14-36)pNPY, (1-4)-Aca-(15-36)pNPY, (1-4)-Aca-(16-36)pNPY, (1-4)-Aca-(17-36)pNPY, (1-4)-Aca-(18-36)pNPY, (1-4)-(31-36)pNPY11, (1-4)-Aca-(31-36)pNPY, (4-1)-(31-36)pNPY, (4-1)-Aca-(31-36)pNPY, $(4-1)_D$-(31-36)pNPY, $(4-1)_D$-Aca-(31-36)pNPY.

Ref: Fournier et al., Mol Pharmacol 45(1):93-101, Jan 1994.

Additional Internal Deletion Mutants, including but not limited to:
des-$AA^{10-17}$-NPY, des-$AA^{10-17}$, Ac-[D-$Lys^9$(ε-Ac-Ala)]NPY, des-$AA^{10-17}$, Ac[D-$Lys^9$(ε-Ac-Ala)]NPY, des-$AA^{10-17}$[$Ala^{7,21}$]NPY, des-$AA^{10-17}$ [$Cys^{7,21}$]NPY, des-$AA^{10-17}$[$Glu^7$,$Lys^{21}$]NPY, des-$AA^{11-17}$[D-$Lys^{10}$(ε-Ac), $Cys^{7,21}$]NPY, des-$AA^{10-17}$[D-$Cys^7$, D-Lys(ε-Ac), $Cys^{21}$]NPY, des-$AA^{10-17}$ [D-$Cys^7$, $Lys^9$(ε-Ac), $Cys^{21}$]NPY, des-$AA^{10-17}$[$Cys^{7,21}$, $Pro^{34}$]NPY, des-$AA^{10-17}$[$Asp^7$, $Dpr^{21}$, $Pro^{34}$]NPY, des-$AA^{10-17}$[$Glu^{7,\ Lys21}$, $Pro^{34}$]NPY, des-$AA^{10-17}$[$Cys^{7,21}$, $Leu^{31}$, $Pro^{34}$]NPY, des-$AA^{10-20}$ [$Cys^{7,21}$, $Pro^{34}$]NPY, des-$AA^{10-17}$[$Cys^{2,27}$]NPY, des-$AA^{10-17}$[$Cys^2$, D-$Cys^{27}$]NPY.

Ref: Kirby et al., J Med Chem 38:4579-86, 1995.

Cyclic agonist of NPY, including but not limited to:
[Lys 25-Glu 29]NPY(Ac-25-36), [Glu 25-Lys 29]NPY(Ac-25-36), [Lys 26-Glu31]NPY(Ac-25-36), [Glu 27-Lys31]NPY(Ac-25-36), [Lys28-Glu 32] NPY(Ac-25-36), [Lys27-Glu34]NPY(Ac-25-36).

Ref: Rist et al., Eur J Biochem 247:1019-1028, 1997.

D-amino acid substitutions: [D-$Tyr^1$]NPY, [D-$Pro^2$]NPY, [D-$Ser^3$]NPY, [D-$Lys^4$]NPY, [D-$Pro^5$]NPY, [D-$Asp^6$]NPY, [D-$Asn^7$]NPY, [D-$Pro^8$]NPY, [D-$Ala^9$]NPY, [D-$Glu^{10}$]NPY, [D-$Asp^{11}$]NPY, [D-$Ala^{12}$]NPY, [D-$Pro^{13}$]NPY, [D-$Ala^{14}$]NPY, [D-$Glu^{15}$]NPY, [D-$Asp^{16}$]NPY, [D-$Leu^{17}$]NPY, [D-$Ala^{18}$]NPY, [D-$Arg^{19}$]NPY, [D-$Tyr^{20}$]NPY, [D-$Tyr^{21}$]NPY, [D-$Ser^{22}$]NPY, [D-$Ala^{23}$]NPY, [D-$Leu^{24}$]NPY, [D-$Arg^{25}$]NPY, [D-$His^{26}$]NPY, [D-$Tyr^{27}$]NPY, [D-$Ile^{28}$]NPY, [D-$Asn^{29}$]NPY, [D-$Leu^{30}$]NPY, [D-$Ile^{31}$]NPY, [D-$Thr^{32}$]NPY, [D-$Arg^{33}$]NPY, [D-$Gln^{34}$]NPY, [D-$Arg^{35}$]NPY, [D-$Tyr^{36}$]NPY, [D-$Tyr^1$, D-$Pro^2$]NPY, [D-$Ser^3$, D-$Lys^4$]NPY, [D-$Pro^5$, D-$Asp^6$]NPY, [D-$Asn^7$, D-$Pro^5$]NPY, [D-$Glu^{10,}$ D-$Asp^{11}$]NPY, [D-$Asp^{11}$, D-$Ala^{12}$]NPY, [D-$Pro^{13}$, D-$Ala^{14}$]NPY, [D-$Glu^{15,}$ D-$Asp^{16}$]NPY, [D-$Met^{17}$, D-$Ala^{18}$]NPY, [D-$Arg^{19}$, D-$Tyr^{20}$]NPY, [D-$Tyr^{21,}$ D-$Ser^{22}$]NPY, [D-$Ala^{23}$, D-$Leu^{24}$]NPY, [D-$Arg^{25}$, D-$His^{26}$]NPY, [D-$Tyr^{27,}$ D-$Ile^{28}$]NPY, [D-$Asn^{29}$, D-$Leu^{30}$]NPY, [D-$Ile^{31}$, D-$Thr^{32}$]NPY, [D-$Arg^{33,}$ D-$Gln^{34}$]NPY, [D-$Arg^{35}$, D-$Tyr^{36}$]NPY.

Ref: Kirby et al., J Med Chem 36:3802-08, 1993; Grundemar et al., Regulatory Peptides 62:131-136, 1996.

TABLE 2-continued

PEPTIDE AGONIST OF PYY

Other NPY Agonist and Analogs

| PEPTIDE | SEQUENCE | |
|---|---|---|
| NPY(3-36) | SKPDNPGEDAPAEDMARYYSALRHYINLITRQRY | (SEQ ID NO: 335) |

Ref: Grandt et al., Regulatory Peptides 67(1):33-7, 1996.

| PEPTIDE | SEQUENCE | |
|---|---|---|
| N-Acetyl NPY(24-36) | LRHYINLITRQRY | (SEQ ID NO: 213) |

Ref: Potter et al., Eur J Pharmacol 267(3):253-262, May 17, 1994.

| PEPTIDE | SEQUENCE | |
|---|---|---|
| N-Acetyl [Leu$^8$, Leu$^{31}$] NPY(24-36) | LRHYLNLLTRQRY | (SEQ ID NO: 214) |

Ref: Potter et al., Eur J Pharmacol 267(3):253-262, May 17, 1994.

| PEPTIDE | SEQUENCE | |
|---|---|---|
| [Leu$^{28}$, Leu$^{31}$] NPY(24-36) | LRHYLNLLTRQRY | (SEQ ID NO: 215) |

Ref: Potter et al., Eur J Pharmacol 267(3):253-262, May 17, 1994.

| PEPTIDE | SEQUENCE | |
|---|---|---|
| [Leu$^{17}$, Gln$^{19}$, Ala$^{21}$, Ala$^{22}$, Gly$^{23}$, Leu$^{28}$, Leu$^{31}$] NPY(13-36) | PAEDLAQYAAELRHYLNLLTRQRY | (SEQ ID NO: 216) |

Ref: Potter et al., Eur J Pharmacol 267(3):253-262, May 17, 1994.

| PEPTIDE | SEQUENCE | |
|---|---|---|
| Cyclo S-S[Cys$^{20}$, Cys$^{24}$]pNPY | SKPDNPGEDAPAEDMARCYSACRHYINLITRQRY | (SEQ ID NO: 315) |

Ref: Soll et aL, Eur J Biochem 268(10):2828-37, May 2001.

| PEPTIDE | SEQUENCE | |
|---|---|---|
| Cyclo-(28/32)-Ac-[Lys$^{28}$-Glu$^{32}$]-(25-36)-pNPY | RHYLNLIGRQRY | (SEQ ID NO: 316) |

Ref: Cabrele et al., J Pept Sci 6(3):97-122, Mar 2000.

| PEPTIDE | SEQUENCE | |
|---|---|---|
| Cyclo-(27/31)-Ac-[Glu$^{27}$-Lys$^{31}$]-(25-36)-pNPY | RHGLNLLGRQRY | (SEQ ID NO: 317) |

Ref: Cabrele et al., J Pept Sci 6(3):97-122, Mar 2000.

| PEPTIDE | SEQUENCE | |
|---|---|---|
| [Tyr$^{32}$, Leu$^{34}$] NPY(27-36) | YINLIYRLRY | (SEQ ID NO: 318) |

Ref: Leban et al., J Med Chem 38:1150-57, 1995.

| PEPTIDE | SEQUENCE | |
|---|---|---|
| [Tyr$^{32}$, Leu$^{34}$] NPY(26-36) | HYINLIYRLRY | (SEQ ID NO: 319) |

Ref: Leban et al., J Med Chem 38:1150-57, 1995.

| PEPTIDE | SEQUENCE | |
|---|---|---|
| [Tyr$^{32}$, Leu$^{34}$] NPY(25-36) | RHYINLIYRLRY | (SED ID NO: 320) |

Ref: Leban et at, J Med Chem 38:1150-57, 1995.

TABLE 2-continued

PEPTIDE AGONIST OF PYY

[Leu³¹] NPY(27-36)  YINLLYRQRY  (SEQ ID NO: 321)

Ref: Leban et al., J Med Chem 38:1150-57, 1995.

| PEPTIDE | SEQUENCE | |
|---|---|---|
| [Tyr³², Leu³⁴](1-4)-Ahr-(27-36)NPY | YPSL-Aha-YINLIYRLRY | (SED ID NO: 322) |

Ref: Leban et al., J Med Chem 38:1150-57, 1995.

| PEPTIDE | SEQUENCE | |
|---|---|---|
| [Tyr³², Leu³⁴]NPY(28-36) | INLIYRLRY | (SEQ ID NO: 323) |

Ref: Leban et al., J Med Chem 38:1150-57, 1995.

| PEPTIDE | SEQUENCE | |
|---|---|---|
| PP (human) | ASLEPEYPGDNATPEQMAQYAAELRRYINMLTRPRY | (SEQ ID NO: 3) |

Ref: Kimmel et al., Endocrinology 83:1323-30, 1968.

Variations of PP

N-Terminal Deletions including but not limited to: PP(26-36), PP(25-36), PP(24-36), PP(23-36), PP(22-36), PP(21-36), PP(20-36), PP(19-36), PP(18-36), PP(17-36), PP(16-36), PP(15-36), PP(14-36), PP(13-36), PP(12-36), PP(11-36), PP(10-36), PP(9-36), PP(8-36), PP(7-36), PP(6-36), PP(5-36), PP(4-36), PP(3-36).

TABLE 3

EXAMPLES OF CONSERVATIVE AMINO ACID SUBSTITUTIONS OF PYY

| PEPTIDE | SEQUENCE | |
|---|---|---|
| Single point mutations of PYY(25-36) | | |
| [Lys²⁵]PPY(25-36) | KHYLNLVTRQRY | (SEQ ID NO: 36) |
| [Thr²⁷]PPY(25-36) | RHTLNINTRQRY | (SEQ ID NO: 37) |
| [Phe²⁷]PPY(25-36) | RHFLNLVTRQRY | (SEQ ID NO: 38) |
| [Ile²⁸]PYY(25-36) | RHYINLVTRQRY | (SEQ ID NO: 39) |
| [Val²⁸]PYY(25-36) | RHYVNLVTRQRY | (SEQ ID NO: 40) |
| [Gln²⁹]PYY(25-36) | RHYLQLVTRQRY | (SEQ ID NO: 41) |
| [Ile³⁰]PYY(25-36) | RHYLNIVTRQRY | (SEQ ID NO: 42) |
| [Val³⁰]PYY(25-36) | RHYLNVVTRQRY | (SEQ ID NO: 43) |
| [Ile³¹]PYY(25-36) | RHYLNLITRQRY | (SEQ ID NO: 44) |
| [Leu³¹]PYY(25-36) | RHYLNLLTRQRY | (SEQ ID NO: 45) |
| [Ser³²]PYY(25-36) | RHYLNLVSRQRY | (SEQ ID NO: 46) |
| [Lys³³]PYY(25-36) | RHYLNLVTKQRY | (SEQ ID NO: 47) |
| [Asn³⁴]PYY(25-36) | RHYLNLVTRNRY | (SEQ ID NO: 48) |
| [Lys³⁵]PYY(25-36) | RHYLNLVTRQKY | (SEQ ID NO: 49) |
| [Thr³⁶]PYY(25-36) | RRYLNLVTRQRT | (SEQ ID NO: 50) |
| [Phe³⁶]PYY(25-36) | RHYLNLVTRQRF | (SEQ ID NO: 51) |

TABLE 3-continued

EXAMPLES OF CONSERVATIVE AMINO ACID SUBSTITUTIONS OF PYY

| PEPTIDE | SEQUENCE | |
|---|---|---|

Double point mutations

| [Lys$^{25}$, Thr$^{27}$]PPY(25-36) | KHTLNLVTRQRY | (SEQ ID NO: 52) |
| [Lys$^{25}$, Phe$^{27}$]PPY(25-36) | KHFLNLVTRQRY | (SEQ ID NO: 53) |
| [Lys$^{25}$, Ile$^{28}$]PPY(25-36) | KHYINLVTRQRY | (SEQ ID NO: 54) |
| [Lys$^{25}$, Val$^{28}$]PPY(25-36) | KHYVNLVTRQRY | (SEQ ID NO: 55) |
| [Lys$^{25}$, Gln$^{29}$]PPY(25-36) | KHYLQLVTRQRY | (SEQ ID NO: 56) |
| [Lys$^{25}$, Ile$^{30}$]PPY(25-36) | KHYLNIVTRQRY | (SEQ ID NO: 57) |
| [Lys$^{25}$, Val$^{30}$]PPY(25-36) | KHYLNVVTRQRY | (SEQ ID NO: 58) |
| [Lys$^{25}$, Ile$^{31}$]PPY(25-36) | KHYLNLITRQRY | (SEQ ID NO: 59) |
| [Lys$^{25}$, Leu$^{31}$]PPY(25-36) | KHYLNLLTRQRY | (SEQ ID NO: 60) |
| [Lys$^{25}$, Ser$^{31}$]PPY(25-36) | KHYLNLVSRQRY | (SEQ ID NO: 61) |
| [Lys$^{25}$, Lys$^{33}$]PPY(25-36) | KHYLNLVTKQRY | (SEQ ID NO: 62) |
| [Lys$^{25}$, Asn$^{34}$]PPY(25-36) | KHYLNLVTRNRY | (SEQ ID NO: 63) |
| [Lys$^{25}$, Lys$^{35}$]PPY(25-36) | KHYLNLVTRQKY | (SEQ ID NO: 64) |
| [Lys$^{25}$, Thr$^{36}$]PPY(25-36) | KHYLNLVTRQRT | (SEQ ID NO: 65) |
| [Lys$^{25}$, Phe$^{36}$]PPY(25-36) | KHYLNLVTRQRF | (SEQ ID NO: 66) |
| [Thr$^{27}$, Ile$^{28}$]PPY(25-36) | RHTINLVTRQRY | (SEQ ID NO: 67) |
| [Thr$^{27}$, Val$^{28}$]PPY(25-36) | RRTVNLVTRQRY | (SEQ ID NO: 68) |
| [Thr$^{27}$, Gln$^{29}$]PPY(25-36) | RHTLQLVTRQRY | (SEQ ID NO: 69) |
| [Thr$^{27}$, Ile$^{30}$]PPY(25-36) | RHTLNIVTRQRY | (SEQ ID NO: 70) |
| [Thr$^{27}$, Val$^{30}$]PPY(25-36) | RHTLNVVTRQRY | (SEQ ID NO: 71) |
| [Thr$^{27}$, Ile$^{31}$]PPY(25-36) | RHTLNLIYRQRY | (SEQ ID NO: 72) |
| [Thr$^{27}$, Leu$^{31}$]PPY(25-36) | RRTLNLLTRQRY | (SEQ ID NO: 73) |
| [Thr$^{27}$, Ser$^{32}$]PPY(25-36) | RHTLNLVSRQRY | (SEQ ID NO: 74) |
| [Thr$^{27}$, Lys$^{33}$]PPY(25-36) | RHTLNLVTKQRY | (SEQ ID NO: 75) |
| [Thr$^{27}$, Asn$^{34}$]PPY(25-36) | RHTLNLVTRNRY | (SEQ ID NO: 76) |
| [Thr$^{27}$, Lys$^{35}$]PPY(25-36) | RHTLNLVTRQKY | (SEQ ID NO: 77) |
| [Thr$^{27}$, Thr$^{36}$]PPY(25-36) | RHTLNLVTRQRT | (SEQ ID NO: 78) |
| [Thr$^{27}$, Phe$^{36}$]PPY(25-36) | RHTLNLVTRQRF | (SEQ ID NO: 79) |
| [Phe$^{27}$, Ile$^{28}$]PPY(25-36) | RHFINLVTRQRY | (SEQ ID NO: 80) |
| [Phe$^{27}$, Val$^{28}$]PPY(25-36) | RRFVNLVTRQRY | (SEQ ID NO: 81) |
| [Phe$^{27}$, Gln$^{29}$]PPY(25-36) | RHFLQLVTRQRY | (SEQ ID NO: 82) |
| [Phe$^{27}$, Ile$^{30}$]PPY(25-36) | RHFLNIVTRQRY | (SEQ ID NO: 83) |
| [Phe$^{27}$, Val$^{30}$]PPY(25-36) | RHFLNVVTRQRY | (SEQ ID NO: 84) |
| [Phe$^{27}$, Ile$^{31}$]PPY(25-36) | RHFLNLITRQRY | (SEQ ID NO: 85) |
| [Phe$^{27}$, Leu$^{31}$]PPY(25-36) | RHFLNLLTRQRY | (SEQ ID NO: 86) |
| [Phe$^{27}$, Ser$^{32}$]PPY(25-36) | RHFLNLVSRQRY | (SEQ ID NO: 87) |

TABLE 3-continued

EXAMPLES OF CONSERVATIVE AMINO ACID SUBSTITUTIONS OF PYY

| PEPTIDE | SEQUENCE | |
|---|---|---|
| [Phe$^{27}$, Lys$^{33}$]PPY(25-36) | RHFLNLVTKQRY | (SEQ ID NO: 88) |
| [Phe$^{27}$, Asn$^{34}$]PPY(25-36) | RHFLNLVTRNRY | (SEQ ID NO: 89) |
| [Phe$^{27}$, Lys$^{35}$]PPY(25-36) | RHFLNLVTRQKY | (SEQ ID NO: 90) |
| [Phe$^{27}$, Thr$^{36}$]PPY(25-36) | RHFLNLVTRQRT | (SEQ ID NO: 91) |
| [Phe$^{27}$, Phe$^{36}$]PPY(25-36) | RHFLNLVTRQRF | (SEQ ID NO: 92) |
| [Gln$^{29}$, Ile$^{30}$]PYY(25-36) | RHYLQIVTRQRY | (SEQ ID NO: 93) |
| [Gln$^{29}$, Val$^{30}$]PYY(25-36) | RHYLQVVTRQRY | (SEQ ID NO: 94) |
| [Gln$^{29}$, Ile$^{31}$]PYY(25-36) | RHYLQLITRQRY | (SEQ ID NO: 95) |
| [Gln$^{29}$, Leu$^{31}$]PYY(25-36) | RHYLQLLTRQRY | (SEQ ID NO: 96) |
| [Gln$^{29}$, Ser$^{32}$]PYY(25-36) | RRYLQLVSRQRY | (SEQ ID NO: 97) |
| [Gln$^{29}$, Leu$^{33}$]PYY(25-36) | RHYLQLVTKQRY | (SEQ ID NO: 98) |
| [Gln$^{29}$, Asn$^{34}$]PYY(25-36) | RHYLQLVTRNRY | (SEQ ID NO: 99) |
| [Gln$^{29}$, Leu$^{35}$]PYY(25-36) | REYLQLVTRQKY | (SEQ ID NO: 100) |
| [Gln$^{29}$, Thr$^{36}$]PYY(25-36) | RHYLQLVTRQRT | (SEQ ID NO: 101) |
| [Gln$^{29}$, Phe$^{36}$]PYY(25-36) | RHYLQLVTRQRF | (SEQ ID NO: 102) |
| [Ile$^{30}$, Ile$^{31}$]PYY(25-36) | RRYLNIITRQRY | (SEQ ID NO: 103) |
| [Ile$^{30}$, Leu$^{31}$]PYY(25-36) | RHYLNILTRQRY | (SEQ ID NO: 104) |
| [Ile$^{30}$, Ser$^{32}$]PYY(25-36) | RRYLNIVSRQRY | (SEQ ID NO: 105) |
| [Ile$^{30}$, Lys$^{33}$]PYY(25-36) | RHYLNIVTKQRY | (SEQ ID NO: 106) |
| [Ile$^{30}$, Asn$^{34}$]PYY(25-36) | RHYLNIVTRNRY | (SEQ ID NO: 107) |
| [Ile$^{30}$, Lys$^{35}$]PYY(25-36) | RHYLNIVTRQKY | (SEQ ID NO: 108) |
| [Ile$^{30}$, Thr$^{36}$]PYY(25-36) | RHYLNIVTRQRT | (SEQ ID NO: 109) |
| [lie$^{30}$, Phe$^{36}$]PYY(25-36) | RHYLNIVTRQRF | (SEQ ID NO: 110) |
| [Val$^{30}$, Ile$^{31}$]PYY(25-36) | RHYLNVITRQRY | (SEQ ID NO: 111) |
| [Val$^{30}$, Leu$^{31}$]PYY(25-36) | RHYLNVLTRQRY | (SEQ ID NO: 112) |
| [Val$^{30}$, Ser$^{32}$]PYY(25-36) | RHYLNVVSRQRY | (SEQ ID NO: 113) |
| [Val$^{30}$, Lys$^{33}$]PYY(25-36) | RHYLNVVTKQRY | (SEQ ID NO: 114) |
| [Val$^{30}$, Asn$^{34}$]PYY(25-36) | RHYLNVVTRNRY | (SEQ ID NO: 115) |
| [Val$^{30}$, Lys$^{35}$]PYY(25-36) | RHYLNVVTRQKY | (SEQ ID NO: 116) |
| [Val$^{30}$, Thr$^{36}$]PYY(25-36) | RHYLNVVTRQRT | (SEQ ID NO: 117) |
| [Val$^{30}$, Phe$^{36}$]PYY(25-36) | RHYLNVVTRQRF | (SEQ ID NO: 118) |
| [Ile$^{31}$, Ser$^{32}$]PYY(25-36) | RHYLNLISRQRY | (SEQ ID NO: 119) |
| [Ile$^{31}$, Lys$^{33}$]PYY(25-36) | RHYLNLITKQRY | (SEQ ID NO: 120) |
| [Ile$^{31}$, Asn$^{34}$]PYY(25-36) | RHYLNLITRNRY | (SEQ ID NO: 121) |
| [Ile$^{31}$, Lys$^{35}$]PYY(25-36) | RHYLNLITRQKY | (SEQ ID NO: 122) |
| [Ile$^{31}$, Thr$^{36}$]PYY(25-36) | RHYLNLITRQRT | (SEQ ID NO: 123) |
| [Leu$^{31}$, Phe$^{36}$]PYY(25-36) | RHYLNLITRQRF | (SEQ ID NO: 124) |

TABLE 3-continued

EXAMPLES OF CONSERVATIVE AMINO ACID SUBSTITUTIONS OF PYY

| PEPTIDE | SEQUENCE | |
|---|---|---|
| [Leu$^{31}$, Ser$^{32}$]PYY(25-36) | RHYLNLLSRQRY | (SEQ ID NO: 125) |
| [Val$^{31}$, Lys$^{33}$]PYY(25-36) | RHYLNLLTKQRY | (SEQ ID NO: 126) |
| [Leu$^{31}$, Asn$^{34}$]PYY(25-36) | RHYLNLLTRNRY | (SEQ ID NO: 127) |
| [Leu$^{31}$, Lys$^{35}$]PYY(25-36) | RHYLNLLTRQKY | (SEQ ID NO: 128) |
| [Leu$^{31}$, Thr$^{36}$]PYY(25-36) | RHYLNLLTRQRT | (SEQ ID NO: 129) |
| [Leu$^{31}$, Phe$^{36}$]PYY(25-36) | RHYLNLLTRQRF | (SEQ ID NO: 130) |
| [Ser$^{32}$, Lys$^{33}$]PYY(25-36) | RHYLNLVSKQRY | (SEQ ID NO: 131) |
| [Ser$^{32}$, Asn$^{34}$]PYY(25-36) | RHYLNLVSRNRY | (SEQ ID NO: 132) |
| [Ser$^{32}$, Lys$^{35}$]PYY(25-36) | RHYLNLVSRQKY | (SEQ ID NO: 133) |
| [Ser$^{32}$, Thr$^{36}$]PYY(25-36) | RHYLNLVSRQRT | (SEQ ID NO: 134) |
| [Ser$^{32}$, Phe$^{36}$]PYY(25-36) | RHYLNLVSRQRY | (SEQ ID NO: 135) |
| [Lys$^{33}$, Asn$^{34}$]PYY(25-36) | RHYLNLVTKNRY | (SEQ ID NO: 136) |
| [Lys$^{33}$, Lys$^{35}$]PYY(25-36) | RHYLNLVTKQKY | (SEQ ID NO: 137) |
| [Lys$^{33}$, Thr$^{36}$]PYY(25-36) | RHYLNLVTKQRT | (SEQ ID NO: 138) |
| [Lys$^{33}$, Phe$^{36}$]PYY(25-36) | RHYLNLVTKQRF | (SEQ ID NO: 139) |
| [Asn$^{34}$, Lys$^{35}$]PYY(25-36) | RHYLNLVTRNKY | (SEQ ID NO: 140) |
| [Asn$^{34}$, Thr$^{36}$]PYY(25-36) | RHYLNLVTRNRT | (SEQ ID NO: 141) |
| [Asn$^{34}$, Phe$^{36}$]PYY(25-36) | RHYLNLVTRNRF | (SEQ ID NO: 142) |
| [Lys$^{35}$, Thr$^{36}$]PYY(25-36) | RHYLNLVTRQKT | (SEQ ID NO: 143) |
| [Lys$^{35}$, Phe$^{36}$]PYY(25-36) | RHYLNLVTRQKF | (SEQ ID NO: 144) |

Point Mutations of PYY(24-36)

| PEPTIDE | SEQUENCE | |
|---|---|---|
| PYY(24-36) | LRHYLNLVTRQRY | (SEQ ID NO: 145) |
| [Ile$^{24}$]PYY(24-36) | IRHYLNLVTRQRY | (SEQ ID NO: 146) |
| [Val$^{24}$]PYY(24-36) | VRRYLNLVTRQRY | (SEQ ID NO: 147) |

Also included as PYY(24-36) mutations are polypeptide variations (amino acid sequence variations) resulting from the combination of any of these three mutants with any of the above listed mutants for PYY(25-36), e.g., [Lys$^{25}$]PPY(24-36) (Amino acid sequence=LKHYLNLVTRQRY (SEQ ID NO: 191)) would result from combining the mutations from SEQ ID NO: 36 with SEQ ID NO: 145.

Point Mutations of PYY(23-36)

| PEPTIDE | SEQUENCE | |
|---|---|---|
| PYY(23-36) | SLRHYLNLVTRQRY | (SEQ ID NO: 148) |
| [Thr$^{23}$]PYY(23-36) | TLRHYLNLVTRQRY | (SEQ ID NO: 149) |

Also included as PYY(23-36) mutations are polypeptide variations (amino acid sequence variations) resulting from the combination of either of these two mutants with any of the above listed mutants for PYY(25-36), and/or any of the above listed mutants for PYY(24-36), e.g., [Lys$^{25}$]PPY(23-36) (Amino acid sequence=SLKHYLNLVTRQRY (SEQ ID NO: 192)) would result from combining the mutations from SEQ ID NO: 36 with SEQ ID NO: 148.

Point Mutations of PYY(22-36)

| PEPTIDE | SEQUENCE |
|---|---|
| PYY(22-36) | ASLRHYLNLVTRQRY (SEQ ID NO: 150) |
| [Ser$^{22}$]PYY(22-36) | SSLRHYLNLVTRQRY (SEQ ID NO: 151) |

Also included as PYY(22-36) mutations are polypeptide variations (amino acid sequence variations) resulting from the combination of either of these two mutants with any of the above listed mutants for PYY(25-36), and/or any of the above listed mutants for PYY(23-36), e.g., [Lys$^{25}$]PPY(22-36) (Amino acid sequence=ASLKHYLNLVTRQRY (SEQ ID NO: 193)) would result from combining the mutations from SEQ ID NO: 36 with SEQ ID NO: 150.

Point Mutations of PYY(21-36)

| PEPTIDE | SEQUENCE |
|---|---|
| PYY(21-36) | YASLRHYLNLVTRQRY (SEQ ID NO: 152) |
| [Thr$^{21}$]PYY(21-36) | TASLRHYLNLVTRQRY (SEQ ID NO: 153) |
| [Phe$^{21}$]PYY(21-36) | FASLRHYLNLVTRQRY (SEQ ID NO: 154) |

Also included as PYY(21-36) mutations are polypeptide variations (amino acid sequence variations) resulting from the combination of any of these three mutants with any of the above listed mutants for PYY(25-36), and/or any of the above listed mutants for PYY(22-36), e.g., [Lys$^{25}$]PPY(21-36) (Amino acid sequence=YASLKHYLNLVTRQRY (SEQ ID NO: 194)) would result from combining the mutations from SEQ ID NO: 36 with SEQ ID NO: 152.

Point Mutations of PYY(20-36)

| PEPTIDE | SEQUENCE |
|---|---|
| PYY(20-36) | YYASLRHYLNLVTRQRY (SEQ ID NO: 155) |
| [Thr$^{20}$]PYY(20-36) | TYASLRHYLNLVThQRY (SEQ ID NO: 156) |
| [Phe$^{20}$]PYY(20-36) | FYASLRHYLNLVTRQRY (SEQ ID NO: 157) |

Also included as PYY(20-36) mutations are polypeptide variations (amino acid sequence variations) resulting from the combination of any of these three mutants with any of the above listed mutants for PYY(25-36), and/or any of the above listed mutants for PYY(21-36), e.g., [Lys$^{25}$]PPY(20-36) (Amino acid sequence=YYASLKHYLNLVTRQRY (SEQ ID NO: 195)) would result from combining the mutations from SEQ ID NO: 36 with SEQ ID NO: 155.

Point Mutations of PYY(19-36)

| PEPTIDE | SEQUENCE |
|---|---|
| PYY(19-36) | RYYASLRHYLNLVTRQRY (SEQ ID NO: 158) |
| [Lys$^{19}$]PYY(19-36) | KYYASLRHYLNLVTRQRY (SEQ ID NO: 159) |

Also included as PYY(19-36) mutations are polypeptide variations (amino acid sequence variations) resulting from the combination of either of these two mutants with any of the above listed mutants for PYY(25-36), and/or any of the above listed mutants for PYY(20-36), e.g., [Lys$^{25}$]PPY(19-36) (Amino acid sequence=RYYASLKHYLNLVTRQRY (SEQ ID NO: 196)) would result from combining the mutations from SEQ ID NO: 36 with SEQ ID NO: 158.

Point Mutations of PYY(18-36)

| PEPTIDE | SEQUENCE |
|---|---|
| PYY(18-36) | NRYYASLRHYLNLVTRQRY (SEQ ID NO: 160) |
| [Gln$^{18}$]PYY(18-36) | QRYYASLRHYLNLVTRQRY (SEQ ID NO: 161) |

Also included as PYY(18-36) mutations are polypeptide variations (amino acid sequence variations) resulting from the combination of either of these two mutants with any of the above listed mutants for PYY(25-36), and/or any of the above listed mutants for PYY(19-36), e.g., [Lys$^{25}$]PPY(18-36) (Amino acid sequence=NRYYASLKHYLNLVTRQRY (SEQ ID NO: 197)) would result from combining the mutations from SEQ ID NO: 36 with SEQ ID NO: 160.

Point Mutations of PYY(17-36)

| PEPTIDE | SEQUENCE |
|---|---|
| PYY(17-36) | LNRYYASLRHYLNLVTRQRY (SEQ ID NO: 162) |
| [Ile$^{17}$]PYY(17-36) | INRYYASLRHYLNLVTRQRY (SEQ ID NO: 163) |
| [Val$^{17}$]PYY(17-36) | VNRYYASLRHYLNLVTRQRY (SEQ ID NO: 164) |

Also included as PYY(17-36) mutations are polypeptide variations (amino acid sequence variations) resulting from the combination of any of these three mutants with any of the above listed mutants for PYY(25-36), and/or any of the above listed mutants for PYY(18-36), e.g., [Lys$^{25}$]PPY(17-36) (Amino acid sequence=LNRYYASLKHYLNLVTRQRY (SEQ ID NO: 198)) would result from combining the mutations from SEQ ID NO: 36 with SEQ ID NO: 162.

| Point Mutations of PYY(16-36) | |
|---|---|
| PEPTIDE | SEQUENCE |
| PYY(16-36) | ELNRYYASLRHYLNLVTRQRY (SEQ ID NO: 165) |
| [Asp$^{16}$]PYY (16-36) | DLNRYYASLRHYLNLVTRQRY (SEQ ID NO: 166) |

Also included as PYY(16-36) mutations are polypeptide variations (amino acid sequence variations) resulting from the combination of either of these two mutants with any of the above listed mutants for PYY(25-36), and/or any of the above listed mutants for PYY(17-36), e.g., [Lys$^{25}$]PPY(16-36) (Amino acid sequence=ELNRYYASLKHYLNLVTRQRY (SEQ ID NO: 199)) would result from combining the mutations from SEQ ID NO: 36 with SEQ ID NO: 165.

| Point Mutations of PYY(15-36) | |
|---|---|
| PEPTIDE | SEQUENCE |
| PYY(15-36) | EELNRYYASLRHYLNLVTRQRY (SEQ ID NO: 167) |
| [Asp$^{15}$]PYY (15-36) | DELNRYYASLRHYLNLVTRQRY (SEQ ID NO: 168) |

Also included as PYY(15-36) mutations are polypeptide variations (amino acid sequence variations) resulting from the combination of either of these two mutants with any of the above listed mutants for PYY(25-36), and/or any of the above listed mutants for PYY(16-36), e.g., [Lys$^{25}$]PPY(15-36) (Amino acid sequence=EELNRYYASLKHYLNLVTRQRY (SEQ ID NO: 200)) would result from combining the mutations from SEQ ID NO: 36 with SEQ ID NO: 167.

| Point Mutations of PYY(14-36) | |
|---|---|
| PEPTIDE | SEQUENCE |
| PYY(14-36) | PEELNRYYASLRHYLNLVTRQRY (SEQ ID NO: 169) |

Also included as PYY(14-36) mutations are polypeptide variations (amino acid sequence variations) resulting from the combination of this PYY(14-36) mutant with any of the above listed mutants for PYY(25-36), and/or any of the above listed mutants for PYY(15-36), e.g., [Lys$^{25}$]PPY(23-36) (Amino acid sequence=PEELNRYYASLKHYLNLVTRQRY (SEQ ID NO: 201) would result from combining the mutations from SEQ ID NO: 36 with SEQ ID NO: 169.

| Point Mutations of PYY(13-36) | |
|---|---|
| PEPTIDE | SEQUENCE |
| PYY(13-36) | SPEELNRYYASLRHYL NLVTRQRY (SEQ ID NO: 170) |
| [Thr$^{13}$]PYY(13-36) | TPEELNRYYASLRHYL NLVTRQRY (SEQ ID NO: 171) |

Also included as PYY(13-36) mutations are polypeptide variations (amino acid sequence variations) resulting from the combination of either of these two mutants with any of the above listed mutants for PYY(25-36), and/or any of the above listed mutants for PYY(14-36), e.g., [Lys$^{25}$]PPY(13-36) (Amino acid sequence=SEELNRYYASLKHYLNLVTRQRY (SEQ ID NO: 202)) would result from combining the mutations from SEQ ID NO: 36 with SEQ ID NO: 170.

| Point Mutations of PYY(12-36) | |
|---|---|
| PEPTIDE | SEQUENCE |
| PYY(12-36) | ASPEELNRYYASLRHY LNLVTRQRY (SEQ ID NO: 172) |
| [Ser$^{12}$]PYY(12-36) | SSPEELNRYYASLRHY LNLVTRQRY (SEQ ID NO: 173) |

Also included as PYY(12-36) mutations are polypeptide variations (amino acid sequence variations) resulting from the combination of either of these two mutants with any of the above listed mutants for PYY(25-36), and/or any of the above listed mutants for PYY(13-36), e.g., [Lys$^{25}$]PPY(12-36) (Amino acid sequence=ASEELNRYYASLKHYLNLVTRQRY (SEQ ID NO: 203)) would result from combining the mutations from SEQ ID NO: 36 with SEQ ID NO: 172.

| Point Mutations of PYY(11-36) | |
|---|---|
| PEPTIDE | SEQUENCE |
| PYY(11-36) | DASPEELNRYYASLRH (SEQ ID NO: 174) YLNLVTRQRY |
| [Glu$^{11}$]PYY(11-36) | EASPEELNRYYASLRH (SEQ ID NO: 175) YLNLVTRQRY |

Also included as PYY(12-36) mutations are polypeptide variations (amino acid sequence variations) resulting from the combination of either of these two mutants with any of the above listed mutants for PYY(25-36), and/or any of the above listed mutants for PYY(12-36), e.g., [Lys$^{25}$]PPY(11-36) (Amino acid sequence=DASEELNRYYASLKHYLNLVTRQRY (SEQ ID NO: 204)) would result from combining the mutations from SEQ ID NO: 36 with SEQ ID NO: 174.

| Point Mutations of PYY(10-36) | |
|---|---|
| PEPTIDE | SEQUENCE |
| PYY(10-36) | EDASPEELNRYYASLR (SEQ ID NO: 176) RYLNLVTRQRY |
| [Asp$^{10}$]PYY(10-36) | DDASPEELNRYYASLR (SEQ ID NO: 177) HYLNLVTRQRY |

Also included as PYY(10-36) mutations are polypeptide variations (amino acid sequence variations) resulting from the combination of either of these two mutants with any of the above listed mutants for PYY(25-36), and/or any of the above listed mutants for PYY(11-36), e.g., [Lys$^{25}$]PPY(10-36)

(Amino acid sequence=EDASEELNRYYASLKHYLNLVTRQRY (SEQ ID NO: 205)) would result from combining the mutations from SEQ ID NO: 36 with SEQ ID NO: 176.

| Point Mutations of PYY(9-36) | |
|---|---|
| PEPTIDE | SEQUENCE |
| PYY(9-36) | GEDASPEELNRYYASLRHYLNLVTRQRY (SEQ ID NO: 178) |

Also included as PYY(9-36) mutations are polypeptide variations (amino acid sequence variations) resulting from the combination of this PPY(9-36) mutant with any of the above listed mutants for PYY(25-36), and/or any of the above listed mutants for PYY(10-36), e.g., [Lys$^{25}$]PPY(9-36) (Amino acid sequence=GEDASPEELNRYYASLKHYLNLVTRQRY (SEQ ID NO: 206)) would result from combining the mutations from SEQ ID NO: 36 with SEQ ID NO: 178.

| Potin Mutations of PYY(8-36) | |
|---|---|
| PEPTIDE | SEQUENCE |
| PYY(8-36) | PGEDASPEELNRYYASLRHYLNLVTRQRY (SEQ ID NO: 179) |

Also included as PYY(8-36) mutations are polypeptide variations (amino acid sequence variations) resulting from the combination of this PPY(8-36) mutant with any of the above listed mutants for PYY(25-36), and/or any of the above listed mutants for PYY(9-36), e.g., [Lys$^{25}$]PPY(8-36) (Amino acid sequence=SEQ ID NO: 207)) would result from combining the mutations from SEQ ID NO: 36 with SEQ ID NO: 179.

| Point Mutations of PYY(7-36) | |
|---|---|
| PEPTIDE | SEQUENCE |
| PYY(7-36) | APGEDASPEELNRYYASL RRYLNLVTRQRY (SEQ ID NO: 180) |
| [Ser$^9$]PYY(7-36) | SPGEDASPEELNRYYASL RHYLNLVTRQRY (SEQ ID NO: 181) |

Also included as PYY(7-36) mutations are polypeptide variations (amino acid sequence variations) resulting from the combination of either of these two mutants with any of the above listed mutants for PYY(25-36), and/or any of the above listed mutants for PYY(8-36), e.g., [Lys$^{25}$]PPY(7-36) (Amino acid sequence=APGEDASEELNRYYASLKHYLNLVTRQRY (SEQ ID NO: 208)) would result from combining the mutations from SEQ ID NO: 36 with SEQ ID NO: 180.

| Point Mutations of PYY(6-36) | |
|---|---|
| PEPTIDE | SEQUENCE |
| PYY(6-36) | EAPGEDASPEELNRYYAS LRHYLNLVTRQRY (SEQ ID NO: 182) |
| [Asp$^6$]PYY(6-36) | DAPGEDASPEELNRYYAS LRHYLNLVTRQRY (SEQ ID NO: 183) |

Also included as PYY(6-36) mutations are polypeptide variations (amino acid sequence variations) resulting from the combination of either of these two mutants with any of the above listed mutants for PYY(25-36), and/or any of the above listed mutants for PYY(7-36), e.g., [Lys$^{25}$]PPY(6-36) (Amino acid sequence=EAPGEDASEELNRYYASLKHYLNLVTRQRY (SEQ ID NO: 209)) would result from combining the mutations from SEQ ID NO: 36 with SEQ ID NO: 182.

| Point Mutations of PYY(5-36) | |
|---|---|
| PEPTIDE | SEQUENCE |
| PYY(5-36) | PEAPGEDASPEELNRYYASLRHYL NLVTRQRY (SEQ ID NO: 184) |

Also included as PYY(5-36) mutations are polypeptide variations (amino acid sequence variations) resulting from the combination of this PPY(5-36) mutant with any of the above listed mutants for PYY(25-36), and/or any of the above listed mutants for PYY(6-36), e.g., [Lys$^{25}$]PPY(5-36) (Amino acid sequence=PEAPGEDASPEELNRYYASLKHYLNLVTRQRY (SEQ ID NO: 210)) would result from combining the mutations from SEQ ID NO: 36 with SEQ ID NO: 184.

| Point Mutations of PYY(4-36) | |
|---|---|
| PEPTIDE | SEQUENCE |
| PYY(4-26) | KPEAPGEDASPEELNRYY ASLRHYLNLVTRQRY (SEQ ID NO: 185) |
| [Arg$^4$]PYY(4-36) | RPEAPGEDASPEELNRYY ASLRHYLNLVTRQRY (SEQ ID NO: 186) |
| [Gln$^4$]PYY(4-36) | QPEAPGEDASPEELNRYY ASLRHYLNLVTRQRY (SEQ ID NO: 187) |
| [Asn$^4$]PYY(4-36) | NPEAPGEDASPEELNRYY ASLRRYLNLVTRQRY (SEQ ID NO: 188) |

Also included as PYY(4-36) mutations are polypeptide variations (amino acid sequence variations) resulting from the combination of any of these four mutants with any of the above listed mutants for PYY(25-36), and/or any of the above listed mutants for PYY(5-36), e.g., [Lys$^{25}$]PPY(4-36) (Amino acid sequence=KPEAPGEDASEELNRYYASLKHYLNL VTRQRY (SEQ ID NO: 211)) would result from combining the mutations from SEQ ID NO: 36 with SEQ ID NO: 185.

| Point Mutations of PYY(3-36) | |
| --- | --- |
| PEPTIDE | SEQUENCE |
| PYY(3-36) | IKPEAPGEDASPEELNRY (SEQ ID NO: 334) YASLRHYLNLVTRQRY |
| [Leu³]PYY(3-36) | LKPEAPGEDASPEELNRY (SEQ ID NO: 189) YASLRHYLNLVTRQRY |
| [Val³]PYY(3-36) | VKPEAPGEDASPEELNRY (SEQ ID NO: 190) YASLRHYLNLVTRQRY |

Also included as PYY(3-36) mutations are polypeptide variations (amino acid sequence variations) resulting from the combination of any of these three mutants with any of the above listed mutants for PYY(25-36), and/or any of the above listed mutants for PYY(4-36), e.g., [Lys$^{25}$]PPY(3-36) (Amino acid sequence=IKPEAPGEDASEE LNRY-YASLKHYLNL VTRQRY (SEQ ID NO: 212)) would result from combining the mutations from SEQ ID NO: 36 with SEQ ID NO: 1.

Also contemplated are PYY agonists (NPY analogs) having the formula:

X-Q-$R_{19}$-$R_{20}$-$R_{21}$-$R_{22}$-$R_{23}$-Leu-$R_{25}$-$R_{26}$-$R_{27}$-$R_{28}$-$R_{29}$-$R_{30}$-$R_{31}$-$R_{32}$-Arg-$R_{34}$-Arg-$R_{36}$-Y wherein X is H or $C^a$ Me or $N^a$ Me or desamino or an acyl group having 7 carbon atoms or less; Q is $R_{17}$-$R_{18}$, $R_{18}$ or desQ; $R_{17}$ is Met, Arg, Nle, Nva, Leu, Ala or D-Ala; $R_{18}$ is Ala, Ser, Ile, D-Ala, D-Ser or D-Ile; $R_{19}$ is Arg, Lys or Gln; $R_{20}$ is Tyr or Phe; $R_{21}$ is Tyr, Glu, His or Ala; $R_{22}$ is Ser, Ala, Thr, Asn or Asp; $R_{23}$ is Ala, Asp, Glu, Gln, Asn or Ser; $R_{25}$ is Arg or Gln; $R_{26}$ is His, Arg or Gln; $R_{27}$ is Phe or Tyr; $R_{28}$ is Ile, Leu, Val or Arg; $R_{29}$ is Asn or Ile; $R_{30}$ is Leu, Met, Thr or Val; $R_{31}$ is Ile, Val or Leu; $R_{32}$ is Thr or Phe; $R_{34}$ is Gln, Pro or His; $R_{36}$ is Phe or Tyr; and Y is $NH_2$ or OH; provided that when Q is $R_{18}$, then at least one of $R_{27}$ and $R_{36}$ is Phe. Analogs of NPY have the following applications: potent postsynaptic treatment of hypertension and cardiogenic shock, the treatment of acute cardiovascular circulatory failure, and the elevation of intracellular calcium. See U.S. Pat. No. 5,026,685.

Certain preferred NPY analogs have the formula: X—$R_{18}$-Arg-Tyr-Tyr-$R_{22}$-$R_{23}$-Leu-Arg-His-Tyr-$R_{28}$-Asn-Leu-$R_{31}$-Thr-Arg-Gln-Arg-Tyr-$NH_2$ (SEQ ID NO: 342), wherein X is H or $C^a$ Me or $N^a$ Me or desamino or an acyl group having 7 carbon atoms or less; $R_{18}$ is Ala or Ser; $R_{22}$ is Ser or Ala; $R_{23}$ is Ala or Ser; $R_{27}$ is Phe or Tyr; $R_{28}$ is Ile or Leu; $R_{31}$ is Ile or Val; and $R_{36}$ is Phe or Tyr; provided that at least one of $R_{27}$ and $R_{36}$ is Phe. See U.S. Pat. No. 5,026,685.

Other contemplated NPY analogs have the formula:

(SEQ ID NO: 343)
X-$R_{17}$-$R_{18}$-Arg-Tyr-Tyr-Ser-Ala-Leu-Arg-His-$R_{27}$-Ile-Asn-Leu-Ile-Thr-Arg-Gln-Arg-$R_{36}$-$NH_2$, wherein $R_{17}$ is Arg or Leu and $R_{18}$ is Ser or Ala or Ile; and wherein X, $R_{27}$ and $R_{36}$ are as previously indicated.

Still other preferred NPY analogs have the formula:

(SEQ ID NO: 344)
X-$R_{18}$-Arg-Tyr-Tyr-Ala-Ser-Leu-$R_{25}$-His-$R_{27}$-Leu-Asn-Leu-Val-Thr-Arg-Gln-Arg-$R_{36}$-$NH_2$, wherein X is desamino or $C^a$ Me or $N^a$ Me and wherein $R_{18}$, $R_{25}$, $R_{27}$ and $R_{36}$ are as previously indicated.
Examples of such NPY agonists include:
pNPY (17-36) having the formula:

(SEQ ID NO: 217)
H-Leu-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide hNPY (17-36) having the formula:

(SEQ ID NO: 218)
H-Met-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [Phe$^{27}$]-NPY (18-36) having the formula:

(SEQ ID NO: 219)
H-Ala-Arg-Tyr-Tyr-Ser-Ala-Leu-Arg-His-Phe-Ile-Asn-Leu-Ile-Thr-Arg-Gln-Arg-Tyr-$NH_2$

The peptide [Ac-D-Ala$^{17}$]-NPY (17-36) having the formula:

(SEQ ID NO: 220)
Ac-D-Ala-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide NPY (19-36) having the formula:

(SEQ ID NO: 221)
H-Arg-Tyr-Tyr-Ser-Ala-Leu-Arg-His-Tyr-Ile-Asn-Leu-Ile-Thr-Arg-Gln-Arg-Tyr-$NH_2$

The peptide [Nle$^{17}$]-NPY (17-36) having the formula:

(SEQ ID NO: 222)
H-Nle-Ala-Arg-Tyr-Tyr-Ser-Ala-Leu-Arg-His-Tyr-Ile-Asn-Leu-Ile-Thr-Arg-Gln-Arg-Tyr-$NH_2$

The peptide [D-Ser$^{18}$]-NPY (18-36) having the formula:

(SEQ ID NO: 223)
H-D-Ser-Arg-Tyr-Tyr-Ser-Ala-Leu-Arg-His-Tyr-Ile-Asn-Leu-Ile-Thr-Arg-Gln-Arg-Tyr-$NH_2$

The peptide [Ala$^{17}$, His$^{21}$]-NPY (17-36) having the formula:

(SEQ ID NO: 224)
H-Ala-Ala-Arg-Tyr-His-Ser-Ala-Leu-Arg-His-Tyr-Ile-Asn-Leu-Ile-Thr-Arg-Gln-Arg-Tyr-$NH_2$

The peptide [D-Ile¹⁸]-NPY (18-36) having the formula:

(SEQ ID NO: 225)
D-Ile-Arg-Tyr-Tyr-Ser-Ala-Leu-Arg-His-Tyr-Ile-Asn-
Leu-Ile-Thr-Arg-Gln-Arg-Tyr-NH₂

The peptide [Ac-Arg¹⁷]-NPY (17-36) having the formula:

(SEQ ID NO: 226)
Ac-Arg-Ala-Arg-Tyr-Tyr-Ser-Ala-Leu-Arg-His-Tyr-
Ile-Asn-Leu-Ile-Thr-Arg-Gln-Arg-Tyr-NH₂

The peptide [Gln¹⁹]-NPY (19-36) having the formula:

(SEQ ID NO: 227)
H-Gln-Tyr-Tyr-Ser-Ala-Leu-Arg-His-Tyr-Ile-Asn-Leu-
Ile-Thr-Arg-Gln-Arg-Tyr-NH₂

The peptide [Phe²⁰]-NPY (18-36) having the formula:

(SEQ ID NO: 228)
H-Ala-Arg-Phe-Tyr-Ser-Ala-Leu-Arg-His-Tyr-Ile-Asn-
Leu-Ile-Thr-Arg-Gln-Arg-Tyr-NH₂

The peptide [$C^\alpha$ MeLeu¹⁷]-pNPY (17-36) having the formula:

(SEQ ID NO: 229)
H-$C^\alpha$-MeLeu-Ala-Arg-Tyr-Tyr-Ser-Ala-Leu-Arg-His-
Tyr-Ile-Asn-Leu-Ile-Thr-Arg-Gln-Arg-Tyr-NH₂

The peptide [$N^\alpha$ MeLeu¹⁷]-pNPY (17-36) having the formula:

(SEQ ID NO: 230)
H-$N^\alpha$ MeLeu-Ala-Arg-Tyr-Tyr-Ser-Ala-Leu-Arg-His-
Tyr-Ile-Asn-Leu-Ile-Thr-Arg-Gln-Gln-Arg-Tyr-NH₂

The peptide [desamino Ala¹⁸]-NPY (18-36) having the formula:

(SEQ ID NO: 231)
desamino-Ala-Arg-Tyr-Tyr-Ser-Ala-Leu-Arg-His-Tyr-
Ile-Asn-Leu-Ile-Thr-Arg-Gln-Arg-Tyr-NH₂

The peptide [For-Ala¹⁸, Glu²³, Arg²⁶]-NPY (18-36) having the formula:

(SEQ ID NO: 232)
For-Ala-Arg-Tyr-Tyr-Ser-Glu-Leu-Arg-Arg-Tyr-Ile-
Asn-Leu-Ile-Thr-Arg-Gln-Arg-Tyr-NH₂

The peptide [Nva¹⁷, Ala²¹, Leu²⁸]-NPY (17-36) having the formula:

(SEQ ID NO: 233)
H-Nva-Ala-Arg-Tyr-Ala-Ser-Ala-Leu-Arg-His-Tyr-Leu-
Asn-Leu-Ile-Thr-Arg-Gln-Arg-Tyr-NH₂

The peptide [Thr²², Gln²³]-NPY (18-36) having the formula:

(SEQ ID NO: 234)
H-Ala-Arg-Tyr-Tyr-Thr-Gln-Leu-Arg-His-Tyr-Ile-Asn-
Leu-Ile-Thr-Arg-Gln-Arg-Tyr-NH₂

The peptide [desamino Leu¹⁷, Asn²³, Val³⁰]-NPY (17-36) having the formula:

(SEQ ID NO: 235)
H-desamino Leu-Ala-Arg-Tyr-Tyr-Ser-Ala-Leu-Arg-
His-Tyr-Ile-Asn-Val-Ile-Thr-Arg-Gln-Arg-Tyr-NH₂

The peptide [Asp²², Ser²³, Thr³⁰]-NPY (18-36) having the formula:

(SEQ ID NO: 236)
H-Ala-Arg-Tyr-Tyr-Asp-Ser-Leu-Arg-His-Tyr-Ile-Asn-
Thr-Ile-Thr-Arg-Gln-Arg-Tyr-NH₂

The peptide [Gln²⁵, Leu³¹, Pro³⁴]-NPY (18-36) having the formula:

(SEQ ID NO: 237)
H-Ala-Arg-Tyr-Tyr-Ser-Ala-Leu-Gln-His-Tyr-Ile-Asn-
Leu-Leu-Thr-Arg-Pro-Arg-Tyr-NH₂

The peptide [Gln² Phe³⁶]-NPY (17-36) having the formula:

(SEQ ID NO: 238)
H-Leu-Ala-Arg-Tyr-Tyr-Ser-Ala-Leu-Arg-Gln-Tyr-Arg-
Asn-Leu-Ile-Thr-Arg-Gln-Arg-Phe-NH₂

The peptide [Phe³⁶]-pPYY (19-36) having the formula:

(SEQ ID NO: 239)
H-Arg-Tyr-Tyr-Ala-Ser-Leu-Arg-His-Tyr-Leu-Asn-Leu-
Val-Thr-Arg-Gln-Arg-Phe-NH₂

The peptide pPYY (18-36) having the formula:

(SEQ ID NO: 240)
H-Ser-Arg-Tyr-Tyr-Ala-Ser-Leu-Arg-His-Tyr-Leu-Asn-
Leu-Val-Thr-Arg-Gln-Arg-Tyr-NH₂

The peptide [Ac-Ser¹⁸, Phe²⁷]-pPYY (18-36) having the formula:

(SEQ ID NO: 241)
Ac-Ser-Arg-Tyr-Tyr-Ala-Ser-Leu-Arg-His-Phe-Leu-
Asn-Leu-Val-Thr-Arg-Gln-Arg-Tyr-NH₂

The peptide [Nle¹⁷, Asn²², Phe²⁷]-NPY (17-36) having the formula:

(SEQ ID NO: 242)
H-Nle-Ala-Arg-Tyr-Tyr-Asn-Ala-Leu-Arg-His-Phe-Ile-

Asn-Leu-Ile-Thr-Arg-Gln-Arg-Tyr-NH₂

The peptide [D-Ala¹⁸, Glu²¹, His³⁴]-NPY (18-36) having the formula:

(SEQ ID NO: 243)
H-D-Ala-Arg-Tyr-Glu-Ser-Ala-Leu-Arg-His-Tyr-Ile-

Asn-Leu-Ile-Thr-Arg-His-Arg-Tyr-NH₂

The peptide [Bz-Leu¹⁷, Pro³⁴, Phe³⁶]-pNPY (17-36) having the formula:

(SEQ ID NO: 244)
Bz-Leu-Ala-Arg-Tyr-Tyr-Ser-Ala-Leu-Arg-His-Tyr-

Ile-Asn-Leu-Ile-Thr-Arg-Pro-Arg-Phe-NH₂

The peptide [Lys¹⁹, Phe²⁷, Val²⁸]-NpY (18-36) having the formula:

(SEQ ID NO: 245)
H-Ala-Lys-Tyr-Tyr-Ser-Ala-Leu-Arg-His-Phe-Val-Asn-

Leu-Ile-Thr-Arg-Gln-Arg-Tyr-NH₂

The peptide [D-Ala¹⁷, Val²⁸, Phe³²]-NPY (17-36) having the formula:

(SEQ ID NO: 246)
D-Ala-Arg-Tyr-Tyr-Ser-Ala-Leu-Arg-His-Tyr-Val-Asn-

Leu-Ile-Phe-Arg-Gln-Arg-Tyr-NH₂

The peptide [C^αMeSer¹⁸, Met³⁰, Phe³⁶]-NPY (18-36) having the formula:

(SEQ ID NO: 247)
H-Ca MeSer-Tyr-Tyr-Ser-Ala-Leu-Arg-His-Tyr-Ile-

Asn-Met-Ile-Thr-Arg-Gln-Arg-Phe-NH₂

The peptide [Arg¹⁷, Ile¹⁸, Phe²⁷,³⁶]-NPY (17-36) having the formula:

(SEQ ID NO: 248)
H-Arg-Ile-Arg-Tyr-Tyr-Ser-Ala-Leu-Arg-His-Phe-Ile-

Asn-Leu-Ile-Thr-Arg-Gln-Arg-Phe-NH₂

The peptide [Ser¹⁸, Phe²⁷]-pNPY (17-36) having the formula:

(SEQ ID NO: 249)
H-Leu-Ser-Arg-Tyr-Tyr-Ser-Ala-Leu-Arg-His-Phe-Ile-

Asn-Leu-Ile-Thr-Arg-Gln-Arg-Tyr-NH₂

The peptide [N^αMeIle¹⁸, Gln²⁵, Phe²⁷]-NPY (18-36) having the formula:

(SEQ ID NO: 250)
N^α MeIle-Arg-Tyr-Tyr-Ser-Ala-Leu-Gln-His-Phe-Ile-

Asn-Leu-Ile-Thr-Arg-Gln-Arg-Tyr-NH₂

The peptide [D-Ser¹⁸, Phe³⁶]-NPY (18-36) having the formula:

(SEQ ID NO: 251)
H-D-Ser-Arg-Tyr-Tyr-Ser-Ala-Leu-Arg-His-Tyr-Ile-

Asn-Leu-Ile-Thr-Arg-Gln-Arg-Phe-NH₂

The peptide [Asp²³, Ar²⁶]-hNPY (17-36) having the formula:

(SEQ ID NO: 252)
H-Met-Ala-Arg-Tyr-Tyr-Ser-Asp-Leu-Arg-Arg-Tyr-Ile-

Asn-Leu-Ile-Thr-Arg-Gln-Arg-Tyr-NH₂

The peptide [Glu²³, Ile²⁹]-NPY (18-36) having the formula:

(SEQ ID NO: 253)
H-Ala-Arg-Tyr-Tyr-Ser-Gln-Leu-Arg-His-Tyr-Ile-Ile-

Leu-Ile-Thr-Arg-Gln-Arg-Tyr-NH₂

The peptide [D-Ala¹⁷]-NPY(17-36)-OH having the formula:

(SEQ ID NO: 254)
D-Ala-Ala-Arg-Tyr-Tyr-Ser-Ala-Leu-Arg-His-Tyr-Ile-

Asn-Leu-Ile-Thr-Arg-Gln-Arg-Tyr-OH.

Other peptide YY agonists have the formula:

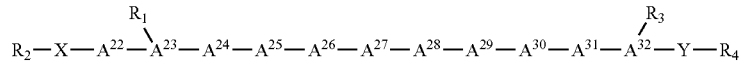

wherein:
X is a chain of 0-5 amino acids, inclusive, the N-terminal one of which is bonded to $R_1$ and $R_2$
Y is a chain of 0-4 amino acids, inclusive, the C-terminal one of which is bonded to $R_3$ and $R_4$
$R_1$ is H, $C_1$-$C_2$ alkyl (e.g., methyl), $C_6$-$C_{18}$ aryl (e.g., phenyl, napthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);
$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$A^{22}$ is an aromatic amino acid, Ala, Aib, Anb, N-Me-Ala, or is deleted;

$A^{23}$ is Ser, Thr, Ala, N-Me-Ser, N-Me-Thr, N-Me-Ala, or is deleted;

$A^{24}$ is Leu, Ile, Vat, Trp, Gly, Aib, Anb, N-Me-Leu, or is deleted;

$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{26}$ is His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{27}$ is an aromatic amino acid other than Tyr;

$A^{28}$ is Leu, Ile, Vat, Trp, Aib, Aib, Anb, or N-Me-Leu;

$A^{29}$ is Asn, Ala, Gln, Gly, Trp, or N-Me-Asn;

$A^{30}$ is Leu, Ile, Val, Trp, Aib, Anb, or N-Me-Leu;

$A^{31}$ is Vat, Ile, Trp, Aib, Anb, or N-Me-Val;

$A^{32}$ is Thr, Ser, N-Me-Set, or N-Me-Thr;

$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$R_4$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof. See U.S. Pat. No. 5,574,010.

Particularly preferred agonists of this formula to be used in the method of the disclosure include:

(SEQ ID NO: 255)
N-60 -Ala-Ser-Leu-Arg-His-Trp-Leu-Asn-Leu-Val-Thr-Arg-Gln-Arg-Tyr-$NH_2$.

Other peptide YY agonists have the formula:

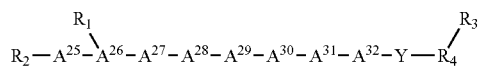

wherein:

the N-terminal amino acid bonds to $R_1$ and $R_2$;

Y is a chain of 0-4 amino acids, inclusive the C-terminal one of which bonds to R3 and R4;

$R_1$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl;

$R_2$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl;

$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl group, or an aryl group), Orn or is deleted;

$A^{27}$ is an aromatic amino acid;

$A^{28}$ is Leu, Ile, Val, Trp, Aib, Anb, or N-Me-Leu;

$A^{29}$ is Asn, Ala, Gin, Gly, Tip, or N-Me-Asn;

$A^{30}$ is Leu, Ile, Val, Trp, Aib, Anb, or N-Me-Leu;

$A^{31}$ is Val, Ile, Tip, Aib, Anb, or N-Me-Val;

$A^{32}$ is Thr, Set, N-Me-Set, or N-Me-Thr or D-Trp;

$R_3$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl; and $R_4$ is H, $C_1$-$C_{12}$ alkyl, $C_6$-$C_{18}$ aryl, $C_1$-$C_{12}$ acyl, $C_7$-$C_{18}$ aralkyl, or $C_7$-$C_{18}$ alkaryl, or a pharmaceutically acceptable salt thereof. Note that, unless indicated otherwise, for all peptide YY agonists described herein, each amino acid residue, e.g., Leu and $A^1$, represents the structure of NH—C(R)H—CO—, in which R is the side chain. Lines between amino acid residues represent peptide bonds which join the amino acids. Also, where the amino acid residue is optically active, it is the L-form configuration that is intended unless D-form is expressly designated.

Other PYY agonists have the formula:

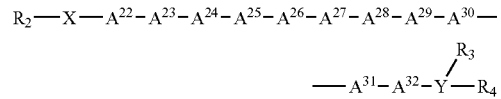

wherein:

X is a chain of 0-5 amino acids, inclusive, the N-terminal one of which is bonded to $R_1$ and $R_2$;

Y is a chain of 0-4 amino acids, inclusive, the C-terminal one of which is bonded to $R_3$ and $R_4$;

$R_1$ is H, $C_1$-$C_{12}$ alkyl (e.g. methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$A^{22}$ is an aromatic amino acid, Ala, Aib, Anb, N-Me-Ala, or is deleted;

$A^{23}$ is Ser, Thr, Ala, Aib, N-Me-Ser, N-Me-Thr, N Me-Ala, or is deleted;

$A^{24}$ is leu, Ile, Val, Trp, Gly, Nle, Nva, Aib, Anb, N-Me-Leu, or is deleted;

$A^{25}$ is Arg, Lys, homo-Arg, diethyl-homo-Arg, Lye-ε-NH—R (where R is H, a branched or straight chain $C_1$-$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl groups or an aryl group), Orn, or is deleted;

$A^{27}$ is an aromatic amino acid other than Tyr;

$A^{28}$ is Leu, Ile, Val, Trp, Nle, Nva, Aib, Anb, or N-Me-Leu;

$A^{29}$ is Asn, Ala, Gin, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl); and $R_4$ is H, $C_1$-$C_{12}$ allyl (e.g., methyl), $C_6$-$C_{18}$ aryl (e.g., phenyl, naphthaleneacetyl), $C_1$-$C_{12}$ acyl (eg., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof In preferred embodiments, $A^{27}$ is Phe, Nal, Bip, Pcp, Tic, Trp, Bth, Thi, or Dip.

In preferred embodiments X is $A^{17}$-$A^{18}$-$A^{19}$-$A^{20}$-$A^{21}$ wherein $A^{17}$ is Cys, Leu, Ile, Val, Nle, Nva, Aib, Anb, or N-Me-Leu;

$A^{18}$ is Cys, Ser, Thr, N-Me-Ser, or N-Me-Thr;

$A^{19}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn;

$A^{20}$ is an aromatic amino acid, or Cys; and $A^{21}$ is an aromatic amino acid, Cys, or a pharmaceutically acceptable salt thereof In yet other preferred embodiments, Y is $A^{33}$-$A^{34}$-$A^{35}$-$A^{36}$ wherein $A^{33}$ is Arg, Lys, homo-Arg, diethyl-homo-Arg, Lys-ε-NH—R (where R is H, a branched or straight chain $C_1$-$C_{10}$ alkyl group, or an aryl group), Cys, or Orn;

$A^{34}$ is Cys, Gln, Asn, Ala, Gly, N-Me-Cl, Aib, or Anb;

$A^{35}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn; and $A^{36}$ is an aromatic amino acid, Cys or a pharmaceutically acceptable salt thereof. See U.S. Pat. No. 5,604,203.

Particular embodiments include compounds has the formula: N-α-Ac-Ala-Ser-Leu-Arg-His-Phe-Leu-Asn-Leu-Val-Thr-Arg-Gin-Arg-Tyr-$NH_2$ (SEQ. ID. NO: 325), H-Ala-Ser-Leu-Arg-His-Phe-Leu-Asn-Leu-Val-Thr-Arg-Gln-Arg-Tyr-$NH_2$ (SEQ. ID. NO: 326), N-α-Ac-Ala-Ser-Leu-Arg-Thr-Arg-Gin-Arg-Tyr-$NH_2$ (SEQ. ID. NO: 327), N-α-Ac-Ala-Ser-Leu-Arg-His-Thi-Leu-Asn-Leu-Val-Thr-Arg-Gin-Arg-Tyr-$NH_2$ (SEQ. ID. NO: 328), N-α-Ac-Tyr-Ser-Leu-Arg-His-Phe-Leu-Asn-Leu-Val-Thr-Arg-Gin-Arg-Tyr-$NH_2$ (SEQ. ID. NO: 329) or a pharmaceutically acceptable salt thereof.

Other PYY agonists have the formula:

(Formula II)

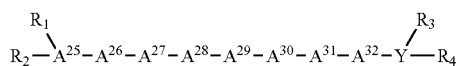

wherein the N-terminal amino acid is bounded to $R_1$ and $R_2$; Y is a chain of 0-4 amino acids, inclusive the C-terminal one of which is bonded to $R_3$ and $R_4$;

$R_1$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$R_2$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl);

$A^{25}$ is Arg, Lys, homo-Arg, diethyl-homo-Arg, Lys-ε-NH—R (where R is H, a branched or straight chain $C_1$-$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$-$C_{10}$ alkyl groups or an aryl group), Orn, or is deleted;

$A^{27}$ is an aromatic amino acid;

$A^{28}$ is Leu, Ile, Val, Trp, Nle, Nva, Aib, Anb, or N-Me-Leu;

$A^{29}$ is Asn, Ala, Gin, Gly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nle, Nva, Aib, Anb, or N-Me-Val;

$A^{32}$ is Thr, Ser, N-Me-Ser, N-Me-Thr, or D-Trp;

$R_3$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl); and $R_4$ is H, $C_1$-$C_{12}$ alkyl (e.g., methyl), $C_6$-$C_{18}$ aryl (e.g., phenyl, naphthaleneacetyl), $C_1$-$C_{12}$ acyl (e.g., formyl, acetyl, and myristoyl), $C_7$-$C_{18}$ aralkyl (e.g., benzyl), or $C_7$-$C_{18}$ alkaryl (e.g., p-methylphenyl), or a pharmaceutically acceptable salt thereof. See U.S. Pat. No. 5,604,203.

In particular embodiments, $A^{27}$ is Phe, Nal, Bip, Pcp, Tic, Trp, Bth, Thi, or Dip.

In particular embodiments X is $A^{33}$-$A^{34}$-$A^{35}$-$A^{36}$ wherein $A^{33}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn;

$A^{34}$ is Gln, Asn, Ala, Gly, N-Me-Gin, Aib, Cys, or Anb;

$A^{35}$ is Arg, Lys, homo-Arg, diethyl-homo-Arg, Lys-ε-NH—R (where R is H, a branched or straight chain $C_1$-$C_{10}$ alkyl group, or $C_6$-$C_{18}$ aryl group), Cys, or Orn; and $A^{36}$ is an aromatic amino acid, Cys, or a pharmaceutically acceptable salt thereof.

Preferably, the compound has the formula: N-α-Ac-Arg-His-Phe-Leu-Asn-Leu-Val-Thr-Arg-Gln-Arg-Tyr-$NH_2$ (SEQ. ID. NO: 324).

Exemplary PYY agonists include:

| | |
|---|---|
| YPAKEAPGEDASPEELSTYYASLR[im-DNP-His$^{26}$]YLNLVTRZRY-$NH_2$<br>PYY(22-36) | (SEQ ID NO: 256) |
| ASLRHYLNLVTRQRY-$NH_2$<br>[Ala$^{32}$]PYY | (SEQ ID NO: 257) |
| ASLRHYLNLV[Ala]RQRY-$NH_2$<br>[Ala$^{23,32}$]PYY | (SEQ ID NO: 258) |
| A[Ala]LRHYLNLV[Ala]RQRY-$NN_2$<br>[Glu$^{28}$]PYY(22-36) | (SEQ ID NO: 259) |
| ASLRHY[Glu]NLVTRQRY-$NH_2$<br>N-α-Ac-PYY(22-36) | (SEQ ID NO: 260) |
| N-α-Ac-ASLRHYLNLVTRORY-$NH_2$<br>N-α-Ac[p.CL.Phe$^{26}$]PYY | (SEQ ID NO: 261) |
| N-α-Ac-ASLR[p.CL.Phe$^{26}$]YLNLVTRQRY-$NH_2$<br>N-α-Ac[Glu$^{28}$]PYY | (SEQ ID NO: 262) |
| N-α-Ac-ASLRHY[Glu]NLVTRQRY-$NH_2$<br>N-α-Ac[Phe$^{27}$]PYY | (SEQ ID NO: 263) |
| N-α-Ac-ASLRH[Phe]ENLVTRQR[N-Me-Tyr]-$NH_2$<br>N-α-Ac[8N-Me-Tyr$^{36}$]PYY | (SEQ ID NO: 264) |

-continued

N-α-Ac-ASLRHYENLVTROR[N-Me-Tyr]-NH₂ (SEQ ID NO: 265)
N-α-myristoyl-PYY(22-36)

N-α-myristoyl-ASLRHYLNLVTRQRY-NH₂ (SEQ ID NO: 266)
N-α-naphthateneacetyl-PYY(22-36)

N-α-naphthateneacetyl-ASLRHYLNLVTRQRY-NH₂ (SEQ ID NO: 267)
N-α-Ac[Phe²⁷]PYY

N-α-Ac-ASLRH[Phe]ENLVTROR[N-Me-Tyr]-NH₂ (SEQ ID NO: 268)
N-α-Ac-PYY(22-36)

N-α-Ac-ASLRHYLNLVTRQRY-NH₂ (SEQ ID NO: 269)
N-α-Ac-[Bth²⁷]PYY(22-36)

N-α-Ac-ASLRH[Bth]LNLVTRQRY-NH₂ (SEQ ID NO: 270)

N-α-Ac-[Bip²⁷]PYY(22-36) (SEQ ID NO: 271)

N-α-Ac-ASLRH[Bth]LNLVTRQRY-NH₂ (SEQ ID NO: 272)
N-α-Ac-[Nal²⁷]PYY(22-36)

N-α-Ac-ASLRH[Bth]LNLVTRQRY-NH₂ (SEQ ID NO: 273)
N-α-Ac-[Trp²⁷]PYY(22-36)

N-α-Ac-ASLRH[Trp]LNLVTRQRY-NH₂ (SEQ ID NO: 274)
N-α-Ac-[Thi²⁷]PYY(22-36)

N-α-Ac-ASLRN[Thi]LNLVTRQRY-NH₂ (SEQ ID NO: 275)
N-α-Ac-[Tic²⁷]PYY(22-36)

N-α-Ac-ASLRH[Tic]LNLVTRQRY-NH₂ (SEQ ID NO: 276)
N-α-Ac-[Phe²⁷]PYY(25-36)

N-α-Ac-[Phe]LNLVTRQRY-NH₂ (SEQ ID NO: 277)
N-α-Ac-[Phe²⁷, Thi²⁷]PYY(22-36)

N-α-Ac-ASLRH[Phe]LNLVTRQR[Thi]-NH₂ (SEQ ID NO: 279)
N-α-Ac-[Thz²⁶, Phe²⁷]PYY(22-36)

N-α-Ac-ASLRH[Thz][Phe]LNLVTRQRY-NH₂ (SEQ ID NO: 280)
N-α-Ac-[Phe²⁷]PYY(22-36)

N-α-Ac-ASLRH[Thz][Phe]LNLVTRQRY-NH₂ (SEQ ID NO: 281)
N-α-Ac-[Phe²⁷]PYY(22-36)

N-α-Ac-[Phe]SLRN[Phe]LNLVTRQRY-NH₂ (SEQ ID NO: 282)
N-α-Ac-[Tyr²², Phe²⁷]PYY(22-36)

N-α-Ac-[Tyr]SLRH[Phe]LNLVTRQRY-NH₂ (SEQ ID NO: 289)
N-α-Ac-[Trp²⁸]PYY(22-36)

N-α-Ac-ASLRH[Trp]NLVTRQRY-NH₂ (SEQ ID NO: 290)
N-α-Ac-[Trp²⁸]PYY(22-36)

N-α-Ac-ASLRHY[Trp]NLVTRQRY-NH₂ (SEQ ID NO: 291)
N-α-Ac-[Trp²⁸]PYY(22-36)

N-α-Ac-ASLRHYLN[Trp]VTRQRY-NH₂ (SEQ ID NO: 292)
N-α-Ac-[Ala²⁶, Phe²⁷]PYY(22-36)

N-α-Ac-ASLR[Ala][Phe]LNLVTRQRY-NH₂ (SEQ ID NO: 293)
N-α-Ac-[Bth²⁷]PYY(22-36)

N-α-Ac-ASLR[Bth]LNLVTRQRY-NH₂ (SEQ ID NO: 294)
N-α-Ac-[Phe²⁷]PYY(22-36)

N-α-Ac-ASLRH[Phe]LNLVTRQRY-NH₂ (SEQ ID NO: 295)
N-α-Ac-[Phe²⁷,³⁶]PYY(22-36)

N-α-Ac-ASLRH[Phe]LNLVTRQR[Phe]-NH₂ (SEQ ID NO: 296)
N-α-Ac-[Phe²⁷, D-Trp³²]PYY(22-36)

N-α-Ac-ASLRH[Phe]LNLV[D-Trp]RQRY-NH₂ (SEQ ID NO: 297)

Other PYY agonists include neurophilic Y Y2 receptor specific peptides having the formula:

```
X1(-X2-X3-X4-X5-X6-X7-X8-X9-X10-X11-X12-X13-X14)_n-
X15
``` wherein

X1 is NH, $CH_3CO$ or one or two naturally occurring amino acids.

X2 is Leu, Ile or Val.
X3 is Arg, Lys or His.
X4 is His, Lys or Arg.
X5 is Tyr or Phe.
X6 is Leu, Ile or Val.
X7 is Asn or Gln.
X8 is Leu, Ile or Val.
X9 is Leu, Ile or Val.
X10 is Thr or Ser.
X11 is Arg, His or Lys.
X12 is Gln or Asn.
X13 is Arg, His or Lys.
X14 is Tyr or Phe.
X15 is COOH, $NH_2$ or one or two naturally occurring amino acids with the terminal amino acid being in the normal or carboxamide form; and
n is 1 to 5. See U.S. Pat. No. 5,696,093.

Exemplary agonists include:

```
                                      (SEQ ID NO: 298)
CH3CO-L-R-H-Y-L-N-L-L-T-R-Q-R-Y-NH2

(SEQ ID NO: 299)
CH3CO-L-R-H-Y-I-N-L-I-T-R-Q-R-Y-NH2

(SEQ ID NO: 300)
NH2-L-R-H-Y-L-N-L-L-T-R-Q-R-Y-NH2

(SEQ ID NO: 301)
NH2-L-R-H-Y-I-N-L-I-T-R-Q-R-Y-NH2
```

Other PYY agonists have the formula:

N-α-$R^1$-[$Nle^{24,28,30}$, $Trp^{27}$, $Nva^{31}$, $\psi^{35/36}$]PYY(22-36)-$NH_2$, N-α-$R^1$-[$Nle^{24,28}$, $Trp^{27,30}$, $Nva^{31}$, $\psi^{35/36}$]PYY(22-36)-$NH_2$, N-α-$R^1$-[$Nle^{24,28,30}$, $Phe^{27}$, $Nva^{31}$, $\psi^{35/36}$]PYY(22-36)-$NH_2$, N-α-$R^1$-[$Nle^{24,28}$, $Phe^{27}$, $Trp^{30}$, $Nva^{31}$, $\psi^{35/36}$]PYY(22-36)-$NH_2$, N-α-$R^1$-[$Trp^{30}$, $\psi^{35,36}$]PYY(25-36)-$NH_2$, N-α-$R^1$-[$Trp^{30}$]PYY(25-36)-$NH_2$, N-α-$R^1$-[$Nle^{24,28}$, $Trp^{30}$, $Nva^{31}$, $\psi^{35/36}$]PYY(22-36)-$NH_2$ and N-α-$R^1$-[$Nle^{28}$, $Trp^{30}$, $Nva^{31}$, $\psi^{35/36}$]PYY(22-36)-$NH_2$ or a pharmaceutically-acceptable salt thereof, wherein $R^1$ is H, $(C_1-C_{12})$alkyl or $(C_1-C_{12})$acyl; and ψ is a pseudopeptide bond selected from the group consisting of —$CH_2$—NH—, —$CH_2$—S—, —$CH_2$—$CH_2$—, —$CH_2$—O— and —$CH_2$—CO—. See U.S. Pat. No. 6,046,162.

Particular compounds of the immediately foregoing group of compounds are where $R^1$ is acetyl and ψ is —$CH_2$—NH—.

A particular group of compounds is selected from a group consisting of

N-α-Ac-[$Nle^{24,28,30}$, $Trp^{27}$, $Nva^{31}$, $\psi^{35/36}$]PYY(22-36)-$NH_2$, (SEQ ID NO: 302)

N-α-Ac-[$Nle^{24,28}$, $Trp^{27,30}$, $Nva^{31}$, $\psi^{35/36}$]PYY(22-36)-$NH_2$, (SEQ ID NO: 303)

N-α-Ac-[$Nle^{24,28,30}$, $Phe^{27}$, $Nva^{31}$, $\psi^{35/36}$]PYY(22-36)-$NH_2$, (SEQ ID NO: 304)

N-α-Ac-[$Nle^{24,28}$, $Phe^{27}$, $Trp^{30}$, $Nva^{31}$, $\psi^{35/36}$]PYY(22-36)-$NH_2$, (SEQ ID NO: 305)

N-α-Ac-[$Trp^{30}$, $\psi^{35/36}$]PYY(25-36)-$NH_2$, (SEQ ID NO: 306)

N-α-Ac-[$Trp^{30}$]PYY(25-36)-$NH_2$ (SEQ ID NO: 307) and

N-α-Ac-[$Nle^{28}$, $Trp^{30}$, $Nva^{31}$, $\psi^{35/36}$]PYY(22-36)-$NH_2$, (SEQ ID NO: 308) or a pharmaceutically acceptable salt thereof.

Another particular compound has the formula N-α-Ac-[$Nle^{24,28}$, $Trp^{30}$, Nva.sup.31, $\psi^{35/36}$]PYY(22-36)-$NH_2$ (SEQ. ID. NO: 309) or a pharmaceutically acceptable salt thereof.

Another PYY agonist has the formula (A),

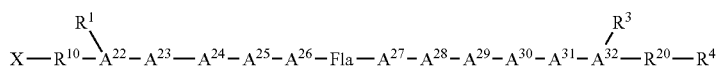

having one or two pseudopeptide bonds where each pseudopeptide bond is independently selected from the group consisting of —$CH_2$—NH—, —$CH_2$—S—, —$CH_2$—$CH_2$—, —$CH_2$—O— and —$CH_2$—CO—; wherein:

$R^{10}$ is a chain of 0-5 amino acids, inclusive, where the N-terminal amino acid is bonded to $R^1$ and $R^2$ by the side chain of the N-terminal amino acid or by the nitrogen of the amino group of the N-terminal amino acid;

$R^{20}$ is a chain of 0-4 amino acids, inclusive, where the C-terminal amino acid is bonded to $R^3$ and $R^4$ by the side chain of the C-terminal amino acid or by the carbon of the carboxyl group of the C-terminal amino acid;

$R^1$, $R^2$, $R^3$ and $R^4$ are each independently selected from the group consisting of H, $(C_1-C_{12})$alkyl, $(C_6-C_{18})$aryl, $(C_1-C_{12})$acyl, phenyl$(C_1-C_{12})$alkyl and $((C_1-C_{12})$alkyl$)_{1-5}$-phenyl;

$A^{22}$ is an aromatic amino acid, Ala, Aib, Anb, N-Me-Ala or is deleted;

$A^{23}$ is Ser, Thr, Ala, N-Me-Ser, N-Me-Thr, N-Me-Ala or is deleted;

$A^{24}$ is Leu, Ile, Nle, Val, Trp, Gly, Aib, Anb, N-Me-Leu or is deleted;

$A^{25}$ is Arg, Lys, homo-Arg, diethyl-homo-Arg, Lys-p.epsilon.-NH-Z, Orn or is deleted;

$A^{26}$ is His, Thr, 3-Me-His, 1-Me-His, β-pyrazolylalanine, N-Me-His, Arg, Lys, homo-Arg, diethyl-homo-Arg, Lys-ε-NH-Z, Orn or is deleted;

$A^{28}$ is Leu, Ile, Nle, Val, Trp, Aib, Anb or N-Me-Leu;

$A^{29}$ is Asn, Ala, Gln, Gly, Trp or N-Me-Asn;

$A^{30}$ is Leu, Ile, Nle, Fla, Val, Trp, Aib, Anb or N-Me-Leu;

$A^{31}$ is Val, Nva, Ile, Trp, Aib, Anb or N-Me-Val; and $A^{32}$ is Thr, Ser, N-Me-Ser or N-Me-Thr;

where Z for each occurrence is independently selected from the group consisting of H, $(C_1-C_{10})$alkyl and $(C_6-C_{18})$aryl; or a pharmaceutically acceptable salt thereof. See U.S. Pat. No. 6,046,167.

A particular group of compounds of the immediately foregoing group of compounds is where $R^{10}$ is $A^{17}$-$A^{18}$-$A^{19}$-$A^{20}$-$A^{21}$;

where $A^{17}$ is Cys, Leu, Ile, Val, Nle, Nva, Aib, Anb or N-Me-Leu;

$A^{18}$ is Cys, Ser, Thr, N-Me-Ser or N-Me-Thr;

$A^{19}$ is Arg, Lys, homo-Arg, diethyl-homo-Arg, Lys-ϵ-NH—R.sup.5, Cys or Orn;

$A^{20}$ is an aromatic amino acid or Cys;

$A^{21}$ is an aromatic amino acid or Cys;

$R^{20}$ is $A^{33}$-$A^{34}$-$A^{35}$-$A^{36}$, $A^{33}$ is Arg, Lys, homo-Arg, diethyl-homo-Arg, Lys-ϵ-NH—$R^5$, Cys or Orn;

$A^{34}$ is Cys, Gin, Asn, Ala, Gly, N-Me-Gln, Aib or Anb;

$A^{35}$ is Arg, Lys, homo-Arg, diethyl-homo-Arg, Lys-ϵ-NH—$R^5$, Cys or Orn; and $A^{36}$ is an aromatic amino acid or Cys;

where $R^5$ for each occurrence is independently selected from the group consisting of $H_1(C_1-C_{10})$alkyl and $(C_6-C_{18})$aryl.

A particular group of compounds of the foregoing group of compounds are the compounds of the formula N-α-Ac-[Fla$^{27}$)]PYY(25-36)-NH$_2$ and N-α-Ac-[Fla$^{27}$]PYY(22-36)-NH$_2$ or a pharmaceutically acceptable salt thereof.

Another group of PYY agonist has the formula:

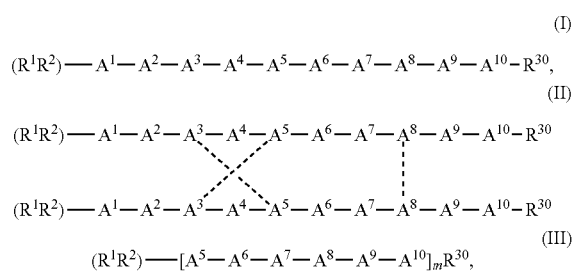

or a pharmaceutically acceptable salt thereof wherein

— represents an optional bond between the amino acids shown connected where each bond is independently selected from the group consisting of —S—S— only when the amino acids connected are Cys-Cys, —CO—NH—, —CH$_2$—NH— and

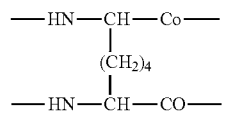

provided that when the optional bond is

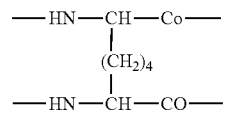

it replaces the two amino acids that the optional bond is attached to; q is 1-4; m is 1 to 4;

$R^{30}$ is OH or —O—$R^1$, provided that when $A^1$ to $A^7$ are deleted then $R^{30}$ is also NH—$R^1$, where $R^{30}$ is attached to the carbon atom of the carboxyl of the C-terminal amino acid;

$R^1$ and $R^2$ for each occurrence are each independently selected from the group consisting of H, $(C_1-C_{12})$alkyl, $(C_6-C_{18})$aryl, $(C_1-C_{12})$acyl, phenyl$(C_1-C_{12})$alkyl and $((C_1-C_{12})$alkyl$)_{1-5}$-phenyl where $R^1$ and $R^2$ are attached to the nitrogen of the amine of the N-terminal amino acid;

$A^1$ is deleted or D- or L- of the following amino acids: Trp, Tyr, Fla, Bth, Nal, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^2$ is deleted or D- or L- of the following amino acids: Ile, Val, Leu, Nle, Anb, Aib, Pro, Gln or Asn;

$A^3$ is deleted or D- or L- of the following amino acids: Asn, Gln, Glu, Asp, Orn, Lys, Dpr or Cys;

$A^4$ is deleted or D- or L- of the following amino acids: Ile, Val, Leu, Nle, Anb, Aib or Pro;

$A^5$ is deleted or D- or L- of the following amino acids: Ile, Val, Leu, Nle, Anb, Aib, Pro, Glu, Asp, Orn, Lys, Dpr or Cys;

$A^6$ is deleted or D- or L- of the following amino acids: Thr, Ser, Trp, Tyr, Fla, Bth, Nal, Tic, Tic-OH, Dip, Bip or optionally substituted Phe where the Phe is optionally substituted with one to five substituents selected from the group consisting of $(C_1-C_4)$alkyl, halo, $(C_1-C_4)$alkoxy, amino and nitro;

$A^7$ is deleted or D- or L- of the following amino acids: Arg, Lys, homo-Arg, dialkyl-homo-Arg, Lys-ϵ-NH—$R^7$ or Orn;

$A^5$ is deleted or D- or L- of the following amino acids: Nva, Val, Ile, Leu, NMe, Anb, Aib, Pro, Gln, Asn, Glu, Asp, Orn, Lys, Dpr or Cys;

$A^9$ is deleted or D- or L- of the following amino acids: Arg, Lys, homo-Arg, dialkyl-homo-Arg, Lys-ϵ-NH—$R^7$ or Orn; and $A^{10}$ is deleted or D- or L- of the following amino acids: Tyr, Trp, Fla, Bth, Nal, Tic, Tic-OH, Dip, Bip, tyramine or optionally substituted Phe where the Phe is optionally substituted with one to five substituents selected from the group consisting of $(C_1-C_4)$alkyl, halo, $(C_1-C_4)$alkoxy, amino and nitro, or the corresponding decarboxylated optionally substituted Phe;

where $R^7$ for each occurrence is independently selected from the group consisting of H.sub.$_1(C_1-C_{10})$alkyl and $(C_6-C_{18})$aryl, provided that not all of $A_1$ to $A_{10}$ are deleted at the same time. See U.S. Pat. No. 6,046,167.

A particular group of compounds of the immediately foregoing group of compounds is

```
                                            (SEQ ID NO: 310)
H--Ile--Asn--Pro--Ile--Tyr--Arg--Leu--Arg--Tyr--OMe (SEQ ID NO: 311)
H--Ile--Asn--Pro--Cys--Tyr--Arg--Leu--Arg--Tyr--Ome
                    |
H--Ile--Asn--Pro--Cys--Tyr--Arg--Leu--Arg--Tyr--Ome, (SEQ ID NO: 312)
H--Cys--Tyr--Arg--Leu--Arg--Tyr--Ome
   |
H--Cys--Tyr--Arg--Leu--Arg--Tyr--OMe,
```

-continued (SEQ ID NO: 313)
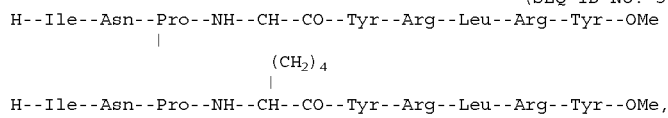

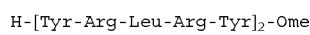

(SEQ ID NO: 314)
H-[Tyr-Arg-Leu-Arg-Tyr]$_2$-Ome or a pharmaceutically acceptable salt thereof PYY and PYY agonists may be produced by recombinant DNA technology by chemical synthesis, from natural sources, or by any combination thereof. PYY and PYY agonists may be modified by well known processes such as amidation, glycosylation, acylation (e.g. acetylation), sulfation, phosphylation, cyclization, lipidization and pegylation. Methods for lipidization with fatty acid derivatives of sulfhydryl-containing compounds are disclosed in U.S. Pat. Nos. 5,936,092; 6,093,692; and 6,225,445. Fatty acid derivatives of sulfhydryl-containing PYY and PYY agonists comprising fatty acid-conjugated products with a disulfide linkage are employed for delivery of the PYY and PYY agonists to neuronal cells and tissues. This modification markedly increases the absorption of the compounds relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties.

Fatty acids, as constituents of phospholipids, make up the bulk of cell membranes. Due to their lipidic nature, fatty acids can easily partition into and interact with the cell membrane in a non-toxic way. Therefore, fatty acids represent potentially a useful carrier ligand for the delivery of proteins and peptides. Strategies that may use fatty acids in the delivery of proteins and peptides include the covalent modification of proteins and peptides and the use of fatty acid emulsions.

To prepare such conjugates, a sulfhydryl-containing PYY and PYY agonist is attached to a fatty acid derivative via a reversible, biodegradable disulfide bond. Such a conjugate is expected to bind to the apical side of a cell membrane, reach the basolateral membrane of the GI-epithelium as a result of membrane transport and turnover, and become released into interstitial fluid as the result of disulfide bond reduction.

Such lipidized PYY and PYY agonist compounds have the general formula

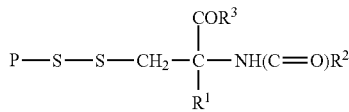

in which P is a residue derived from a PYY or PYY agonist; $R^1$ is hydrogen, lower alkyl or aryl; $R^2$ is a lipid-containing moiety and $R^3$ is —OH, a lipid-containing moiety or an amino acid chain comprising one or 2 amino acids and terminating in —CO$_2$H or —COR$^2$. See U.S. Pat. No. 5,936,092. These conjugates are particularly useful for increasing the absorption and prolonging blood and tissue retention of PYY and PYY agonists.

Typical alkyl groups include $C_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Preferred aryl groups are $C_{6-14}$ aryl groups and typically include phenyl, naphthyl, fluorenyl, phenanthryl, and anthracyl groups.

The term "lipid-containing moiety" refers to either a lipid group per se or a hydrocarbon-based group (in particular, one or more amino acids) comprising a lipid group. By the term "lipid group" is meant a hydrophobic substituent consisting of 4 to 26 carbon atoms, preferably 5 to 19 carbon atoms. Suitable lipid groups include, but are not limited to, the following: palmityl ($C_{15}H_{31}$,), oleyl ($C_{15}H_{29}$), stearyl ($C_{17}H_{35}$), cholate; and deoxycholate.

PCT Application No. WO 00/34236 describes drug-carrier conjugates and synthetic strategies for their production, as well as synthetic methods, intermediates, and final products useful for the uptake and release of biologically-active amino group containing compounds. Such lipidized PYY and PYY agonist compounds have general Formula I

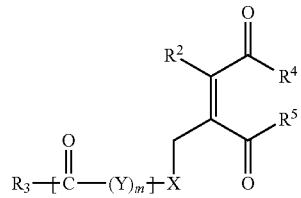

in which $R^2$ is selected from the group consisting of hydrogen, halo, alkyl, or aryl, wherein the alkyl or aryl groups are optionally substituted with one or more alkoxy, alkoxyalkyl, alkanoyl, nitro, cycloalkyl, alkenyl, allyl, alkanoyloxy, alkyl or halogen atoms;

$R^3$ is a lipophilic group; one of $R^4$ and $R^5$ is a PYY or a PYY agonist and the other of $R^4$ and $R^5$ is OR$^6$ where $R^6$ is hydrogen, an alkali metal or a negative charge;

X is oxygen or sulfur;

Y is a bridging natural or unnatural amino acid; n is zero or 1; and m is an integer from zero to 10.

Typical alkyl groups include $C_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Typical alkoxy groups include oxygen substituted by any of the alkyl groups mentioned above.

Typical alkoxyalkyl groups include any of the above alkyl groups substituted by an alkoxy group, such as methoxymethyl, ethoxymethyl, propoxymethyl, butoxymethyl, pentoxymethyl, hexoxymethyl, methoxyethyl, methoxypropyl, methoxybutyl, methoxypentyl, methoxyhexyl, and the like.

Preferred aryl groups are $C_{6-14}$ aryl groups and typically include phenyl, naphthyl, fluorenyl, phenanthryl, and anthracyl groups.

Typical alkoxy substituted aryl groups include the above aryl groups substituted by one or more of the above alkoxy groups, e.g., 3-methoxyphenyl, 2-ethoxyphenyl, and the like.

Typical alkyl substituted aryl groups include any of the above aryl groups substituted by any of the $C_{1-6}$ alkyl groups, including the group $Ph(CH_2)n$, where n is 1-6, for example, tolyl, o-, m-, and p-xylyl, ethylphenyl, 1-propylphenyl, 2-propylphenyl, 1-butylphenyl, 2-butylphenyl, t-butylphenyl, 1-pentylphenyl, 2-pentylphenyl, 3-pentylphenyl.

Typical alkenyl groups include $C_{2-6}$ alkenyl groups, e.g. ethenyl, 2-propenyl, isopropenyl, 2-butenyl, 3-butenyl, 4-pentenyl, 3-pentenyl, 2-pentenyl, 5-hexenyl, 4-hexenyl, 3-hexenyl, and 2-hexenyl groups.

Typical alkynyl groups include $C_{2-6}$ alkynyl groups e.g. enthynyl, 2-propenyl, 2-butynyl, 3-butynyl, 4-pentynyl, 3-pentynyl, 2-pentynyl, 5-hexynyl, 4hexynyl, 3-hexynyl, and 2-hexynyl groups.

Typical alkenyl or alkynyl substituted aryl groups include any of the above $C_{6-14}$ aryl groups substituted by any of the above $C_{2-6}$ alkenyl or $C_{2-6}$ alkynyl groups, e.g., ethenylphenyl, 1-propenylphenyl, 2-propenylphenyl, 1butenylphenyl, 2-butenylphenyl, 1-pentenylphenyl, 2-pentenylphenyl, 3-pentenylphenyl, 1-hexenylphenyl, 2-hexenylphenyl, 3-hexenylphenyl, ethynylphenyl, 1-propynylphenyl, 2-propynylphenyl, 1-butynylphenyl, 2-butynylphenyl, 1-pentynylphenyl, 2-pentynylphenyl, 3-pentynylphenyl, 1-hexynylphenyl, 2-hexynylphenyl, 3-hexynylphenyl groups.

Typical halo groups include fluorine, chlorine, bromine, and iodine.

Typical halo substituted alkyl groups include $C_{1-6}$ alkyl groups substituted by one or more fluorine, chlorine, bromine, or iodine atoms, e.g., fluoromethyl, difluoromethyl, trifluoromethyl, pentafluoroethyl, 1,1-difluoroethyl, and trichloromethyl groups.

Typical alkanoyl groups include $C_{1-5}C(=O)$— alkanoyl groups, e.g., acetyl, propionyl, butanoyl, pentanoyl, and hexanoyl groups, or by an arylalkanoyl group, e.g., a $C_{1-5}C(=O)$— alkanoyl group substituted by any of the above aryl groups.

Typical cycloalkyl groups include $C_{3-8}$ cycloalkyl groups including cyclopropyl, cyclobutyl, cyclopentyl, cyclohexyl, cycloheptyl and cyclooctyl groups.

The term "lipophilic group" as used herein refers to either a naturally occurring lipid per se, a hydrophobic branched or unbranched hydrocarbon comprising about 4 to about 26 carbon atoms, preferably about 5 to about 19 carbon atoms, a fatty acid or ester thereof, or a surfactant. Suitable lipophilic groups include, but are not limited to, long chain alkanoyl groups including: palmityl ($C_{15}H_{31}$), oleyl ($C_{15}H_{29}$), stearyl ($C_{17}H_{35}$), lauryl ($C_{11}H_{23}$), cholyl, and myristyl ($C_{13}H_{27}$)

The term "natural or unnatural amino acid" as used herein refers to any of the 21 naturally occurring amino acids as well as D-form amino acids, blocked L-and D-form amino acids such as those blocked by amidation or acylation, substituted amino acids (e.g., those substituted with a sterically hindered alkyl group or a cycloalkyl group such as cyclopropyl or cyclobutyl) in which the substitution introduces a conformational restraint in the amino acid. The preferred naturally occurring amino acids for use in the present disclosure as amino acids or components of a peptide or protein are alanine, arginine, asparagine, aspartic acid, citrulline, cysteine, cystine, y-glutamic acid, glutamine, glycine, histidine, isoleucine, norleucine, leucine, lysine, methionine, ornithine, phenylalanine, proline, hydroxyproline, serine, threonine, tryptophan, tyrosine, valine, γ-carboxyglutamate, or O-phosphoserine. The preferred non-naturally occurring amino acids for use in the present disclosure as amino acids or components of peptides or proteins are any of the β-amino acids, e.g., α-alanine, γ-amino butyric acid, γ-amino butyric acid, γ-(aminophenyl)butyric acid, α-amino isobutyric acid, ε-amino caproic acid, τ-amino heptanoic acid, amino benzoic acid, aminophenyl acetic acid, aminophenyl butyric acid, cysteine (ACM), methionine sulfone, phenylglycine, norvaline, ornithine, δ-ornithine, ρnitro-phenylalanine, 1,2,3,4-terahydroisoquinoline-3-carboxylic acid and thioproline.

The present disclosure is also directed to methods of preparing lipidized conjugates of PYY and PYY agonists, pharmaceutical compositions comprising lipidized conjugates of PYY and PYY agonists, and methods of increasing the delivery of amino group-containing PYY and PYY agonists into a cell.

Also provided by the disclosure are chemically modified derivatives of PYY and PYY agonists which may provide additional advantages such as increased solubility, stability and circulating time of the polypeptide, or decreased immunogenicity (see U.S. Pat. No. 4,179,337). Such modified derivatives include PYY and PYY agonists modified by pegylation. The terms "pegylated" and "pegylation" refer to the process of reacting a poly(alkylene glycol), preferably an activated poly(alkylene glycol), with a facilitator such as an amino acid, e.g. lysine, to form a covalent bond. Although "pegylation" is often carried out using poly(ethylene glycol) or derivatives thereof, such as methoxy poly(ethylene glycol), the term is not intended to be so limited here, but is intended to include any other useful poly(alkylene glycol), such as, for example poly(propylene glycol).

The chemical moieties for derivitization may also be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999.

The polyethylene glycol molecules (or other chemical moieties) should be attached to the polypeptides or proteins with consideration of effects on functional or antigenic domains of the polypeptides or proteins. There are a number of attachment methods available to those skilled in the art, e.g., EP 0 401 384 (coupling PEG to G-CSF), see also Malik et al., *Exp. Hematol* 20:1028-1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins and polypeptides via linkage to any of a number of amino acid residues. For example, polyethylene glycol can be linked to proteins and polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or protein or to more than one type of amino acid residue (e.g., lysine, histidine, aspartic acid, glutamic acid, cysteine and combinations thereof) of the protein or polypeptide.

One may specifically desire proteins and polypeptides chemically modified at the N-terminus. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins and polypeptides may be accomplished by any number of means. For example, polyethylene glycol may be attached to the protein or polypeptide either directly or by an intervening linker. Linkerless systems for attaching polyethylene glycol to proteins and polypeptides are described in Delgado et al., *Crit. Rev. Thera. Drug Carrier Sys.* 9:249-304, 1992; Francis et al., *Intern. J, of Hematol.* 68:1-18, 1998; U.S. Pat. Nos. 4,002,531; 5,349,052; WO 95/06058; and WO 98/32466.

One system for attaching polyethylene glycol directly to amino acid residues of proteins and polypeptides without an intervening linker employs tresylated MPEG, which is produced by the modification of monmethoxy polyethylene glycol (MPEG) using tresylchloride ($ClSO_2CH_2CF_3$). Upon reaction of the protein or polypeptide with tresylated MPEG, polyethylene glycol is directly attached to amine groups of the protein or polypeptide. Thus, the disclosure includes protein-polyethylene glycol conjugates produced by reacting proteins and polypeptides with a polyethylene glycol molecule having a 2,2,2-trifluoreothane sulphonyl group.

Polyethylene glycol can also be attached to proteins and polypeptides using a number of different intervening linkers. For example, U.S. Pat. No. 5,612,460 discloses urethane linkers for connecting polyethylene glycol to proteins. Protein-polyethylene glycol conjugates wherein the polyethylene glycol is attached to the protein or polypeptide by a linker can also be produced by reaction of proteins or polypeptides with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins and polypeptides are described in WO 98/32466.

The number of polyethylene glycol moieties attached to each protein or polypeptide (i.e., the degree of substitution) may also vary. For example, the pegylated proteins and polypeptides may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein or polypeptide molecule. Methods for determining the degree of substitution are discussed, for example, in Delgado et al., *Crit. Rev. Thera. Drug Carrier Sys.* 9:249-304, 1992.

The proteins and polypeptides containing substantially non-antigenic polymers, preferably poly(alkylene glycols) may be prepared, for example, as described in U.S. Pat. Nos. 5,428,128; 6,127,355; and 5,880,131.

To effect covalent attachment of poly(ethylene glycol) (PEG) to a protein or polypeptide, the hydroxyl end groups of the PEG must first be converted into reactive functional groups. This process is frequently referred to as "activation" and the product is called "activated PEG." Methoxy poly (ethylene glycol) (mPEG), distally capped with a reactive functional group is often used. One such activated PEG is succinimidyl succinate derivative of PEG (SS-PEG). See also Abuchowski et al., *Cancer Biochem. Biophys.* 7:175-186, 1984; and U.S. Pat. No. 5,122,614 which discloses poly(ethylene glycol)-N-succinimide carbonate and its preparation.

Alternative substantially non-antigenic polymers that may be employed in the practice of the present disclosure include materials such as dextran, polyvinyl pyrrolidones, polysaccharides, starches, polyvinyl alcohols, polyacrylamides, or other similar non-immunogenic polymers. Those of ordinary skill in the art will realize that the foregoing are merely illustrative and not intended to restrict the type of polymeric substances suitable for use herein.

In one aspect of the disclosure, the polymer is introduced into the peptide or protein molecule after being functionalized or activated for reaction and attachment to one or more amino acids. By activation, it is understood by those of ordinary skill in the art that the polymer is functionalized to include a desired reactive group. See, for example, U.S. Pat. Nos. 4,179,337 and 5,122,614. In this embodiment, the hydroxyl end groups of poly(alkylene glycols) are converted and activated into reactive functional groups.

In another aspect of the disclosure, the polymer is conjugated to a facilitator moiety prior to being introduced into the polypeptide or protein molecule. The facilitator moiety is preferably an amino acid such as lysine, however, non-amino acid moieties are also contemplated. Within the aspect, there are included multifunctionalized organic moieties such as alkyls or substituted alkyls. Such moieties can be prepared to have a nucleophilic functional group such as an amine and an electrophilic group such as an acid as well as a suitably functionalized region for conjugating with the desired polymer or polymers.

The facilitator moieties allow easier inclusion of a polymer into the peptide or protein molecule during synthesis. For example, poly(alkylene glycols) coupled to facilitator amino acids or amino acid residues in polypeptides or proteins by means of suitable coupling agents are illustrative. A useful review of a number of coupling agents known in the art appears in Dreborg et al., *Critical Reviews in Therapeutic Drug Carrier Systems* 6(4):315-165, 1990, see especially, pp. 317-320.

Pegylated PYY peptides and agonists can also be of the general formula

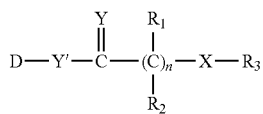

wherein:

D is a residue of a PYY peptide or agonist;

X is an electron withdrawing group;

Y and Y' are independently O or S;

(n) is zero (0) or a positive integer, preferably from 1 to about 12;

$R_1$ and $R_2$ are independently selected from the group consisting of H, $C_{1-6}$ alkyls, aryls, substituted aryls, aralkyls, heteroalkyls, substituted heteroalkyls, and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

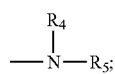

and $R_4$ and $R_5$ are independently selected from the group consisting of H, $C_{1-6}$ alkyls, aryls, substituted aryls, aralkyls, heteroalkyls, substituted heteroalkyls and substituted $C_{1-6}$ alkyls or jointly form a cyclic $C_5$-$C_7$ ring. See U.S. Pat. No. 6,127,355.

Typical alkyl groups include $C_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Preferred aryl groups are $C_{6-14}$ aryl groups and typically include phenyl, naphthyl, fluorenyl, phenanthryl, and anthracyl groups.

Typical alkyl substituted aryl groups include any of the above aryl groups substituted by any of the $C_{1-6}$ alkyl groups, including the group $Ph(CH_2)_n$, where n is 1-6, for example, tolyl, o-, m-, and p-xylyl, ethylphenyl, 1-propylphenyl, 2-propylphenyl, 1-butylphenyl, 2-butylphenyl, t-butylphenyl, 1-pentylphenyl, 2-pentylphenyl, 3-pentylphenyl.

Typical cycloalkyl groups include $C_{3-8}$ cycloalkyl groups including cyclopropyl, cyclobutyl, cyclopentyl, cyclohexyl, cycloheptyl and cyclooctyl groups.

Typical electron withdrawing groups include O, $NR_1$, S, SO and $SO_2$, wherein $R_1$ is defined above.

GLP-1 and Agonists Thereof

GLP-1 is produced from preproglucogon, which is a 160 amino acid polypeptide, in the central nervous system (CNS) and the intestine. It is released into the circulation in response to nutrient intake. Physiological actions of GLP-1 in man include stimulation of insulin release, suppression of gastric acid secretion and slowing of gastric emptying.

GLP-1 (1-37) (SEQ ID NO: 336) is the initial product of the processing of preproglucagon. GLP-1 (1-37) is amidated by post-translational processing to yield GLP-1 (1-36) NH (SEQ ID NO 337), or is enzymatically processed to give GLP-1 (7-37) (SEQ ID NO: 338). GLP-1 (7-37) can be amidated to give GLP-1 (7-36) amide (SEQ ID NO: 339). The sequences of human GLP-1 are given below:

```
GLP-1 (1-37):
                                     (SEQ ID NO: 336)
His Asp Glu Phe Glu Arg His Ala Glu Gly Thr Phe
Thr Ser Asp Val Ser Ser Tyr Leu Glu Gly Gly Ala
Ala Lys Glu Phe Ile Ala Trp Leu Val Lys Gly Arg
Gly.

GLP-1 (1-36) amide:
                                     (SEQ ID NO: 337)
His Asp Glu Phe Glu Arg His Ala Glu Gly Thr Phe
Thr Ser Asp Val Ser Ser Tyr Leu Glu Gly Gly Ala
Ala Lys Glu Phe Ile Ala Trp Leu Val Lys Gly Arg
NH2, GLP-1 (7-37):
                                     (SEQ ID NO: 338)
His Ala Glu Gly Thr Phe Thr Ser Asp Val Ser Ser
Tyr Leu Glu Gly Gly Ala Ala Lys Glu Phe Ile Ala
Trp Leu Val Lys Gly Arg Gly.

GLP-1 (7-36) amide:
                                     (SEQ ID NO: 339)
His Ala Glu Gly Thr Phe Thr Ser Asp Val Ser Ser
Tyr Leu Gln Gly Gly Ala Ala Lys Glu Phe Ile Ala
Trp Leu Val Lys Gly Arg NH2.
```

A GLP-1 agonist is a peptide, small molecule, or chemical compound that preferentially binds to the GLP-1 receptor and stimulates the same biological activity as does GLP-1. In one embodiment, an agonist for the GLP-1 receptor binds to the receptor with an equal or greater affinity than GLP-1. In another embodiment, an agonist selectively binds the GLP-1 receptor, as compared to binding to another receptor. Exendin-4, which is a 39-amino acid peptide isolated from the salivary glands of the Gila monster (*Heloderma suspectum*) (Eng J et al J Biol Chem 267:7402-7405, 1992) is an example of an agonist at the GLP-1 receptor. Molecules derived from exendin-4 and that also have GLP-1 agonist activity are further examples of GLP-1 agonists. GLP-1 agonists include GLP-1 related peptides and peptides that result from natural or synthetic enzymatic or chemical processing of preproglucagon or of a GLP-1 peptide or a related peptide.

Any compound that is described as being a GLP-1 agonist maybe used in the present invention, as may any compound that is tested for GLP-1 agonist activity, for example, as described above, and found to function as a GLP-1 agonist. A recombinant GLP-1 receptor suitable for use in screening is disclosed in WO93/19175. Many GLP-1 agonists are known and are described in the art. Examples of published patent specifications that disclose GLP-1 agonists are the following: WO2002/67918, WO2002/66479, WO2002/03978, WO2001/89554, WO2001/14386, WO2001/66135, WO2001/35988, WO2001/14368, WO2001/04156, WO2000/78333, WO2000/59887, WO2000/42026, EP 0955314, and WO99/43707. Examples of GLP-1 agonists are Arg34, Lys26(N-epsilon-(gamma-Glu(N-alpha-hexadecanoyl)))-GLP-1 (7-37), IP7-GLP-1 (7-37)OH.

GLP-1 or an agonist thereof may be administered according to the present invention peripherally at a dose of, for example, 0.1 nmoles or more per kg body weight of the subject, for example, 0.2 nmoles or more, for example, 0.4 nmoles or more, for example, 0.6 nmoles or more, for example, 0.8 nmoles or more, for example, 1.0 nmole or more, for example, 1.2 nmoles or more, for example, 1.4 nmoles or more, for example, 1.6 nmoles or more, for example, 1.8 nmoles or more, for example, 2.0 nmoles or more, for example, 2.2 nmoles or more, for example, 2.4 nmoles or more, for example, 2.6 nmoles or more, for example, 2.8 nmoles, for example, 3.0 nmoles or more, for example, up to 3.2 nmoles per kg body weight. The amount used may be up to 3.0 nmoles per kg body weight, for example, up to 2.8 nmoles, for example, up to 2.6 nmoles, for example, up to 2.4 nmoles, for example, up to 2.2 nmoles, for example, up to 2.0 nmoles, for example, up to 1.8 nmoles, for example, up to 1.4 nmoles, for example, up to 1.2 nmoles, for example, up to 1.0 nmoles, for example, up to 0.8 nmoles, for example, up to 0.6 nmoles, for example, up to 0.4 nmoles, for example, up to 0.2 nmoles per kg body weight. The dose is generally in the range of from 0.1 to 3.2 nmoles per kg body weight, for example, within any combination of upper and lower ranges given above.

We have shown that intracerebroventricular (ICV) administration of GLP-1 to rats potently inhibits food intake. This effect is blocked by the specific GLP-1 receptor antagonist, exendin 9-39. GLP-1 receptors are found in the brainstem, arcuate nucleus and PVN. Following ICV GLP-1 administration, c-fos is expressed in the arcuate nucleus and PVN. However, peripheral administration of GLP-1 in man and rat also inhibits food intake and results in c-fos expression in the brainstem of rats. As is disclosed herein, the effect on 1-hour food intake in non-fasted rats of IP administration of GLP-1 is not influenced by the presence of concomitant exendin 9-39, a GLP-1 receptor agonist, in the arcuate nucleus of the rat. This indicates that circulating GLP-1 acts via the brainstem rather than the arcuate nucleus.

These and other findings suggest that the main site for appetite inhibition by peripheral GLP-1 is the dorsal vagal complex, acting in part directly through the area postrema. However, the physiological importance of this in man is currently unclear.

As disclosed herein, when administered to humans, PYY was found to reduce appetite. When infused into humans at physiological post-prandial levels, $PYY_{3-36}$ significantly decreased appetite and reduced food intake by a third over 12 hours, and even by a third over 24 hours. Both the effect itself and the duration of the effect are surprising and unpredictable, as they occurred for many hours after the hormone had been cleared from the circulation. The effects, which are produced at physiological levels of the peptide, are strong indications that PYY acts in vivo to regulate feeding behavior.

As disclosed herein, peripheral administration of $PYY_{3-36}$ in the rat caused an increase of c-fos immunoreactivity in the arcuate nucleus of the hypothalamus and a decrease in hypothalamic neuropeptide Y (NPY) mRNA. Further, electrophysiological studies demonstrated that $PYY_{3-36}$ inhibits synaptic activity of the NPY nerve terminals and thus activates POMC neurons, which are known to receive inhibitory NPY synaptic inputs.

Without being bound by theory, these results demonstrate that the gut hormone $PYY_{3-36}$ can act via the neuropeptide Y Y2 receptor. This hypothesis is supported by the observation that when $PYY_{3-36}$ was administered to neuropeptide Y Y2 receptor null mice (Y2R gene knock out mice), no inhibition of feeding was observed. Administration of $PYY_{3-36}$ to wild type littermates of the Y2R null mice was fully effective in inhibiting feeding.

Thus, a novel gut-brain pathway that inhibits feeding after meals is described. Without being bound by theory, the natural pathway involves release of PYY from the gut, its conversion to $PYY_{3-36}$, which acts as an agonist on the neuropeptide Y Y2 receptor (NPY Y2 receptor) in the brain. The NPY Y2 receptor acts as a inhibitory pre-synaptic receptor reducing release of neuropeptide Y, which is a most potent stimulator of feeding, and also acting on the anorexigenic melanocortin systems, the result of the NPY Y2 receptor activity being to suppress appetite and decrease food intake. The action of $PYY_{3-36}$ may occur in the arcuate nucleus of the hypothalamus, but other areas may be also be involved.

The results obtained show that $PYY_{3-36}$, a gut hormone that circulates in the blood, inhibits appetite at physiological concentrations, and that the inhibitory effect is observed even for some hours after the hormone has been cleared from the blood. This effect has been observed in all species tested, i.e. in mouse, rat and human. The circulating gut hormone appears to act via hypothalamic circuits. The reduction of messenger RNA, necessary for the synthesis of brain appetite regulating hormones, in particular of hypothalamic NPY mRNA may be a possible mechanism for the long action of $PYY_{3-36}$.

When $PYY_{3-36}$ was co-administered parenterally, either EP or IV with GLP-1, a clear synergistic reduction in food intake was produced. This contrasts with the results obtained with oxyntomodulin, where there was no synergistic effect, only a sum of the individual effects. As indicated above, $PYY_{3-36}$ is considered to act via the arcuate nucleus. Oxyntomodulin is also considered to act via that region of the brain. GLP-1, however, is believed to act via the brainstem, as explained above. While not being limited to the following, it appears that, when agents that act via different areas of the brain and/or by different neurological routes are administered parenterally, they produce a synergistic affect, whereas when they act by the same area and/or route they do not.

These results indicate the importance in vivo of the interaction of gut hormones on the regulation of appetite and food intake. The present invention demonstrates that, surprisingly, it is possible to regulate appetite and food intake more effectively by informed choice of agents.

The disclosure is illustrated by the following non-limiting Examples.

EXAMPLES

Example 1

Material and Methods

Generation of POMC-EGFP mice: The EGFP cassette contains its own Kozak consensus translation initiation site along with SV40 polyadenylation signals downstream of the EGFP coding sequences directing proper processing of the 3' end of the EGFP mRNA. The EGFP cassette was introduced by standard techniques into the 5' untranslated region of exon 2 of a mouse Pomc genomic clone containing 13 kb of 5' and 2 kb of 3' flanking sequences (Young et al., *J Neurosci* 18, 6631-40, 1998). The transgene was microinjected into pro-nuclei of one-cell stage embryos of C57BL/6J mice (Jackson Laboratories) as described (Young et al., *J Neurosci* 18, 6631-40, 1998). One founder was generated and bred to wildtype C57BL/6J to produce $N_1$ hemizygous mice. In addition, $N_2$ and subsequent generations of mice homozygous for the transgene were also generated. The mice are fertile and have normal growth and development.

Immunofluorescence and GFP co-localization: Anesthetized mice were perfused transcardially with 4% paraformaldehyde and free-floating brain sections prepared with a vibratome. Sections were processed for immunofluorescence and colocalization of GFP fluorescence using standard techniques. Primary antisera and their final dilutions were rabbit anti-β-endorphin, 1:2500 v/v; rabbit anti-NPY, 1:25,000 v/v (Alanex Corp.); rabbit anti-ACTH, 1:2000 v/v; and mouse anti-TH, 1:1000 v/v (Incstar). After rinsing, sections were incubated with 10 mg/ml biotinylated horse anti-mouse/rabbit IgG (Vector Laboratories) followed by Cy-3 conjugated streptavidin, 1:500 v/v (Jackson Immunoresearch Laboratories). Photomicrographs were taken on a Zeiss Axioscop using FITC and RITC filter sets (Chroma Technology Corp.).

Electrophysiology (Example 2): 200 μm thick coronal slices were cut from the ARC of four-week old male POMC-EGFP mice. Slices were maintained in (in M) [NaCl, 126; KCl, 2.5; $MgCl_2$, 1.2; $CaCl_2.2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour(hr) prior to recordings. Recordings were made in Krebs at 35° C. Slices were visualized on an Axioskop FS2 (Zeiss) through standard infra red optics and using epifluoresence through a FITC filter set (see FIG. 1c). Whole cell recordings were made from fluorescent neurons using an Axopatch 1D amplifier (Axon Instruments) and Clampex 7 (Axon Instruments). Resting membrane potentials were determined using an event detection protocol on a PowerLab system (AD Instruments, Mountain View, Calif.) to average expanded traces of the membrane potential. Drugs were applied to the bath over the times indicated. The resting membrane potential was stable for up to an hour in cells treated with Krebs alone. I-V relationships for the Met-Enk currents were established using a step protocol; (−60 mV holding potential, sequentially pulsed (40 ms) from −120 to −50 mV, cells were returned to −60 mV for 2 s between voltage steps). The protocol was repeated after Met Enk addition. The net current was the difference between the two I-V relationships. This protocol was repeated in Krebs with 6.5 mM $K^+$. I-V relationships to identify the postsynaptic leptin current were performed similarly with slow voltage ramps (5 mV/s from −100 to −20 mV) before and 10 minutes after the addition of leptin (100 nM). GABAergic IPSCs were recorded using a CsCl internal electrode solution (in mM) [CsCl, 140; Hepes, 10; $MgCl_2$, 5; Bapta, 1; (Mg)-ATP, 5; (Na)GTP, 0.3]. Both mini IPSCs and large amplitude (presumably multisynaptic) IPSCs were observed in the untreated slices. TTX (1 μM) abolished large IPSCs. Data were acquired before and after addition of drug for the times indicated on the figures at a −50 mV holding potential in 2 s. sweeps every 4 s. Mini postsynaptic currents were analyzed using Axograph 4 (Axon Instruments). IPSCs and excitatory postsynaptic currents (EPSCs) were distinguished on the basis of their decay constants; additionally picrotoxin (100 μM) blocked all IPSCs. POMC neurons receive a low EPSC tone and the frequency was not modulated by any of the treatments described here.

Immunostaining for light and electron microscopy: Double immunocytochemistry for NPY and POMC using different color diaminobenzidine(DAB) chromogens was carried out on fixed mouse hypothalami according to published protocols (Horvath et al., *Neuroscience* 51, 391-9, 1992). For electron microscopy, preembedding immunostaining for β-endorphin was using an ABC Elite kit (Vector Laboratories) and a DAB reaction followed by post-embedding labeling of GABA and NPY using rabbit anti-GABA, 1:1000 v/v and gold conjugated (10 nm) goat anti-rabbit IgG or sheep anti-NPY and gold conjugated (25 nm) goat anti-sheep IgG. Finally, sections were contrasted with saturated uranyl acetate (10 minutes) and lead citrate (20-30 s) and examined using a Philips CM-10 electron microscope.

Animals: Male Wistar rats (200-250 g), 7-8 weeks old (Charles River Laboratories, United Kingdom) were maintained under controlled temperature (21-23° C.) and light conditions (lights on 07:00-19:00) with ad libitum access to water and food (RM1 diet; SDS Ltd., Witham, United Kingdom) except where stated. Arcuate and paraventricular nuclei cannulations and injections were performed as previously described (Glaum et al., *Mol. Pharmacol.* 50, 230-5, 1996; Lee et al., *J. Physiol* (*Lond*) 515, 439-52; 1999; Shiraishi et al., *Nutrition* 15, 576-9, 1999). Correct intranuclear cannula placement was confirmed histologically at the end of each study period (Glaum et al., *Mol. Pharmacol.* 50, 230-5, 1996; Lee et al., *J. Physiol* (*Lond*) 515, 439-52, 1999; Shiraishi et al., *Nutrition* 15, 576-9, 1999). All animal procedures were approved under the British Home Office Animals (Scientific Procedures) Act, 1986. All injection studies on fasting animals were performed in the early light-phase (0800-0900). All dark-phase feeding studies injections were performed just prior to lights off.

Male Pomc-EGFP mice were studied at 5-6 weeks of age and were generated as described above. Y2r-null mice were generated using Cre-lox P mediated recombination, which results in the germline deletion of the entire coding region of the Y2 receptor. All Y2r-null mice were maintained on a mixed C57/B16-129SvJ background. Male mice aged 8-12 weeks and between 20-30 g bodyweight were kept under controlled temperature (21-23° C.) and light conditions (lights on 06:00-18:00) with ad libitum access to water and food (Gordon's Speciality Stock feeds) except where stated. All studies were performed in the early light-phase (0700-0800).

Intraperitoneal injections: Rats were accustomed to IP injection by injections of 0.5 ml saline on the two days prior to study. For all studies, animals received an IP injection of $PYY_{3-36}$, GLP-1 or saline in 500 μl (for rats) or 100 μl (for mice).

Electrophysiology: Whole cell patch clamp recordings were made from POMC neurons in the hypothalamus of 180 μm thick coronal slices from Pomc-EGFP mice, as previously reported (Cowley et al., *Nature* 411, 480-484, 2001). "Loose cell-attached" recordings were made using extracellular buffer in the electrode solution, and maintaining seal resistance between 3-5 Mohm throughout the recording. Firing rates were analysed using mini-analysis protocols (Mini-Analysis, Jaejin Software, NJ). Vehicle controls were used in this system, previously validated for the electrophysiological actions of neuropeptides (Cowley et al., *Nature* 411, 480-484, 2001). Data were analysed by ANOVA, Neuman-Keuls posthoc comparison, and Wilcoxon Signed Rank Test.

Hypothalamic explants: Male Wistar rats were killed by decapitation and the whole brain immediately removed, mounted with the ventral surface uppermost and placed in a vibrating microtome (Biorad, Microfield Scientific Ltd., Devon, UK). A 1.7 mm slice was taken from the base of the brain to include the PVN and the ARC and immediately transferred to 1 ml of artificial CSF (aCSF) (Kim et al., *J. Clin. Invest.* 105, 1005-11, 2000) equilibrated with 95% $O_2$ and 5%

$CO_2$ and maintained at 37° C. After an initial 2-hour equilibration period, with aCSF replaced every 60 minutes, the hypothalami were then incubated for 45 minutes in 600 μl aCSF (basal period) before being exposed to the Y2A (50 nM) in 600 μl aCSF. Finally, the viability of the tissue was verified by a 45 minute exposure to 56 mM KCL; isotonicity was maintained by substituting $K^+$ for $Na^+$. At the end of each period, the aCSF was removed and frozen at −20° C. until assayed for NPY and αMSH by radioimmunoassay.

C-fos expression: C-fos expression was measured in adult Wistar rats and Pomc-EGFP mice 2 hours after 1P administration of saline or $PYY_{3-36}$ (5 μg/100 g) using standard immunohistochemical techniques (Hoffman et al., *Front. Neuroendocrinol.* 14, 173-213, 1993). Data were obtained from 3 rats and 5 mice in each group. For the Pomc-EGFP mice 5 anatomically matched arcuate nucleus sections (Franklin et al., *The Mouse Brain in Stereotaxic Coordinates*, Academic Press, San Diego, 1997) were counted from each animal, and images acquired using a Leica TSC confocal microscope (Grove et al., *Neuroscience* 100, 731-40, 2000).

RNase protection assay (RPA): Total RNA was extracted from hypothalami (Trizol, Gibco). RPAs were performed (RPAIII kit, Ambion) using 5 μg RNA and probes specific for NPY, αMSH and β actin (internal standard). For each neuropeptide, the ratio of the optical density of the neuropeptide mRNA band to that of β actin was calculated. Neuropeptide mRNA expression levels are expressed relative to saline control (mean±s.e.m. n=4 per group). The statistical analysis used was ANOVA, with Bonferroni post hoc analysis.

Plasma assays: Human leptin was measured using a commercially available radioimmunoassay (RIA) (Linco Research, USA). All other plasma hormone levels were measured using established in-house RIAs (Tarling et al., *Intensive Care Med.* 23, 256-260, 1997). Glucose concentrations were measured using a YSI 2300STAT analyser (Yellow Springs Instruments Inc., Ohio, USA). Plasma paracetamol levels were measured using an enzymatic colorimetric assay (Olympus AU600 analyzer).

Human Studies: $PYY_{3-36}$ was purchased from Bachem (California, USA). The Limulus Amoebocyte Lysate assay test for pyrogen was negative and the peptide was sterile on culture. Ethical approval was obtained from the Local Research Ethics Committee (project registration 2001/6094) and the study was performed in accordance with the principles of the Declaration of Helsinki. Subjects gave informed written consent.

Each subject was studied on two occasions with at least 1 week between each study. Volunteers filled out a food diary for three days prior to each infusion, and for the following 24 hours. All subjects fasted and drank only water from 20:00 on the evening prior to each study. Subjects arrived at 08:30 on each study day, were cannulated and then allowed to relax for 30 minutes prior to the onset of the study protocol. Blood samples were collected every 30 minutes into heparinised tubes containing 5,000 Kallikrein Inhibitor Units (0.2 ml) of aprotinin (Bayer) and centrifuged. Plasma was separated and then stored at −70° C. until analysis. Subjects were infused with either saline or 0.8 pmol.kg$^{-1}$.min$^{-1}$ $PYY_{3-36}$ for 90 minutes (about 72 pmol total infusion), in a double blind randomized crossover design.

Two hours after the termination of the infusion, subjects were offered an excess free-choice buffet meal (Edwards et al., *Am. J. Physiol. Endocrinol. Metab.* 281, E155-E166, 2001), such that all appetites could be satisfied. Food and water were weighed pre- and postprandially and caloric intake calculated. Appetite ratings were made on 100 mm visual analogue scores (VAS) with the text expressing the most positive and the negative rating anchored at each end (Raben et al., *Br. J. Nutr.* 73, 517-30, 1995). VAS was used to assess hunger, satiety, fullness, prospective food consumption and nausea. Caloric intake following saline and $PYY_{3-36}$ were compared using a paired t test. The postprandial response curves were compared by ANOVA using repeated paired measures, with time and treatment as factors.

Measurements of Energy Expenditure: To determine the actions of PYY on energy expenditure the OXYMAX system is utilized with rodents following PYY injection into a treatment cohort. This system is also utilized with rodents following a saline injection (control cohort). The equipment measures $O_2$ consumption and $CO_2$ production; the efficiency with which the body produces $CO_2$ from $O_2$ gives a reliable index of caloric or metabolic efficiency. A similar system is used with human volunteers.

Example 2

Neural Network in the Arcuate Nucleus

Figure 1B:
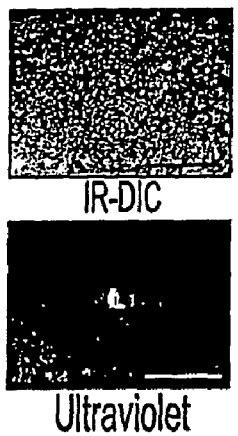
FIG. 1b is a digital image showing the identification of a single POMC neuron by EGFP fluorescence (upper) and IR-DIC microscopy (lower) in a living ARC slice prior to electrophysiological recordings.
Figure 1C:
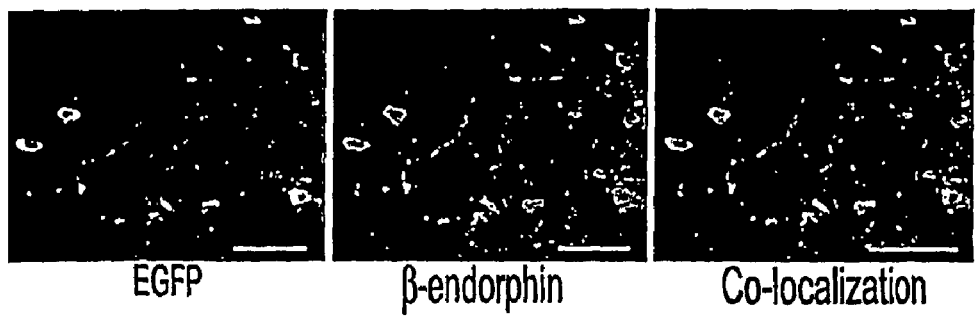
FIG. 1c is a set of digital images showing the co-localization (bright, on right) of EGFP (left) and β-endorphin immunoreactivity (middle) in ARC POMC neurons. Scale bars: b & c, 50 μm.
Figure 1D:
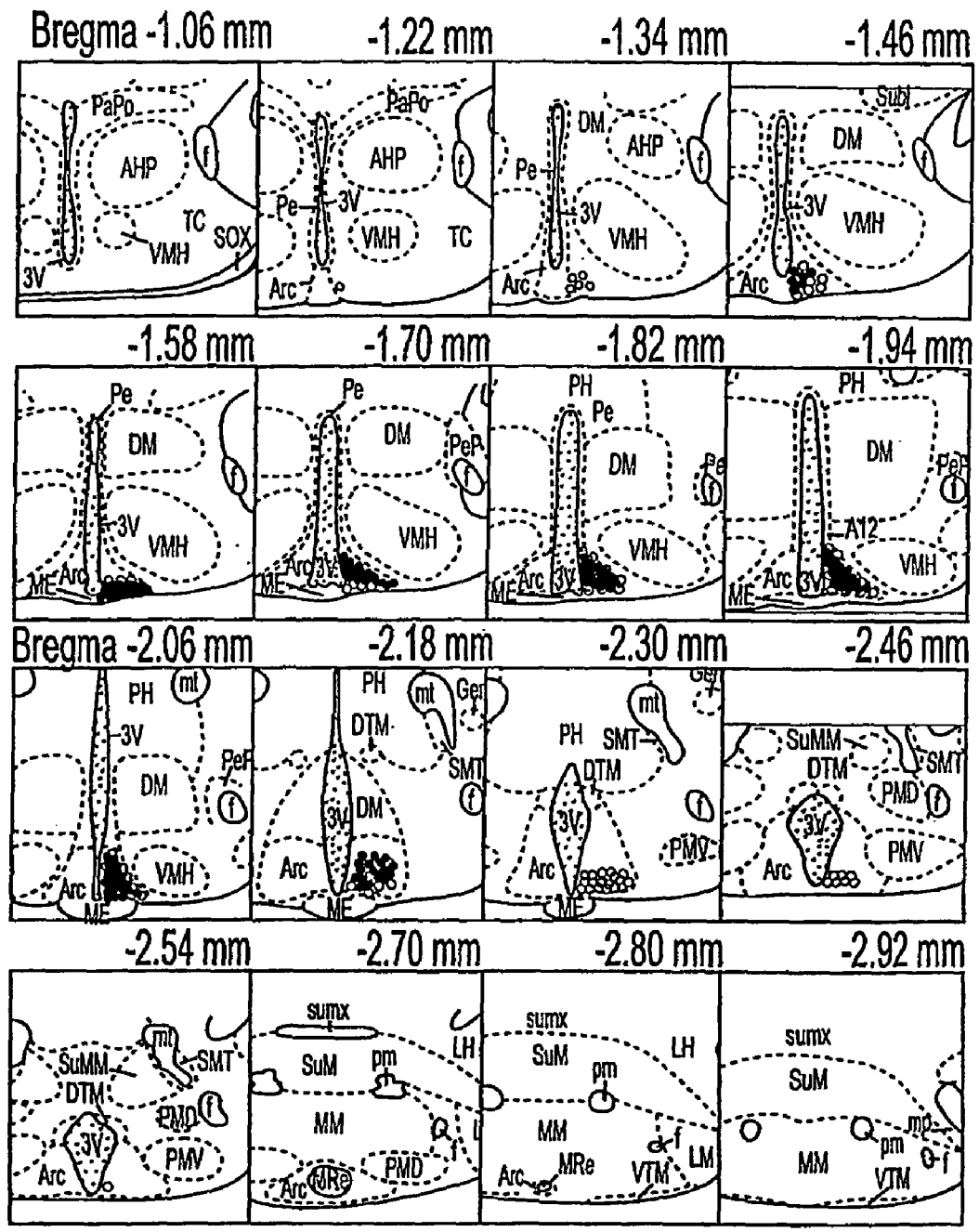
FIG. 1d is a set of diagrams showing the distribution of EGFP-positive neuronal soma throughout the ARC nucleus. ○=5 cells, •=10 cells.

A strain of transgenic mice was generated expressing green fluorescent protein (EGFP Clontech), under the transcriptional control of mouse Pomc genomic sequences that include a region located between −13 kb and −2 kb required for accurate neuronal expression (Young et al., *J Neurosci* 18, 6631-40, 1998) (FIG. 1a). Bright green fluorescence (509 nm) was seen in the two CNS regions where POMC is produced: the ARC and the nucleus of the solitary tract. Under ultraviolet (450-480 nm) excitation POMC neurons were clearly distinguished from adjacent, non-fluorescent neurons (FIG. 1b) visualized under infrared optics. Double immunofluorescence revealed>99% cellular co-localization of EGFP and POMC peptides within the ARC (FIG. 1c). There was close apposition of both tyrosine hydroxylase (TH)- and NPY-stained terminals on EGFP-expressing POMC neurons, but no evidence of co-localization of the TH or NPY immunoreactivity with EGFP. Total fluorescent cell counts performed on coronal hypothalamic sections revealed 3148±62 (mean±SEM: n=3) POMC-EGFP neurons distributed through the entire ARC (Franklin et al., *The Mouse Brain in Stereotaxic Coordinates*, Academic Press, San Diego, 1997) (FIG. 1d). POMC neurons in the mouse are located both medially and ventrally within the ARC, in contrast to a predominantly lateral position in the rat ARC.

Figure 2A:
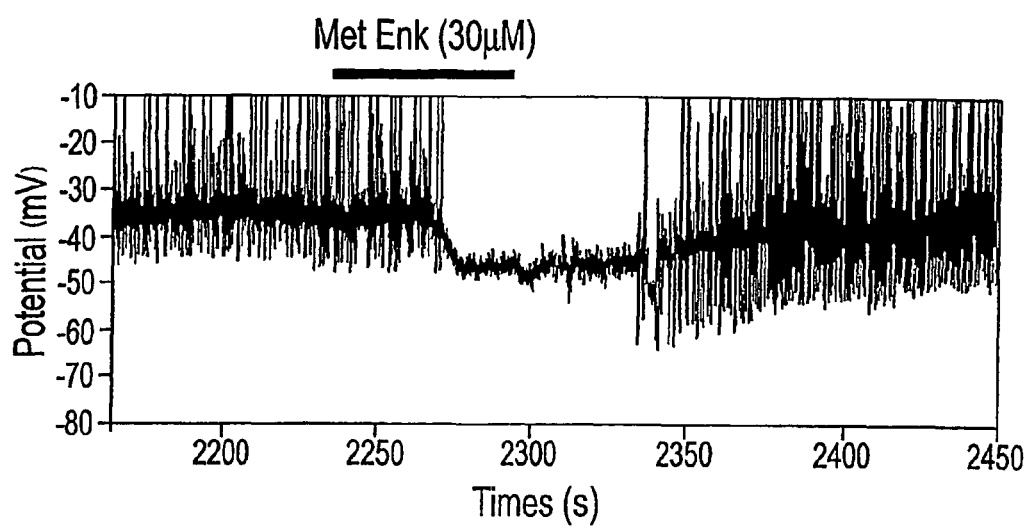
FIG. 2a is a tracing showing met-enkephalin hyperpolarizes POMC neurons and inhibits all action potentials. The horizontal bar indicates the time when 30 μM Met-Enk was bath-applied to the slice.
Figure 2B:
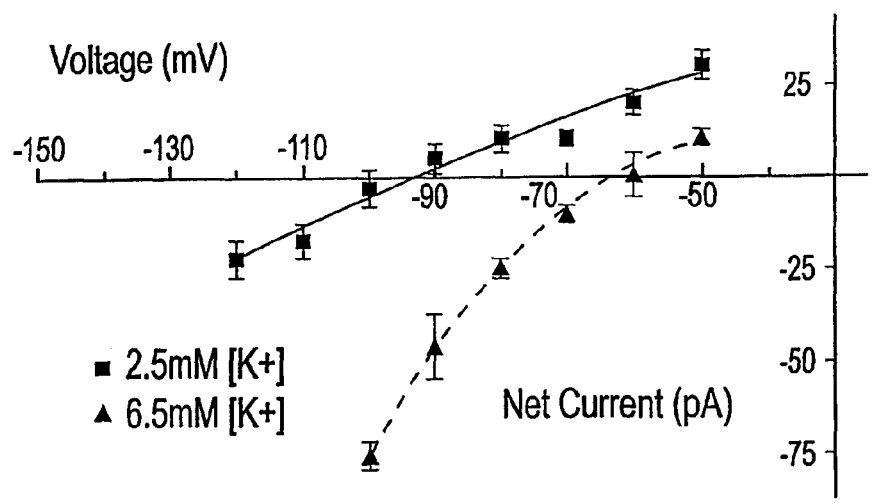
FIG. 2b is a graph showing met-enkephalin current and reversal potential is shifted by extracellular $K^+$ concentration.
Figure 2C:
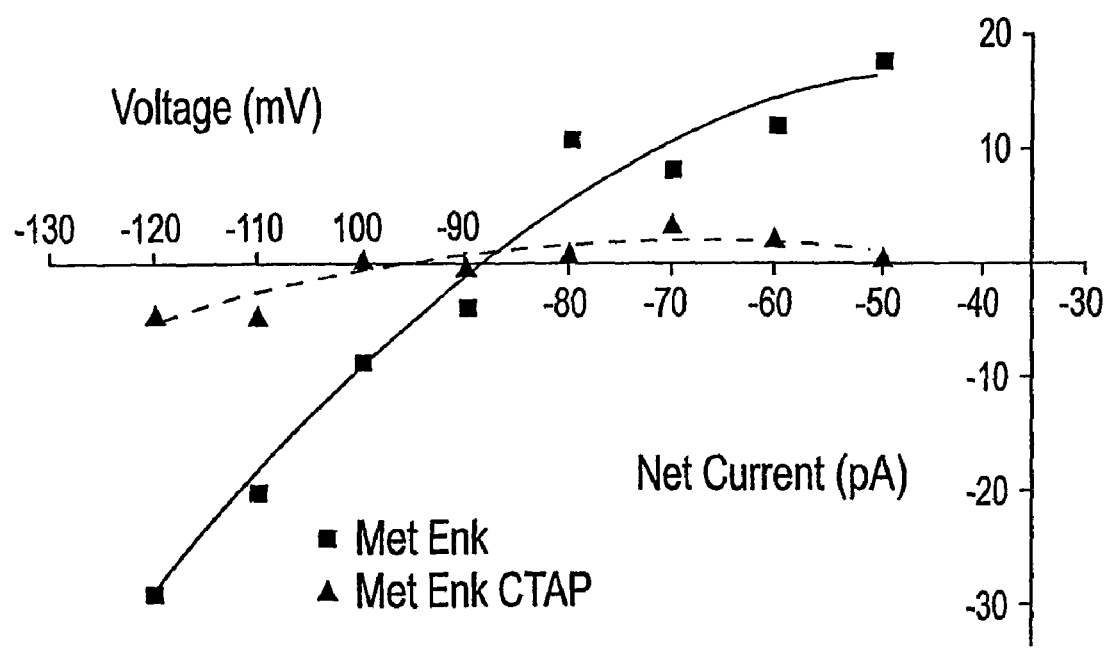
FIG. 2c is a graph showing met-enkephalin activates MOP-Rs on POMC neurons. A Met-Enk (30 μM) current was observed and the MOP-R specific antagonist CTAP (1 μM) was applied for 1 minute. Following CTAP Met-Enk elicited no current. The figure is representative of three experiments.

POMC-EGFP neurons in hypothalamic slices had a resting membrane potential of −40 to −45 mV and exhibited frequent spontaneous action potentials. The non-selective opioid agonist met-enkephalin (Met-Enk: 30 μM; Sigma) caused a rapid (35-40 s), reversible hyperpolarization (10-20 mV) of the membrane potential of POMC cells (n=10) and prevented spontaneous action potential generation (FIG. 2a). In normal (2.5 mM $K^+$) Krebs buffer, the reversal-potential of the inwardly-rectifying opioid current was approximately −90 mV, while in 6.5 mM $K^+$ Krebs the reversal-potential was shifted to approximately −60 mV (n=3: FIG. 2b). The μ opioid receptor (MOP-R) antagonist CTAP (1 μM; Phoenix Pharmaceuticals) completely prevented the current induced by Met-Enk in POMC cells (n=3: FIG. 2c). These characteristics indicate the opioid current was due to activation of MOP-R and increased ion conductance through G protein coupled, inwardly-rectifying potassium channels (GIRK) (Kelly et al., *Neuroendocrinology* 52, 268-75, 1990). The similar opioid responses in EGFP-labeled POMC neurons to that of a guinea pig (Kelly et al., *Neuroendocrinology* 52, 268-75, 1990) or mouse (Slugg et al., *Neuroendocrinology* 72, 208-17, 2000). POMC cells, identified by post-recording immunohistochemistry, suggests that expression of the EGFP transgene does not compromise either expression of receptors nor their coupling to second messenger systems in POMC neurons.

Figure 3A:
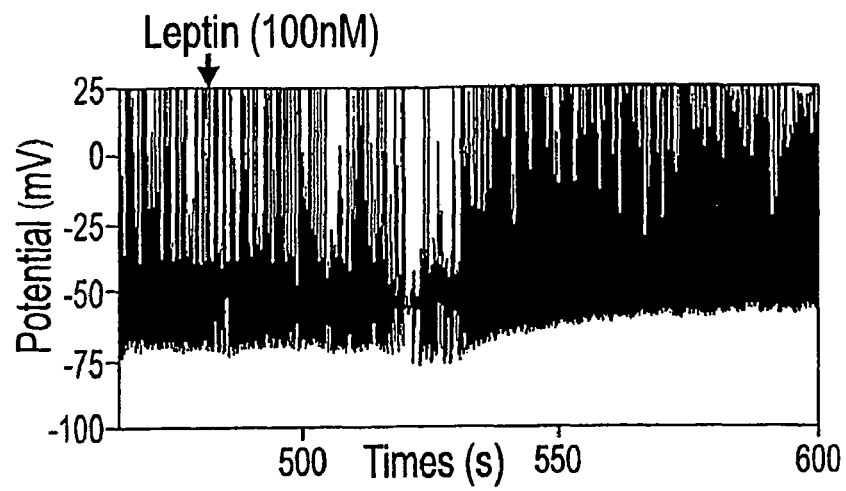
FIG. 3a is a tracing demonstrating that leptin depolarizes POMC neurons and increases the frequency of action potentials within 1 to 10 minutes of addition. The figure is a representative example of recordings made from 77 POMC neurons.
Figure 3B:
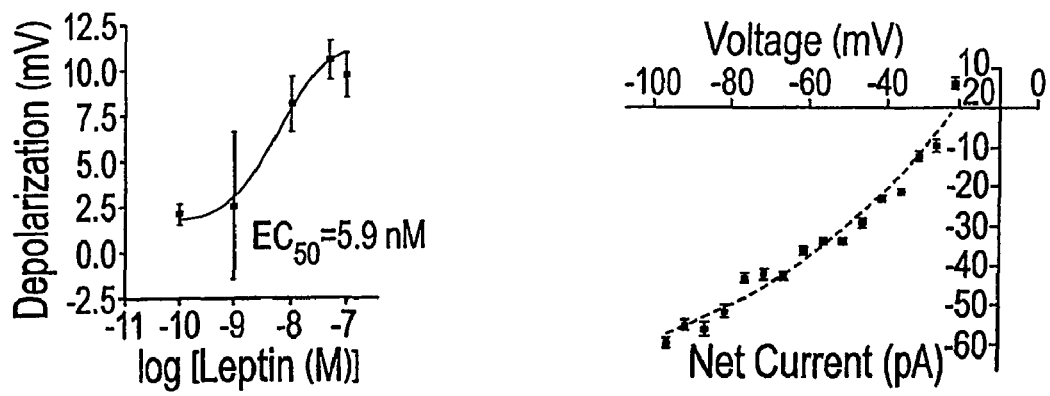
FIG. 3b is a graph showing that leptin causes a concentration dependent depolarization of POMC cells. The depolarization caused by leptin was determined at 0.1, 1, 10, 50, and 100 nM ($EC_{50}$=5.9 nM) in (8, 7, 9, 3, 45) cells respectively.
Figure 3C:
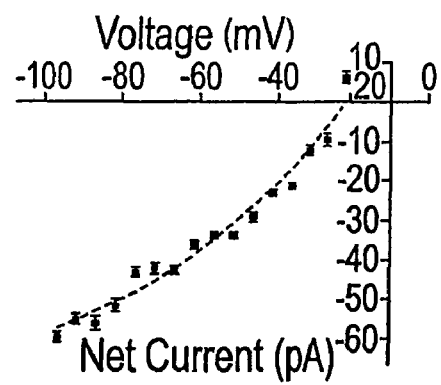
FIG. 3c is a graph showing that leptin depolarizes POMC cells by activating a nonspecific cation current. The figure is representative of the response in 10 cells.
Figure 3D:
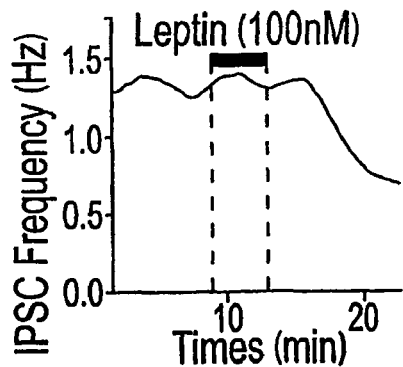
FIG. 3d is a graph showing that leptin decreases the frequency of IPSCs in POMC cells. The figure is an example of 5 cells in which leptin (100 nM) decreased the frequency of IPSCs.
Figure 3E:
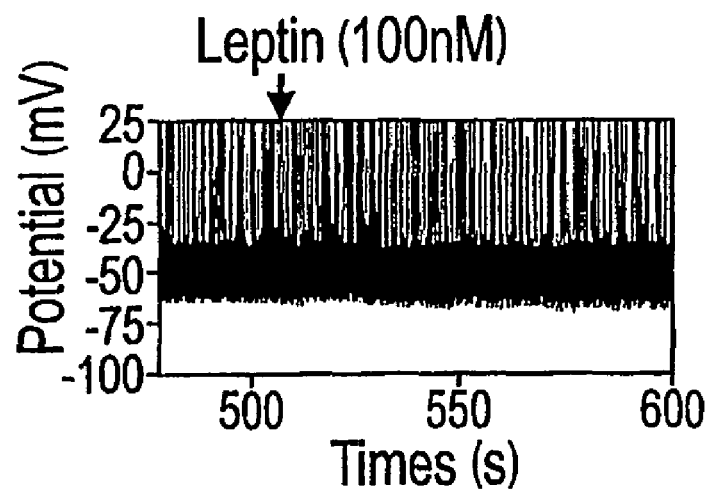
FIG. 3e is a tracing demonstrating that leptin had no effect on 5 adjacent non-fluorescent ARC neurons.
Figure 3F:
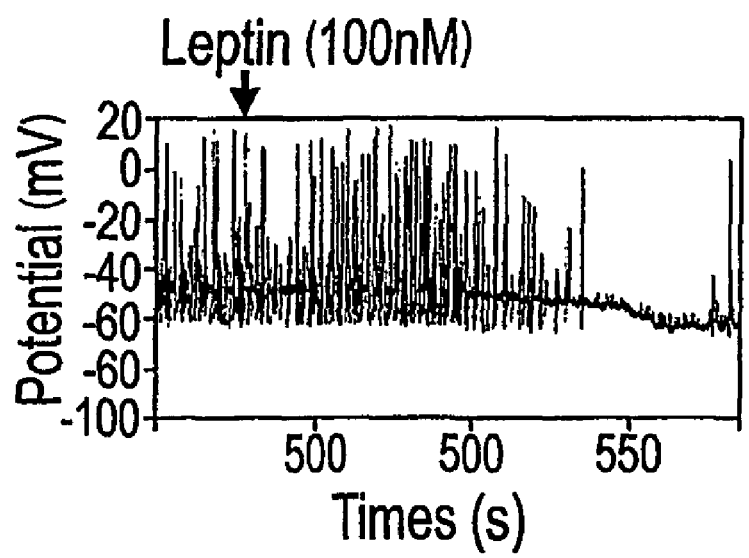
FIG. 3f is a tracing showing that leptin hyperpolarized 5 non-fluorescent ARC neurons.

Next, the direct effects of leptin on identified POMC cells in slice preparations were investigated. Leptin (0.1-100 nM) depolarized 72 of 77 POMC cells by 3-30 mV (FIG. 3a, mean±SEM depolarization at 100 nM leptin=9.7±1.2 mV, n=45) within 2-10 minutes, in a concentration responsive manner (FIG. 3b). There were two components to the depolarization and neither were fully reversible within 40 minutes. Firstly, the depolarization was due to a small inward current which reversed at approximately −20 mV (FIG. 3c), suggesting the involvement of a non-specific cation channel (Powis et al., *Am J Physiol* 274, R1468-72, 1998). Secondly, leptin treatment decreased the GABAergic tone onto POMC cells. GABAergic inhibitory postsynaptic currents (IPSCs) were observed in POMC cells and leptin (100 nM) decreased their frequency by 25% (FIG. 3d) in 5 out of 15 cells suggesting that it acted presynaptically to reduce GABA release (leptin had no effect on IPSCs in 10 out of 15 POMC neurons). The effect on IPSC frequency occurred with a similar lag to the effect on membrane potential. Thus, leptin not only directly depolarizes POMC neurons but also acts at GABAergic nerve terminals to reduce the release of GABA onto POMC neurons, allowing them to adopt a more depolarized resting potential. The consistent depolarization of POMC cells by leptin was specific because leptin had no effect on 5 of 13 adjacent non-fluorescent cells tested (FIG. 3e), while it hyperpolarized 5 (FIG. 3f) and depolarized 3 other non-POMC neurons in the ARC. The electrophysiological effects of leptin reported here are consistent with leptin's biological actions; leptin rapidly causes release of α-MSH from rat hypothalami (Kim et al., *J Clin Invest* 105, 1005-11, 2000), presumably by activating POMC neurons.

Figure 4A:
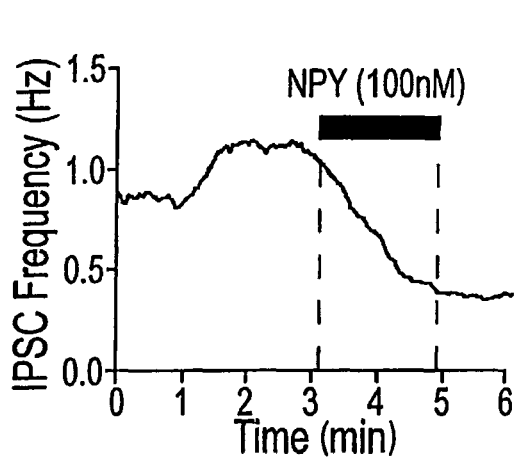
FIG. 4a is a graph showing that NPY decreases the frequency of mini IPSCs in POMC neurons.

Previous reports of neuronal hyperpolarization by leptin (Glaum et al., *Mol Pharmacol* 50, 230-5, 1996; Spanswick et al., *Nature* 390, 521-5, 1997), and the demonstrated co-localization of GABA and NPY (Horvath et al., *Brain Res* 756, 283-6, 1997) within subpopulations of ARC neurons, led us to speculate that leptin hyperpolarizes NPY/GABA cells that directly innervate POMC neurons, and thus reduces GABAergic drive onto POMC cells. Both the leptin and NPY Y2 receptors are expressed on NPY neurons in the ARC (Hakansson et al., *J Neurosci* 18, 559-72, 1998; Broberger et al., *Neuroendocrinology* 66, 393-408, 1997). Furthermore, activation of Y2 receptors inhibits NPY release from NPY neurons (King et al., *J Neurochem* 73, 641-6, 1999), and presumably would also diminish GABA release from NPY/GABA terminals. This is an alternative pharmacological approach, independent of leptin, to test the hypothesized innervation of POMC neurons by GABAergic NPY neurons. Indeed, NPY (100 nM; Bachem) decreased the frequency of GABAergic IPSCs by 55% within 3 minutes, in all 12 POMC cells tested (FIG. 4a). Both NPY and leptin still inhibited IPSCs in the presence of tetrodotoxin (TTX) (6 of 6 and 3 of 5 cells respectively), indicating that some of the inhibition of IPSCs was occurring through direct effects at presynaptic nerve terminals. POMC neurons express the NPY Y1 receptor (Broberger et al., *Neuroendocrinology* 66, 393-408, 1997) and NPY also hyperpolarized all POMC neurons tested, by an average of 9±6 mV (n=3).

Figure 4B:
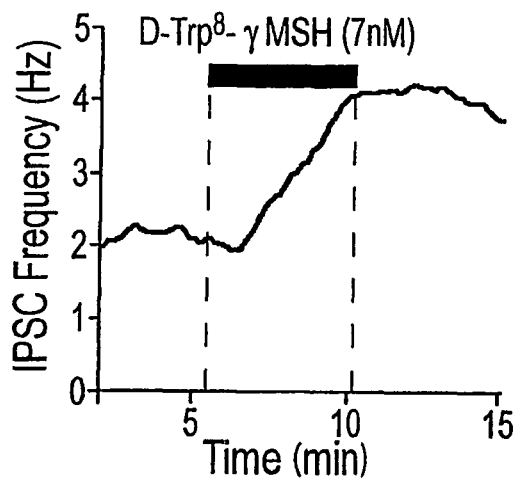
FIG. 4b is a graph demonstrating that D-Trp$^8$-γMSH (7 nM), a dose that selectively activates MC3-R, increases the frequency of GABAergic IPSCs in POMC neurons.
Figure 4C:
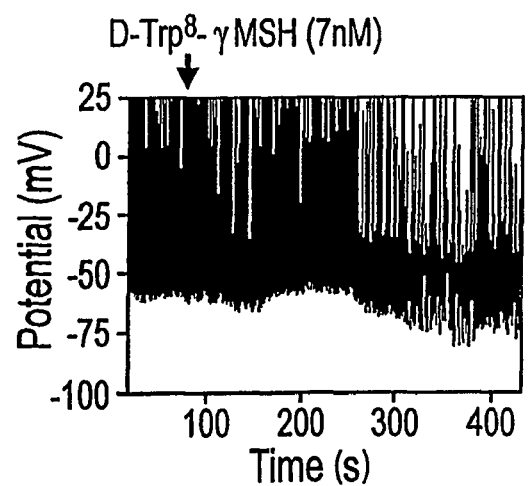
FIG. 4c is a tracing showing that D-Trp$^8$-γMSH hyperpolarizes POMC neurons.

Another pharmacological test to confirm the origin of GABAergic innervation on POMC neurons from NPY/GABA terminals was to test the effect of the recently characterized and highly selective MC3-R agonist D-Trp$^8$-γMSH (Grieco et al., *J Med Chem* 43, 4998-5002, 2000) on local GABA release. D-Trp$^8$-γMSH (7 nM) increased the frequency of GABAergic IPSCs (280±90%) recorded from 3 of 4 POMC neurons (FIG. 4b). It had no effect on one cell. The positive effect of MC3-R activation, together with the negative effects of NPY and leptin, demonstrate the dynamic range of the NPY/GABA synapse onto POMC neurons and point to the important role of this synapse in modulating signal flow within the ARC. D-Trp$^8$-γMSH (7 nM) also hyperpolarized (−5.5±2.4 mV) 9 of 15 POMC neurons tested and decreased the frequency of action potentials (FIG. 4c); the remaining cells showed no significant response to D-Trp$^8$-γ MSH. These effects could be due entirely to increased GABA release onto the POMC cells, or could be due to an additional postsynaptic action of D-Trp$^8$-γMSH on POMC neurons, approximately half of which also express the MC3-R (Bagnol et al., *J Neurosci (Online)* 19, RC26, 1999). Thus, MC3-R acts in a similar autoreceptor manner to MOP-Rs on POMC neurons, diminishing POMC neuronal activity in response to elevated POMC peptides.

To further determine that the IPSCs in POMC neurons were due to local innervation by NPY/GABA cells, multilabel immunohistochemistry was performed using light and electron microscopy. Although independent NPY (Csiffary et al., *Brain Res* 506, 215-22, 1990) and GABA (Horvath et al., *Neuroscience* 51, 391-9, 1992) innervation of POMC cells has been reported, co-localization of NPY and GABA in nerve terminals forming synapses onto POMC cells has not been shown. Similar to the rat (Csiffary et al., *Brain Res* 506, 215-22, 1990), a dense innervation of POMC cells by NPY axon terminals was detected in the mouse (FIG. 4d). Electron microscopy confirmed the coexpression of NPY and GABA in axon terminals and revealed that these boutons established synapses on the perikarya of all 15 ARC POMC neurons analyzed (representative example, FIG. 4e).

A detailed model of regulation of this circuit shows dual mechanisms of leptin action in the ARC, interactions between NPY/GABA and POMC neurons, and autoregulatory feedback from opioid and melanocortin peptides as well as NPY (FIG. 4f). In this model, leptin directly depolarizes the POMC neurons and simultaneously hyperpolarizes the somata of NPY/GABA neurons, and diminishes release from NPY/GABA terminals. This diminished GABA release disinhibits the POMC neurons, and result in an activation of POMC neurons and an increased frequency of action potentials.

Example 3

Administration of PYY Inhibits Food Intake

The orexigenic NPY and the anorectic alpha melanocortin stimulating hormone (α-MSH) systems of the hypothalamic arcuate nucleus are involved in the central regulation of appetite (Schwartz et al., *Nature* 404, 661-671, 2000). However the potential mechanisms signaling meal ingestion directly to these hypothalamic-feeding circuits are unclear. $PYY_{3-36}$ is a gut-derived hormone that is released postprandially in proportion to the calories ingested (Pedersen-Bjergaard et al., *Scand. J. Clin. Lab. Invest.* 56, 497-503, 1996). The effects of peripheral administration of $PYY_{3-36}$ on feeding were investigated.

Figure 5A:
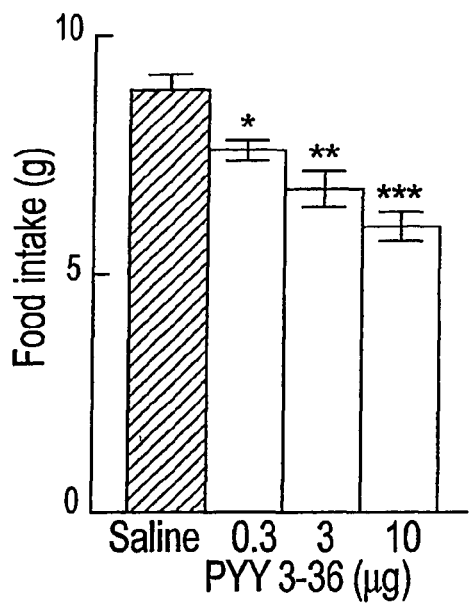
FIG. 5a is a bar graph of dark-phase feeding tabulating food intake after intraperitoneal injection of $PYY_{3-36}$. Freely feeding rats were injected with $PYY_{3-36}$ at the doses indicated (μg/100 g), or saline, just prior to 'lights off' and 4-hour cumulative food intake was measured. Results are the mean±s.e.m. (n=8 per group), *=p<0.05, =p<0.01, *=<0.001 compared to saline.
Figure 5B:
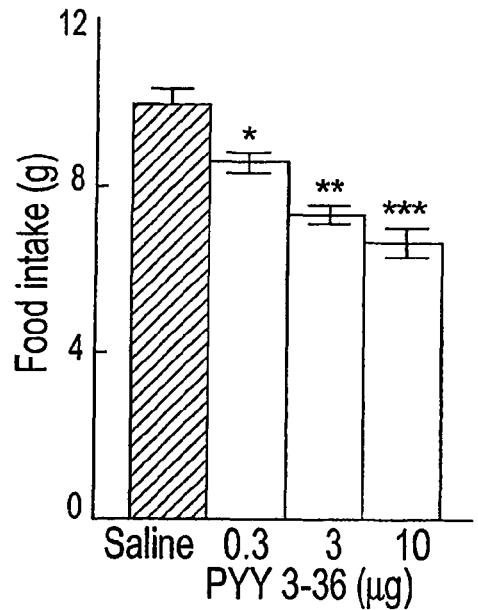
FIG. 5b is a bar graph of food intake after intraperitoneal injection of $PYY_{3-36}$. Fasted rats were injected with $PYY_{3-36}$ at the doses indicated (μg/100 g), or saline, and 4-hour cumulative food intake was measured. Results are shown as the mean±s.e.m. (n=8 per group), *=p<0.05, =p<0.01, *=<0.001 compared to saline.
Figure 5C:
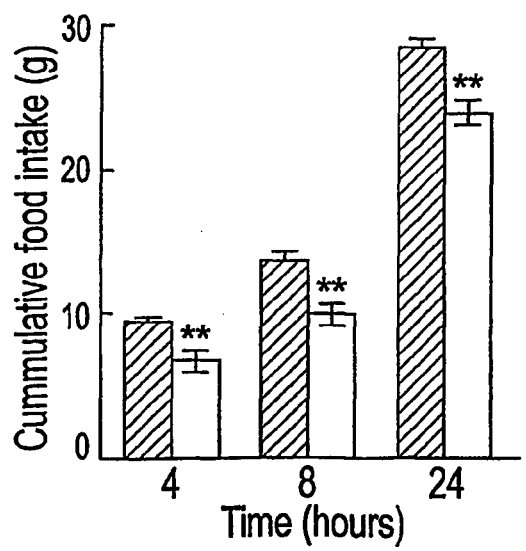
FIG. 5c is a bar graph of cumulative food intake after intraperitoneal injection of saline or $PYY_{3-36}$. Fasted rats were injected with either saline (closed bars) or $PYY_{3-36}$ 5 μg/100 g (open bars) and cumulative food intake measured at the time points indicated. Results are expressed as mean±s.e.m. (n=12 per group), =p<0.01 compared to saline.
Figure 5D:
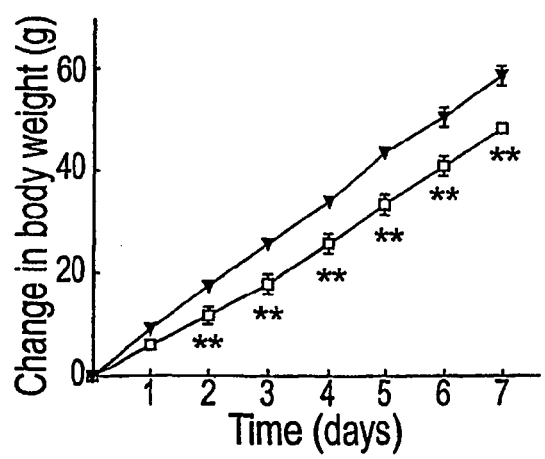
FIG. 5d is a line graph of body weight gain during chronic treatment with $PYY_{3-36}$. Rats were injected intraperitoneally with $PYY_{3-36}$ 5 μg/100 g (open squares) or saline (filled inverted triangles) twice daily for 7 days. Body weight gain was calculated each day. Results are expressed as mean±s.e.m. (n=12 per group) =p<0.01 compared to saline.

An intraperitoneal injection (IP) of $PYY_{3-36}$ to freely feeding rats, prior to the onset of the dark-phase, significantly decreased subsequent food intake (FIG. 5a). A similar inhibition of feeding was seen following IP injection in rats fasted for 24 hours (FIG. 5b). A time course of the plasma $PYY_{3-36}$ levels achieved following IP injection of $PYY_{3-36}$ demonstrated a peak level at 15 minutes post injection, which was within the normal postprandial range (peak $PYY_{3-36}$ levels 15 minutes post IP injection of 0.3 µg/100 g=99.3±10.4 pmol/l vs. peak postprandial level=112.1±7.8 pmol/l, n=8-10 per group), suggesting that physiological concentrations of $PYY_{3-36}$ inhibit feeding. $PYY_{3-36}$ did not affect gastric emptying (percentage of food ingested remaining in the stomach at 3 hours: $PYY_{3-36}$=36±1.9%, saline=37.4±1.0% n=12 ) (Barrachina et al., *Am. J. Physiol.* 272, R1007-11, 1997). $PYY_{3-36}$ administered IP twice daily for 7 days reduced cumulative food intake (7-day cumulative food intake: $PYY_{3-36}$= 187.6±2.7 g vs. saline=206.8±2.3, n=8 per group, P<0.0001) and decreased body weight gain (FIG. 5d) ($PYY_{3-36}$= 48.2±1.3 g vs. saline=58.7±1.9, n=8 per group, P<0.002).

Example 4

PYY Administration Affects c-fos Expression

To investigate whether this inhibition of food intake involved a hypothalamic pathway, c-fos expression was examined in the arcuate nucleus, an important center of feeding control (Schwartz et al., *Nature* 404, 661-671, 2000; Cowley et al., *Nature* 411, 480-484, 2001), following a single IP injection of $PYY_{3-36}$. There was a 2-fold increase in the number of cells positive for c-fos in the lateral arcuate of the rat ($PYY_{3-36}$=168±2, saline=82.7±5, n=3, P<0.0001). Likewise in Pomc-EGFP-transgenic mice (Cowley et al., *Nature* 411, 480-484, 2001) IP administration of $PYY_{3-36}$ resulted in a 1.8-fold increase in the number of arcuate cells positive for c-fos (FIG. 6b), compared with saline control animals (FIG. 6a) ($PYY_{3-36}$=250±40, saline=137±15, n=5, P<0.05). IP $PYY_{3-36}$ caused a 2.6 fold increase in the proportion of POMC neurons that express c-fos ($PYY_{3-36}$=20.4±2.9%, saline=8±1.4%, n=5, P<0.006) (FIGS. 6c and d).

These observations suggested that $PYY_{3-36}$ may act via the arcuate nucleus. Thus, the actions of $PYY_{3-36}$, and its effects upon NPY and POMC circuits in the hypothalamus, were studied. In view of the sustained inhibition of food intake and the effects on weight gain following peripheral administration of $PYY_{3-36}$ both Pomc and Npy hypothalamic messenger RNA (mRNA) were measured using RNase protection assays. A significant decrease in Npy mRNA in response to $PYY_{3-36}$ was observed 6 hours post IP injection, compared with saline treated animals (saline=17.3±2.0, $PYY_{3-36}$=8.8±1.0, relative optical density units, P<0.02). A non-significant increase occurred in Pomc mRNA levels.

Example 5

Y2 Receptors $PYY_{3-36}$ shows a 70% amino acid sequence identity to NPY and acts through NPY receptors (Soderberg et al., *J. Neurochem.* 75, 908-18, 2000). The Y2R is a putative inhibitory presynaptic receptor and is highly expressed on the arcuate NPY neurons (Broberger et al., *Neuroendocrinology* 66, 393-408, 1997), though not on the neighboring POMC neurons. $PYY_{3-36}$ is a high affinity agonist at the Y2 receptor (Grandt et al., *Regul. Pept.* 51, 151-159, 1994). It was hypothesized that peripheral $PYY_{3-36}$ inhibits food intake via the Y2R in the arcuate nucleus, an area known to be directly accessible to circulating hormones (Kalra et al., *Endocr. Rev.* 20, 68-100, 1999).

Figure 7A:
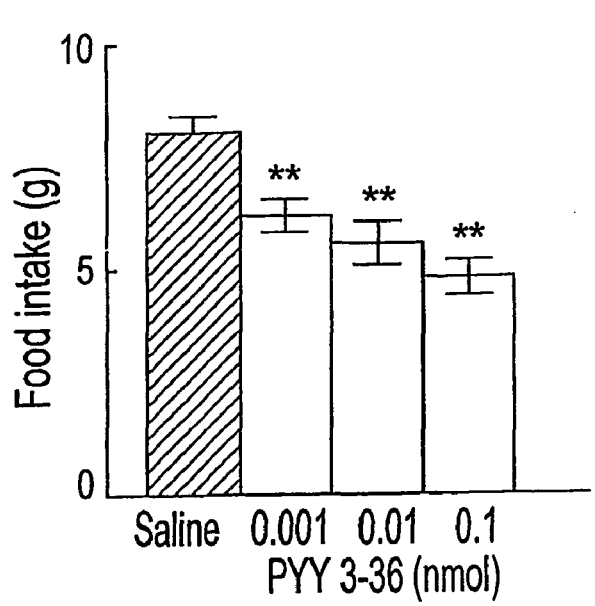
FIG. 7a is a bar graph of food intake following intra-arcuate $PYY_{3-36}$ injection. Fasted rats were injected with saline or $PYY_{3-36}$ into the arcuate nucleus at the doses indicated. Post-injection 2-hour food intake was measured, **=p<0.01 compared to saline.

To investigate this hypothesis, $PYY_{3-36}$ was injected directly into the arcuate nucleus (Kim et al., *Diabetes* 49, 177-82, 2000). In rats fasted for 24 hours, food intake was significantly decreased by doses as low as 100 fmol (FIG. 7a), resulting in a similar inhibition to that seen following IP administration. To establish whether these effects were via the Y2R, aY2R selective agonist was used (Potter et al., *Eur. J. Pharmacol.* 267, 253-262, 1994), N-acetyl ($Leu^{28}$, $Leu^{31}$) NPY (24-36) [Y2A]. Its affinity was confirmed using receptor-binding studies (Small et al., *Proc. Natl. Acad. Sci. U.S.A.* 94, 11686-91, 1997) on cell lines expressing the NPY Y1, Y2 and Y5 receptors (Y2 $IC_{50}$=1.3±0.2 nM, Y1 $IC_{50}$>5000 nM, Y5 $IC_{50}$>5000 nM). Intra-arcuate nucleus injection of Y2A in rats previously fasted for 24 hours dose-dependently (100 fmol-1 nmol) inhibited food intake (chow ingested 2 hours post-injection, 0.1 nmol Y2A=6.2±0.5 g, saline=8.2±0.6 g, n=8 per group, P<0.05).

Figure 7B:
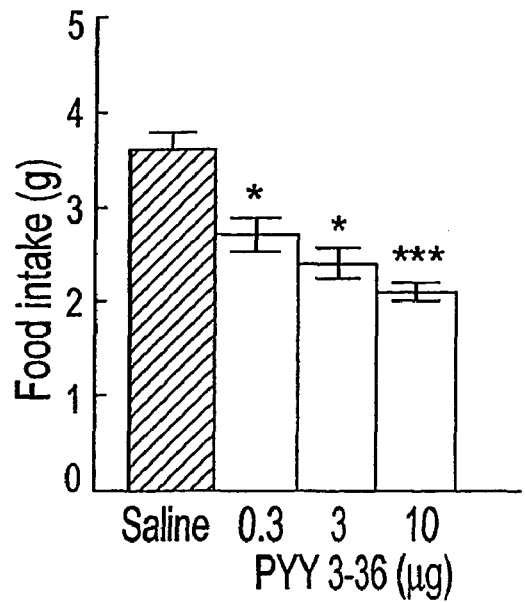
FIGS. 7b and 7c are bar graphs of feeding response to $PYY_{3-36}$ in Y2r-null mice following IP administration: wild type littermates mice (FIG. 7b) and Y2r-null mice (FIG. 7c), fasted for 24 hours, were injected with $PYY_{3-36}$ at the doses indicated (μg/100 g), or saline, and 4-hour cumulative food intake was measured. Results are the mean±s.e.m. (n=5 per group), *=p<0.05, **=p<0.01 compared to saline.
Figure 7C:
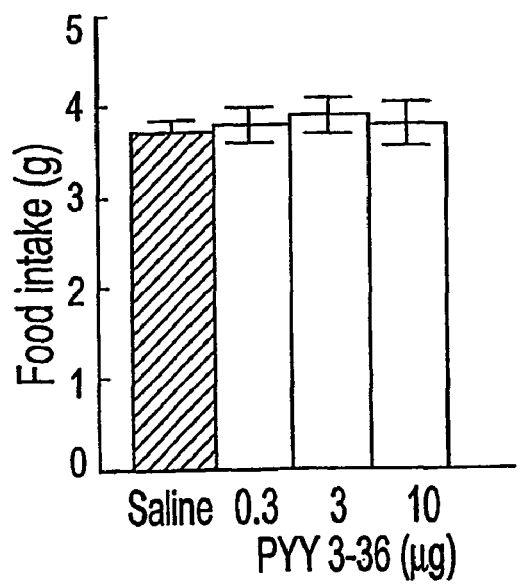

To confirm the anatomical specificity of this effect Y2A (100 fmol-1 nmol) was injected into the paraventricular nucleus (PVN) (Kim et al., *J. Clin. Invest.* 105, 1005-11, 2000) of rats fasted for 24 hours and found no alteration of food intake (2 hour post-injection saline=8.3±0.4 g, 0.1 nmol Y2A=8.0±0.6 g, n=8 per group). To further determine the role of the Y2R in the feeding inhibition caused by peripheral $PYY_{3-36}$, the effect of $PYY_{3-36}$ on Y2r-null mice and littermate controls was examined. $PYY_{3-36}$ inhibited daytime feeding in a dose responsive manner in fasted male wild-type mice but did not inhibit food intake in fasted male Y2r-null mice (FIGS. 7b and 7c). Food intake measured in response to a fast demonstrated that male Y2r-null mice eat significantly more at 2, 4 and 24 hours compared with their littermate controls (24-hour cumulative food intake; Y2r-null mice=7.1±0.48 g vs. wild-type=5.3±0.7 g, n=8 per group, P<0.05).

Figure 8A:
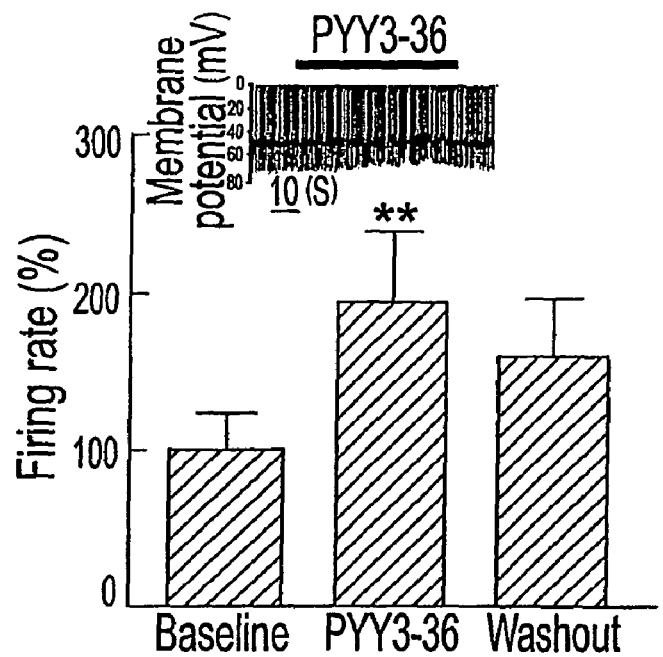
FIG. 8a is a tracing showing the effect of $PYY_{3-36}$ (10 nM) on the frequency of action potentials in POMC neurons (whole-cell configuration recordings; n=22) *p<0.05. $PYY_{3-38}$ was administered at time D for 3 minutes; baseline, −3 to 0 minute; $PYY_{3-36}$, 2-5 minutes; and wash-out, 8-11 minutes.

The electrophysiological response of hypothalamic POMC neurons to administration of both $PYY_{3-36}$ and Y2A was examined. These neurons were identified using mice with targeted expression of green fluorescent protein in POMC neurons (Cowley et al., *Nature* 411,480-484,2001). $PYY_{3-36}$ disinhibited the POMC neurons, resulting in a significant depolarization of 19 of the 22 POMC neurons tested (FIG. 8a inset) (10.3±2.1 mV depolarization, n=22, P<0.0003). A similar depolarization was seen with Y2A (8.7±1.8 mV depolarization, n=9, P<0.002). The depolarization caused by $PYY_{3-36}$ stimulated a significant increase in the frequency of action potentials in POMC neurons (FIG. 8a) (93% increase over control, P<0.05, n=22). In the whole cell mode the effect of $PYY_{3-36}$ was sometimes reversed upon washout, but only after a long latency (30 minutes). A similar washout of leptin effects upon these neurons was observed.

Figure 8B:
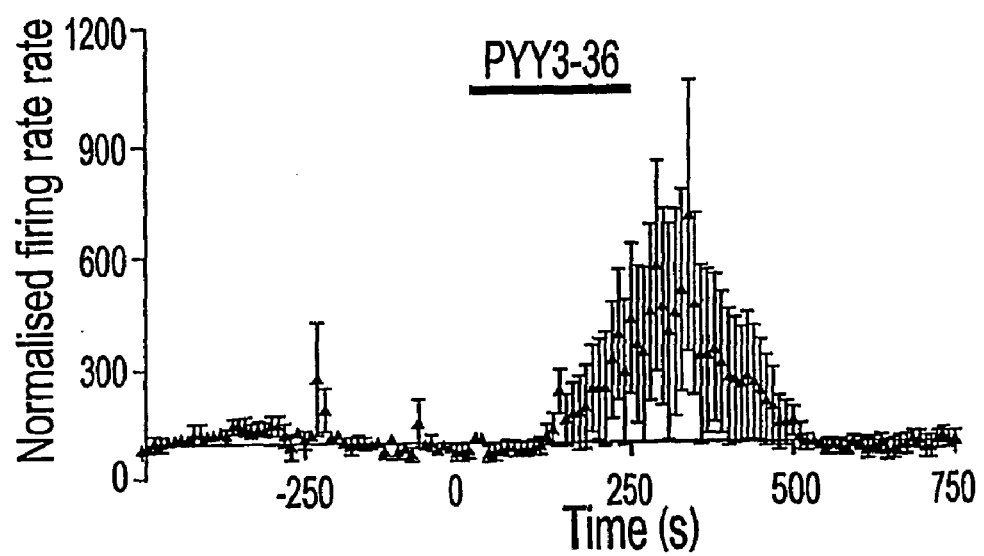
FIG. 8b is a graph of the effect if $PYY_{3-38}$ (10 nM) on the frequency of action potentials in loose cell-attached patch recordings (n=8). Data from individual cells were normalized to the firing rate for the 200 s before $PYY_{3-38}$ addition.
Figure 8C:
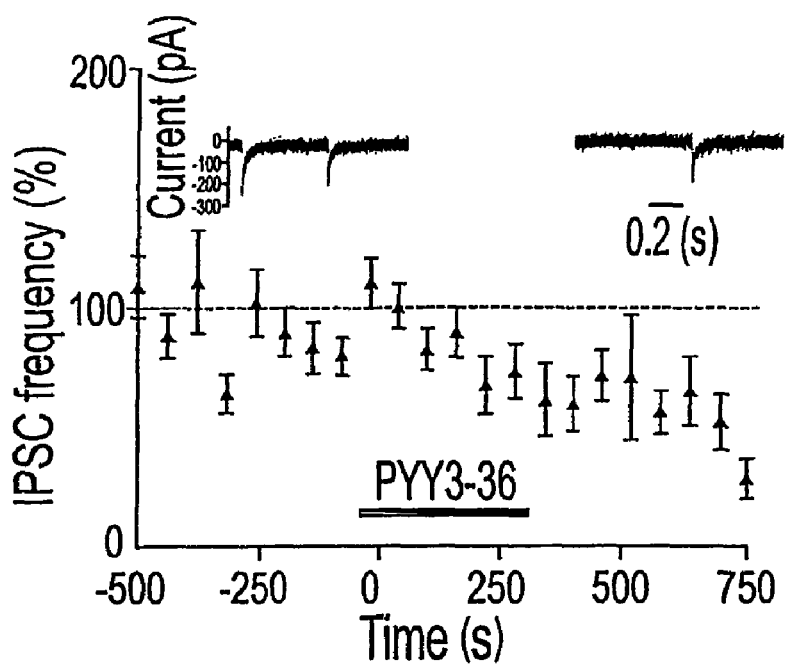
FIG. 8c is a tracing and a graph of the effect of $PYY_{3-36}$ (50 nM) on spontaneous IPSCs onto POMC neurons (n=13). Inset shows a representative recording of IPSCs before and after $PYY_{3-36}$ (50 nM), respectively. Results in FIG. 8a-8c are expressed as mean∀s.e.m.
Figure 8D:
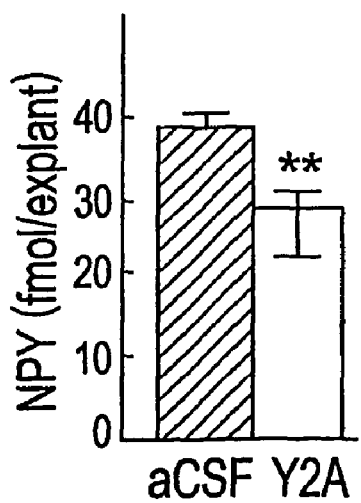
FIG. 8d and 8e are bar graphs showing NPY (FIG. 8d) and %-MSH (FIG. 8e) released from hypothalamic explants in response to Y2A. Hypothalamic slices were incubated with artificial CSF (aCSF), with or without 50 nM Y2A, for 45 minutes. Results are expressed mean∀s.e.m. (n=40); \*\*=p<0.01; \*\*\*=p<0.001 compared to saline.
Figure 8E:
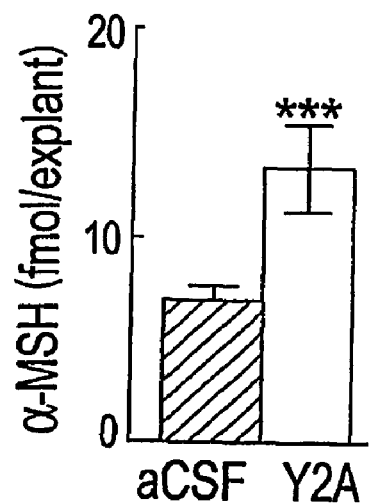

To exclude effects of cellular rundown, or seal deterioration, the effects of $PYY_{3-36}$ in the "loose cell-attached" (or extracellular) configuration was examined. $PYY_{3-36}$ caused a reversible 5-fold increase in the frequency of action potentials in loose cell-attached recordings of POMC neurons (FIG. 8b). This increase in firing rate occurred with the same latency as $PYY_{3-36}$ reduced the frequency of inhibitory postsynaptic currents (IPSCs) onto all 13 POMC neurons tested (FIG. 8c) (51.9±9.2% reduction, n=13, P<0.0001), indicating a reduced frequency of GABA release onto POMC neurons. Interestingly, the firing rate of POMC neurons returned to basal, in spite of continued inhibition of IPSCs. A similar effect upon IPSC frequency was seen with Y2A (44.4±9.3% reduction, n=8, P<0.004) suggesting this effect to be via Y2R. $PYY_{3-36}$ (25 nM) caused a hyperpolarization (5.2±1.16 mV, P<0.004, n=5) of unidentified, but presumably NPY-containing, non-POMC, neurons in the arcuate nucleus. There is a tonic GABAergic inhibition of POMC neurons by NPY neurons (Cowley et al., *Nature* 411, 480-484, 2001) and these results suggest that $PYY_{3-36}$ acts by inhibiting NPY neurons, thus decreasing this GABAergic tone and consequentially disinhibiting POMC neurons. The effect of Y2A on peptide secretion was also examined using hypothalamic explants (Kim et al., *J. Clin. Invest.* 105, 1005-11, 2000). Y2A significantly decreased NPY release, with a concomitant increase in α-MSH release from hypothalamic explants (FIGS. 8*d* and 4*e*). Taken together, these observations suggest that $PYY_{3-36}$ modulates both the NPY and melanocortin systems in the arcuate nucleus.

Example 6

Human Studies

Because of the importance of the melanocortin system in man (Barsh et al., *Nature* 404, 644-651, 2000) and the profound effects of $PYY_{3-36}$ on both feeding and weight change seen in rodents, the effects of $PYY_{3-36}$ on appetite and food intake were investigated in human subjects. Twelve healthy fasted, non-obese volunteers (six men and six women, mean age 26.7±0.7 years, BMI=24.6±0.94 $kg.m^{-2}$) were infused with $PYY_{3-36}$ (0.8 $pmol.kg^{-1}.min^{-1}$) or saline for 90 minutes in a double-blind placebo controlled crossover study.

Figure 9A:
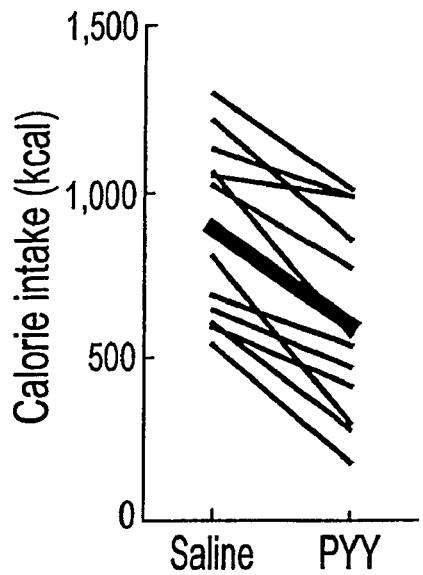
FIG. 9a is a graph of the calorie intake from a "free-choice" buffet meal 2 hours after infusion with saline or $PYY_{3-36}$. The thin lines indicate individual changes in calorie intake for each subject between saline and $PYY_{3-36}$ administration. The thick line represents mean change between the two infusions (n=12).
Figure 9B:
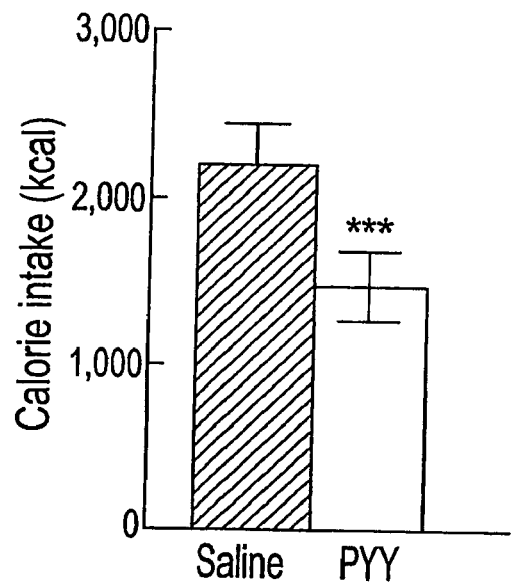
FIG. 9b is a graph of the 24-hour calorie intake following infusion with saline or $PYY_{3-36}$. Total calorie intake, as assessed by food diaries, is shown for the 24-hour period following either saline or $PYY_{3-36}$ infusion. Data is given as mean±s.e.m. (n=*2,\*\*\*=p<0.0001 compared to saline.
Figure 9C:
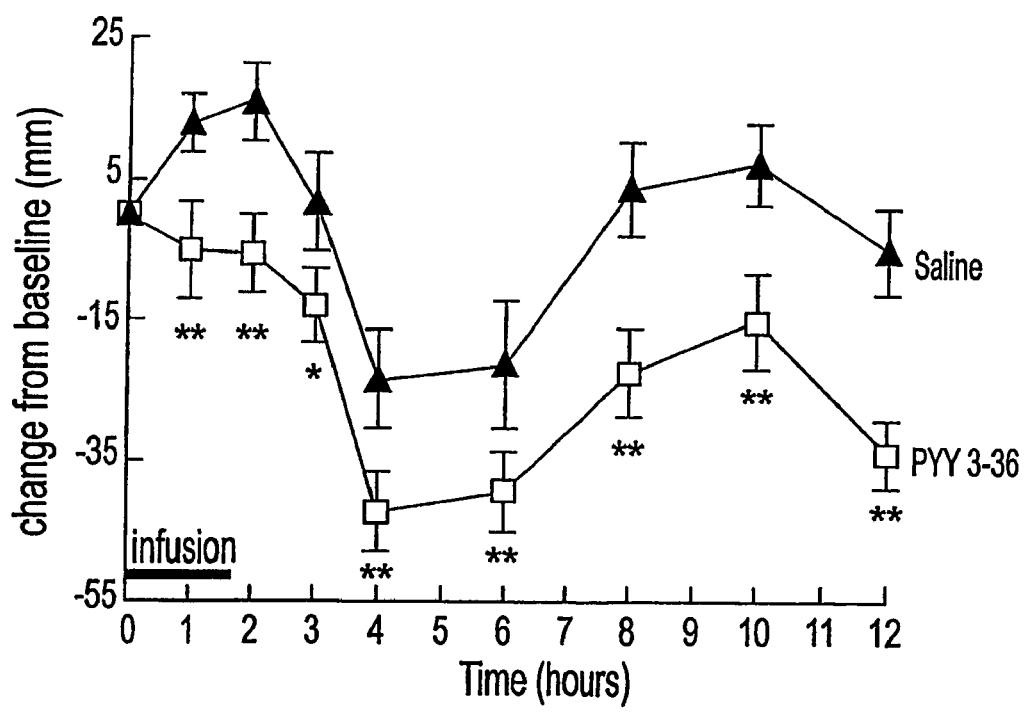
FIG. 9c is a graph of the appetite score (relative scale). Visual analogue scores (Raben et al., *Br. J. Nutr.* 73, 517-30, 1995) show perceived hunger during and after infusions. The results are presented as change from baseline scores and are the mean±s.e.m. for all 12 subjects.

$PYY_{3-36}$ plasma concentrations increased from mean basal concentration of 8.3±1.0 pM to 43.5±3 pM during the $PYY_{3-36}$ infusion and mimicked postprandial levels (Pedersen-Bjergaard et al., *Scand. J. Clin. Lab. Invest.* 56, 497-503, 1996; Adrian et al., *Gastroenterology* 89, 1070-1077, 1985). Post-infusion, $PYY_{3-36}$ concentrations returned to basal within 30 minutes. $PYY_{3-36}$ infusion resulted in a significant decrease in hunger scores (Raben et al., *Br. J. Nutr.* 73, 517-30, 1995) (FIG. 9*c*), but not in the scores for sleepiness or sickness. Calorie intake during a free-choice buffet meal (Tarling et al., *Intensive Care Med.* 23, 256-260, 1997) two hours after the termination of the infusion was reduced by over a third compared to saline (36±7.4%, p<0.0001) (FIG. 9*a*). There was no effect upon fluid intake and no difference in sensations of fullness or nausea reported by the volunteers. $PYY_{3-36}$ administration had no effect on gastric emptying, as estimated by the paracetamol absorption method (Edwards et al., *Am. J. Physiol. Endocrinol. Metab.* 281, E155-E166, 2001; Tarling et al., *Intensive Care Med.* 23, 256-260, 1997), or on plasma glucose, plasma leptin, GLP-1, or insulin. Analysis of the food diaries revealed a significant inhibition of food intake in the 12-hour period following the $PYY_{3-36}$ infusion (saline=2205±243 kcal, $PYY_{3-36}$=1474±207 kcal). However, food intake during a 12 to 24 hour period between the two groups was virtually identical. Overall there was a 33% decrease in cumulative total calorie consumption in the 24-hour period following the $PYY_{3-36}$ infusion (FIG. 9*b*). These findings demonstrate that infusion of $PYY_{3-36}$, matching postprandial levels, caused a marked inhibition of both appetite and food intake in man.

In an additional study, two groups of healthy subjects (n=12 per group, 6 males and 6 females), one with increased Body Mass Index (BMI) (mean=32.73±0.93 kg/m2) and another group with low BMI (mean=20.49±2.05 kg/m2), were studied on two occasions with at least 1 week between each study. All subjects fasted and drank only water from 20:00 hours on the evening prior to each study. Subjects arrived at 08:30 on each study day, were cannulated and then allowed to relax for 30 minutes prior to the onset of the study protocol. Subjects were infused with either saline or 0.8 pmol.kg1.min-1 $PYY_{3-36}$ for 90 minutes, in a double blind randomized crossover design. Two hours after the termination of the infusion, subjects were offered an excess free-choice buffet meal, such that all appetites could be satisfied. Food and water were weighed pre- and postprandially and caloric intake calculated. Caloric intake following saline and $PYY_{3-36}$ were compared using a paired t test (p<0.001). The number of calories ingested following administration of $PYY_{3-36}$ differed significantly from the number of calories ingested following administration of saline for both the overweight group and the lean group. The overweight group showed a 28.8±4.3% reduction and the lean group a 31.1±4.4% reduction. However, the reduction for the overweight group did not differ significantly from the reduction for the lean group. These findings demonstrate that infusion of $PYY_{3-36}$, matching postprandial levels, caused a marked inhibition of both appetite and food intake in both lean and overweight subjects.

Figure 10:
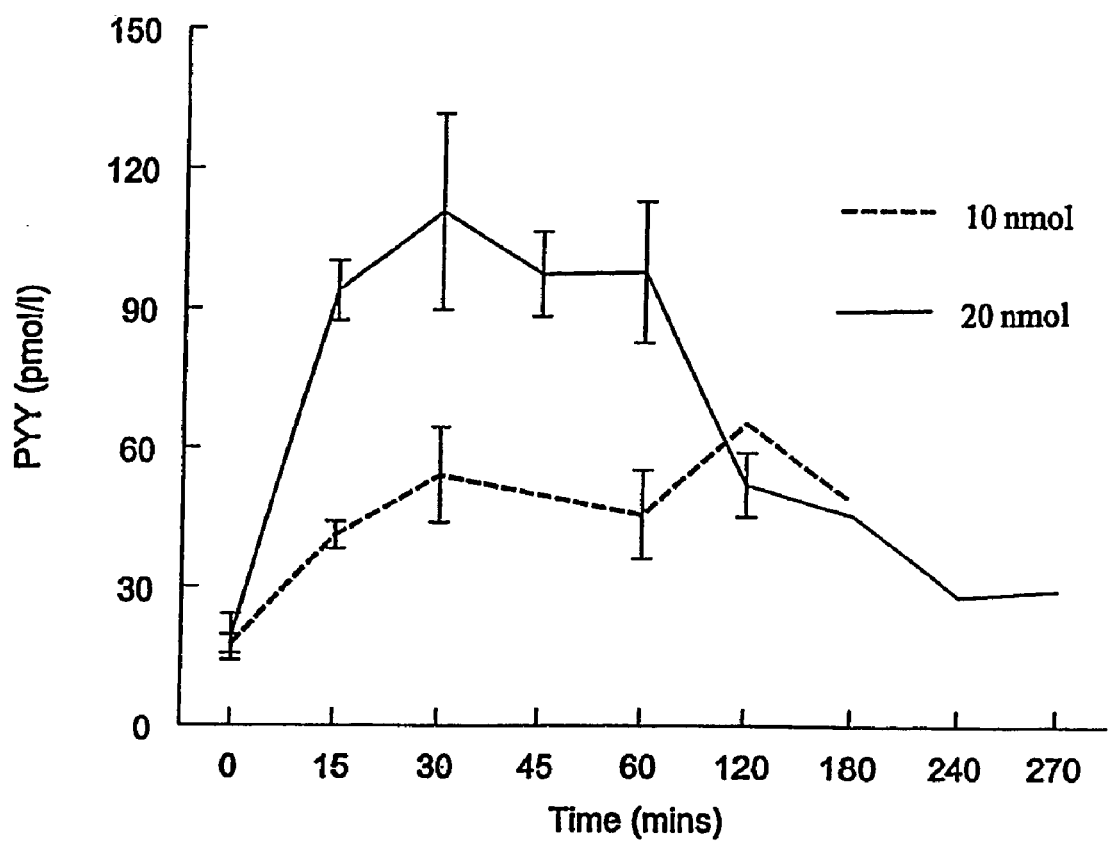
FIG. 10 shows plasma $PYY_{3-36}$ levels following subcutaneous administration of 10 nmols $PYY_{3-36}$ (broken line) and 20 nmols $PYY_{3-36}$ (solid line).

Administration of $PYY_{3-36}$ at doses of 10 nmoles and 20 nmoles (in saline) subcutaneously to human subjects resulted in raised plasma levels of $PYY_{3-36}$ as shown in FIG. 10.

Without being bound by theory, cells within the arcuate nucleus could detect circulating peripheral satiety signals and relay these signals to other brain regions (Butler et al., *Nature Neuroscience* 4, 605-611, 2001). This is supported by the observation that leptin modifies the activity of both the POMC and NPY arcuate neurons (Cowley et al., *Nature* 411, 480-484, 2001). The results disclosed herein demonstrate, through a combination of electrophysiological and hypothalamic explant studies, that the gut hormone, $PYY_{3-36}$, can directly influence hypothalamic circuits, resulting in coordinate changes in POMC and NPY action. The results presented here demonstrate that NPY neurons in the ARC are not protected by the blood/brain barrier, and thus are accessible to circulating molecules. Furthermore, $PYY_{3-36}$ administered directly into this brain region reduces food intake.

The data disclosed herein demonstrates that postprandial levels of $PYY_{3-36}$ inhibit food intake in more than one mammalian species (e.g. rodents and human subjects) for up to 12 hours, thereby demonstrating a role in regulation of food intake. This role can be described as a long term role, such as over a period of several hours (e.g. at least two, three, four, eight, or twelve hours, or from about two to about fifteen hours). This is in contrast to previously characterized gut-derived 'short-term' satiety signals, e.g. cholecystokinin (Schwartz et al., *Nature* 404, 661-671, 2000; Moran, *Nutrition* 16, 858-865, 2000), the effects of which are relatively short-lived (e.g., from about 1-4 hours).

The failure of $PYY_{3-36}$ to inhibit food intake in the Y2r-null mice provides evidence that $PYY_{3-36}$ reduces food intake via a Y2R dependent mechanism. The results disclosed herein suggest the existence of a novel gut-hypothalamic pathway in the regulation of feeding, involving postprandial $PYY_{3-36}$ acting at the arcuate Y2R. Thus, PYY, and analogs thereof, such as $PYY_{3-36}$ provide novel therapeutic agents for the treatment of obesity.

Example 7

Parenterally Administered GLP-1

GLP-1 i.e. GLP-1 (7-36) amide (25 nmol/kg) or saline (control) was administered parenterally to non-fasted rats prior to the onset of the dark phase. Exendin 9-39 (20 nmoles/kg) or saline (control) injected into the arcuate nucleus of non-fasted rats. Food intake one hour later was measured.

Figure 11:
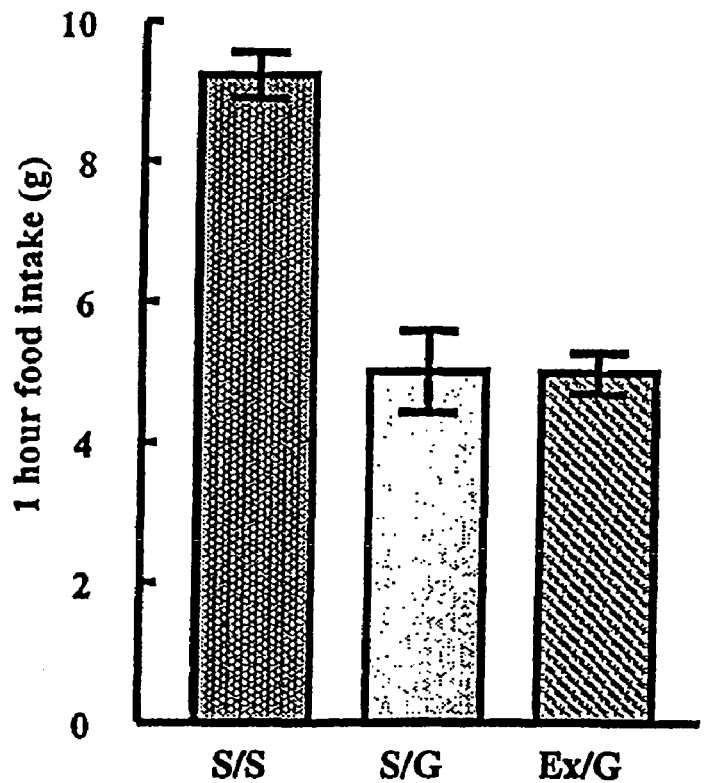
FIG. 11 shows the effect on 1-hour food intake in non-fasted rats of IP administration of GLP-1 in the presence or absence of concomitant exendin 9-39 in the arcuate nucleus of the rat. S=Saline, G=GLP-1 (25 nmol/kg), and Ex=exendin 9-39 (20 nmoles/kg).

The results as shown in FIG. 11 demonstrate that the effect on 1-hour food intake in non-fasted rats of IP administration of GLP-1 is not influenced by the presence of concomitant exendin 9-39, a GLP-1 receptor agonist, in the arcuate nucleus of the rat. This indicates that circulating GLP-1 acts via the brainstem rather than the arcuate nucleus. These and other findings suggest that the main site for appetite inhibition by peripheral GLP-1 is the dorsal vagal complex, acting in part directly through the area postrema.

Example 8

Co-Administration of PYY3-36 and GLP-1 in Rats $PYY_{3-36}$ and GLP-1 i.e. GLP-1 (7-36) amide were injected (intraperitoneally) into non-fasted rats prior to the onset of the dark phase. GLP-1 and $PYY_{3-36}$ were administered separately at the following doses: GLP-1 30 µg/kg=1×G or 60 µg/kg=2×G in 500 µl saline; $PYY_{3-36}$ (3 µug/kg=1×P or 6 µg/kg=2×P in 500 µl saline). $PYY_{3-36}$ and GLP-1 were co-administrated IP (P+G group) at doses of GLP-1 30 µg/kg and $PYY_{3-36}$ 3 µg/kg combined.

Figure 12:
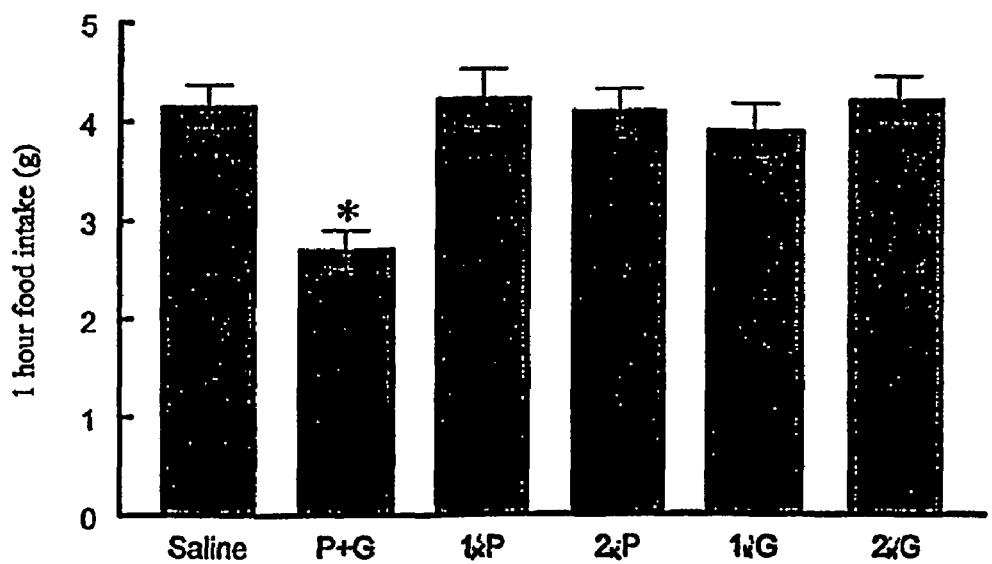
FIG. 12 shows the effects of co-administration of $PYY_{3-36}$ and GLP-1 on 1-hour food intake in non-fasted rats injected (intraperitoneally) prior to the onset of the dark phase. IP GLP-1 (30 μg/kg=1×G or 60 μg/kg=2×G in 500 μl saline) or IP $PYY_{3-36}$ (3 μg/kg=1×P or 6 μg/kg=2×P in 500 μl saline). Co-administration (P+G group) is GLP-1 30 μg/kg and $PYY_{3-36}$ 3 μg/kg combined.

The results set out in FIG. 12 show that there is a clear synergistic effect on the reduction of food intake when $PYY_{3-36}$ and GLP-1 were co-administered (P+G). However, when the procedure was carried out substituting oxyntomodulin for GLP-1, the results obtained for reduction of food intake when $PYY_{3-36}$ and oxynotomdulin were co-administered were only the sum of the individual effects. No synergistic effect was observed.

Example 9

Co-Administration of $PYY_{3-36}$ and GLP-1 in Humans 10 healthy volunteers (4 men and 6 women) having a mean age of 24.7 (±0.8) years and a mean BMI of 22.7 (±0.6) kg/m² were recruited. The volunteers were asked to fast and to drink only water from 9 pm on the night preceding all study days. Each volunteer attended for four study days. The volunteers arrived at 9.30 am and the venflons were inserted. A rest period from 10.00 to 10.30 followed. Intrvenous infusion started at 10.30, and a buffet lunch was provided between 12.00 and 12.30. infusion was terminated at 12.30, and the volunteers went home at 13.30.

The volunteers were given the following intra-venous infusions for 120 minutes (90 minutes pre-meal) in random order: Saline, GLP-1, $PYY_{3-36}$, $PYY_{3-36}$+GLP-1. The dose of both GLP-1 and PYY3-36 was 0.4 pmol/kg/min. The study was double blinded. GLP-1 is i.e. GLP-1 (7-36) amide The results of the food intake from the free buffet meal are given in the Table below Food intake from free buffet meal (Kcal)

|  | Saline | G | P | P + G |
|---|---|---|---|---|
| mean | 997 | 950 | 848 | 724 |
| Sem | 68.0 | 81.3 | 105.2 | 66.6 |
| p v saline |  | 0.336318995 | 0.069375886 | 3.00605E-06 |
| p v P + G |  | 0.003622523 | 0.044418337 |  |
| % reduction from saline |  | 5% | 15% | 27% | using paired t tests for all statistical comparisons

These result demonstrate a synergistic effect when PYY3-36 and GLP-1 are co-administered.

The results obtained in Examples 4 and 5 above demonstrate that $PYY_{3-36}$ acts via the arcuate nucleus. Oxynotmodulin is also considered to act via that region of the brain. The results obtained in Example 8 above indicates that GLP-1 acts via the brainstem. It appears from the results obtained in this Example that, when agents such as $PYY_{3-36}$ and GLP-1 that act via different areas of the brain and/or by different neurological routes are administered parenterally, they produce a synergistic affect, whereas when they act by the same area and/or route such as $PYY_{3-36}$ and oxynotmodulin, they do not. The synergistic effect on food intake obtained when PYY and GLP-1 were co-administered to humans confirms the observation made in rats.

These results indicate the importance in vivo of the interaction of gut hormones on the regulation of appetite and food intake. The present invention demonstrates that, surprisingly, it is possible to regulate appetite and food intake more effectively by informed choice of agents.

It will be apparent that the precise details of the methods or compositions described may be varied or modified without departing from the spirit of the described disclosure. We claim all such modifications and variations that fall within the scope and spirit of the claims below.

The invention claimed is:

1. A method for decreasing calorie intake, food intake or appetite in a human subject in need thereof, which comprises peripherally administering prior to a meal to said subject $PYY_{3-36}$ (peptide YY amino acids 3 to 36) from 5 to 100 nmoles per 70 to 75 kilogram body weight of the subject and a therapeutically effective amount of GLP-1 (glucagon-like peptide 1) or an agonist thereof.

2. A method as claimed in claim 1, wherein the $PYY_{3-36}$ and the GLP-1 or agonist thereof are administered to said subject sequentially.

3. A method as claimed in claim 2, wherein the $PYY_{3-36}$ and the GLP-1 or agonist thereof are administered to said subject via different routes.

4. A method as claimed in claim 1, wherein the subject is overweight.

5. A method as claimed in claim 1, wherein the subject is obese.

6. A method as claimed in claim 1, wherein the subject is diabetic.

7. A method as claimed in claim 1, wherein the peripheral administration is subcutaneous, intravenous, intramuscular, intranasal, transdermal, intraperitoneal, oral, topical, transmucosal, or sublingual administration or pulmonary inhalation.

8. A method for decreasing calorie intake, food intake or appetite in a human subject in need thereof, which comprises peripherally administering prior to a meal to said subject $PYY_{3-36}$ (peptide YY amino acids 3 to 36) from 45 to 135 pmoles per kilogram body weight of the subject and a therapeutically effective amount of GLP-1 (glucagon-like peptide 1) or an agonist thereof.

9. A method as claimed in claim 8, wherein about 72 pmoles of $PYY_{3-36}$ per kilogram body weight of the subject are peripherally administered.

10. A method as claimed in claim 1, wherein the $PYY_{3-36}$ or the GLP-1 or agonist thereof is peripherally administered to the subject at least 30 minutes prior to a meal.

11. A method as claimed in claim 1, wherein the GLP-1 agonist is exendin-4 or a derivative thereof that is a GLP-1 agonist.

12. A method as claimed in claim 1, further comprising administering a therapeutically effective amount of amfepramone (diethylpropion), phentermine, mazindol, phenylpropanolamine, fenfluramine, dexfenfluramine, or fluoxetine to said subject.

13. A method as claimed in claim 1, wherein the $PYY_{3-36}$ and the GLP-1 or agonist thereof are administered to said subject simultaneously.

14. A method as claimed in claim 1, which comprises administering $PYY_{3-36}$ to the subject subcutaneously at a dose of 10 nmoles, 20 nmoles, 30 nmoles or 40 nmoles per 70 to 75 kilograms body weight of the subject.

15. A method as claimed in claim 1, which comprises administering $PYY_{3-36}$ to the subject subcutaneously at a dose of 20 to 60 nmoles per 70 to 75 kilogram body weight of the subject.

16. A method as claimed in claim 1, which comprises administering $PYY_{3-36}$ to the subject subcutaneously at a dose of 35 to 45 nmoles per 70 to 75 kilogram body weight of the subject.

17. A method as claimed in claim 7, wherein the peripheral administration is subcutaneous administration.

18. The method as claimed in claim 1, wherein the peripheral administration is peripheral injection in a pulse dose.

19. The method as claimed in claim 1, wherein the peripheral administration is administration in a sustained or controlled release preparation or from a pump or implantable drug infusion device.

20. A method as claimed in claim 1, wherein the $PYY_{3-36}$ is peripherally administered to the subject at least 30 minutes prior to a meal.

21. A method as claimed in claim 1, wherein the $PYY_{3-36}$ is modified by amidation, glycosylation, acylation, sulfation, phosphylation, cyclization, lipidization or pegylation.

22. A method as claimed in claim 1, wherein 0.1 to 3.2 nmoles of the GLP-1 or agonist thereof per kilogram body weight of the subject is peripherally administered.

23. A method for treating obesity in a human subject in need of treatment, which comprises peripherally administering prior to a meal to said subject $PYY_{3-36}$ (peptide YY amino acids 3 to 36) from 5 to 100 nmoles per 70 to 75 kilogram body weight of the subject and a therapeutically effective amount of GLP-1 (glucagon-like peptide 1) or an agonist thereof.

24. The methods of claim 1, 8 or 23, wherein $PYY_{3-36}$ comprises peptide YY amino acids 3 to 36 of SEQ ID NOs:1, 5-12, 189 or 190, or a single point mutation or a double point mutation thereof.

25. A method as claimed in claim 1, wherein the peripheral administration is intravenous administration.

26. The method of claim 1, wherein the peripheral administration is subcutaneous administration.

27. The method of claim 1, wherein the peripheral administration is oral administration.

28. The method of claim 1, wherein the peripheral administration is by pulmonary inhalation.

* * * * *